(12) United States Patent
Campos et al.

(10) Patent No.: US 10,752,730 B2
(45) Date of Patent: Aug. 25, 2020

(54) QUANTITATIVE INTRAMOLECULAR FISSION IN OLIGOACENES, MATERIALS, AND METHODS OF USE THEREOF

(71) Applicants: THE TRUSTEES OF COLUMBIA UNIVERSITY IN THE CITY OF NEW YORK, New York, NY (US); BROOKHAVEN SCIENCE ASSOCIATES, LLC, Upton, NY (US)

(72) Inventors: Luis Miguel Campos, Brooklyn, NY (US); Matthew Y. Sfeir, Bethpage, NY (US); Samuel Nathan Sanders, New York, NY (US); Elango Kumarasamy, New York, NY (US); Andrew Brian Pun, New York, NY (US); Michael Louis Steigerwald, Martinsville, NJ (US)

(73) Assignees: The Trustees of Columbia University in the City of New York, New York, NY (US); Bookhaven Science Associates, LLC, Upton, NY (US)

( * ) Notice: Subject to any disclaimer, the term of this patent is extended or adjusted under 35 U.S.C. 154(b) by 57 days.

(21) Appl. No.: 15/536,964

(22) PCT Filed: Dec. 17, 2015

(86) PCT No.: PCT/US2015/066529
§ 371 (c)(1),
(2) Date: Jun. 16, 2017

(87) PCT Pub. No.: WO2016/100754
PCT Pub. Date: Jun. 23, 2016

(65) Prior Publication Data
US 2018/0258217 A1 Sep. 13, 2018

Related U.S. Application Data

(60) Provisional application No. 62/124,404, filed on Dec. 17, 2014.

(51) Int. Cl.
*C08G 61/10* (2006.01)
*H01L 51/00* (2006.01)
(Continued)

(52) U.S. Cl.
CPC .............. *C08G 61/10* (2013.01); *C07C 50/24* (2013.01); *C07F 7/0803* (2013.01);
(Continued)

(58) Field of Classification Search
CPC ....................................................... C08G 61/10
(Continued)

(56) References Cited

PUBLICATIONS

Kang, Jihoon et al., "Strucure and Properties of Small Molecule-Polymer Blend Semiconductors for organic Thin Film Transistors," J. Am. Chem. Soc., vol. 130, pp. 12273-12275, 2008.
(Continued)

*Primary Examiner* — Duc Truong
(74) *Attorney, Agent, or Firm* — Hunton Andrews Kurth LLP

(57) ABSTRACT

The present invention provides soluble, stable singlet fission (SF) compounds, compositions, materials, methods of their use, and methods for their preparation that provide efficient intramolecular singlet fission (iSF) and multiple excitons. The SF compound may be a dimer, an oligomer, or a polymer of polyoligoacenes, where for example, the compound achieves a triplet yield reaching about 200% per absorbed photon. In this system, SF does not depend on intermolecular inter-actions. Instead, SF is an intrinsic property of the molecule and therefore occurs independent of intermolecular interactions. Singlet fission has the potential to significantly improve the photocurrent in single junction solar cells and thus raise the Shockley-Queisser power conversion efficiency limit from about 33% to about 46% or greater. Quantitative SF yield at room temperature has only
(Continued)

been observed in crystalline solids or aggregates of higher acenes.

11 Claims, 125 Drawing Sheets

(51) Int. Cl.
C07C 50/24 (2006.01)
C07F 7/08 (2006.01)
(52) U.S. Cl.
CPC ........ *C07F 7/0805* (2013.01); *H01L 51/0035* (2013.01); *H01L 51/0052* (2013.01); *H01L 51/0055* (2013.01); *H01L 51/0056* (2013.01); *H01L 51/0058* (2013.01); *H01L 51/0094* (2013.01); *C07C 2603/52* (2017.05); *C08G 2261/144* (2013.01); *C08G 2261/226* (2013.01); *C08G 2261/312* (2013.01); *C08G 2261/314* (2013.01); *C08G 2261/411* (2013.01); *C08G 2261/90* (2013.01); *C08G 2261/91* (2013.01); *C08G 2261/92* (2013.01); *C08G 2261/94* (2013.01); *C08G 2261/95* (2013.01); *Y02E 10/549* (2013.01)
(58) Field of Classification Search
USPC .................................................. 528/39, 394
See application file for complete search history.

(56) References Cited

PUBLICATIONS

Mannsfeld, Stefan C.B. et al., "Thin Film Structure of Triisopropylsilylethynyl-Functionalized Pentacene and Tetraceno[2,3-b]thiophene from Grazing Incidence X-Ray Diffraction," Adv. Mater, vol. 23, pp. 127-131, 2011.
Kline, Joseph R. et al., "Controlling the Microstructure of Solution-Processable Small Molecules in Thin-Film Transistors through Substrate Chemistry," Chem. Matter, vol. 23, pp. 1194-1203, 2011.
Banerjee, Moloy et al., "Synthesis, Optical, and Electronic Properties of Soluble Poly-p-phenylene Oligomers as Models for Molecular Wires," J. Sm. Chem. Soc., vol. 131, pp. 1780-1786, 2009.
You, Jingbi et al., "A Polymer Tandem Solar Cell with 10.6% Power Conversion Efficiency," Nat. Commun, vol. 4, pp. 1-10, 2013.
Ashton, Peter R. et al., "Molecular Belts. 2. Substrate-Directed Syntheses of Belt-Type and Cage-Type Structures," J. Am. Chem. Soc., vol. 115, pp. 5422-5429, 1993.
Coropceanu, Veaceslav et al., "Charge Transport in Organic Semiconductors," Chem. Rev., vol. 107, pp. 926-952, 2007.
Wu, Weiping et al., " . . . Conjugated Molecules with Fused Rings for Organic Field-Effect Transistors: Design, Synthesis and Applications," Chem. Soc. Rev., vol. 39, pp. 1489-1502, 2010.
Okamoto, Toshihiro et al., "2,9-Dibromopentacene: Synthsis and the Role of Substituent and Symmetry on Solid-State Order," Synthetic Metals, vol. 160, pp. 2447-2451, 2010.
Kumarasamy, Elango et al., "Nonbiaryl and Heterobiaryl Atropisomers: Molecular Templates with Promise for Atropselective Chemical Transformations," Chem. Rev., vol. 115, pp. 11239-11300, 2015.
Xiao, Shengxiong et al., "Supersized Contorted Aromaticst," Chem. Sci., vol. 4, pp. 2018-2023, 2013.
Benard, Christophe P. et al., "Double Diels-Alder Strategies to Soluble 2,9- and 2,9,6,13-Tetraethynylpentacenes, Photolytic [4+4] Cycloadditions, and Pentacene Crystal Packing," J. Org. Chem., vol. 72, pp. 7229-7236, 2007.
Zhao, Yuewei et al., "Photochemical Formation of Substituted Pentacenes," J. Org. Chem., vol. 73, pp. 5506-5513, 2008.
Lu, Jun et al., "Synthesis, Structure, and Resolution of Exceptionally Twisted Pentacenes," J. Am. Chem. Soc., vol. 128, pp. 17043-17050, 2006.
Takahashi, Tamotsu et al., "Straightforward Method for Synthesis of Highly Alkyl-Substituted Naphthacene and Pentanene Derivatives by Homologation," J. Am. Chem. Soc., vol. 122, pp. 12876-12877, 2000.
Goto, Kiyohiko et al., "Intermolecular Oxidative Annulation of 2-Aminoanthracenes to Diazaacenes and Aza[7] helicenes," Angew. Chem. Int. Ed., vol. 51, pp. 10333-10336, 2012.
Sheldrick, George M. "A Short History of SHELX," Acta Cryst., vol. A64, pp. 112-122, 2008.
Dolomanov, Oleg V. et al., "OLEX2: A Complete Structure Solution, Refinement and Analysis Program," J. Appl. Cryst., vol. 42, pp. 339-341, 2009.
Clark, R.C. et al., "The Analytical Calculation of Absorption in Multifaceted Crystals," Acta Cryst., vol. A51, pp. 887-897, 1995.
Busing, William R. et al., "High-Speed Computation of the Absorption Correction for Single Crystal Diffraction Measurement," Acta Cryst, vol. 10, pp. 180-182, 1957.
Resch-Genger, Ute et al., "Determination of the Photoluminescence Quantum yield of Dilute Dye Solutions (IUPAC Technical Report)," Pure Appl. Chem., vol. 85, No. 10. pp. 2005-2026, 2013.
Brouwer, Albert M. et al., "Standards for Photoluminescence Quantum Yield Measurements in Solution (IUPAC Technical Report)" Pure Appl. Chem., vol. 83, No. 12, pp. 2213-2228, 2011.
Plunkett, Kyle N. et al., "Expeditious Synthesis of Contorted Hexabenzocoronenes," Organic Letters, vol. 11, No. 11, pp. 2225-2228, 2009.
Angliker, Herbert et al., "Electronic Spectra of Hexacene in Solution," Chemical Physics Letters, vol. 87, No. 2, pp. 208-212, Mar. 19, 1982.
Bensasson, R. et al., "Triplet-Triplet Extinction Coefficients vis Energy Transfer," Trans. Faraday Soc., vol. 67, pp. 1904-1915, 1971.
Snellenburg, Joris J. et al., "Glotaran: A Java-based Graphical user Interface for the R Package TIMP," Journal of Statistical Software, vol. 49, Issue 3, pp. 1-22, Jun. 2012.
Walker, Brian J. et al., "Singlet Exciton Fission in Solution," Nature Chemistry, vol. 5., pp. 1019-1024, Dec. 2013.
Greyson, Eric C. et al., "Singlet Exciton Fission for Solar Cell Applications: Energy Aspects of Interchromophore Coupling," J. Phys. Chem., vol. 114, pp. 1223-14232, 2010.
Payne, Marcia M. et al., "Stable, Crystalline Acenedithiophenes with up to Seven Linearly Fused Rings," Organic letters, vol. 6, No. 19, pp. 3325-3328, 2004.
Miao, Qian et al., "Organization of Acenes with a Cruciform Assembly Motif," J. Am. Chem. Soc., vol. 128, pp. 1340-1345, 2006.
Lehnherr, Dan et al., "Pentacene Oligomers and Polymers: Functionalization of Pentacene to Afford Mono-, Di-, Tri-, and Polymeric Materials," Organic letters, vol. 9, No. 22, pp. 4583-4586, 2007.
Lehnherr, Dan et al., "Exploring Electronically Polarized Pentacenes," Organic Letters, vol. 10, No. 19, pp. 4163-4166, 2008.
Lehnherr, Dan et al., "Synthesis and Electronic Properties of Conjugated Pentacene Dimers," Organic Letters, vol. 10, No. 21, pp. 4779-4782, 2008.
Swartz, Christopher R et al., "Synthesis and Characterization of Electron-Deficient Pentacenes," Organic Letters, vol. 7, No. 15, pp. 3163-3166, 2005.
Chen, Jihua et al., "The Influence of Side Chains on the Structures and Properties of Functionalized Pentacenes," Journal of Materials Chemistry, vol. 18, No. 17, pp. 1937-2052, May 7, 2008.
Mullen, K. et al., "Electronic Materials: The Oligomer Approach," Wiley-VCH: New York, pp. 1-625, 1998.
Liu, Feng et al., "Multifaceted Regioregular Oligo(thieno[3,4-b]thiophene)s Enabled by Tunable Quinoidization and Reduced Energy Band Gap," J. Am. Chem. Soc., vol. 137, pp. 10357-10366, 2015.
Zhang, Lei et al., "Synthesis, Electronic Structure, Molecular Packing/Morphology Evolution, and Carrier Mobilities of Pure Oligo-/Poly(alkythiophenes)," J. Am. Chem. Soc., vol. 135, pp. 844-854, 2013.

(56) References Cited

PUBLICATIONS

Vinzenz Koch, Felix Peter et al., "Thermal and Structural Characteristics of Oligo(3-hexylthiophene)s . . . ,)" J. Am. Chem. Soc., vol. 135, 13699-13709, 2013.

Koch, V.P. Felix et al., "'Fibonacci's Route' to Regioregular Oligo(3-hexylthiophene)s" J. Am. Chem. Soc., vol. 135, pp. 13695-13698, 2013.

Capozzi, Brian et al., "Length-Dependent Conductance of Oligothiophenes," J. Am. Chem. Soc., vol. 136, pp. 10486-10492, 2014.

Porz, Michael et al., "TIPS-Tetracene- and TIOPS-Pentacene-Annulated Poly(norbornadiene)s: Synthesis and Properties," Maromol. Rapid Commun., vol. 34, pp. 1611-1617, 2013.

Tokito, Shizuo et al., "Acene Containing Polyfluorenes for red, green, and blue emission in organic light-emitting diodes," Proc. SPIE-Int. Soc. Opt. Eng., vol. 4105, pp. 69-74, 2001.

Lehnherr, Dan et al., "A Modular Synthetic Approach to Conjugated Pentacene Di-, Tri-, and Tetramers," Angew. Chem. Int. Ed., vol. 49, pp. 6190-6194, 2010.

Lehnherr, Dan et al., "Synthesis of Soluble Oligo- and Polymeric Pentacene-based Materials," Tetrahedron, vol. 64, pp. 11449-11461, 2008.

Okamoto, Toshihiro et al., "Synthesis of Solution-Soluble Pentacene-Containing Conjugated Copolymers," J. Am. Chem. Soc., vol. 129, pp. 10308-10309, 2007.

Lehnherr, Dan et al., "Pentacene-Based Dendrimers: Synthesis and Thin Film Photoconductivity measurements of Branched Pentacene Oligomers," J. Org. Chem., vol. 74, pp. 5017-5024, 2009.

Maliakal, Ashok et al., "Photochemical Stability of Pentacene and a Substituted Pentacene in Solution and in Thin Films," Chem. Mater., vol. 16, pp. 4980-4986, 2004.

Fudickar, Werner et al., "Why Triple Bonds Protect Acenes from Oxidatoin and Decomposition," J. Am. Chem. Soc., vol. 134, pp. 15071-15082, 2012.

Bendikov, Michael et al., "Tetrathiafulvalenes, Oligoacenenes, and Their Buckminsterfullerene Derivatives; The Brick and Mortar of Organic Electronics," Chem. Rev., vol. 104, pp. 4891-4945, 2004.

Anthony, John E. "Functionalized Acenes and Heteroacenes for Organic Electronics," Chem. Rev., vol. 106, pp. 5028-5048, 2006.

Shu, Ying et al., "A Survey of Electron-Deficient Pentacenes as Acceptors in Polymer Bulk Heterojunction Solar Cells," Chem. Sci., vol. 2, pp. 363-368, 2011.

Herwig, Peter T. et al., "A Soluble Pentacene Precursors: Synthesis, Solid-State Conversion into Pentacene and Application in a Field-Effect Transistor," Adv. Mater, vol. 11, No. 6, pp. 480-483, 1999.

Jo, Sae Byeok et al., "Boosting Photon Harvesting in Organic Solar Cells with Highly Oriented Molecular Crystals via Graphene-Organic Heterointerface," vol. 9, No. 8., pp. 8206-8219, 2015.

Afzali, Ali et al., "High-Performance, Solution-Processed Organic Thin Film Transistors from a Novel Pentacene Precursor," J. Am. Chem. Soc., vol. 124, pp. 8812-8813, 2002.

Park, Sung Kyu et al., "High Mobility Solution Processed 6, 13-bis(triisoproply-silylethynyl) Pentancene Organic thin film Transistors," Applied Physics Letters, vol. 91, pp. 063514-1-063514-3, 2007.

Lin, Yen-Yi et al., "Pentacene-Based Organic Thin-film Transistors," IEEE Transactions on Electron Devices, vol. 44, No. 8, pp. 1325-1331, Aug. 1997.

Bunz, H.F. Uwe "The Larger Linear N-Heteroacenes," Acc. Chem. Res., vol. 48, pp. 1676-1686, 2015.

Sundar, Vikram et al., "Elastomeric Transistor Stamps: Reversible Probing of Charge Transport in Organic Crystals," Science, vol. 303, pp. 1644-1646, Mar. 12, 2004.

Tsefrikas, Vikki M. et al., "Geodesic Polyarenes by Flash Vacuum Pyrolysis," Chem. Rev., vol. 106, pp. 4868-4884, 2006.

Ball, Melissa et al., "Contorted Polycyclic Aromatics," Acc. Chem. Res., vol. 48, pp. 267-276, 2015.

Zade, Sanjio S. et al., "Heptacene and Beyond: The Longest Characterized Acenes," Angew. Chem. Int. Ed., vol. 49, pp. 4012-4015, 2010.

Anthony, John E. "The Larger Acenes: Versatile Organic Semiconductors," Angew. Chem. Int. Ed., vol. 47, pp. 452-483, 2008.

Ito, Kaname et al., "Oligo(2,6-anthrylene)s: Acene-Oligomer Approach for Organic Field-Effect Transistors," Angew. Chem., vol. 115, No. 10, pp. 1191-1194, 2003.

Katz, Howard E. et al., "Synthetic Chemistry for Ultrapure, Processable, and high-Mobility Organic Transistor Semiconductors," Acc. Chem. Res., vol. 34, pp. 359-369, 2001.

Purushothaman, Balaji et al., "Snythesis and Stability of Soluble Hexacenes," Orangic Letters, vol. 12, No. 9, pp. 2060-2063, 2010.

Payne, Marcia M. et al., "Functionalized Higher Acenes: Hexacene and Heptacene," J. Am. Chem. Soc., vol. 127, pp. 8028-8029, 2005.

Anthony, John E. et al., "Functionalized Pentacene: Improved Electronic Properties from Control of Solid-State Order," J. Am. Chem. Soc., vol. 123, pp. 9482-9483, 2001.

Anthony, John E. et al., "A Road Map to Stable, Soluble, Easily Crystallized Pentacene Derivatives," Organic Letters, vol. 4, No. 1, pp. 15-18, 2002.

Fudickar, Werner et al., "Why Triple Bonds Protect Acenes from Oxidation and Decomposition," J. Am. Chem. Soc., vol. 134, pp. 15071-15082, 2012.

Englman, Robert et al., "The energy gap law for radiationless transitions in large molecules," Molecular Physics, vol. 18, No. 2, pp. 145-164, 1970.

Casper, Jonathan V. et al., "Application of the Energy Gap Law to Nonradiactive, Excited-State Decay," J. Phys. Chem., vol. 87, pp. 952-957, 1983.

Wilson, Joanne S. et al., "The Energy Gap Law for Triplet States in Pt-Containing Conjugated Polymers and Monomers," J. Am. Chem. Soc., vol. 123, pp. 9412-9417, 2001.

Yang, Le et al., "Solution-Processable Singlet Fission Photovoltaic Devices," Nano Lett., vol. 15, pp. 354-358, 2014.

Houk, K.N. et al., "Polyacene and Cyclacene Geometries and Electronic Structures: Bond Equalization, Vanishing Band Gaps, and Triplet Ground States Contrast with Polyacetylene," J. Org. Chem., vol. 66, pp. 5517-5521, 2001.

Stern, Hannah L. et al., "Identification of a triplet pair Intermediate in Singlet exciton fission in Solution," PNAS, vol. 112, No. 25, pp. 7656-7661, Jun. 23, 2015.

Pensack, Ryan D. et al., "Exciton Delocalization Drives Rapid Singlet Fission in Nanoparticles of Acene Derivatives," J. Am. Chem. Soc., vol. 137, pp. 6790-6803, 2015.

Roberts, Sean T. et al., "Efficient Singlet Fission Discovered in a Disordered Acene Film," J. Am. Chem. Soc., vol. 134, pp. 6388-6400, 2012.

Mastron, Joseph N. et al., "Aqueous Colloidal Acene Nanoparticles: A New Platform for Studying Singlet Fission," J. Phys. Chem., vol. 117, pp. 15519-15526, 2013.

Geacintov, N.E. et al., "Heterofission of Pentacene Excited Singlets in Pentacene-Doped Tetracene Crystals," Chemical Physics Letters, vol. 11, No. 4, pp. 504-508, Nov. 1, 1971.

Chabr, M. et al., "Singlet Exciton Trapping and Heterofission in Tetracene Doped Anthracene Crystals," Chemical Physics Letters, vol. 49, No. 3, pp. 599-603, Aug. 1, 1977.

Trlifaj, M. et al., "Nonradiative Heterofission of a Singlet Host Exciton into a Pair of Triplet Electronic Excitations in Doped Aromatic Hydrocarbon Molecular Crystals," Czech. J. Phys., vol. 27, pp. 190-199, 1977.

Alguire, Ethan C. et al., "Exploring Non-Condon Effects in a Covalent Tetracene Dimer: How Important are Vibrations in Determining the Electronic Coupling for Singlet Fission?" J. Phys. Chem., vol. 119, pp. 299-311, 2015.

Greyson, Eric C. et al., "Maximizing Singlet Fission in Organic Dimers: Theoretical Investigation of Triplet Yield in the Regime of Localized Excitation and Fast Coherent Electron Transfer," J. Phys. Chem., vol. 114, pp. 14168-14177, 2010.

Muller, Astrid M. et al., "Exciton Fission and Fusion in Bis(tetracene) Molecules with Difference Covalent Linker Structures," J. Am. Chem. Soc., vol. 129, pp. 14240-14250, 2007.

Muller, Astrid M. et al., "Evidence for Exciton Fission and Fusion in a Covalently Linked Tetracene dimer," Chemical Physics Letters, vol. 421, pp. 518-522, 2006.

(56) References Cited

PUBLICATIONS

Vallett, Paul J. et al., "Tunable Electronic Coupling and Driving Force in Structurally Well-Defined Tetracene Dimers for Molecular Singlet Fission: A Computational Exploration using Density Functional Theory," J. Phys. Chem., vol. 117, pp. 10824-10838, 2013.

Burdett, Jonathan J. et al., "The Dynamics of Singlet Fission in Crystalline Tetracene and Convalent Analogs," Accounts of Chemical Research, vol. 46, No. 6, pp. 1312-1320, 2013.

Musser, Andrew J. et al., "Activated Singlet Exciton Fission in a Semiconducting Polymer," J. Am. Chem. Soc., vol. 135, pp. 12747-12754, 2013.

Gradinaru, Claudiu C. et al., "An Unusual Pathway of Excitation Energy Deactivation in Carotenoids: Singlet-to-triplet Conversion on an Ultrafast timescale in a photosynthetic antenna," PNAS, vol. 98, No. 5, pp. 2364-2369, Feb. 27, 2001.

Chan, Wai-Lun et al., "The Quantum Coherent Mechanism for Singlet Fission: Experiment and Theory," Accounts of Chemical Research, vol. 46, No. 6, pp. 1321-1329, 2013.

Chan, Wai-Lun et al., "Observing the Multiexciton State in Singlet Fission and Ensuing Ultrafast Multielectron Transfer," Science, vol. 334, pp. 1541-1545, Dec. 16, 2011.

Yost, Shane R. et al., "A transferable model for singlet-fission kinetics," Nature Chemistry, vol. 6, pp. 492-497, Jun. 2014.

Lee, O.J. et al., "Ultrafast Switching of a Nanomagnet by a Combined out-of-place and in-plane polarized spin current pulse," Applied Physics Letters, vol. 95, pp. 012506-1-012506-3, 2009.

Zeng, Tao et al., "The Low-Lying Electronic States of Pentacene and Their Roles in Singlet Fission," J. Am. Chem. Soc., vol. 136, pp. 5755-5764, 2014.

Singh, S. et al., "Laser Generation of Excitons and Fluoresence in Anthracene Crystals," The Journal of Chemical Physics, vol. 42, No. 1, pp. 330-342, Jan. 1, 1965.

Varnavski, Oleg et al., "High Yield Ultrafast Intramolecular Singlet Exciton Fission in a Quinoidal Bithiophene," J. Phys. Chem. Lett., vol. 6, pp. 1375-1384, 2015.

Lukman, Steven et al., "Tuneable Singlet Exciton Fission and Triplet-Triplet Annihilation in an Orthogonal Pentacene Dimer," Adv. Funct. Mater, vol. 25, pp. 5452-5461, 2015.

International Search Report for International Application No. PCT/US2015/066529 dated Feb. 26, 2017.

International Written Opinion for International Application No. PCT/US2015/066529 dated Feb. 26, 2017.

SN Sanders et al. "Quantitative Intramolecular Singlet Fission in Bipentacenes," J. Am. Chem. Soc. vol. 137, pp. 8965-8972, Jun. 23, 2015.

Zirzlmeier, Johannes et al., "Singlet Fission in Pentacene Dimers," PNAS, vol. 112, No. 17, pp. 5325-5330, Apr. 28, 2015.

Sanders, Samuel N. et al., "Quantitative Intramolecular Singlet Fission in Bipentacenes," J. Am. Chem. Soc., vol. 137, pp. 8965-8972, 2015.

Low, Jonathan et al., "Correlating Structure and Function in Organic Electronics: From Single Molecule Transport to Singlet Fission," Chem. Mater., vol. 27, pp. 5453-5463, 2015.

Monahan, N. et al., "Chrage Transfor-Mediated Singlet Fission," Annu. Rev. Phys. Chem., vol. 66, pp. 601-618, 2015.

Aryanpour, Karan et al., "Theory of Primary Photoexcitations in Dono-Acceptor Copolymers," arXiv:1508.00071v2 [cond-mat.meshall], Dec. 31, 2015.

Busby, Erik et al., "Fast Singlet Exciton Decay in Push-Pull Molecules Containing Oxidized Thiophenes," J. Am. Chem., pp. 7644-7650, 2015.

Busby, Erik et al., A Design Strategy for Intramolecular singlet fission mediated by charge-transfer states in donor-acceptor organic materials, Nature Materials, vol. 14, pp. 426-433, Apr. 2015.

Shockley, William et al., "Detailed Balance limit of Efficiency of . . . ," Journal of Applied Physics, vol. 32, No. 3, pp. 510-519, Mar. 1961.

Nozik, A.J. et al., "Quantum dot Solar Cells," Physica, vol. 14, pp. 115-120, 2002.

Green, Martin A. et al., "Third Generation Photovoltaics Ultra-high Conversion Efficiency at Low Cost," Prog. Photovolt: Res. Appl., vol. 9, pp. 123-135, 2001.

Lee, Jiye et al., "Singlet Exciton Fission Photovoltaics," Accounts of Chemical Research, vol. 46, No. 6, pp. 1300-1311, 2013.

Congreve, Daniel N. et al., "External Quantum Efficiency Above 100% in a Singlet-Exciton-Fisson-based Organic Photovoltaic Cell," Science, vol. 340, pp. 334-337, Apr. 19, 2013.

Paci, Irina et al., "Singlet Fission for Dye-Sensitized Solar Cells: can a Suitable Sensitizer be found?" J. Am. Chem. Soc., vol. 128, pp. 16546-16553, 2006.

Smith, Millicent B. et al., "Singlet Fission," Chem. Rev., vol. 110, pp. 6891-6936, 2010.

Smith, Millicent B. et al., "Recent Advances in Singlet Fission," Annu. Rev. Phys. Chem., vol. 64, pp. 361-386, 2013.

Hanna, M.C. et al., "Solar Conversion Efficiency of Photovoltaic and Photoelectrolysis cells with Carrier Multiplication Absorbers," Journal of Applied Physics, vol. 100, pp. 074510-1-074510-7, 2006.

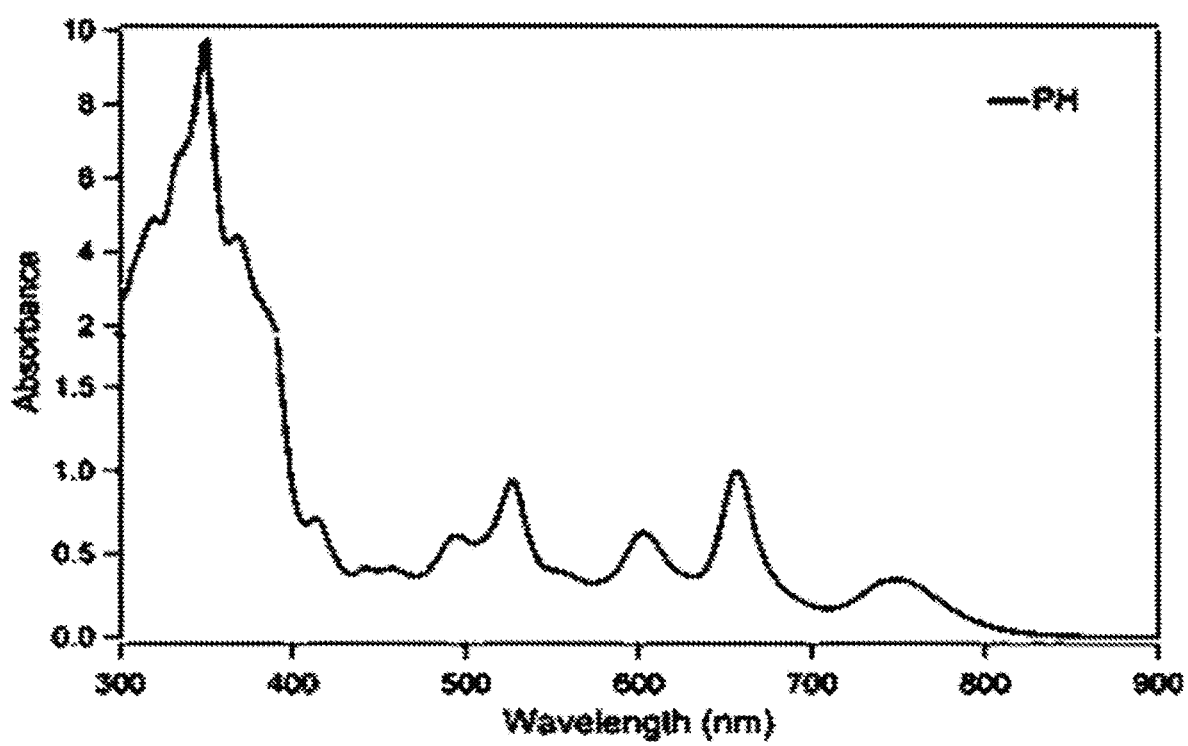

FIG. 34A

| atom | x | y | z |
|---|---|---|---|
| C1 | 0.0614752681 | -0.0213004662 | 0.0742138490 |
| C2 | 0.0877178925 | -0.0352050930 | 1.4971101911 |
| C3 | 1.2984201134 | -0.1632977385 | 2.2086594281 |
| C4 | 1.3416218128 | -0.1792523734 | 3.5976992747 |
| C5 | 2.5726330549 | -0.3100990136 | 4.3214916599 |
| C6 | 2.5865350268 | -0.3233947625 | 5.6870175180 |
| C7 | 1.3662763876 | -0.2062807118 | 6.4252169914 |
| C8 | 0.1708725251 | -0.0795277705 | 5.7767494897 |
| C9 | 0.1072887379 | -0.0606775515 | 4.3444899370 |
| C10 | -1.0940924975 | 0.0665067250 | 3.6558208624 |
| C11 | -1.1511345845 | 0.0835885467 | 2.2459843840 |
| C12 | -2.3863308522 | 0.2133011136 | 1.5510942357 |
| C13 | -2.4122613664 | 0.2256069358 | 0.1269541962 |
| C14 | -3.6219486970 | 0.3515816070 | -0.5870030989 |
| C15 | -3.6637638391 | 0.3648233156 | -1.9763393748 |
| C16 | -4.8938734254 | 0.4921573288 | -2.7022868906 |
| C17 | -4.9059050419 | 0.5026263589 | -4.0679753670 |
| C18 | -3.6844741271 | 0.3860681041 | -4.8045034362 |
| C19 | -2.4899695807 | 0.2626534773 | -4.1539747596 |
| C20 | -2.4286819975 | 0.2467446348 | -2.7215475352 |
| C21 | -1.2287505712 | 0.1223513036 | -2.0307736500 |
| C22 | -1.1734408660 | 0.1069210971 | -0.6210776372 |
| C23 | 1.2742288604 | -0.1344972663 | -0.6588798217 |
| C24 | 2.3146772007 | -0.2314065759 | -1.2949598667 |
| Si25 | 3.8792545925 | -0.3742095103 | -2.2572341056 |
| C26 | 4.0535796475 | 1.1478632924 | -3.3626268019 |
| C27 | 5.3256097867 | -0.4698704308 | -1.0450878087 |
| C28 | 3.8035253574 | -1.9413355611 | -3.3095978246 |
| C29 | -3.6030068395 | 0.3316081630 | 2.2770632931 |
| C30 | -4.6571002373 | 0.4340592260 | 2.8894692477 |
| Si31 | -6.2533273918 | 0.5968062603 | 3.7946342390 |
| C32 | -5.9039180408 | 0.5562519416 | 5.6505293892 |
| C33 | -7.0542291991 | 2.2390885503 | 3.3156242758 |
| C34 | -7.3738482819 | -0.8447820919 | 3.3086696925 |
| H35 | 2.2216447068 | -0.2518980951 | 1.6464027798 |
| H36 | 3.4961534756 | -0.3987345314 | 3.7565970727 |
| H37 | 3.5254711973 | -0.4232656605 | 6.2233329524 |
| H38 | 1.3987044334 | -0.2191902641 | 7.5107189727 |
| H39 | -0.7560254567 | 0.0093576293 | 6.3360881650 |
| H40 | -2.0208082632 | 0.1552003305 | 4.2124042982 |
| H41 | -4.5460016988 | 0.4401650073 | -0.0262852898 |
| H42 | -5.8184854041 | 0.5804509931 | -2.1390834547 |
| H43 | -5.8442840488 | 0.5997848800 | -4.6058084599 |

FIG. 34B

| atom | x | y | z |
|---|---|---|---|
| H44 | -3.7154492872 | 0.3966643701 | -5.8901123128 |
| H45 | -1.5621303174 | 0.1741232979 | -4.7117857518 |
| H46 | -0.3013552657 | 0.0337670559 | -2.5858046307 |
| H47 | -5.4267445827 | -0.3842935324 | 5.9444153361 |
| H48 | -5.2425823049 | 1.3762282819 | 5.9486740172 |
| H49 | -6.8345127593 | 0.6521875709 | 6.2217395353 |
| H50 | -6.4110021259 | 3.0850998089 | 3.5777953464 |
| H51 | -8.0100343988 | 2.3696603039 | 3.8357063500 |
| H52 | -7.2487072722 | 2.2889715316 | 2.2393662589 |
| H53 | -6.9172116357 | -1.8056062423 | 3.5669032073 |
| H54 | -7.5738597576 | -0.8490627943 | 2.2322710590 |
| H55 | -8.3366784323 | -0.7794073342 | 3.8282724448 |
| H56 | 3.2165665062 | 1.2306359175 | -4.0634606752 |
| H57 | 4.9778186305 | 1.0952754035 | -3.9493310896 |
| H58 | 4.0842518293 | 2.0672699040 | -2.7694222790 |
| H59 | 5.3761574123 | 0.4243026321 | -0.4153071429 |
| H60 | 5.2354730633 | -1.3399621437 | -0.3867071303 |
| H61 | 6.2769951572 | -0.5543854230 | -1.5828986935 |
| H62 | 4.7217312462 | -2.0573779345 | -3.8965630447 |
| H63 | 3.6892615099 | -2.8332224919 | -2.6853455335 |
| H64 | 2.9607878631 | -1.9127667186 | -4.0078536431 |

FIG. 35A

| atom | x | y | z |
|---|---|---|---|
| C1 | 0.1455346705 | 0.9571596286 | 0.0344901516 |
| C2 | 0.1060656725 | 0.6377343109 | 1.4315000573 |
| C3 | 1.3588167874 | 0.4268578866 | 2.1255415012 |
| C4 | 2.5820674292 | 0.5467745970 | 1.3882340263 |
| C5 | 2.5727932969 | 0.8537897690 | 0.0572843078 |
| C6 | 1.3347914952 | 1.0618411523 | -0.6291855193 |
| C7 | 1.3352806301 | 0.1185933216 | 3.4813026030 |
| C8 | 0.1310961494 | 0.0084267200 | 4.2067295768 |
| C9 | -1.1252980624 | 0.2209409063 | 3.5108674212 |
| C10 | -1.0896784990 | 0.5283903515 | 2.1341469710 |
| C11 | -2.3533102573 | 0.1237391718 | 4.2249626089 |
| C12 | -2.3554447258 | -0.1678856677 | 5.6202611715 |
| C13 | -1.0987749857 | -0.3817226984 | 6.3150366645 |
| C14 | 0.1279324116 | -0.2961381173 | 5.5997077020 |
| C15 | -1.1278255981 | -0.6517558291 | 7.7007626182 |
| C16 | -2.3172413212 | -0.6981086655 | 8.4145791426 |
| C17 | -3.5695187395 | -0.4803066125 | 7.7266539535 |

FIG. 35B

| atom | x | y | z |
|---|---|---|---|
| C18 | -3.5552593132 | -0.2344889545 | 6.3574143370 |
| C19 | -2.3585759420 | -0.9264566304 | 9.8291079265 |
| C20 | -3.5375458989 | -0.9199678613 | 10.5113354447 |
| C21 | -4.7944672572 | -0.6931232887 | 9.8428907818 |
| C22 | -4.7813487310 | -0.4947638012 | 8.4807654069 |
| C23 | 1.3618486853 | -0.5029588970 | 6.2753796554 |
| C24 | 2.4293231209 | -0.6774482076 | 6.8462686419 |
| C25 | -3.5862227223 | 0.3395068041 | 3.5503834942 |
| C26 | -4.6507905027 | 0.5287733999 | 2.9779347587 |
| H27 | 2.2708307527 | -0.0392493843 | 4.0064989189 |
| H28 | -2.0285124044 | 0.6872800849 | 1.6149939717 |
| H29 | 3.5190215381 | 0.3888997455 | 1.9143073448 |
| H30 | -0.7946095216 | 1.1159531059 | -0.4858584132 |
| H31 | 3.5064665142 | 0.9429243740 | -0.4899429510 |
| H32 | 1.3480487457 | 1.3056543022 | -1.6875034676 |
| H33 | -0.1877283123 | -0.8105808967 | 8.2174635083 |
| H34 | -4.4921782256 | -0.0681435508 | 5.8373347151 |
| H35 | -1.4205050095 | -1.0794648407 | 10.3560123666 |
| H36 | -5.7095849302 | -0.3504406129 | 7.9382801706 |
| H37 | -3.5337518245 | -1.0526257940 | 11.5881575682 |
| C38 | -6.0552016871 | -0.6455284246 | 10.6127582145 |
| C41 | -6.2211083056 | -1.3450660031 | 11.7866268694 |
| C42 | -7.4402407646 | -1.2977263563 | 12.5306285120 |
| C43 | -8.5323406226 | -0.4959626606 | 12.0236005862 |
| C44 | -8.3339433951 | 0.2234375337 | 10.8023254630 |
| C45 | -7.1526722195 | 0.1552637317 | 10.1311740020 |
| H46 | -5.4247966314 | -1.9773609554 | 12.1659377860 |
| C47 | -7.6118970016 | -1.9935925924 | 13.7243719424 |
| H48 | -9.1445762920 | 0.8421820458 | 10.4287023872 |
| H49 | -7.0157940870 | 0.7427696975 | 9.2307341268 |
| C50 | -8.8181023998 | -1.9434646237 | 14.4562908669 |
| H51 | -6.7976059151 | -2.5959862951 | 14.1114900318 |
| C52 | -9.9119010113 | -1.1402918974 | 13.9395833327 |
| C53 | -9.7235446103 | -0.4378425679 | 12.7313823905 |
| C54 | -11.1431980434 | -1.0716231832 | 14.6481366126 |
| H55 | -10.5411865517 | 0.1643089085 | 12.3504059473 |
| C56 | -11.3162606936 | -1.8000664848 | 15.8596853284 |
| C57 | -12.2107296928 | -0.2700880197 | 14.1585971951 |
| C58 | -10.2206494843 | -2.5978941298 | 16.3816820877 |
| C59 | -8.9818492651 | -2.6515871557 | 15.6810162718 |
| C60 | -10.4197299858 | -3.3085505537 | 17.5827187968 |
| C61 | -7.8942996099 | -3.4021802361 | 16.2064908239 |
| C62 | -11.6259943106 | -3.2722999852 | 18.2738877193 |

FIG. 35C

| atom | x | y | z |
|---|---|---|---|
| H63 | -9.6019390540 | -3.9050544567 | 17.9723642575 |
| C64 | -12.7185073781 | -2.4773421619 | 17.7541412793 |
| C65 | -12.5335585289 | -1.7678946886 | 16.5722809076 |
| C66 | -13.9552767865 | -2.4542252168 | 18.4780648585 |
| H67 | -13.3479280847 | -1.1712054610 | 16.1770732713 |
| C68 | -14.1039469933 | -3.1669066318 | 19.6337651827 |
| H69 | -14.7736341739 | -1.8568411233 | 18.0854310914 |
| H70 | -15.0463167695 | -3.1420563985 | 20.1730997341 |
| C71 | -13.0248864671 | -3.9531552638 | 20.1473195643 |
| C72 | -11.8288474589 | -4.0029370960 | 19.4902448398 |
| H73 | -13.1656079424 | -4.5126210375 | 21.0675780788 |
| H74 | -11.0081837011 | -4.5998444640 | 19.8774507574 |
| C75 | -6.9406271593 | -4.0287998730 | 16.6469774116 |
| C77 | -13.1428489501 | 0.4173530204 | 13.7653198570 |
| Si78 | -14.5623427538 | 1.4458342640 | 13.1984223914 |
| C81 | -14.2056306745 | 2.0507627120 | 11.4454504920 |
| H82 | -13.2995368518 | 2.6646313986 | 11.4128849776 |
| H83 | -14.0671873439 | 1.2106047326 | 10.7574433239 |
| H84 | -15.0352774283 | 2.6597869341 | 11.0686177156 |
| C84 | -14.7575012698 | 2.9114979539 | 14.3739856215 |
| H85 | -13.8542962033 | 3.5300694966 | 14.3903265872 |
| H86 | -15.5953631806 | 3.5471775364 | 14.0651529461 |
| H87 | -14.9505506180 | 2.5763687841 | 15.3981936434 |
| C87 | -16.1205416548 | 0.3775157962 | 13.2187149313 |
| H88 | -16.9904093774 | 0.9525354592 | 12.8811683110 |
| H89 | -16.0145033354 | -0.4894621426 | 12.5587034276 |
| H90 | -16.3359823042 | 0.0056739291 | 14.2258163423 |
| Si90 | -5.4766253112 | -4.9497018508 | 17.2830752945 |
| C93 | -4.3743704989 | -3.7569603712 | 18.2481596912 |
| H94 | -4.0272859247 | -2.9335454260 | 17.6155885344 |
| H95 | -4.9076944054 | -3.3217720413 | 19.0992925742 |
| H96 | -3.4908186152 | -4.2772412490 | 18.6355633038 |
| C96 | -4.5318882250 | -5.6631529023 | 15.8109457553 |
| H97 | -4.1869830437 | -4.8726372852 | 15.1364237119 |
| H98 | -3.6508643416 | -6.2198009128 | 16.1503175467 |
| H99 | -5.1580210854 | -6.3481259298 | 15.2304800495 |
| C99 | -6.0732156245 | -6.3415001146 | 18.4114260446 |
| H100 | -5.2231353906 | -6.9137012663 | 18.8002097851 |
| H101 | -6.6309354221 | -5.9499577510 | 19.2684470026 |
| H102 | -6.7269448326 | -7.0360845335 | 17.8745002184 |
| Si101 | 4.0556310507 | -0.9230176608 | 7.6758896837 |
| C105 | 4.2895460059 | -2.7628641227 | 8.0334038106 |
| H106 | 3.5027688933 | -3.1448691044 | 8.6915988093 |

FIG. 35D

| atom | x | y | z |
|---|---|---|---|
| H107 | 4.2676678034 | -3.3512722610 | 7.1103756627 |
| H108 | 5.2538771453 | -2.9419990402 | 8.5230095722 |
| C108 | 5.4121360268 | -0.3086053715 | 6.5136033145 |
| H109 | 5.4066387444 | -0.8626270698 | 5.5691557903 |
| H110 | 5.2844665778 | 0.7533839026 | 6.2807703442 |
| H111 | 6.4007165741 | -0.4352766874 | 6.9694149318 |
| C111 | 4.0720140914 | 0.0671041744 | 9.2843884804 |
| H112 | 5.0287737709 | -0.0549101748 | 9.8048979137 |
| H113 | 3.9275319837 | 1.1352910143 | 9.0934380327 |
| H114 | 3.2782404789 | -0.2609374991 | 9.9634728994 |
| Si114 | -6.2587879434 | 0.8137587035 | 2.1244222370 |
| C117 | -6.1507876718 | 2.4316538073 | 1.1555159043 |
| H118 | -5.9458300701 | 3.2786752442 | 1.8179875616 |
| H119 | -5.3550824152 | 2.3948802115 | 0.4043957957 |
| H120 | -7.0937750571 | 2.6331721573 | 0.6345000752 |
| C120 | -7.6222305698 | 0.9182926446 | 3.4280728238 |
| H121 | -7.4385062728 | 1.7365737397 | 4.1317472121 |
| H122 | -8.5959784973 | 1.0947208861 | 2.9569691102 |
| H123 | -7.6942999030 | -0.0102825556 | 4.0039055118 |
| C123 | -6.5903076426 | -0.6274724738 | 0.9495676987 |
| H124 | -7.5422052309 | -0.4867610322 | 0.4245800997 |
| H125 | -5.8017961228 | -0.7166690484 | 0.1953755817 |
| H126 | -6.6430467173 | -1.5769968146 | 1.4914740174 |

FIG. 36A

| atom | x | y | z |
|---|---|---|---|
| C1 | -1.6275169647 | -1.5724507288 | -0.4684944911 |
| C2 | -1.3115933405 | -1.3919526413 | 0.9183195441 |
| C3 | -0.1241545508 | -2.0335527845 | 1.4488711533 |
| C4 | 0.6856311785 | -2.8195265072 | 0.5621528187 |
| C5 | 0.3464160394 | -2.9639232634 | -0.7533368626 |
| C6 | -0.8272627161 | -2.3321664339 | -1.2763680736 |
| C7 | -2.1045731795 | -0.6224116720 | 1.7663219106 |
| C8 | -1.7928643984 | -0.4421392760 | 3.1317805014 |
| C9 | -0.6056196267 | -1.0905322055 | 3.6662311763 |
| C10 | 0.1905424677 | -1.8666674522 | 2.7942994810 |
| C11 | -2.6140154606 | 0.3517033857 | 3.9870241126 |
| C12 | -2.2717681109 | 0.5232394930 | 5.3557679073 |
| C13 | -1.0953301286 | -0.1400921519 | 5.8967409897 |
| C14 | -0.2735755168 | -0.9343871444 | 5.0444777173 |
| C15 | -3.0528087046 | 1.3315009088 | 6.2125488672 |
| C16 | -2.7412089238 | 1.4960696614 | 7.5555831192 |

FIG. 36B

| atom | x | y | z |
|---|---|---|---|
| C17 | -1.5952707630 | 0.8031439149 | 8.1080143094 |
| C18 | -0.8032789896 | 0.0198298902 | 7.2690144793 |
| C19 | -1.3154613201 | 0.9399822561 | 9.5047151364 |
| C20 | -2.0902795524 | 1.7282442637 | 10.3263945669 |
| C21 | -3.2073883843 | 2.4344886273 | 9.7523107303 |
| C22 | -3.5217199890 | 2.3167846118 | 8.4327134118 |
| C23 | -1.8249951097 | 1.8397937553 | 11.7783498125 |
| C24 | -2.0484241030 | 3.0108485333 | 12.4649176363 |
| C25 | -1.8365964476 | 3.1118839445 | 13.8755971765 |
| C26 | -1.4063713887 | 1.9382788690 | 14.6011923717 |
| C27 | -1.1591031757 | 0.7371176814 | 13.8581171574 |
| C28 | -1.3532706767 | 0.6899885816 | 12.5106081378 |
| C29 | -2.0570183416 | 4.2955718650 | 14.5742427789 |
| C30 | -1.9168674335 | 4.3752739886 | 15.9742290316 |
| C31 | -1.5479930091 | 3.1773550969 | 16.7062843412 |
| C32 | -1.2770329916 | 1.9966052514 | 15.9822538610 |
| C33 | -1.4820006574 | 3.2062247550 | 18.1269890819 |
| C34 | -1.8114743186 | 4.3983469615 | 18.8387211971 |
| C35 | -2.1497229481 | 5.6054204095 | 18.1046936369 |
| C36 | -2.1703486981 | 5.5879287859 | 16.6824568648 |
| C37 | -2.4888542594 | 6.7660598583 | 18.8309023706 |
| C38 | -2.5301262601 | 6.7783479386 | 20.2176124887 |
| C39 | -2.1878883560 | 5.5823635286 | 20.9528567656 |
| C40 | -1.8387366072 | 4.4327010938 | 20.2478059850 |
| C41 | -2.2428761642 | 5.6103078652 | 22.3821093051 |
| C42 | -2.6328991376 | 6.7346415669 | 23.0737291103 |
| C43 | -2.9669708882 | 7.9181341507 | 22.3229983335 |
| C44 | -2.9171511272 | 7.9382779896 | 20.9637739308 |
| C45 | -1.1222190255 | 2.0235683535 | 18.8331918254 |
| C46 | -0.8228081999 | 0.9950890927 | 19.4277612998 |
| Si47 | -0.3788523565 | -0.5570583474 | 20.3194740206 |
| C48 | 1.4338217687 | -0.9762884544 | 19.9699287491 |
| C49 | -2.4702871814 | 6.7748544198 | 15.9571818362 |
| C50 | -2.7013840624 | 7.7937281432 | 15.3187429048 |
| Si51 | -3.0142471456 | 9.3242450740 | 14.3399345085 |
| C52 | -4.4005372721 | 10.3037357097 | 15.1707609368 |
| C53 | -2.7253809741 | 6.7581588062 | 24.5509915906 |
| C54 | -3.6426469302 | 7.5610599611 | 25.1884245395 |
| C55 | -3.7369549126 | 7.6223835850 | 26.6125578310 |
| C56 | -2.8369442530 | 6.8191347489 | 27.4123639372 |
| C57 | -1.8983052058 | 5.9804939774 | 26.7247983944 |
| C58 | -1.8474748863 | 5.9477346932 | 25.3615173950 |
| C59 | -2.9125957544 | 6.8970135405 | 28.7988942171 |

FIG. 36C

| atom | x | y | z |
|---|---|---|---|
| C60 | -3.8495458540 | 7.7294573191 | 29.4560592521 |
| C61 | -4.7675035622 | 8.5171740664 | 28.6482557148 |
| C62 | -4.6737282123 | 8.4345690860 | 27.2442249692 |
| C63 | -3.9092896325 | 7.8097100250 | 30.8772979734 |
| C64 | -4.8747126498 | 8.6489791350 | 31.5124416603 |
| C65 | -5.8003319765 | 9.4258302378 | 30.7012993687 |
| C66 | -5.7329126737 | 9.3541066889 | 29.2792354099 |
| C67 | -6.7524717834 | 10.2425086643 | 31.3519503060 |
| C68 | -6.8304409040 | 10.3300171619 | 32.7397235667 |
| C69 | -5.9029264077 | 9.5594055275 | 33.5494401653 |
| C70 | -4.9598266046 | 8.7470612591 | 32.9194324068 |
| C71 | -5.9919389026 | 9.6626111856 | 34.9779655917 |
| C72 | -6.9307760608 | 10.4689399821 | 35.5650868330 |
| C73 | -7.8475450747 | 11.2280283841 | 34.7644157984 |
| C74 | -7.7986717645 | 11.1606068682 | 33.3997583500 |
| C75 | -2.9885264603 | 7.0509191865 | 31.6554558377 |
| C76 | -2.1838909681 | 6.4004927157 | 32.3129048961 |
| Si77 | -0.9518803736 | 5.4283641712 | 33.2773942745 |
| C78 | -0.0407823339 | 6.6001935416 | 34.4491480011 |
| C79 | -6.6350817531 | 10.1155403090 | 28.4799101491 |
| C80 | -7.4080322001 | 10.7603825440 | 27.7794292583 |
| Si81 | -8.5704020061 | 11.7242653405 | 26.7177479179 |
| C82 | -8.9020279585 | 13.3930194052 | 27.5421202385 |
| C83 | 0.8796618660 | -1.5802694987 | 5.5757547254 |
| C84 | 1.8686450963 | -2.1419009575 | 6.0307973949 |
| Si85 | 3.3597410730 | -2.9925931695 | 6.7072377844 |
| C86 | 2.8119465276 | -4.2508897807 | 8.0080502660 |
| C87 | -3.7852015667 | 0.9682317288 | 3.4651883182 |
| C88 | -4.7915892123 | 1.4825095303 | 2.9965488935 |
| Si89 | -6.3073499970 | 2.2390463303 | 2.2720226291 |
| C90 | -7.8151998588 | 1.5310986901 | 3.1635320765 |
| C91 | 0.2600220925 | 4.6374757293 | 32.0599406087 |
| C92 | -1.8643065668 | 4.0959610631 | 34.2571688095 |
| C93 | -10.1841861633 | 10.7538195972 | 26.5369686360 |
| C94 | -7.7677980337 | 11.9744201127 | 25.0234980580 |
| C95 | -1.4257973778 | 10.3472006520 | 14.2947536311 |
| C96 | -3.5235712787 | 8.8272813821 | 12.5876527749 |
| C97 | -1.5064182580 | -1.9477371555 | 19.7108382533 |
| C98 | -0.6232975886 | -0.2730331271 | 22.1716941740 |
| C99 | -6.3614525609 | 1.8090820229 | 0.4359292137 |
| C100 | -6.2311595331 | 4.1134030239 | 2.5036974247 |
| C101 | 4.5007288811 | -1.7018787102 | 7.4860324472 |
| C102 | 4.2490351959 | -3.8735440134 | 5.2901812522 |

FIG. 36D

| atom | x | y | z |
|------|---|---|---|
| H103 | -2.3759895725 | 5.1809513445 | 14.0345642499 |
| H104 | -0.9709972068 | 1.1086633038 | 16.5272863614 |
| H105 | -2.3796787870 | 3.8995063835 | 11.9340134104 |
| H106 | -0.8319078860 | -0.1478099815 | 14.3972008985 |
| H107 | -1.1951058888 | -0.2414469520 | 11.9740098916 |
| H108 | -2.7447854864 | 7.6664407148 | 18.2814615927 |
| H109 | -1.6013420110 | 3.5245957442 | 20.7908767681 |
| H110 | -3.1753255048 | 8.8424135730 | 20.4200594155 |
| H111 | -1.9983711852 | 4.6958085413 | 22.9144765440 |
| H112 | -3.2388531327 | 8.8191734422 | 22.8635648919 |
| H113 | -4.3435158266 | 8.1577082143 | 24.6095305152 |
| H114 | -1.2111232138 | 5.3767733693 | 27.3148486713 |
| H115 | -1.1087934578 | 5.3228169496 | 24.8681018662 |
| H116 | -5.3568787093 | 9.0262284064 | 26.6420938385 |
| H117 | -2.2320502984 | 6.3037740082 | 29.4037723751 |
| H118 | -7.4430407908 | 10.8196797498 | 30.7422656768 |
| H119 | -4.2669735915 | 8.1650394763 | 33.5220766444 |
| H120 | -5.2951639260 | 9.0846314409 | 35.5840626319 |
| H121 | -6.9882966997 | 10.5396364050 | 36.6488770450 |
| H122 | -8.5852775694 | 11.8613497628 | 35.2533858184 |
| H123 | -8.4940482188 | 11.7359614237 | 32.7886513241 |
| H124 | -0.2582089846 | 3.9724682443 | 31.3580774133 |
| H125 | 0.7874397726 | 5.3977788081 | 31.4728107609 |
| H126 | 1.0130603955 | 4.0444517509 | 32.5924440949 |
| H127 | -2.4271160128 | 3.4313318947 | 33.5920223479 |
| H128 | -1.1559915702 | 3.4844303263 | 34.8275297329 |
| H129 | -2.5727218883 | 4.5373772133 | 34.9683457192 |
| H130 | 0.7075355062 | 6.0575033485 | 35.0403386473 |
| H131 | 0.4781986792 | 7.3885563954 | 33.8913077710 |
| H132 | -0.7332876541 | 7.0840908944 | 35.1506838422 |
| H133 | -10.0094319207 | 9.7770200980 | 26.0711739206 |
| H134 | -10.6553393900 | 10.5801897290 | 27.5118009314 |
| H135 | -10.9002415153 | 11.3035297379 | 25.9119607585 |
| H136 | -7.5583170774 | 11.0147498268 | 24.5349164788 |
| H137 | -8.4317483402 | 12.5491684591 | 24.3637624404 |
| H138 | -6.8198116148 | 12.5209806240 | 25.1082958916 |
| H139 | -9.5880293522 | 13.9984145767 | 26.9342020011 |
| H140 | -9.3568314807 | 13.2663738800 | 28.5318529026 |
| H141 | -7.9731444514 | 13.9630986112 | 27.6696457975 |
| H142 | -1.1017170602 | 10.6245242382 | 15.3044675955 |
| H143 | -0.6083689408 | 9.7915691974 | 13.8234958023 |
| H144 | -1.5784870473 | 11.2708475828 | 13.7229614744 |
| H145 | -2.7317902095 | 8.2551129180 | 12.0917887051 |

FIG. 36E

| atom | x | y | z |
|---|---|---|---|
| H146 | -4.4308403604 | 8.2125042190 | 12.5944034247 |
| H147 | -3.7263368073 | 9.7144511841 | 11.9755897172 |
| H148 | -4.6198461085 | 11.2178383275 | 14.6056108348 |
| H149 | -5.3245436743 | 9.7173229499 | 15.2280330789 |
| H150 | -4.1253399548 | 10.5968372173 | 16.1907627417 |
| H151 | -2.5604041569 | -1.7140037805 | 19.9001768666 |
| H152 | -1.3905287160 | -2.1198534682 | 18.6367205984 |
| H153 | -1.2698893486 | -2.8873888919 | 20.2248589800 |
| H154 | -1.6629485191 | -0.0157432445 | 22.4011673228 |
| H155 | -0.3675214012 | -1.1764089516 | 22.7381672683 |
| H156 | 0.0142449267 | 0.5382514056 | 22.5382810580 |
| H157 | 1.7289213108 | -1.8944771380 | 20.4930760530 |
| H158 | 1.6093375493 | -1.1325917434 | 18.9009193744 |
| H159 | 2.0984680386 | -0.1714705238 | 20.3061272956 |
| H160 | -0.4478374913 | 0.4195695501 | 9.9026174880 |
| H161 | -3.8339132876 | 3.0357438187 | 10.4051916634 |
| H162 | -4.3902056693 | 2.8298815683 | 8.0279080486 |
| H163 | 0.0660703196 | -0.4873269545 | 7.6755071450 |
| H164 | -3.9217279722 | 1.8340002957 | 5.8002181909 |
| H165 | 1.0775905534 | -2.3464408853 | 3.1945366166 |
| H166 | -2.9925639251 | -0.1401063775 | 1.3709146547 |
| H167 | 1.5784719690 | -3.3002817158 | 0.9565066004 |
| H168 | 0.9693316977 | -3.5620844013 | -1.4137125728 |
| H169 | -1.0771026171 | -2.4622144398 | -2.3255170903 |
| H170 | -2.5195099048 | -1.0908172763 | -0.8633890523 |
| H171 | -5.4897675642 | 2.2088017821 | -0.0894800525 |
| H172 | -6.3789288920 | 0.7256427353 | 0.2831947913 |
| H173 | -7.2564355458 | 2.2305241135 | -0.0346839597 |
| H174 | -5.3596045775 | 4.5414822115 | 1.9984839457 |
| H175 | -7.1254790031 | 4.5940190301 | 2.0897511522 |
| H176 | -6.1697773604 | 4.3799448909 | 3.5618138302 |
| H177 | -8.7397744761 | 1.9648659754 | 2.7650307108 |
| H178 | -7.8718543681 | 0.4439319789 | 3.0425844369 |
| H179 | -7.7808986200 | 1.7433085515 | 4.2354317695 |
| H180 | 3.9993253494 | -1.1637622148 | 8.2985915722 |
| H181 | 5.3978950686 | -2.1779403661 | 7.9012512549 |
| H182 | 4.8263063564 | -0.9620151049 | 6.7462524936 |
| H183 | 4.5640415968 | -3.1658719675 | 4.5150411175 |
| H184 | 5.1454540938 | -4.3882731158 | 5.6573055838 |
| H185 | 3.6029301214 | -4.6231310834 | 4.8190646700 |
| H186 | 3.6812211762 | -4.7635218104 | 8.4377862944 |
| H187 | 2.2692323290 | -3.7685898631 | 8.8293567305 |
| H188 | 2.1531296481 | -5.0114311511 | 7.5732437739 |

FIG. 37A

| atom | x | y | z |
|---|---|---|---|
| C1 | 1.5398275243 | 1.9522184576 | 0.7547902159 |
| C2 | 1.3312735230 | 1.4694082448 | 2.0906495186 |
| C3 | 2.4915705934 | 1.1281304047 | 2.8875893186 |
| C4 | 3.7934438963 | 1.2891038622 | 2.3062265946 |
| C5 | 3.9433863361 | 1.7528897133 | 1.0324138138 |
| C6 | 2.7970660948 | 2.0900065901 | 0.2430503921 |
| C7 | 2.3133794960 | 0.6625743758 | 4.1834555442 |
| C8 | 1.0349336656 | 0.5149066748 | 4.7599393602 |
| C9 | -0.1304990837 | 0.8572935039 | 3.9599668292 |
| C10 | 0.0636029821 | 1.3238075471 | 2.6413200439 |
| C11 | -1.4320965262 | 0.7270699949 | 4.5188888481 |
| C12 | -1.5956986622 | 0.2775102394 | 5.8575312630 |
| C13 | -0.4299684933 | -0.0593102347 | 6.6584071980 |
| C14 | 0.8719812212 | 0.0526559659 | 6.0979834255 |
| C15 | -0.6267362841 | -0.4702924296 | 7.9925563047 |
| C16 | -1.8904512105 | -0.5472927700 | 8.5646863463 |
| C17 | -3.0536069063 | -0.2243052915 | 7.7653479324 |
| C18 | -2.8760918489 | 0.1653037651 | 6.4462554866 |
| C19 | -2.0745223083 | -0.8926614227 | 9.9392511097 |
| C20 | -3.3152595606 | -0.9037147998 | 10.5278201599 |
| C21 | -4.4673002138 | -0.6086194829 | 9.7105463502 |
| C22 | -4.3405794438 | -0.2934362076 | 8.3934314744 |
| C23 | -3.4670656053 | -1.1289030643 | 11.9801338825 |
| C24 | -4.4451489689 | -0.4837559595 | 12.6989044059 |
| C25 | -4.5326157575 | -0.5861871785 | 14.1218588252 |
| C26 | -3.5729441837 | -1.4131976970 | 14.8217872010 |
| C27 | -2.5979784014 | -2.1166907842 | 14.0413208052 |
| C28 | -2.5414412829 | -1.9767838624 | 12.6897200705 |
| C29 | -3.6002217343 | -1.4589077289 | 16.2071500320 |
| C30 | -4.5125791486 | -0.6946556511 | 16.9653873535 |
| C31 | -5.4876703063 | 0.1243502199 | 16.2606381537 |
| C32 | -5.4741372350 | 0.1324019889 | 14.8499817625 |
| C33 | -6.4032453686 | 0.9324027104 | 16.9944485102 |
| C34 | -6.3296403968 | 0.9767950016 | 18.4127724138 |
| C35 | -5.3366624983 | 0.1791068972 | 19.1130264669 |
| C36 | -4.4622768729 | -0.6751421539 | 18.3852725334 |
| C37 | -5.2400930655 | 0.3075028865 | 20.5108259610 |
| C38 | -6.0466395133 | 1.1770504250 | 21.2334454952 |
| C39 | -7.0643943650 | 1.9379193994 | 20.5428508600 |
| C40 | -7.1835662073 | 1.8101255787 | 19.1671317670 |
| C41 | -7.8888364202 | 2.8173919650 | 21.3191880620 |
| C42 | -7.6816973624 | 2.9820240359 | 22.6539647721 |
| C43 | -6.6247101899 | 2.2829264883 | 23.3445029596 |

FIG. 37B

| atom | x | y | z |
|---|---|---|---|
| C44 | -5.8703001605 | 1.3804525062 | 22.6351282775 |
| C45 | -7.3571380172 | 1.7248891270 | 16.3020186773 |
| C46 | -8.1737487924 | 2.4097558903 | 15.7031634947 |
| C47 | -3.5144174507 | -1.4782646311 | 19.0747409764 |
| C48 | -2.6983555896 | -2.1622878441 | 19.6760621018 |
| C49 | -6.3434857011 | 2.5807675720 | 24.7641238444 |
| C50 | -7.3451452794 | 2.8984513345 | 25.6472828872 |
| C51 | -7.0862230737 | 3.1979541440 | 27.0199723405 |
| C52 | -5.7195924089 | 3.1763952233 | 27.4940283355 |
| C53 | -4.6908461708 | 2.8493339558 | 26.5510871458 |
| C54 | -4.9846814019 | 2.5607477762 | 25.2548127412 |
| C55 | -5.4497979471 | 3.4597517212 | 28.8253042489 |
| C56 | -6.4763411489 | 3.7446034726 | 29.7536452462 |
| C57 | -7.8490885000 | 3.7534990486 | 29.2797009499 |
| C58 | -8.1053570120 | 3.4876063100 | 27.9183674704 |
| C59 | -6.1960837105 | 3.9924274305 | 31.1298870979 |
| C60 | -7.2586257596 | 4.1972217375 | 32.0581303568 |
| C61 | -8.6308321344 | 4.1960656623 | 31.5790220132 |
| C62 | -8.9084431364 | 3.9992783735 | 30.1971019165 |
| C63 | -9.6699233303 | 4.3426672787 | 32.5206787985 |
| C64 | -9.4216141016 | 4.4353061223 | 33.8802493080 |
| C65 | -8.0604675124 | 4.4339736368 | 34.3726050565 |
| C66 | -7.0234965905 | 4.3506068141 | 33.4448942356 |
| C67 | -7.8378787000 | 4.4534311931 | 35.7896381841 |
| C68 | -8.8774097512 | 4.4252185221 | 36.6973657769 |
| C69 | -10.2247424250 | 4.4576988344 | 36.1762491621 |
| C70 | -10.4802255585 | 4.4770446936 | 34.8432259778 |
| C71 | -4.8479431043 | 3.9791269031 | 31.5806653113 |
| C72 | -3.6838539509 | 3.9613576525 | 31.9538620078 |
| C73 | -10.2490088132 | 4.0056389023 | 29.7245626098 |
| C74 | -11.4007715031 | 4.0021513302 | 29.3130847836 |
| C75 | -8.6836980612 | 4.3164706324 | 38.1643741553 |
| C76 | -7.4395155601 | 3.8198338962 | 38.7113638213 |
| C77 | -7.2694409211 | 3.6361379193 | 40.0497854938 |
| C78 | -8.3278883829 | 3.9042382557 | 40.9853220787 |
| C79 | -9.5754649593 | 4.4088529896 | 40.4583141638 |
| C80 | -9.6945636663 | 4.6192636810 | 39.0476112607 |
| C81 | -10.6300250096 | 4.6415569532 | 41.3338619256 |
| C82 | -10.5300381475 | 4.3884456089 | 42.7181022403 |
| C83 | -9.2719826817 | 3.8907741542 | 43.2487359737 |
| C84 | -8.2050164990 | 3.6692624776 | 42.3474935119 |
| C85 | -9.1456142837 | 3.6232537798 | 44.6413154694 |
| C86 | -10.2456926999 | 3.8438148890 | 45.5182241122 |

FIG. 37C

| atom | x | y | z |
|---|---|---|---|
| C87 | -11.5065333589 | 4.3290189722 | 44.9882210386 |
| C88 | -11.6365871001 | 4.5913048659 | 43.5933878791 |
| C89 | -12.5812249280 | 4.5221533110 | 45.8804131228 |
| C90 | -12.4712588593 | 4.2638392585 | 47.2403454576 |
| C91 | -11.2128829321 | 3.7807327802 | 47.7679870041 |
| C92 | -10.1467407982 | 3.5878844065 | 46.9004215859 |
| C93 | -11.1151703385 | 3.5157367251 | 49.1745724503 |
| C94 | -12.1816372824 | 3.7124896123 | 50.0022372021 |
| C95 | -13.4267274516 | 4.1910661328 | 49.4803341660 |
| C96 | -13.5644121802 | 4.4566123487 | 48.1494224640 |
| C97 | -7.9232978996 | 3.1196417770 | 45.1615388669 |
| C98 | -6.8740072138 | 2.6755870726 | 45.6047774242 |
| C99 | -12.8837692760 | 5.0295367510 | 43.0729874910 |
| C100 | -13.9730347458 | 5.3920448311 | 42.6508944393 |
| C101 | 2.0113811015 | -0.2817508581 | 6.8799687982 |
| C102 | 3.0063914070 | -0.5631986208 | 7.5333403267 |
| C103 | -2.5730630730 | 1.0667362818 | 3.7431805195 |
| C104 | -3.5522651184 | 1.3656977377 | 3.0752246838 |
| H105 | -9.1355180900 | 3.4948173482 | 27.5791712729 |
| H106 | -4.4247037826 | 3.4567572837 | 29.1771378055 |
| H107 | -8.3813302138 | 2.9031063209 | 25.3216606596 |
| H108 | -3.6609930908 | 2.8542979659 | 26.8967137698 |
| H109 | -4.1849109746 | 2.3503495050 | 24.5531311980 |
| H110 | -10.6930363989 | 4.3413515698 | 32.1597732184 |
| H111 | -5.9947167259 | 4.3487730544 | 33.7888439856 |
| H112 | -11.5035107429 | 4.4743294558 | 34.4780032681 |
| H113 | -6.8046626588 | 4.4710183488 | 36.1210144275 |
| H114 | -11.0549372852 | 4.4175761205 | 36.8723782889 |
| Si115 | -1.9230968905 | 3.9323175826 | 32.5008877874 |
| H116 | -10.6343297060 | 5.0292450969 | 38.6902698810 |
| H117 | -6.3305667813 | 3.2443943093 | 40.4336099298 |
| H118 | -6.6399326641 | 3.5499120795 | 38.0308116332 |
| H119 | -11.5737428932 | 5.0152642453 | 40.9506114438 |
| H120 | -7.2693217716 | 3.2901393766 | 42.7433030613 |
| H121 | -13.5213102634 | 4.8836383960 | 45.4779975559 |
| H122 | -9.1999530509 | 3.2253185073 | 47.2860354949 |
| H123 | -10.1664985256 | 3.1528405779 | 49.5617438715 |
| H124 | -12.0956694259 | 3.5073920421 | 51.0655388338 |
| H125 | -14.2621441160 | 4.3400029560 | 50.1586585452 |
| H126 | -14.5060727373 | 4.8194790166 | 47.7467671474 |
| Si127 | -5.2917990172 | 2.0029397558 | 46.2707705898 |
| H128 | -5.1057134477 | 0.7906660015 | 23.1330396137 |
| H129 | -8.6618809734 | 3.3821128303 | 20.8039483736 |

FIG. 37D

| atom | x | y | z |
|---|---|---|---|
| H130 | -8.2823485286 | 3.6937373439 | 23.2119431833 |
| H131 | -7.9345533782 | 2.3832169086 | 18.6341095245 |
| H132 | -4.4773855269 | -0.2672636053 | 21.0252255768 |
| H133 | -6.1964804282 | 0.7506764508 | 14.3296801237 |
| H134 | -2.8781937256 | -2.0693475839 | 16.7388743194 |
| H135 | -1.8923824700 | -2.7609043161 | 14.5602298549 |
| H136 | -1.7925646413 | -2.5184895982 | 12.1202209313 |
| H137 | -5.1411809852 | 0.1843518851 | 12.1997297546 |
| Si138 | -1.4635215076 | -3.1994556754 | 20.5719204581 |
| Si139 | -9.3906166598 | 3.4556514224 | 14.7944060661 |
| H140 | -5.4519271271 | -0.6652574039 | 10.1632141366 |
| H141 | -5.2168599429 | -0.0814402004 | 7.7874259737 |
| H142 | -1.1837968851 | -1.0880831305 | 10.5293150078 |
| H143 | -3.7393503575 | 0.4146659164 | 5.8384825986 |
| H144 | 0.2473164739 | -0.7162979630 | 8.5858829654 |
| H145 | -0.8106100452 | 1.5771175424 | 2.0518056112 |
| H146 | 3.1799908477 | 0.4058295189 | 4.7830728117 |
| H147 | 4.6583711307 | 1.0318652319 | 2.9113158580 |
| H148 | 4.9357926034 | 1.8705975540 | 0.6064040773 |
| H149 | 2.9393229097 | 2.4577296336 | -0.7691328358 |
| H150 | 0.6671903675 | 2.2071030858 | 0.1590729259 |
| Si151 | -5.0458813303 | 1.8141277330 | 2.0913358691 |
| Si152 | 4.4851354894 | -0.9793183712 | 8.5558857297 |
| Si153 | -13.1275561167 | 3.9938465498 | 28.6637359456 |
| Si154 | -15.6229171233 | 5.9205804364 | 42.0176671549 |
| C155 | -4.8306854768 | 2.9728458590 | 47.8247779411 |
| C156 | -5.5300996815 | 0.1754319525 | 46.6864306300 |
| C157 | -3.9564358268 | 2.2022634112 | 44.9502181002 |
| C158 | -16.7859709065 | 6.1464252208 | 43.4895797214 |
| C159 | -15.4296653112 | 7.5508652502 | 41.0837350846 |
| C160 | -16.2887237882 | 4.5784841012 | 40.8669875206 |
| C161 | -1.0828412685 | 2.4262340645 | 31.7311084849 |
| C162 | -1.0755200230 | 5.5174312090 | 31.9197992492 |
| C163 | -1.8739351245 | 3.8203948966 | 34.3856803474 |
| C164 | -14.3116998632 | 3.7479765937 | 30.1145495383 |
| C165 | -13.4689910438 | 5.6480667377 | 27.8171911482 |
| C166 | -13.3027814671 | 2.5765206686 | 27.4259931438 |
| C167 | -0.5199081550 | -4.2369394694 | 19.3065901112 |
| C168 | -0.2708148286 | -2.0624777009 | 21.4962577152 |
| C169 | -2.3713775666 | -4.3239348207 | 21.7879774804 |
| C170 | -10.4377935823 | 4.3832665266 | 16.0629554959 |
| C171 | -8.4419259325 | 4.6769668902 | 13.7096996225 |
| C172 | -10.4830501758 | 2.3394002397 | 13.7322437361 |

FIG. 37E

| atom | x | y | z |
|---|---|---|---|
| C173 | 3.8922081459 | -1.6681015256 | 10.2122091750 |
| C174 | 5.5194497287 | -2.2720488381 | 7.6468147418 |
| C175 | 5.5011472038 | 0.5897994097 | 8.8313251131 |
| C176 | -6.5688629658 | 1.5507456645 | 3.1781414074 |
| C177 | -4.9133806672 | 3.6278625085 | 1.5799911419 |
| C178 | -5.1260388204 | 0.7037932033 | 0.5651514345 |
| H179 | -1.6569495240 | -4.9517845505 | 22.3340286875 |
| H180 | -2.9374043030 | -3.7432372939 | 22.5237933150 |
| H181 | -3.0736366101 | -4.9854627811 | 21.2702513354 |
| H182 | 0.4781446828 | -2.6522409002 | 22.0372650662 |
| H183 | 0.2594950171 | -1.3958829144 | 20.8082840170 |
| H184 | -0.7967950676 | -1.4402153484 | 22.2277331060 |
| H185 | 0.2291590394 | -4.8631867883 | 19.8053874410 |
| H186 | -1.1925653699 | -4.8989947551 | 18.7512281814 |
| H187 | 0.0024294390 | -3.6019115437 | 18.5835638171 |
| H188 | -14.3171121095 | 2.5528048261 | 27.0096919247 |
| H189 | -12.6018957099 | 2.6830811784 | 26.5910438648 |
| H190 | -13.1123949800 | 1.6091858751 | 27.9019701553 |
| H191 | -14.4905480470 | 5.6704040592 | 27.4190158259 |
| H192 | -13.3620968244 | 6.4831137284 | 28.5171527534 |
| H193 | -12.7798682001 | 5.8188784115 | 26.9835714043 |
| H194 | -15.3490823677 | 3.7276229321 | 29.7601194522 |
| H195 | -14.1163205038 | 2.8043681200 | 30.6341925927 |
| H196 | -14.2244770691 | 4.5601379057 | 30.8440875068 |
| H197 | -0.0326160455 | 2.3753902807 | 32.0408877968 |
| H198 | -1.5694359581 | 1.4959759056 | 32.0413423330 |
| H199 | -1.1074235623 | 2.4690890187 | 30.6370800836 |
| H200 | -0.8372424390 | 3.7946701321 | 34.7415719952 |
| H201 | -2.3645300226 | 4.6826401416 | 34.8495019060 |
| H202 | -2.3741137105 | 2.9146590430 | 34.7430733612 |
| H203 | -0.0265150426 | 5.5290581209 | 32.2390563217 |
| H204 | -1.0950403015 | 5.6044900576 | 30.8284029340 |
| H205 | -1.5635498474 | 6.4046987270 | 32.3360387596 |
| H206 | -2.9994503250 | 1.8079045898 | 45.3106587149 |
| H207 | -4.2159860340 | 1.6617536012 | 44.0336058168 |
| H208 | -3.8090750503 | 3.2555238617 | 44.6904708733 |
| H209 | -4.6028066371 | -0.2500023103 | 47.0883240532 |
| H210 | -6.3157139270 | 0.0360168325 | 47.4363232210 |
| H211 | -5.8081621895 | -0.4018070837 | 45.7986064187 |
| H212 | -3.8873014395 | 2.6017612089 | 48.2417983499 |
| H213 | -4.7059921968 | 4.0386938324 | 47.6078010488 |
| H214 | -5.5988877581 | 2.8753561700 | 48.5989613337 |
| H215 | -16.3973716949 | 7.8822991403 | 40.6887547926 |

FIG. 37F

| atom | x | y | z |
| --- | --- | --- | --- |
| H216 | -15.0456637928 | 8.3397899172 | 41.7385128701 |
| H217 | -14.7400451304 | 7.4500254579 | 40.2392368298 |
| H218 | -17.2677899721 | 4.8680621089 | 40.4675781343 |
| H219 | -15.6180568355 | 4.4077534705 | 40.0184833344 |
| H220 | -16.4094484507 | 3.6273740955 | 41.3956502550 |
| H221 | -17.7801558743 | 6.4550989402 | 43.1449222118 |
| H222 | -16.9018361215 | 5.2155897923 | 44.0544409038 |
| H223 | -16.4170031365 | 6.9154201226 | 44.1764848168 |
| H224 | 4.7453917788 | -1.9171209434 | 10.8544442025 |
| H225 | 3.2726709920 | -0.9393923702 | 10.7452126104 |
| H226 | 3.3000090838 | -2.5788911827 | 10.0744013727 |
| H227 | 6.3872510206 | 0.3696591743 | 9.4382906052 |
| H228 | 5.8435659531 | 1.0162036357 | 7.8827542893 |
| H229 | 4.9187307947 | 1.3561973779 | 9.3528994202 |
| H230 | 6.4049100555 | -2.5359751655 | 8.2371207850 |
| H231 | 4.9474700272 | -3.1885253943 | 7.4692521336 |
| H232 | 5.8637638837 | -1.8977675861 | 6.6770732511 |
| H233 | -5.7893746707 | 3.9259890847 | 0.9918764089 |
| H234 | -4.8551488835 | 4.2846978453 | 2.4541793649 |
| H235 | -4.0229482230 | 3.8052663540 | 0.9679786683 |
| H236 | -6.0004053452 | 0.9548870547 | -0.0463582392 |
| H237 | -4.2354941080 | 0.8203482854 | -0.0612807695 |
| H238 | -5.2028346494 | -0.3517963336 | 0.8450738707 |
| H239 | -7.4834102247 | 1.8040801927 | 2.6288301648 |
| H240 | -6.6503196243 | 0.5073768598 | 3.5006303787 |
| H241 | -6.5310822813 | 2.1791869965 | 4.0740791186 |
| H242 | -9.1380901566 | 5.3144757048 | 13.1525367884 |
| H243 | -7.7997910178 | 5.3269353133 | 14.3128319580 |
| H244 | -7.8067252415 | 4.1593352582 | 12.9833067128 |
| H245 | -11.1759416213 | 5.0196173397 | 15.5608558547 |
| H246 | -10.9802957891 | 3.6908672922 | 16.7146991394 |
| H247 | -9.8170005861 | 5.0264481314 | 16.6955046591 |
| H248 | -11.2110071830 | 2.9368602722 | 13.1709245581 |
| H249 | -9.8899884827 | 1.7698363414 | 13.0091227470 |
| H250 | -11.0378162868 | 1.6240258516 | 14.3482202769 |

Scheme 1

Scheme 3

Scheme 4

QUANTITATIVE INTRAMOLECULAR FISSION IN OLIGOACENES, MATERIALS, AND METHODS OF USE THEREOF

CROSS REFERENCE TO RELATED APPLICATIONS

This application is a national phase of and claims the benefit and priority from International Patent Application No. PCT/US2015/066529 filed on Dec. 17, 2015, which relates to and claims the benefit of priority from U.S. Provisional Patent Application No. 62/124,404, filed Dec. 17, 2014, entitled, "Quantitative Intramolecular Fission in Oligoacenes," the disclosures of which is are incorporated herein by reference in its their entireties.

STATEMENT REGARDING FEDERALLY SPONSORED RESEARCH OR DEVELOPMENT

The present invention was made with government support under contract number CAREER, DMR-1351293 awarded by the National Science Foundation, contract number DGE 11-44155 awarded by the National Science Foundation, Graduate Research Fellowships Program, contract number N00014-15-1-2532 awarded by the Office of Naval Research, Department of Navy, contract number DE-SC0012704 awarded by the U.S. Department of Energy, and contract number DE-ACO2-98CH10886 awarded by the U.S. Department of Energy. The United States government may have certain rights in this invention.

NAMES OF PARTIES TO A JOINT RESEARCH AGREEMENT

The claimed invention was made by, on behalf of, and/or in connection with Brookhaven Science Associates, LLC to a joint research agreement within the meaning of 35 U.S.C. § 103(c). The claimed invention was made as a result of activities undertaken within the scope of the agreement.

TECHNICAL FIELD

The present invention relates to molecules and polymers that undergo ultrafast, intramolecular singlet fission in oligoacene derivatives and have an enhanced fission yield.

BACKGROUND

Singlet exciton fission has attracted renewed interest in the last decade due to its potential to enhance power conversion efficiencies of single junction solar cells beyond the Shockley-Queisser Limit.[1-6] The third-generation of solar cells is based on materials that operate by non-conventional photophysical mechanisms to overcome the Shockley-Queisser limit.[7-9] The recent discovery of an efficient intramolecular singlet fission (iSF) process in conjugated polymers and small molecules has dramatically increased the quantity and variety of materials that exhibit this process.[2] In molecules and polymers, singlet fission (SF) is the process whereby two triplets are generated from a single photon.[17] The mechanism of triplet pair formation and decay may be quite different in dimers of oligoacenes relative to their monomer counterparts in the solid state, where singlet fission is an intermolecular process (xSF). For example, donor-acceptor polymers are presumed to undergo SF via charge transfer (CT) states, similar to the leading hypothesis for the mechanism for solid stateSF.[10,18-20] However, there is no intrinsic CT character in molecular dimers, yet that have been reported to undergo SF at faster rates than the molecular systems.

Devices fabricated from singlet fission molecules have exceeded 100% external quantum efficiency,[1,5] but many fundamental challenges remain: a) there are a limited number of materials that undergo SF; b) appropriate heterojunctions must be engineered to extract the multiple excitons; and c) device architectures that exploit SF must be engineered. While the resurgent interest in SF has been catalyzed by solar cells, multiexcitonic materials can be also widely applicable in other optoelectronic thin-film technologies.[21]

Acenes are of great interest in the field of organic electronics due to their tunable optoelectronic properties, high charge carrier mobilities, and the observation of singlet exciton fission (SF) in crystals of tetracene and higher acenes.[12,63-70] However, one major hurdle to the implementation of SF materials in devices is the need for intermolecular interactions. While various acenes have been shown to undergo quantitative intermolecular singlet fission (xSF), a significant impediment in these materials is that SF depends on intermolecular coupling. Such dependence on packing interactions prevents these materials from being widely applicable. For example, acenes can undergo SF only when neighboring chromophores are appropriately coupled by a charge-transfer (CT) state in crystalline solids or highly concentrated solutions—intermolecular singlet fission (xSF).[5, 20,24] However, practical applications of xSF materials are difficult because the process relies on intermolecular coupling between chromophores that depend sensitively on crystalline structure and film morphology. A more suitable approach that would enable high-throughput screening of materials is to employ intramolecular singlet fission (iSF) active layers. iSF has rarely been observed in organic materials, with yields lower than 30% or as an endothermic process.[25,26]

The design of organic materials based on strong-donor/strong-acceptor copolymers and small molecules that facilitate iSF through a photoexcited state with strong CT-character, exhibit up to 170% triplet yield in a polymer.[10] Such design principles were founded on the CT-mediated mechanism of xSF. Interestingly, there is another strategy in molecular materials that stems from the fundamental concept of xSF, which involves the covalent coupling of two SF chromophores. To date, several groups have attempted to model or synthesize dimers for iSF, but experimental triplet yields have been low (<10%).[2,3,27-31]

Molecular dimers made up of two covalently linked SF-capable monomers have been considered as candidates for iSF[28,32]. However, early work on tetracene dimers showed low iSF yields, presumably because of the endothermicity of the iSF process or the connectivity employed.[29-30] Pentacene dimers, on the other hand, have recently been reported to undergo iSF quantitatively.[13,15] Pentacene is of particular interest, as it is a benchmark material for organic field effect transistors (OFETs) and organic photovoltaics (OPVs), as well as fundamental studies of various optoelectronic properties.[71-76] However, pentacene has only limited stability and solubility in common organic solvents and is unstable in the presence of oxygen,[47] making it difficult to process by high throughput techniques.[65,77,78] To overcome these limitations, several functionalized pentacenes have been reported, which exhibit enhanced solubility, stability, and tunable electronic properties.[72,79,80] Despite these improvements, over the course of nearly 80 years of significant research in pentacene chemistry and physics, there has been only one report of short conjugated oligomers, a scarce number of conjugated pentacene-containing polymers, and a pentacene homopolymer remains unknown.[81-86] The potential to develop families of oligoacene dimers through systematic studies provides motivation to revisit the concept of singlet fission in oligoacene "mixtures", which was briefly explored in the 1970s when several groups studied crystals of one type of acene doped that had been doped with another type of acene.[32-34]

There are various important aspects that are still being actively investigated in terms of electronic structure, excited state energies and dynamics.[22,35-37] Thus it is important to elucidate the mechanistic and energetic requirements for iSF in order to optimize the design of practical SF chromophores. Therefore, there is still a need for simple, stable, and soluble molecules that exhibit quantitative singlet fission, preferably, for example, molecules that undergo ultrafast iSF. Such fast iSF combined with triplet pair lifetimes as long as hundreds of picoseconds may enable harvesting of two triplets or two electron hole pairs for devices with enhanced photocurrents.

BRIEF SUMMARY

An object of the present invention provide molecules, compounds, or materials that are capable of or undergo quantitative singlet fission. Further objects of the present invention provide the design of new compounds or materials that, considering the energetic requirement for iSF, embody an excitation energy of the singlet of at least twice the energy of the triplet ($E[S_1] \geq 2E[T_1]$).

Other embodiments of the invention provide molecules, compounds, or materials such as for example oligoacene dimers comprising two oligoacene monomers, that are preferably the same or different, covalently linked where the relevant singlet energy for iSF is given by the lower singlet state energy monomer, and the resulting triplet pair is the sum of the individual monomer triplet energies. The fundamental equation for energy conservation is $E(S_1[X]) \geq 2E(T_1[X])$ or $E(S_1[X]) \geq E(T_1[X]) + E(T_1[Y])$, in, for example, a dimer comprising monomer X coupled to Y.

A soluble, stable singlet fission material, comprising an oligoacene of at least two covalently bound oligoacene monomers with or without a spacer, wherein the lower singlet exciton energy of one oligoacene monomer is greater than about or equal to about the sum of the energies of the triplet excitons of each of the at least two oligoacene monomers.

A soluble, stable singlet fission material, comprising:

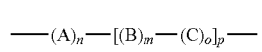

Formula 1 wherein A and C are each any oligoacene or acene monomer, wherein A and C are the same or different oligoacene or acene,
wherein B is a spacer,
wherein n, m, o, and p are each 0 or any positive integer, except when n is 0, then o is greater than or equal to 1 and when o is 0, then n is greater than or equal to 1, and
wherein the lower singlet exciton energy of one acene monomer is essentially greater than about or essentially equal to about, or essentially greater than or essentially equal to, or greater than or equal to about the sum of the energies of the triplet excited states of each oligoacene or acene monomer.

Further embodiments are directed to oligomers of and polymers of polyoligoacenes that undergo intramolecular singlet fission, where the oligomers and polymers are singlet fission materials. The fundamental equation for energy conservation applies, where the singlet energy or approximate singlet energy of the lowest energy monomer is greater than or equal to, or about greater than or about equal to, the sum of the individual monomer triplet energies. The singlet fission molecules, compounds, or materials of the invention may comprise of at least 2-100 acene monomers, for example, at least 2, 3, 4, 5, 6, 7, 8, 10, 20, or more oacene monomers, sufficient to form a dimer, trimer, tetramer, pentamer, hexamer, heptamer, oligomer, or polymer of oligoacene monomers. Moreover, the oligoacene monomer itself may comprise of 2, 3, 4, 5, 6, 7, 8, or more fused benzene rings thereby forming a napthalene, antracene, tetracene, pentacene, hexacene, heptacene, octacene, etc. Oligomers may comprise of 2-10 monomers or repeating units, while polymers may comprise of more than 10 monomers or repeating units. Polymers that are useful may comprise of 20 or more monomers or repeating units, preferably the same oligoacene monomer, but may also include different oligoacenes monomers forming asymmetric polyoligoacenes.

Accordingly, embodiments of the present invention provide compounds and materials, including organic molecules, such as oligomers and polymers, capable of singlet fission and, more particularly, undergo efficient intramolecular singlet fission at a speed of less than or equal to about 5 nanoseconds and a triple pair decay time of, preferably as long as or longer than about 1 microsecond, such that intermolecular coupling is no longer a design constraint. Compounds and materials of the embodiments of the invention exhibit efficient intramolecular singlet fission that generate two triplets per photon absorbed in very high yields, e.g., yields of greater than about 100%, greater than about 140%, greater than about 170%, or even higher, preferably about 200%.

Another object of the invention is directed to an electronic, optical, or electrooptical component or device comprising the SF material, compound, or composition, and the uses of the SF material, compound or composition. The technology of various embodiments of the present invention may be applicable to similar families of small molecules, oligomers, polymers, and materials that undergo iSF, and provides development of new materials that lead to solution processing so that high throughput techniques may be used to study fundamental photophysical phenomena and further be applied to various types of electronic, optical, electrooptical, or optoelectronic components or devices.

BRIEF DESCRIPTION OF THE DRAWINGS

The patent or application file contains at least one drawing executed in color. Copies of this patent or patent application publication with color drawings will be provided by the U.S. Patent & Trademark Office upon request and payment of the necessary fee.

FIGS. 23A to 23C shows steady state UV-visible absorption performed on dilute solutions of PA, PT, and PH heterodimer in chloroform and normalized to the pentacene absorption near 660 nm.

FIG. 32A shows UV-vis spectra of oligomers 1Pc-3Pc measured in chloroform (12.5 μM). FIG. 32B shows UV-vis of oligomers 4Pc-7Pc (12.5 μM) and PolyPc (arbitrary units for comparison) measured in chloroform. FIGS. 32C and 32D UV-Vis of oligomers and PolyPc, drop cast from chloroform on a glass slide and plotted with the onset of absorption peak near 670 nm normalized to a value of 1.

FIGS. 33A to 33B show steady state UV-visible absorption spectra for oligopentacenes: 1Pc, 2Pc, anti-3Pc, and syn-3Pc; FIGS. 33C to 33E show steady state UV-visible absorption spectra for oligopentacenes: mix-3Pc 4PC, 5Pc, 6Pc, and 7Pc. The molarity listed in the legend is not the molarity of the oligomer, but rather the molarity of pentacene monomer for ease of comparison.

FIG. 34A and FIG. 34B show the Cartesian coordinates for Monomer (1Pc). Final total energy (B3LYP, 6-31 g**): −1816.5363 hartrees. Final geometry in angstroms for each atom.

FIG. 35A, FIG. 35B, FIG. 35C, and FIG. 35D show the Cartesian coordinates for Dimer (2Pc). Final total energy (B3LYP, 6-31 g**): −3631.8779 hartrees. Final geometry in angstroms for each atom.

FIG. 36A, FIG. 36B, FIG. 36C, FIG. 36D, and FIG. 36E show the Cartesian coordinates for Trimer (3Pc). Final total energy (B3LYP, 6-31G**): −5447.2189 hartrees. Final geometry in angstroms for each atom.

FIG. 37A, FIG. 37B, FIG. 37C, FIG. 37D, FIG. 37E, and FIG. 37F show the Cartesian coordinates for Tetramer (4Pc) at its optimum geometry. Final total energy (B3LYP, 6-31G**): −7262.5565 hartrees. Final geometry in angstroms for each atom.

DETAILED DESCRIPTION

Figure 1:
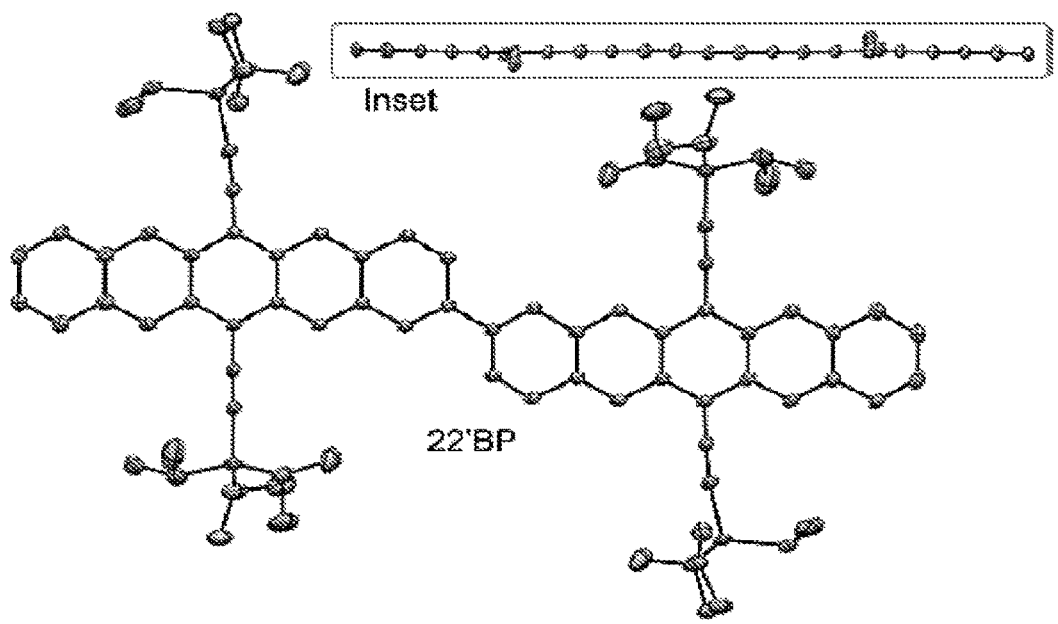
FIG. 1 shows the ORTEP representation of the molecular structure of the bipentacene derivative 22'BP and its side view (inset, iso-propyl (iPr) groups removed for clarity).

Embodiments of the invention pertain to the observation of ultrafast intramolecular singlet fission (SF) with slow triplet decay in oligoacene derivatives. A preferred embodiment is directed to a singlet fission molecule, compound or material that is capable of undergoing singlet fission, preferably efficient singlet fission, where the material displays essentially exoergic or essentially isoergic properties.

Another embodiment of the present invention provides the design of new compounds, molecules, or materials that express an excitation energy of a singlet of at least twice the energy of the triplet (E[$S_1$]≥2E[$T_1$]) or the sum of the monomer triplet energies: E($S_1$[X])≥E($T_1$[X]) E($T_1$[Y]). The novel SF material is also preferably capable of generating multiple excitons (e.g., multiple triplet pairs in organic molecules).

For example, a dimer of triisopropylsilylacetylene pentacene (TIPS pentacene) was observed to undergo quantitative intramolecular singlet fission. This assignment is based on transient absorption spectroscopy experiments which show the dissappearance of the initially photoexcited singlet and correlated rise of a triplet in dilute solution between a measured range of about 5 micromolar and about 56 micromolar concentration in chloroform, and without any dependence on concentration or other processes occurring.

More generally, while intramolecular SF was observed in a TIPS pentacene dimer, higher acene oligomers with appropriate solubilizing chains, such as a dimer of tri-tert butyl silyl acectylene protected hexacene also undergoes this process. Furthermore, longer oligomers such as a trimer or polymer of a linear acene (i.e. for example, tetracene, pentacene, etc.) also perform intramolecular singlet fission. Similarly, a combination, such as a hexacene covalently linked to a tetracene, may also perform singlet fission.

Another embodiment is directed to a facile and scalable method for the synthesis of solution processable higher oligomers of pentacenes (2Pc-7Pc), in addition to the first pentacene homopolymer. Exploiting the arene functional handle allows for a constant ratio of solubilizing/stabilizing units to pentacene as oligomer length increases, which results in excellent solubility in common organic solvents. Regiopure pentacene trimers (syn-3Pc and anti-3Pc) were also synthesized and compared to the regiomixture trimer (nix-3Pc), revealing several interesting characteristics: while there were no significant changes in the solution UV-vis spectroscopy, the solid-state UV-Vis signature was strongly affected by regioisomerism. Changes are attributable to the different packing interactions of the different regioisomers, as characterized by GIWAXS (see, FIG. 68, FIGS. 69A-69D; EXAMPLES 33 and 37). The crystallinity of anti-3Pc was significantly greater than mix-Pc and syn-Pc. GIWAXS also revealed minimal ordering in the higher oligomers, likely due to the presence of a large number of regioisomers. In all cases, crystalline order was increased upon thermal annealing. The solution UV-vis spectroscopy revealed the occurrence of high-energy peak in the region between 425 nm and 550 nm that intensifies as the length of the oligomer increases. This absorption, which effectively increases the absorption profile in the visible region, is attributed to an inter-pentacene π to π* transition. Cyclic voltammetry revealed an increase in the HOMO level for each homologous addition of pentacene, with polymer-like behavior approached at an oligomer length of four. The DSC and TGA experiments reveal that the oligopentacenes are thermally stable and have consistent decomposition temperature irrespective of oligomer length (371-382° C.). Except for 2Pc, all the oligomers displayed no phase transition during the heating cycle while 2Pc had non-reversible phase transition. These oligo- and poly-pentacenes may advantageously be used in various semiconductor applications and have beneficial charge transport properties.

The potential for singlet fission to raise the Shockley-Queisser solar energy conversion efficiency limit from about 33% to about 45% has led to great interest in this process. This invention demonstrates a material which performs this process in quantitative yield, and also works on an intramolecular basis, which was a significant barrier to implementation of first generation, intermolecular singlet fission in devices. This invention creates two triplet excitons from a singlet exciton regardless of morphology or intermolecular interactions. This multiple exciton generation has the potential to raise current in single junction solar cells or in photodetectors. In both cases, external quantum efficiencies over 100% can be obtained which are impossible without such multiple exciton generation processes.

In one embodiment, the invention provides a family of compounds that undergoes intramolecular singlet fission (iSF) with triplet yields reaching more than about 100%, preferably greater than or about 200%, per absorbed photon, independent of intermolecular interactions. For example, a pentacene-based chromophore achieved a triplet yield reaching about 200% per absorbed photon. Yet a further embodiment may be directed to these compounds which may undergo singlet fission in a solid state, as well as creating longer oligomers, and oligomers of different acenes (e.g., tetracene, pentacene, and hexacene).

A further embodiment is directed to a, or at least one, molecule, compound, or material having the following pentacene-tetracene structure.

Another embodiment is directed to a, or at least one, molecule, compound, or material having the following pentacene-hexacen structure.

Figure 71:
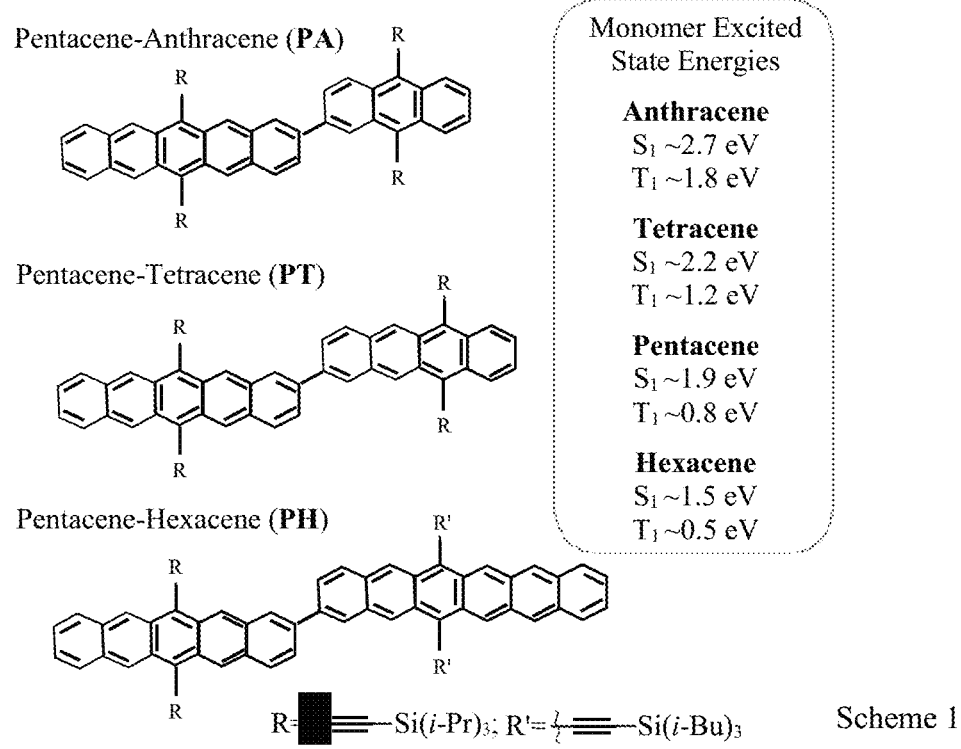
FIG. 71 shows asymmetric systems where two different oligoacene monomers are covalently linked.

Another embodiment provides for asymmetric systems where two different oligoacene monomers are covalently linked (Scheme 1; FIG. 71). Scheme 1 identifies oligoacene heterodimers and the excited state energies of the respective monomers. This design feature of two different oligoacene monomers covalently linked allows for systematic adjustments of the energetics of the iSF process, affecting both the driving force for singlet fission and the total energy of the resulting triplet pair. In these heterodimers, the relevant singlet energy for iSF is given by the lower singlet state energy monomer, and the resulting triplet pair is a sum of the individual monomer triplets. Therefore, the fundamental equation for energy conservation is $E(S_1[X]) \geq E(T_1[X])+E(T_1[Y])$, in, for example, a dimer comprising monomer X coupled to Y. For example, the pentacene-tetracene heterodimer is nearly isoergic ($S_1$[Pentacene]~1.9 eV, $T_1$[Pentacene] ~0.8 eV, $T_1$[Tetracene]~1.2 eV), while the previously reported bipentacene molecule is exoergic ($S_1$[Pentacene]>2×$T_1$[Pentacene]).[13,38-41] The pentacene-hexacene is also exoergic, where the singlet energy of the hexacene is used in the energy calculation because it has a lower singlet energy than that of the pentacene (i.e., about 1.5 eV<about 1.9 eV, respectively) is greater than the total sum of the triplet pair energies (about 1.3 eV) of the individual pentacene and hexacene, i.e., about 0.8 eV and about 0.5 eV, respectively. ($S_1$[Hexacene]~1.5 eV>~1.3 eV: ($T_1$[Pentacene]~0.8 eV+$T_1$[Hexacene]~0.8 eV)). Furthermore, since pentacene-anthracene is significantly endoergic ($E(S_1$[Pentacene])<$E(T_1$[Pentacene])+$E(T_1$[Anthracene])), it is not expected to undergo iSF. Asymmetric dimers as described here undergo fast and efficient iSF, provided that the singlet state is greater than and not significantly lower in energy than the resulting triplet pair. Since the process itself generates entropy, there is a little standard deviation which is allowable, as long as the singlet energy is essentially greater than or equal to the sum of the triplet energies of the monomers or repeating units. Subsequent decay of the triplet pairs formed in iSF-capable heteterodimers is primarily non-radiative, and it obeys the energy gap law for non-radiative recombination.[42-44]

A further embodiment is directed to the investigation of singlet fission in oligoacene heterodimers. The conjugated molecules shown in Scheme 1 were synthesized via Suzuki coupling chemistry (see, Examples 6 and 7).[13] The compounds are labeled as PA, PT, PH, where P, A, T and H refer to pentacene, anthracene, tetracene, and hexacene respectively. The singlet fission results were also compared to the bipentacene (BP), in which two pentacenes are similarly covalently attached at the 2-position. The inclusion of tri-isopropylsilyl acetylene (TIPS), or in the case of hexacene, tri-isobutyl silyl acetylene groups (TIBS), renders these heterodimers soluble and relatively stable in solution.[45-49]

An advantage of the described invention over existing materials that depend on intermolecular interactions, is that a quantitative singlet fission yield may be used neat, in a solution or in a mixture, where the inventive compound, composition, or material, used interchangeably here, is stable and soluble. Whereas, the existing intermolecular coupling-dependent materials only work in crystals or as aggregates, and are therefore difficult to implement. A soluble, stable singlet fission material, where the singlet energy of a lower energy monomer is greater than or equal to, or greater than about or equal to about the sum of the triple monomer energies. Useful singlet fission materials comprise of at least dimers of oligoacenes, preferably tetracenes or larger, including pentacene, hexacene, heptacene, and the like; asymmetric dimers of oligoacenes, such as but not limited to pentacene-tetracene (PT), pentacene-hexacene (PH), pentacene-heptacene, and the like; and polyoligoacenes including oligomers and polymers. Oligomers comprise of 2 to 10 monomers or repeating units, while polymers comprise of more than 10 monomers or repeating units, preferably 15, and more preferably 20 monomers or repeating units. Useful soluble, stable singlet fission materials also include hetero-oligomers and hetero-polymers, and more preferably homo-oligomers and homo-polymers.

In order to understand the effects of increasing the oligomerization length on the fundamental properties of oligoacenes, including oligomers and polymers, building blocks to access oligomers (2-7 monomer or repeating units) as well as polypentacene were developed. (See, Example 17) Obtaining well-defined oligomeric materials is particularly attractive because they reveal detailed structure-property relationships, as in the case of thiophenes.[87-92] To date, pentacene has only been incorporated in alternating copolymers or as a pendant group on a polymer chain, not as a homopolymer.[81-86] An attractive strategy where the pentacenes were not directly coupled, but included a diacetylene spacer in an alternating fashion linked at the 6 and 13 positions was also developed.[84] Unfortunately, higher oligomers (n>4) could not be synthesized employing this strategy due to limited solubility, which results from the decreasing ratio of the solubilizing trialkylsilane unit to pentacene, upon oligomerization. This decreasing ratio can also be detrimental to stability, as the bulky alkylsilyl groups protect against the primary degradation pathways of dimerization and photooxidation.[79] An alternative strategy is needed to access higher oligomers of conjugated pentacene and polypentacene in order to study, for example, optoelectronic properties.

Singlet fission materials having an increasing number of monomers or repeating units may result in an increasing speed, i.e., faster, of conversion of singlet to triplet pair. For useful singlet fission materials, the materials should have singlet fission that occurs at a speed of less than about 5 nanoseconds. Singlet fission may occur at a speed as fast as about 300 femtoseconds ($10^{15}$ of a second). Also, the triplet pairs converted from the singlet should not decay too quickly. The longer the triple pairs remain, the better for efficient singlet fission materials. Preferably decay occurs as slow as microseconds, and preferably is slower than picoseconds. For example, a preferred decay occurring in the microseconds range may be about 1 microsecond to about 2 microseconds, but slower than about 200 to about 500 picoseconds. The decay time of a pentacene-hexacene dimer is about 200 picoseconds, a bipentacene dimer is about 500 picoseconds, and a pentacene-tetracene dimer is about 1.5 nanoseconds.

In one embodiment, a, or at least one, preferred soluble, stable singlet fission material comprises at least an oligoacene dimer of two covalently bound oligoacene monomers, or an oligoacene of at least two covalently bound oligoacene monomers, where the material has a singlet exciton energy of greater than or equal to, greater than about or equal to about, or essentially greater than or essentially equal to, the energy of two triplet excitons, or the energy of the sum of the triplet excited states of each oligoacene monomer, and the singlet exciton energy is that of the lowest energy monomer.

Another embodiment is directed to a soluble, stable singlet fission material comprising a, or at least one, molecule, compound, or material having the structure or compound of Formula 1, where Formula 1 may be repeated to form a chain:

Formula 1 where:
A and C is any acene or acene monomer, for example but not limited to, preferably anthracene, tetracene, pentacene, or any higher acene, where A and C may be the same or different acene or acene monomer, and the different acene monomers may be homo- or the same monomers, or hetero- or asymmetric acene monomers;
wherein A and C are covalently bound to each other, or via spacer B, at one position of any available or possible positions of the A and C acene monomers, and the positions that do not covalently bind A and C to each other, or via spacer B, are occupied by a hydrogen, a halogen, or a cyano substituent, and
B is a spacer, for example but not limited to, phenyl, benzene, a conjugated spacer such as thiophene, benzodithiophene (BDT), -ene, or any similar conjugated spacer, and non-conjugated spacers including, but not limited to, bicyclooctane, saturated carbon, and the like;
n, m, o, and p are each 0 or any positive integer, preferably m is 0 or 1-10, except
when n is 0, o is greater than or equal to 1, i.e., when n=0, o≥1 and o≠0 (i.e., o cannot be 0 when n is 0), and when o is 0, n is greater than or equal to 1, i.e., when o=0, n≥1 and n≠0; and
where the A-C covalently bound dimer, with or without a spacer, B, may add an additional acene monomer that is covalently bound to preferably form an oligomer of polyacenes or a polymer of polyacenes, such as for example a trimer, tetramer, a pentamer, a hexamer, a heptamer, an octomer, and the like;
wherein dimers or repeat units A and C or A and A or C and C each has acene monomers that are covalently bound, conjugated, joined, and the like, to each other or via a spacer, B, at one position of any available or possible positions of the A oligoacene monomer and the C oligoacene monomer, and the positions that do not covalently bind the A and/or C monomers are instead occupied by a hydrogen, H, a halgen, such as for example Bromine (Br), a cyano substituent, or the like; and wherein the lower singlet exciton energy of one oligoacene or acene monomer is essentially greater than about or essentially equal to about, or greater than about or equal to about, or greater than or equal to the sum of the energies of the triplet excited states of each oligoacene or acene monomer. The singlet fission material described here and in Formulas 1, 2, and 3, may have an oligoacene monomer of A and/or C, where the material comprises an oligoacene of at least an anthracene or a tetracene, or an anthracene or a tetracene backbone, including but is not limited to a backbone of a pentacene, a hexacene, a heptacene, or greater oligoacene, preferably at least a tetracene or a pentacene. Each of A and C may comprise of a polyoligoacene that is the same or different from each other; where A is

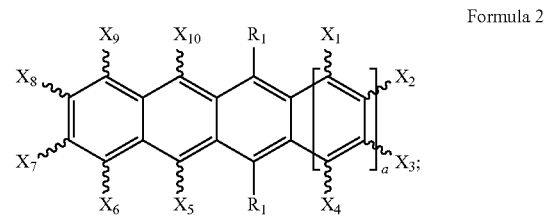

Formula 2 wherein C is

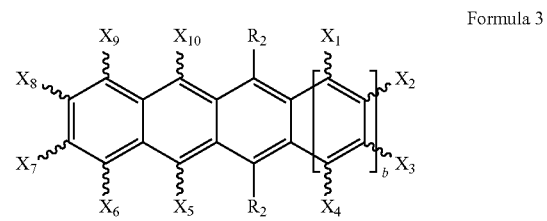

Formula 3 wherein A and C may be covalently bound, conjugated, or joined at any one of positions $X_1$, $X_2$, $X_3$, $X_4$, $X_5$, $X_6$, $X_7$, $X_8$, $X_9$, or $X_{10}$ of A and C, and the covalently bound position of A is not necessarily the same as the position of C, for example, A and C may be covalently bound, conjugated, or joined at positions $X_1$ of A and $X_1$ of C, $X_2$ of A and $X_2$ of C, $X_1$ of A and $X_2$ of C, $X_2$ of A and $X_1$ of C, $X_2$ of A and $X_7$ of C, $X_7$ of A and $X_2$ of C, and the like. The remaining positions that do not have the covalently bound, conjugated, or joined A and C are occupied by a hydrogen (H), a halogen, such as for example Bromine (Br), or a cyano substituent. For example, A and C may be covalently bound, conjugated, or joined at the X positions of each, and the remaining $X_2$, $X_3$, $X_4$, $X_5$, $X_6$, $X_7$, $X_8$, $X_9$, and $X_{10}$ positions of each of A and C are instead occupied by a hydrogen, a halogen, such as for example Bromine (Br), or a cyano substituent, or A and C may be covalently bound at the positions and the remaining $X_1$, $X_3$, $X_4$, $X_5$, $X_6$, $X_7$, $X_8$, $X_9$, and $X_{10}$ positions of each of A and C are instead occupied by a hydrogen or another element, or A and C may be covalently bound at the X and $X_2$ positions of A and C, respectively and the remaining $X_2$, $X_3$, $X_4$, $X_5$, $X_6$, $X_7$, $X_8$, $X_9$, and $X_{10}$ positions of A and the remaining $X_1$, $X_3$, $X_4$, $X_5$, $X_6$, $X_7$, $X_8$, $X_9$, and $X_{10}$ positions of C are instead occupied by a hydrogen or other preferred element.

In Formula 2 and Formula 3, a and b is 0 or any positive integer, preferably a and b are 0, 1, 2, or 3, preferably forming up to a heptacene, a and b each may be any integer that is the same or identical, or different from each other, where a=b or a≠b, and a and b may be 0, 1, 2, 3, 4, 5, 6, etc., where each positive integer for a and b adds, conjugates, joins, fuses, or otherwise binds a benzene ring to the monomer of Formula 2 or Formula 3, thereby lengthening each of the monomers, and with each increasing integer another benezene ring is fused, joined, or added to the oligoacene monomer.

When a or b is 0 or 1, $R_1$ of Formula 2 and $R_2$ of Formula 3 are each tri-isopropylsilyl acetylene (TIPS) or

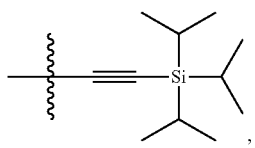 [SMILES: *C#C[Si](C(C)C)(C(C)C)C(C)C]

or in an alternative depiction, where iPr is an isopropyl group;
when a orb is a positive integer of greater than or equal to 2, i.e., 2, 3, or a positive integer greater than 2, $R_1$ of Formula 2 and $R_2$ of Formula 3 are each a bulky group, preferably a bulky group occupying a physical space larger than TIPS such as, but not limited to a bulky group selected from the group consisting of: tri-isobutylsilyl acetylene (TIBS) or

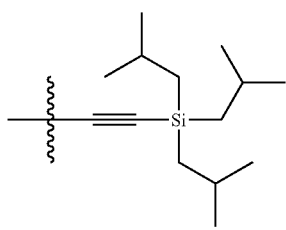 [SMILES: *C#C[Si](CC(C)C)(CC(C)C)CC(C)C]

or in an alternative depiction,

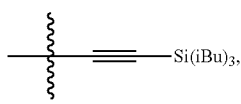

where iBu is an isobutyl group, tricyclohexylsilyl acetylene or:

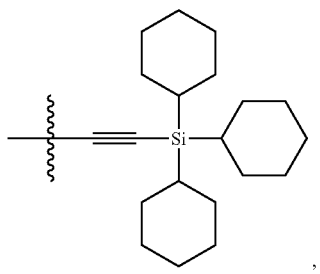 [SMILES: *C#C[Si](C1CCCCC1)(C1CCCCC1)C1CCCCC1]

tricyclopentylsilyl acetylene or

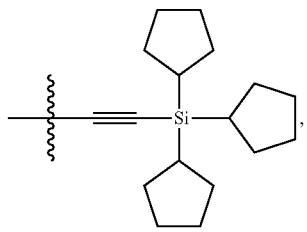 [SMILES: *C#C[Si](C1CCCC1)(C1CCCC1)C1CCCC1]

n-octyl-diisopropylsilylethynyl (NODIPS) or

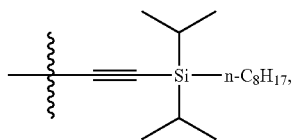

n-octadecyl-diisopropylsilylethynyl ((NODDIPS) or

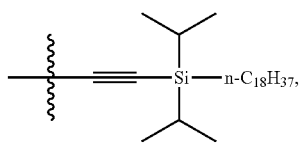

and combinations thereof, where $R_1$ and $R_2$ are the same or different.

The size of the $R_1$ and $R_2$ depends on the length of the oligoacene, where TIPS is preferably the substituent for oligoacenes smaller than pentacene, i.e., having less than 5 benzene rings as shown in Formulas 2 and 3. TIBS, NODIPS, and NODDIPS are considered to be bulky compounds and are preferably the $R_1$ and $R_2$ substituents for oligoacenes having 5 or more benzene rings, i.e., pentacene or larger monomers.

A further embodiment of the invention comprising a, or at least one, singlet fission molecule, compound, or material, all of which are used interchangeably, of Formula 1, where the material is exoergic, essentially exoergic, isoergic, or essentially isoergic. The material preferably generates multiple excitons.

Yet another embodiment is directed to a, or at least one, material selected from the group consisting of: pentacene-hexacene, 22'BP, pentacene-tetracene, 1-200 pentacenes, such as for example, an oligomer of pentacenes, preferably 2-10 monomers in length, a pentacene polymer of 11-200 monomers in length, 1-200 tetracenes, such as for example, an oligomer of tetracenes, preferably 2-10 monomers in length, or a tetracene polymer of 11-200 monomers in length, a hetero polymer of pentacenes, tetracenes, and/or hexacenes of 1-200 monomers in length, such as for example, an oligomer or polymer of pentacene-tetracene repeating units and variations thereof, an oligomer or polymer of pentacene-hexacene repeating units and variations thereof, an oligomer or polymer of tetracene-hexacene repeating units and variations thereof, an oligomer or polymer of pentacene-tetracene-hexacene repeating units and variations thereof, and any combinations thereof, where variations may include different linear orders of the monomers and the presence of one or more spacers, preferably 1-10 spacers in between each of the acene monomers.

The more consecutive spacers joining the oligoacene monomers increases the lifetime of the triplet pairs, reducing or minimizing the degradation. A preferred spacer includes 1-10, preferably 1-5 thiophene rings, alkene rings, benzene-benzene rings, and double bonds.

In a further embodiment, the singlet fission material exhibits a singlet fission yield of greater than about 100%, greater than about 120%, greater than about 140%, or greater than about 200%.

Yet another embodiment is directed a, or at least one, soluble, stable singlet fission material comprising an oligoacene of at least two covalently bound oligoacene monomers, where the lower singlet exciton energy of one oligoacene monomer is greater than or equal to, greater than about or equal to about, or essentially greater than or essentially equal to the energy of the sum of the triplet excited states of each oligoacene monomer, where the material may be used in an electronic, optical, or electrooptical component or device.

A further embodiment is directed to an electronic, optical, or electrooptical component or device, such as for example but not limited to, photodetectors, solar cells, and components or devices utilizing photocatalytic processes, comprising a, or at least one, soluble, stable singlet fission material described here, as well as in Formula 1, where the electronic, optical, or electrooptical component or device is efficient, more efficient than current components or devices, and overcomes the Shockley-Queisser efficiency limit.

Another embodiment is directed to pentacene-based chromophores possessing the desired characteristics. Pentacene has surfaced as the prototypical material since its SF triplet quantum yield is quantitative, preferably more than about 100%, and most preferably about 200%.[23]

A further embodiment is directed to a soluble 2,2'bipentacene molecule (22'BP, FIG. 1). The energy of 22'BP was calculated to be about 0.26 eV exothermic in SF, using a similar method as Greyson and co-workers (See, Examples).[50] While the connectivity of the pentacenes in 22'BP is similar to tetracene dimers proposee,[50] 22'BP has key distinctions: a) xSF in pentacene is known to be exothermic; and b), triisopropysilylacetylene (TIPS) groups were included to render the products soluble and stable, resulting in a high-yielding and scalable synthesis (See, Examples). Here, 22'BP exhibited the maximum iSF yield, about 200%.

Another embodiment is directed to a soluble, stable singlet fission material comprising a polymer of homo-oligoacenes, for example, a polytetracene having 20 repeating units or monomers, where the energy of the tetracene.

Figure 2:
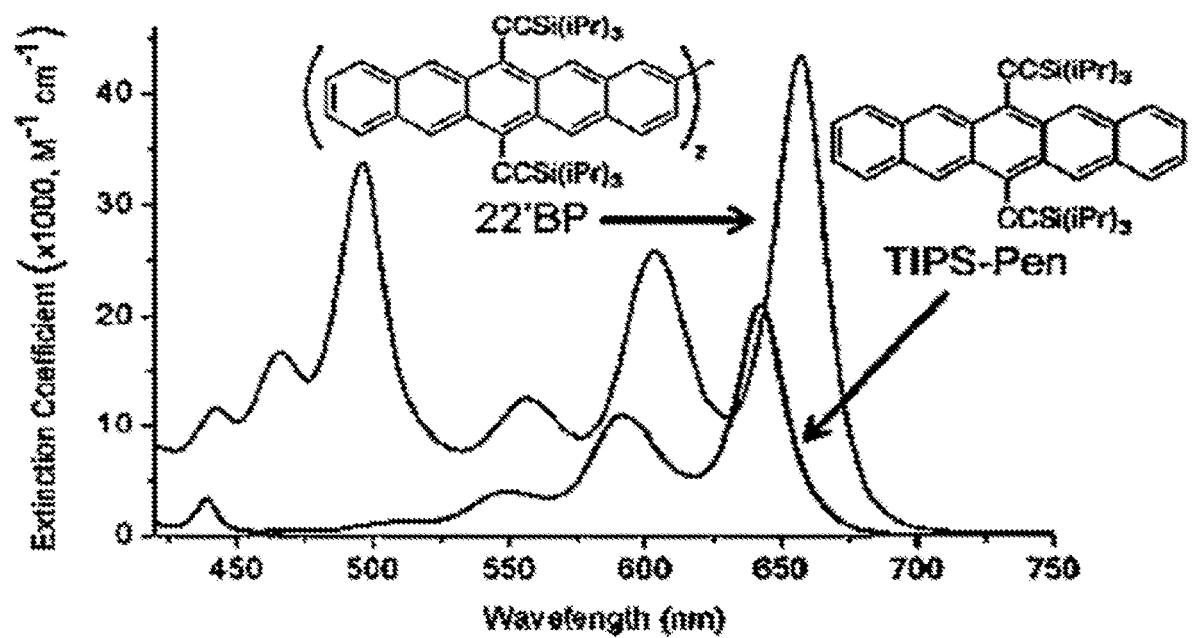
FIG. 2 shows UV-vis spectra of 22'BP and 6,13-bis ((triisopropylsilyl)ethynyl) pentacene (TIPS-Pen) dissolved in chloroform.
Figure 10:
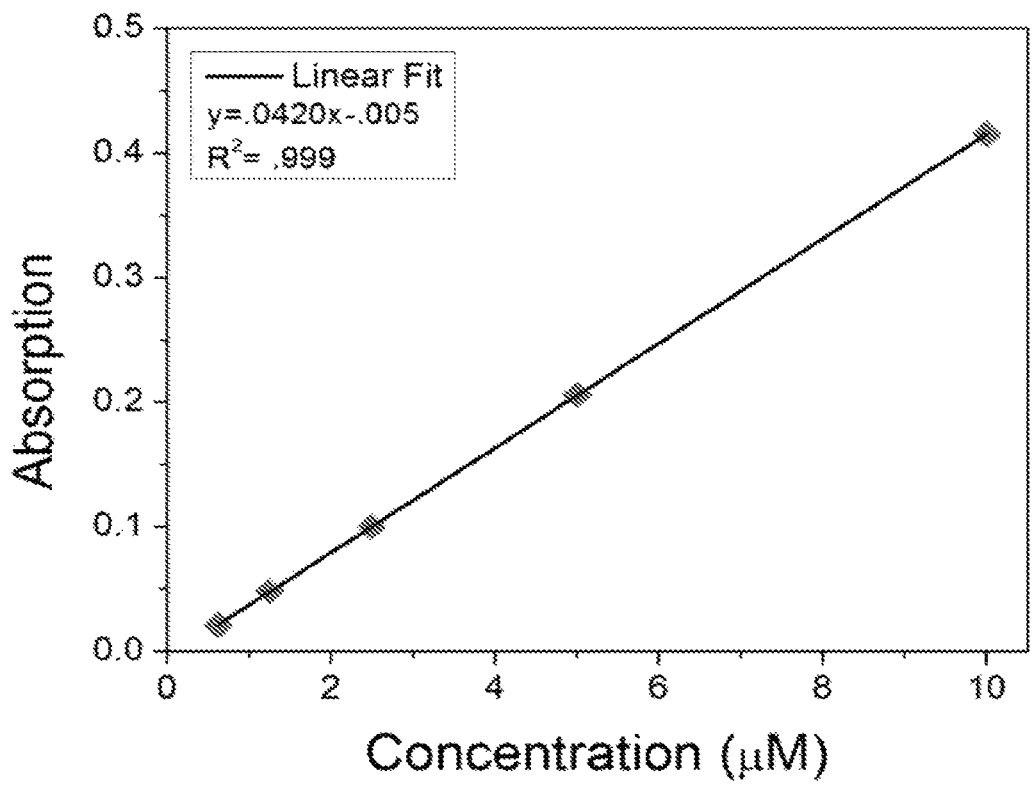
FIG. 10 shows Beer's law of 22'BP in p-xylene yielding a molar extinction coefficient of 42000 $M^{-1}cm^{-1}$.

FIG. 1 shows the crystal structure of 22'BP (synthetic and crystallographic details are provided in the Examples). Steady state absorption spectroscopy of 22'BP in chloroform is compared to that of a single pentacene chromophore, TIPS-Pen (FIG. 2). The molar extinction coefficient of 22'BP was determined to be 43,000 $M^{-1}cm^{-1}$, almost exactly twice that of TIPS-Pen. Additionally, a new set of high-energy peaks appear in the dimer, broadening the absorption to include a greater portion of the visible spectrum. Finally, concentration-dependence studies of 22'BP do not indicate any aggregation effects, which typically manifest as red-shifting of the absorption spectrum (FIG. 10). Ensuring that no aggregates are formed is an important aspect to ensure that the photophysical measurements are probing molecules that are fully dissolved.[51]

To study the transient photophysics of this system, ultrafast broadband transient absorption spectroscopy (TAS) was employed, which measures the differential absorption spectrum between a material in its excited and ground state electronic configuration (details in the Examples). Using this technique, a rapid conversion of photoexcited singlets into triplets occurring on a sub-picosecond timescale was observed. These two distinct populations were clearly observed in a 2D pseudo-color (ΔA) plots of TA spectra as a function of probe wavelength and delay time (FIG. 3A), where photoinduced absorption (PIA) features at about 470 nm and about 560 nm rapidly evolved into a new feature at about 515 nm. The amplitude of the feature at 515 nm rose for a few picoseconds and then decayed with a several hundred picoseconds time constant back to the ground state (FIG. 3B) during which the shape of the transient spectra remained constant. The negative feature at about 660 nm persisted for the duration of the conversion from singlet to triplet and resulted from ground state bleaching of the lowest energy optical transition that was seen in the linear absorption spectrum (FIG. 2).

Based on the known TAS of TIPS-Pen and related compounds, the features that decay on the sub-picosecond timescale to the singlet state and the slow decaying features to the triplet state were assigned.[9] The triplet spectrum was clearly isolated at times greater than about >~5 picoseconds, after which features associated with the singlet manifold decayed. However, to isolate the rapidly decaying singlet features and get an accurate time scale for fission, global analysis methods with a sequential kinetic decay model $(S_1 \rightarrow 2T_1 \rightarrow S_0)$ was used.[52] The deconvoluted spectra that result from global analysis are shown in FIG. 3C and the resulting species concentration profiles as a function of time are shown in FIG. 3D (solid lines). A triplet PIA feature was observed to overlap spectrally with the position of the ground state bleach. As a result, the ground state recovery did not strictly correlate with the magnitude of the bleach feature as a function of time. In other words, the net change in the bleach during the singlet decay was primarily due to the rise of the overlapping triplet PIA, and not due to the loss of excited state population.

A time constant for the correlated singlet decay and triplet rise of 760 femtosecond from global analysis was extracted. From the spectral deconvolution, regions were identified in the unprocessed data at which the singlet (563 nm) and the triplet (731 nm) kinetics could be preferentially observed. These regions did not correspond to the peaks of the singlet and triplet PIA features. The extracted raw kinetic traces at these wavelengths were compared against the computed population profiles (FIG. 3D) and good agreement was found with our model that correlates the rise of the triplet with the decay of the singlet. Similarly, the data at both wavelengths fit well with a common set of time constants that agree with those determined from global fitting (details in the Examples).

Because of the rapid conversion of singlets into triplets in dilute solution and the similarity to the fission processes observed in crystalline pentacene derivatives, this dynamical process was assigned to iSF[22] with a triplet yield (of about 200%) that is comparable to the best xSF solid-state systems. This was based on the fact that the singlet lifetime is over four orders of magnitude shorter than the corresponding singlet lifetime of TIPS-Pen, and no other species besides the singlet and triplet were identified in the transient absorption data. As further confirmation, radiative losses were directly measured using steady-state photoluminescence; accounting for less than about 0.03% of the excited state population decay (details in Examples). Similarly, the presence of additional non-radiative decay channels was ruled out, which have been shown to disrupt the correlation between the singlet decay and triplet rise.[10] Similar to the steady state absorption data, the transient absorption dynamics were independent of concentration spanning an order of magnitude (FIG. 3B). The lowest concentration measured by TAS, 5 µM, was about 15,000 times lower than concentrations needed for efficient intermolecular, diffusion controlled SF previously reported in the literature.[51] Furthermore, diffusion controlled fission occurred at markedly slower rates and produced triplets that lasted orders of magnitude longer due to their ability to diffuse apart. All this information, taken together, supports the assignment of intramolecular singlet fission in 22'BP.

Figure 4:
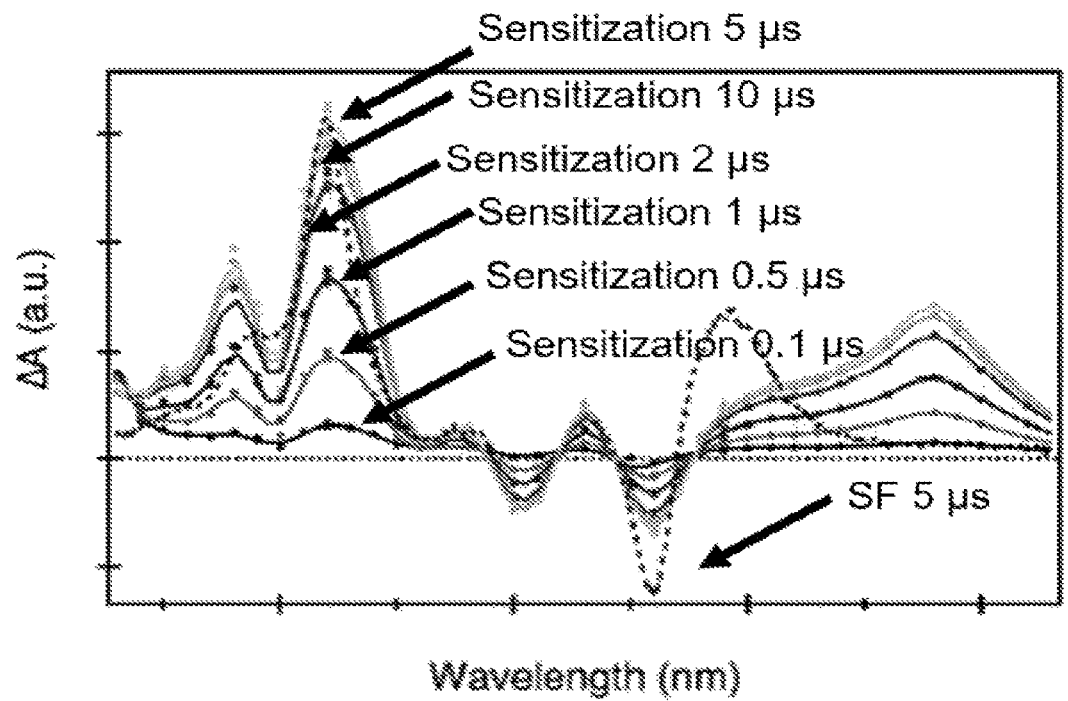
FIG. 4 shows triplet spectra of 22'BP obtained by pulsed radiolysis triplet sensitization (single triplet), showing unprocessed data (solid lines) in the presence of naphthalene triplet sensitizer at various time intervals, and the two-triplets spectrum arising from iSF (dashed line).

As iSF occurs in dilute solution, the transient spectra and dynamics associated with triplet pairs (produced via fission) and individual triplets in 22'BP, which are produced via pulse radiolysis triplet sensitization (PR) experiments were compared[10,53] Most strikingly, the recombination timescale of triplet pairs (about 500 picoseconds) is several orders of magnitude faster than that of individual triplets (several microseconds, FIG. 4). This is in agreement with recent reports of fast triplet-triplet annihilation processes in single molecules.[10] The transient spectra for one and two triplets were not completely identical, particularly on the low energy side of the ground state bleach. The low energy PIA feature (typically assigned to T1→T2) is red-shifted by about 200 meV in the sensitization experiment, though much better agreement is seen in the higher energy (T1→T3) triplet PIA feature.

The fission rate was established to be independent of pump fluence in the measured range (up to 100 µJ/cm$^2$), solvent, and excitation wavelength (FIGS. 6-8), though minor, changes in spectral shape when varying the solvent from chloroform to p-xylene (FIG. 3C and FIG. 4).

Figure 6:
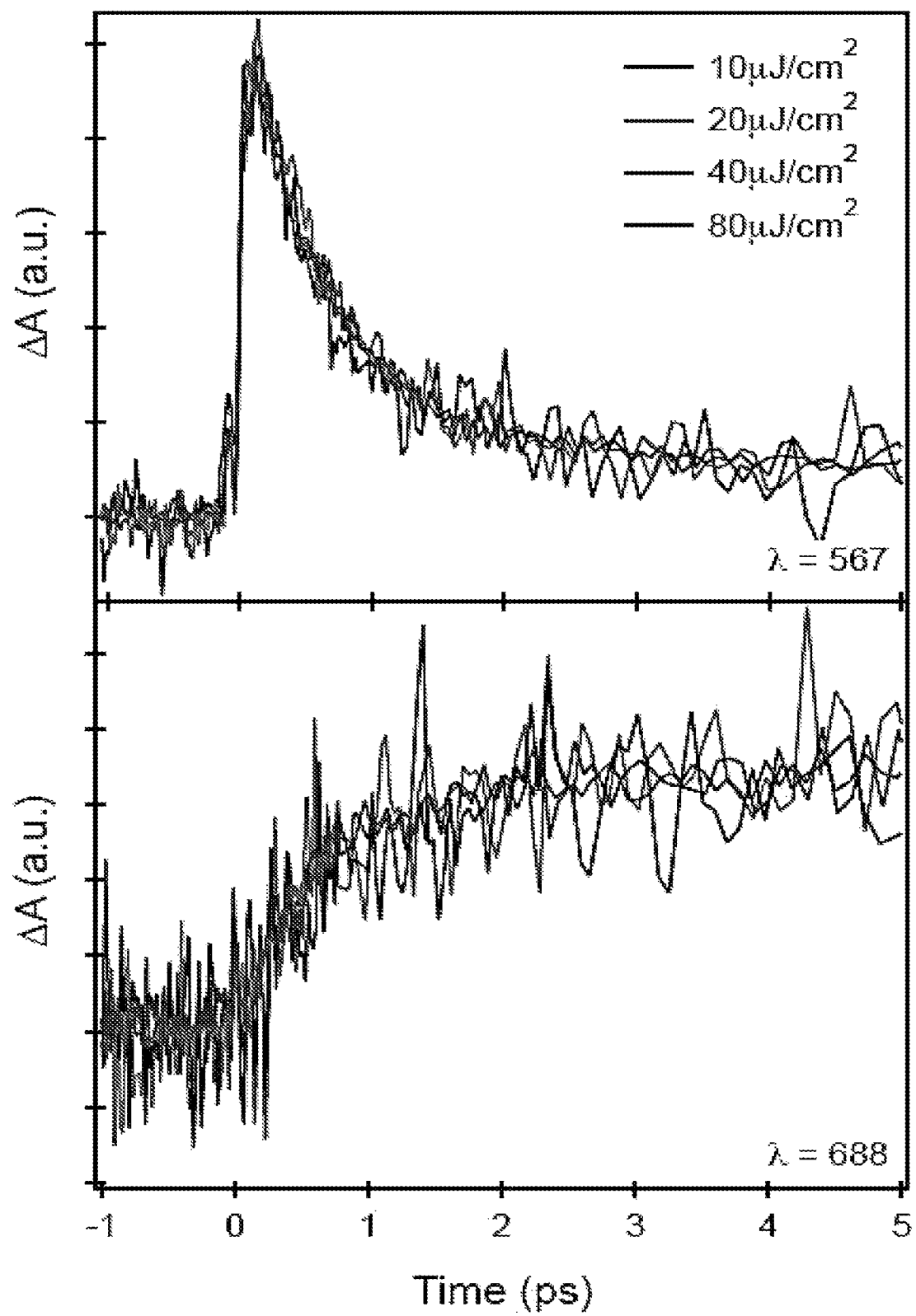
FIG. 6 shows a comparison of normalized kinetic slices at 567 nm and 688 nm, excited with 600 nm pump with varying pump fluence.

Fluence Independent Dynamics:

All dynamical behavior is independent of excitation fluence within the measured range (up to about 100 µJ/cm$^2$). Single wavelengths kinetics at 567 nm (dominated by singlet response) and 688 nm (dominated by triplet response) are shown in FIG. 6 (c=50 µM in chloroform) as a function of the 600 nm pump fluence.

Figure 3:
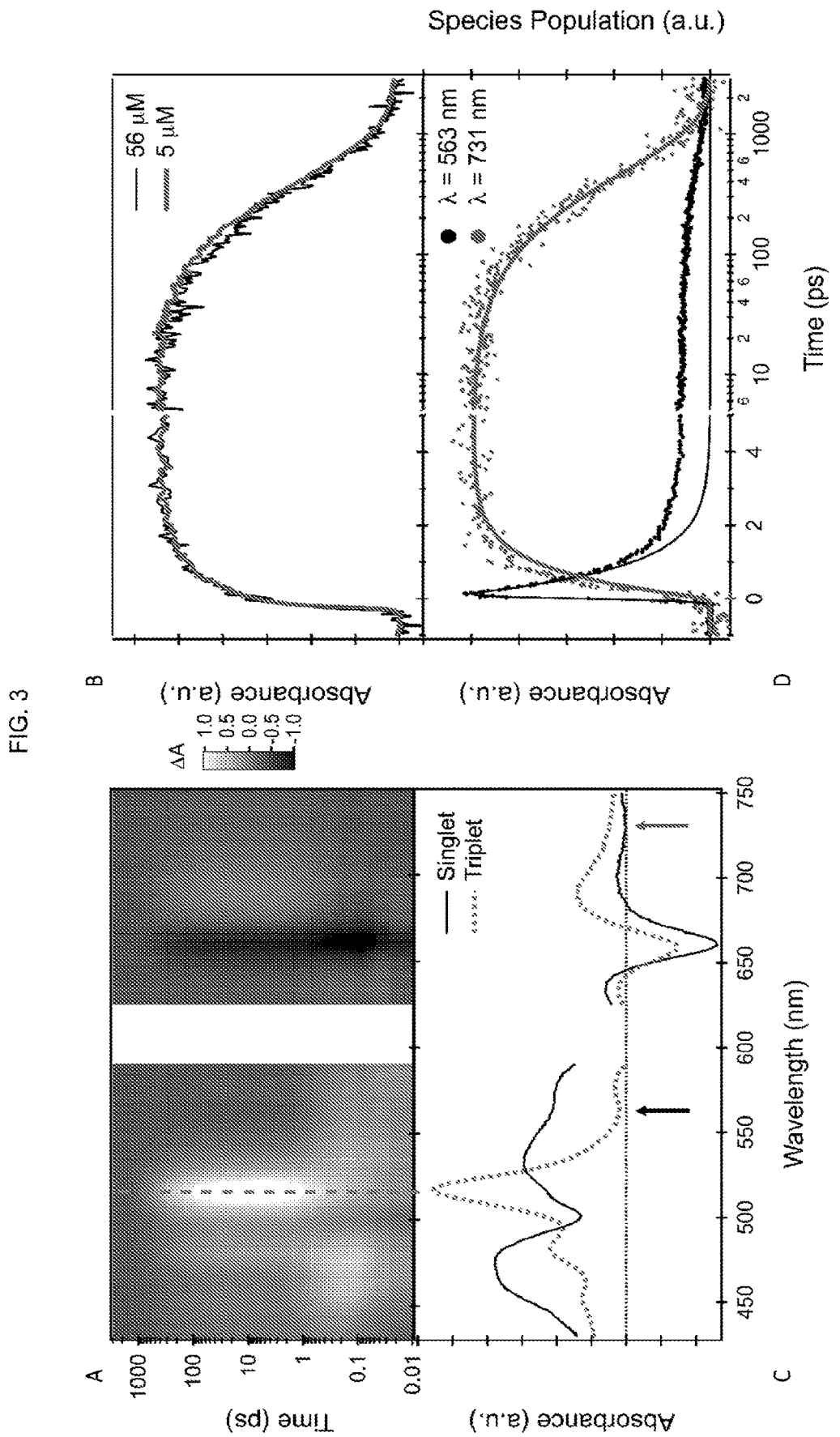
FIG. 3 shows (A) normalized transient absorption data on 56 μM 22'BP in chloroform (600 nm pump). Due to the presence of pump wavelength scatter, small portions of the data have been excluded for clarity. (B) A normalized spectral slice at 517 nm (dashed line in Panel A) showing that the carrier dynamics are independent of concentration over an order of magnitude. (C) Deconvoluted transient spectra of singlet and triplet species as solved by global analysis (details in the Examples). It should be noted that differences in the magnitude of bleach in panel (C) are attributable not to reduction in bleach but rather overlap with the triplet spectrum. (D) Population evolution from global analysis are compared to raw data at wavelengths where primarily singlet (563 nm, black arrow in (C)) and triplet (731 nm, red arrow in (C)) dynamics are observed. The discrepancy at 563 nm is due to the ~20% overlap with a triplet photoinduced absorption feature. Direct fits of the data are found in FIG. 5.
Figure 7:
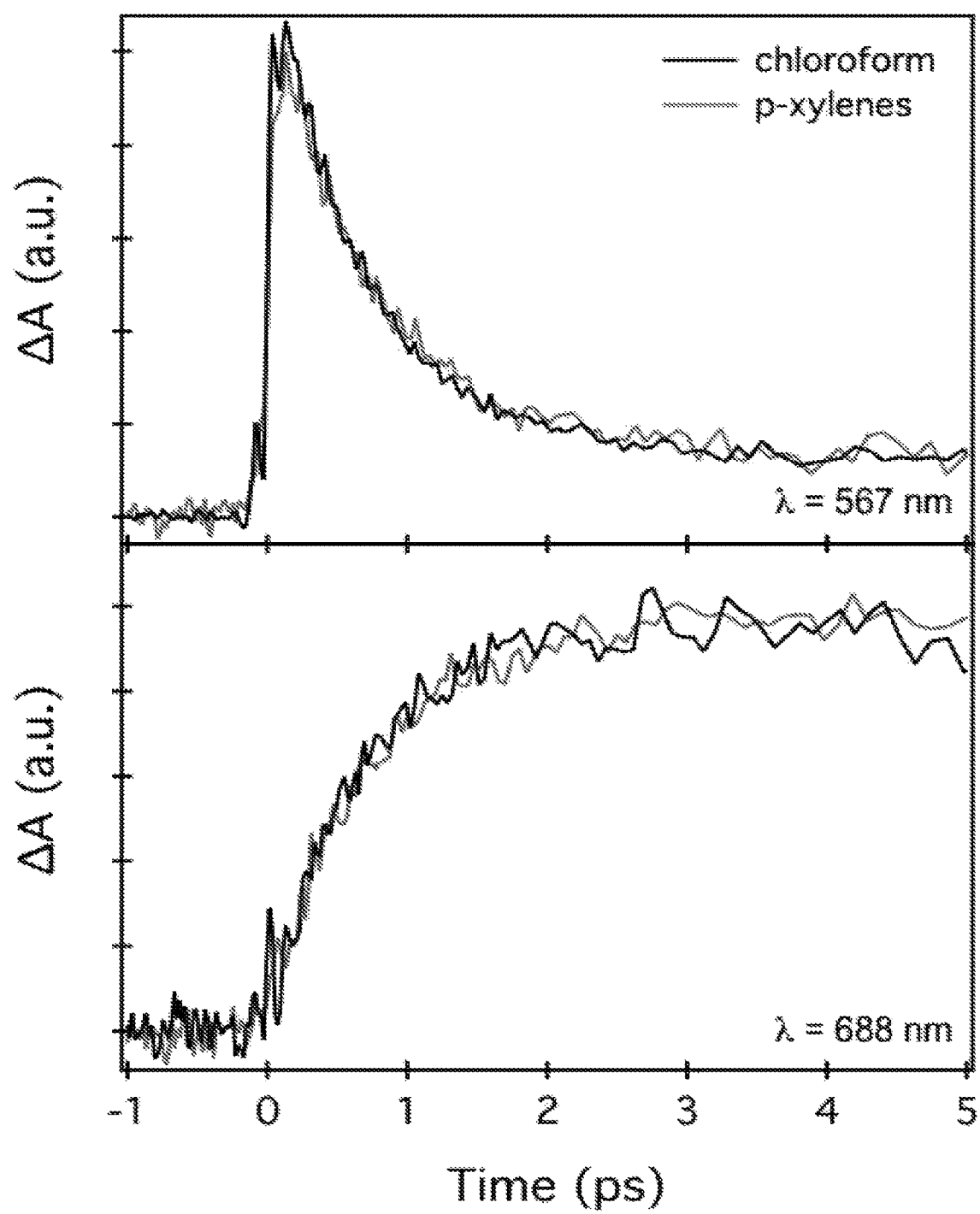
FIG. 7 shows a comparison of kinetic slices at 567 nm and 688 nm, excited with 600 nm pump in chloroform and p-xylenes.
Figure 8:
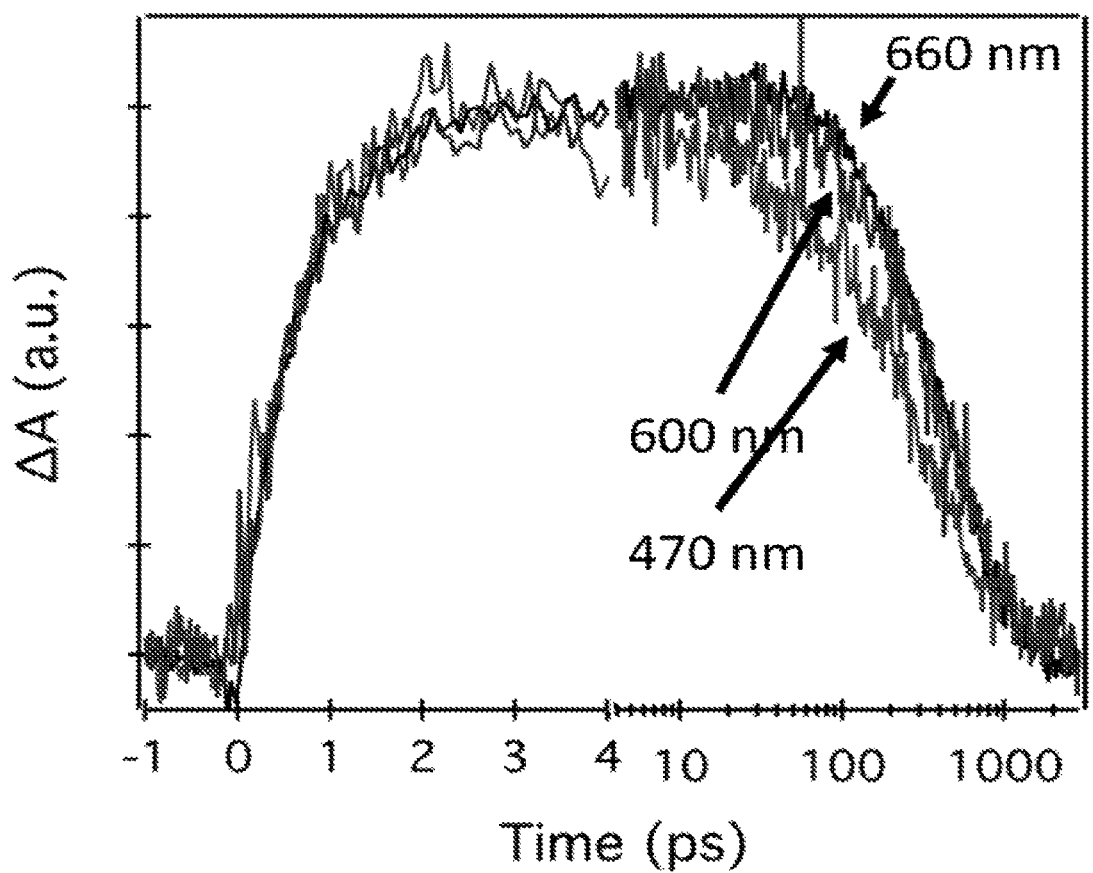
FIG. 8 shows kinetic data at 688 nm for difference pump photon wavelengths. An identical fission rate is seen in all three traces.

Solvent Independent Dynamics:

The fission rate and triplet decay dynamics are independent of solvent, although slight differences are seen in the relative amplitude of triplet photoinduced absorption features (FIG. 3 and FIG. 4). In FIG. 7, kinetic traces extracted from the raw data set of the rise at 567 nm (dominated by singlet response) and 688 nm (dominated by triplet response).

Excitation Wavelength Dependence

The singlet fission rate showed no dependence on photon energy, remaining constant at about 760 fs. However, the relaxation of the triplet pair, confined to a singlet molecule, was found to show more complex dynamics at higher excitation energy. Single wavelength kinetics at 688 nm (600 nm pump) are shown in FIG. 7, where the constant rise of the triplet can be clearly seen along with a weakly energy-dependent recombination process. While in FIG. 8, an identical fission rate is observed in all three photon wavelengths.

Steady State Absorption Spectroscopy

Figure 9:
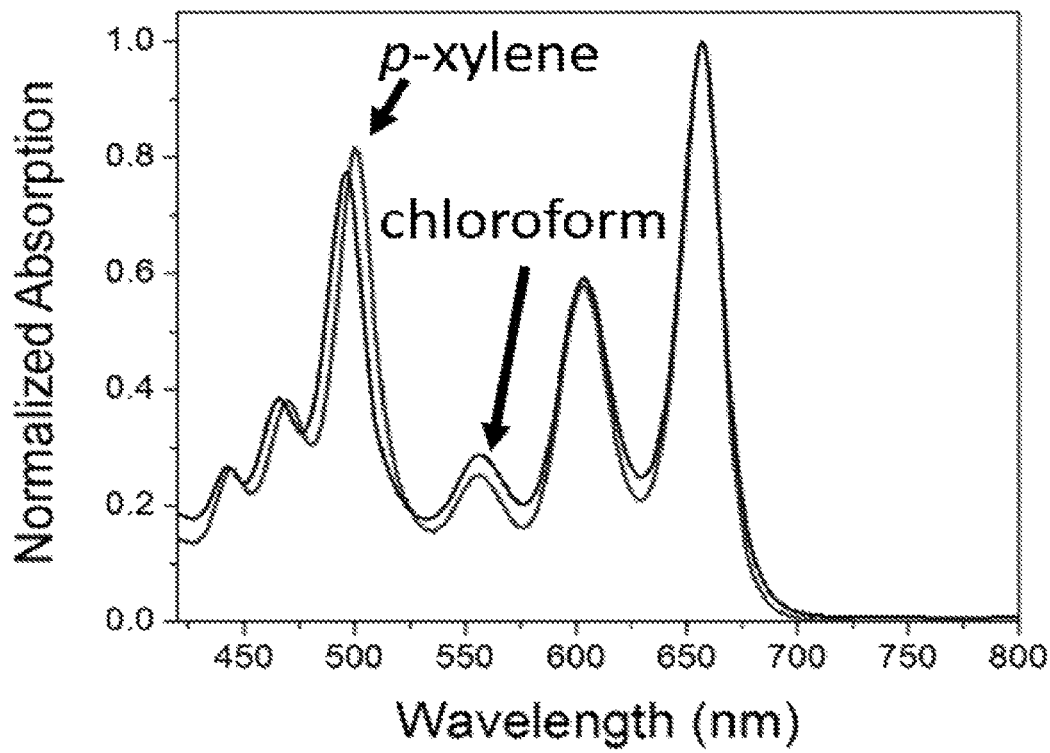
FIG. 9 shows a normalized steady state absorption revealing no evidence of aggregation or change in spectral shape.
Figure 11:
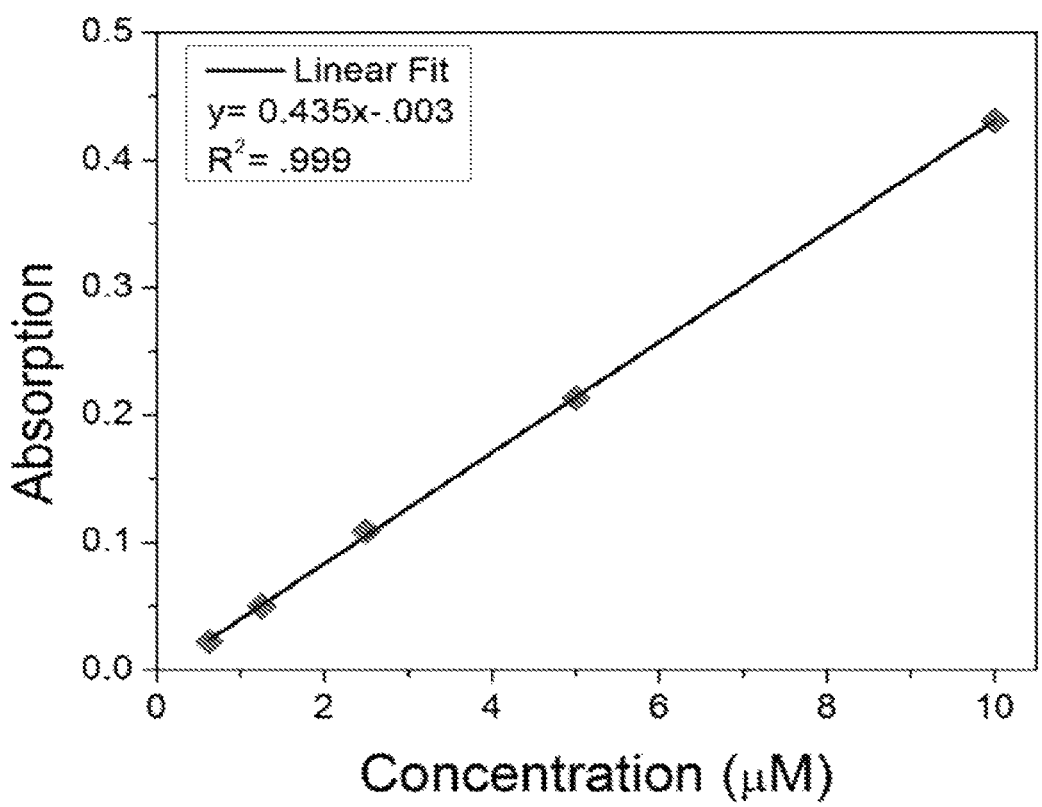
FIG. 11 shows Beer's law of 22'BP in chloroform yielding a molar extinction coefficient of 43500 $M^{-1}cm^{-1}$.
Figure 12:
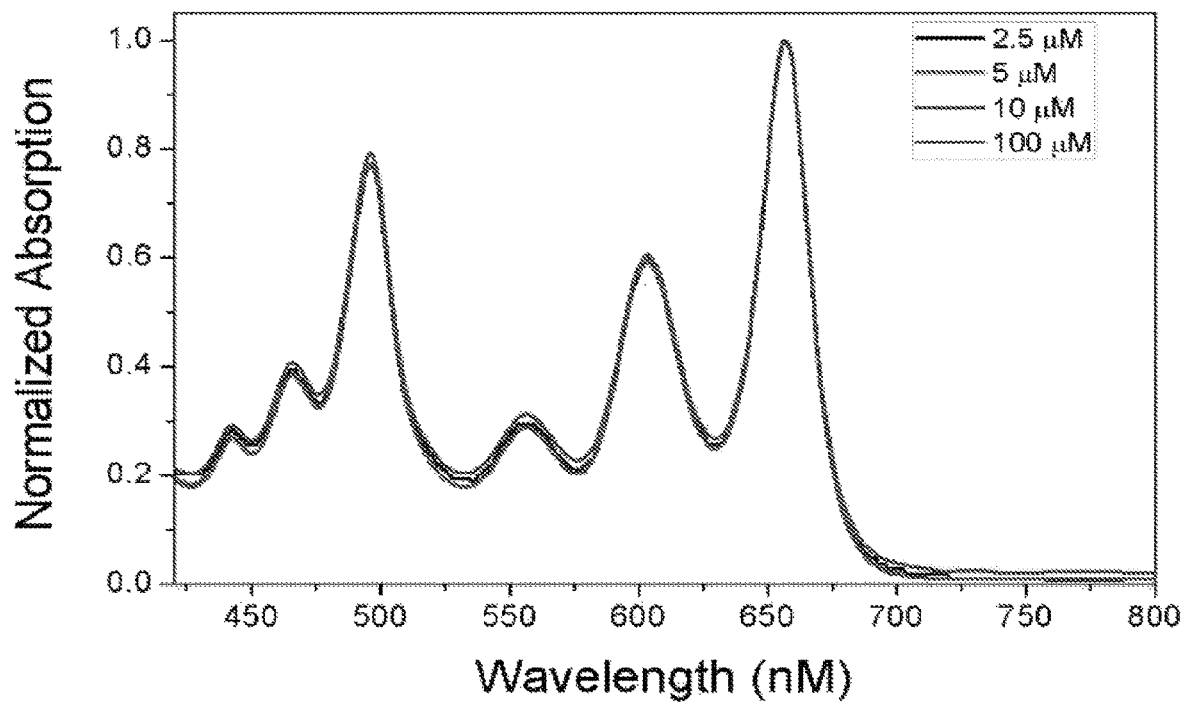
FIG. 12 shows a normalized steady state absorption revealing no evidence of aggregation or change in spectral shape.

Spectra were taken at various concentrations and the absorption of the $\lambda_{max}$ was used in conjunction with Beer's law to determine molar extinction coefficients (FIGS. 9-12). FIGS. 9 and 12 show that the normalized steady state absorption resulted in no evidence of aggregation or change in spectral shape. FIGS. 10 and 11 show that Beer's law of 22'BP has a molar extinction coefficient of 42000 M$^{-1}$cm$^{-1}$ and 43500 M$^{-1}$ cm$^{-1}$ in p-xylene and in chloroform, respectively.

Figure 13:
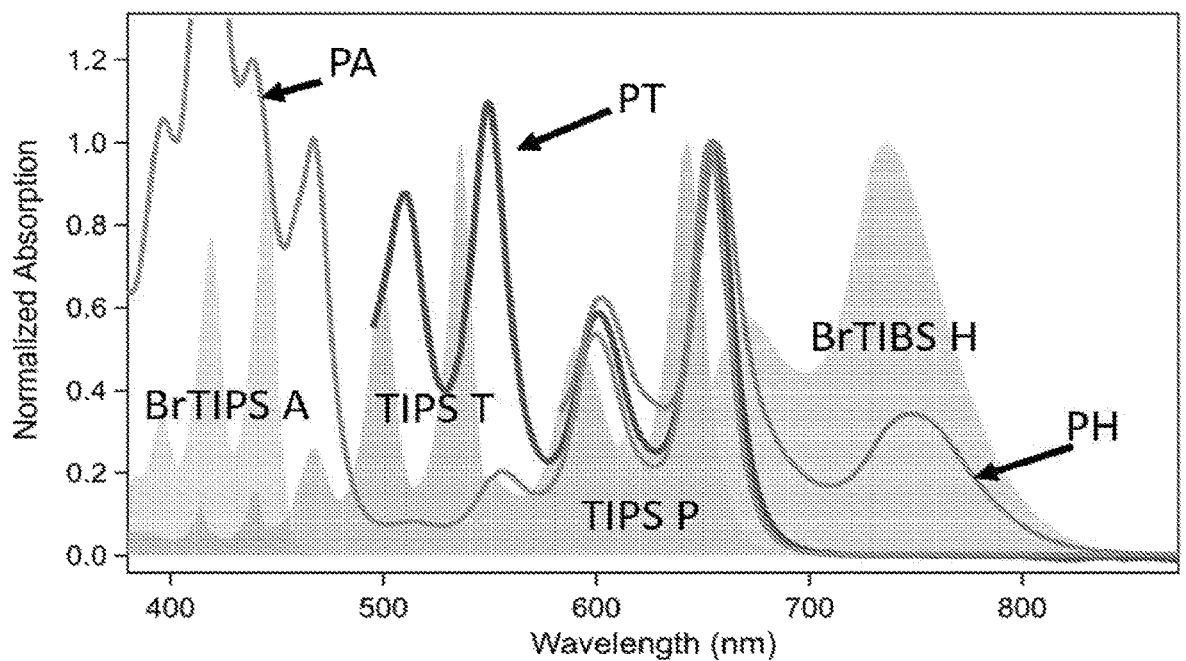
FIG. 13 shows steady-state absorption spectra of Pentacene-Antracene (PA), Pentacene-Tetracene (PT) and Pentacene-Hexacene (PH), along with a TIPS-anthracene derivative, TIPS-tetracene, TIPS-pentacene and a TIBS-hexacene derivative. (tri-isopropylsilyl acetylene (TIPS); tri-isobutyl (iBu group) silyl acetylene groups (TIBS)). Absorption spectra are taken in chloroform and normalized at the pentacene absorption feature. From left to right of the filled in peaks, the spectra shows Br TIPS A, TIPS T, TIPS P, and Br TIBS H. From left to right of the lines, the spectra shows PA (starting around wavelength ~375 nm), PT (starting around wavelength ~500 nm), and PH (starting around wavelength ~575 nm).
Figure 23A:
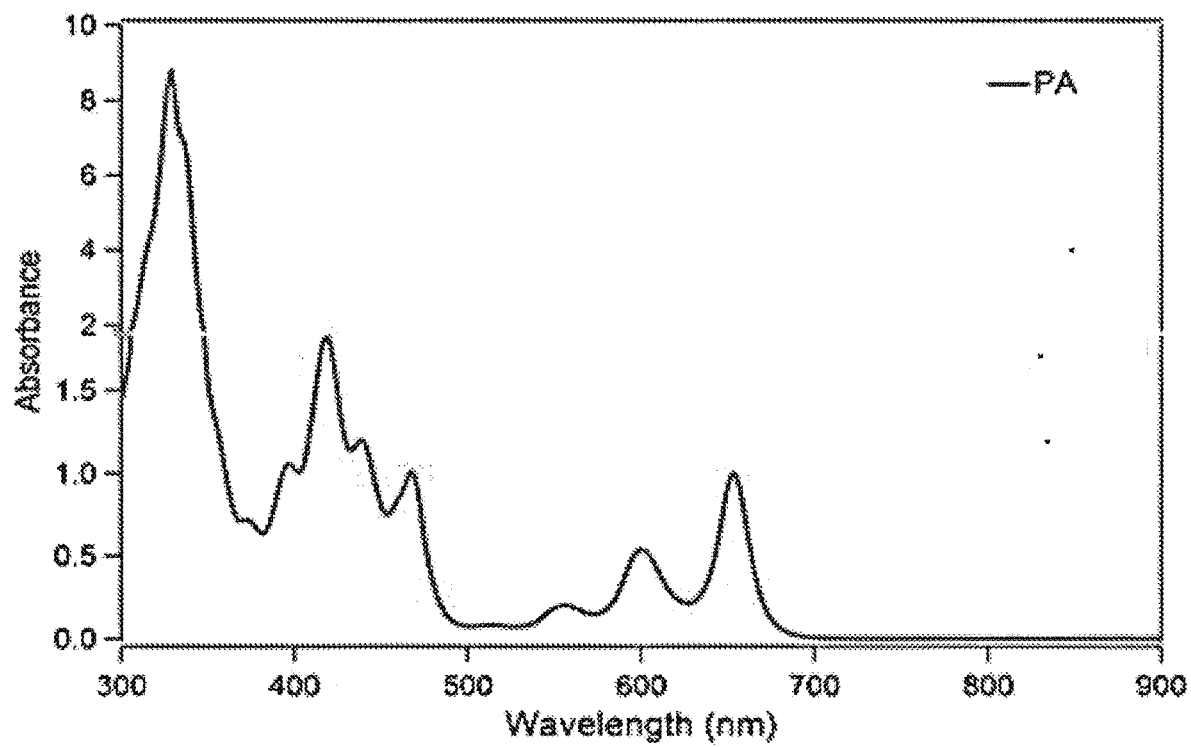
Figure 23B:
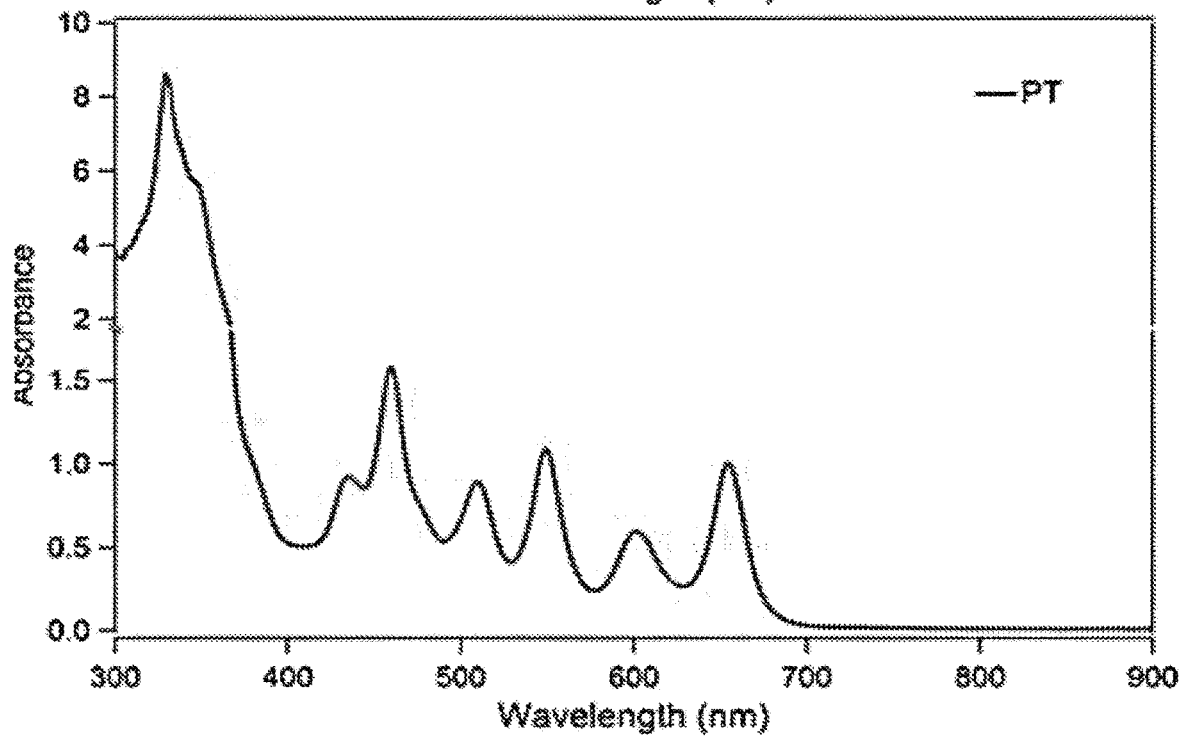
Figure 24A:
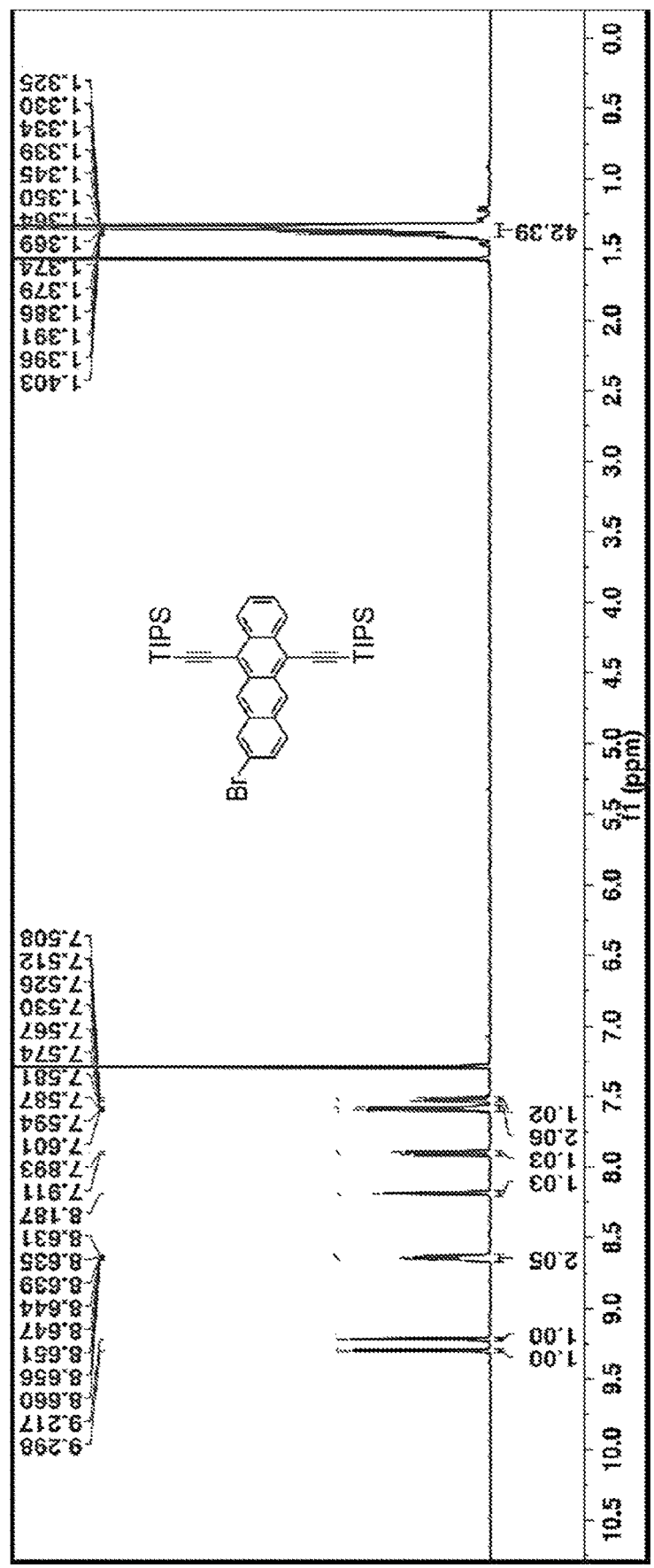
FIG. 24A shows proton nuclear magnetic resonance ($^1H$ NMR) of Bromo-TIPS-Tetracene 4 of Example 9 characterized by $^1$H-NMR (500 MHz, CDCl$_3$, δ ppm): 9.29 (s, 1H), 9.22 (s, 1H), 8.66-8.63 (m, 2H), 8.19 (s, 1H), 7.91-7.89 (m, 1H), 7.60-7.57 (m, 2H), 7.53-7.51 (m, 1H) and 1.40-1.33 (m, 42H).
Figure 24B:
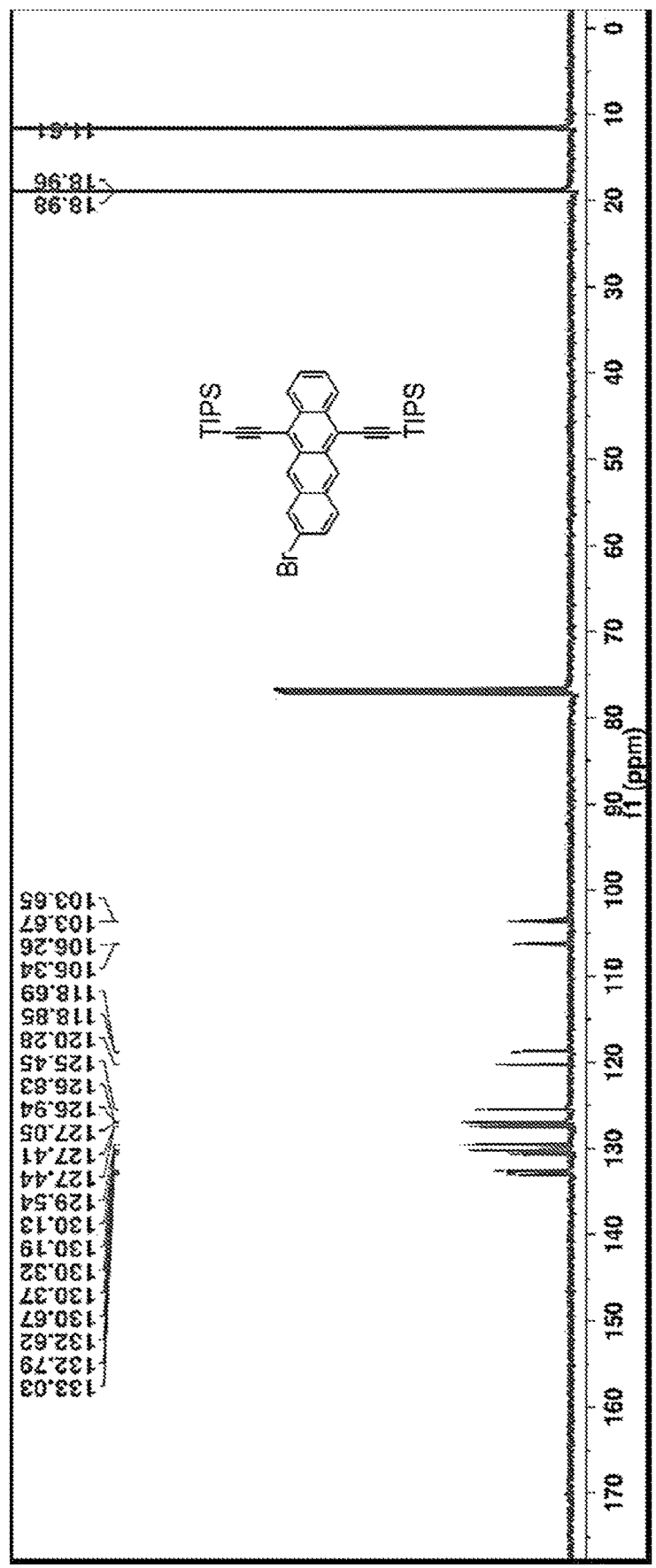
FIG. 24B shows carbon-13 nuclear magnetic resonance ($^{13}$C NMR) of Bromo-TIPS-Tetracene 4 of Example 9 characterized by $^{13}$C-NMR (125 MHz, CDCl$_3$, δ ppm): 133.0, 132.8, 132.6, 130.7, 130.4, 130.3, 130.2, 130.1, 129.5, 127.4, 127.4, 127.1, 126.9, 126.8, 125.5, 120.3, 118.9, 118.7, 106.3, 106.2, 103.67, 103.65, 18.98, 18.96 and 11.6.
Figure 25A:
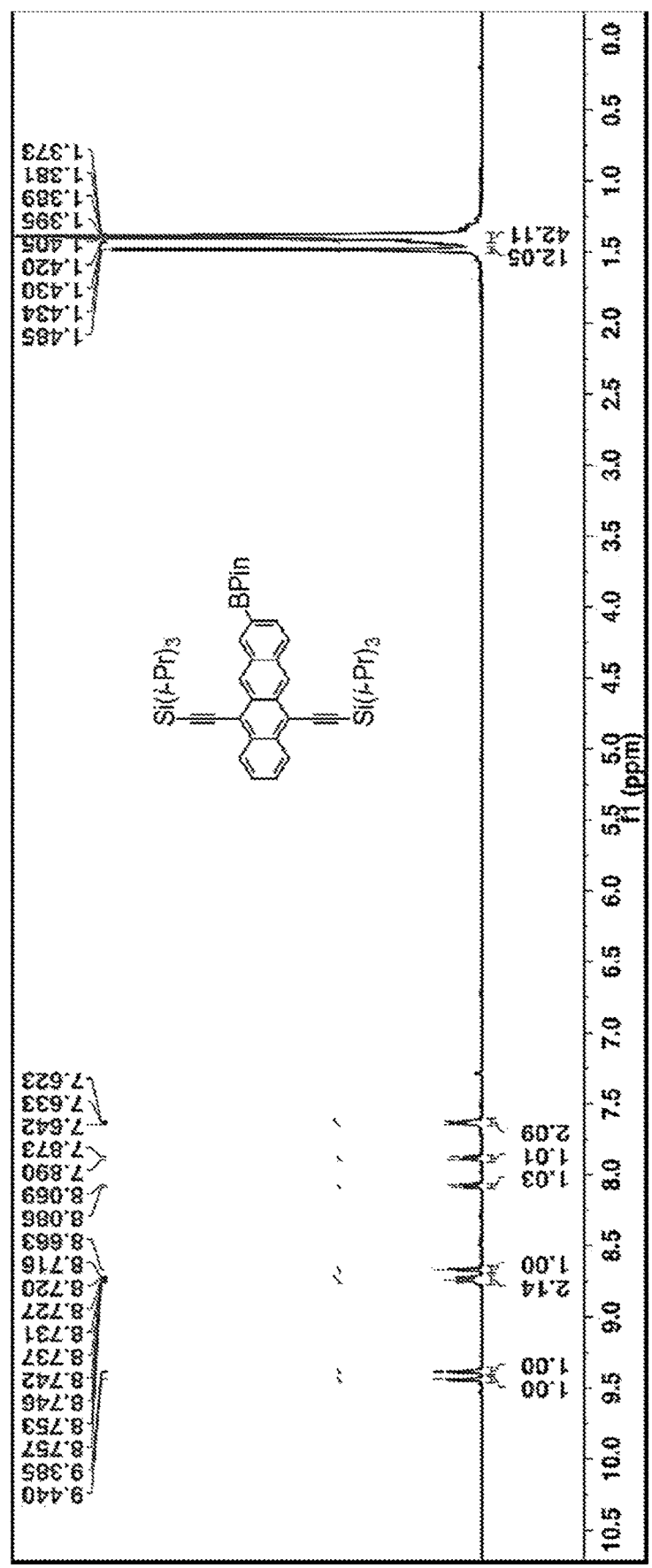
FIG. 25A shows $^1$H NMR of BPIN-TIPS-Tetracene 5 of Example 10 characterized by $^1$H-NMR (500 MHz, CDCl$_3$, δ ppm): 9.44 (s, 1H), 9.39 (s, 1H), 8.76-8.72 (m, 2H), 8.66 (s, 1H), 8.09-8.07 (m, 1H), 7.89-7.87 (m, 1H), 7.64-7.62 (m, 2H), 1.49 (s, 12H) and 1.43-1.37 (m, 42H).
Figure 25B:
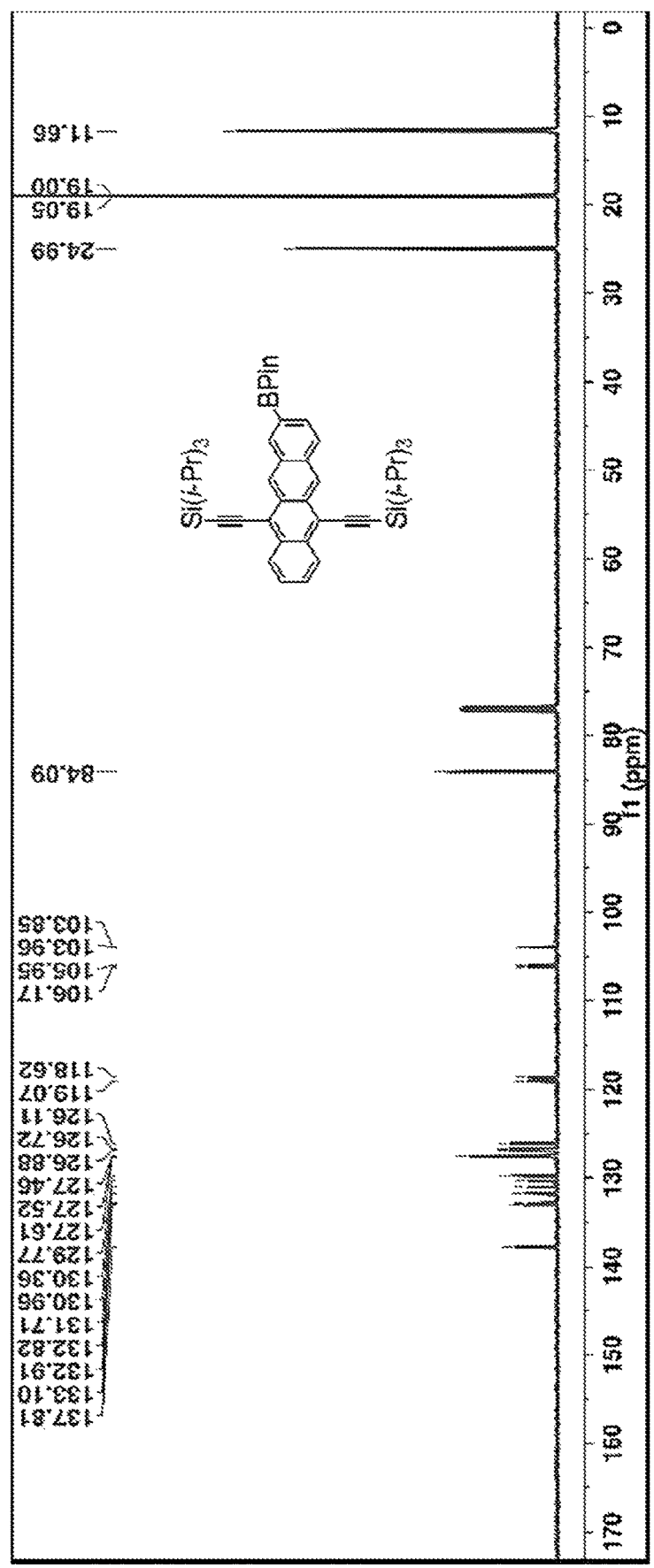
FIG. 25B shows $^{13}$C NMR of BPIN-TIPS-Tetracene 5 of Example 10 characterized by $^{13}$C-NMR (125 MHz, CDCl$_3$, δ ppm): 133.0, 132.8, 132.6, 130.7, 130.4, 130.3, 130.2, 130.1, 129.5, 127.4, 127.4, 127.1, 126.9, 126.8, 125.5, 120.3, 118.9, 118.7, 106.3, 106.2, 103.67, 103.65, 18.98, 18.96 and 11.6.
Figure 26A:
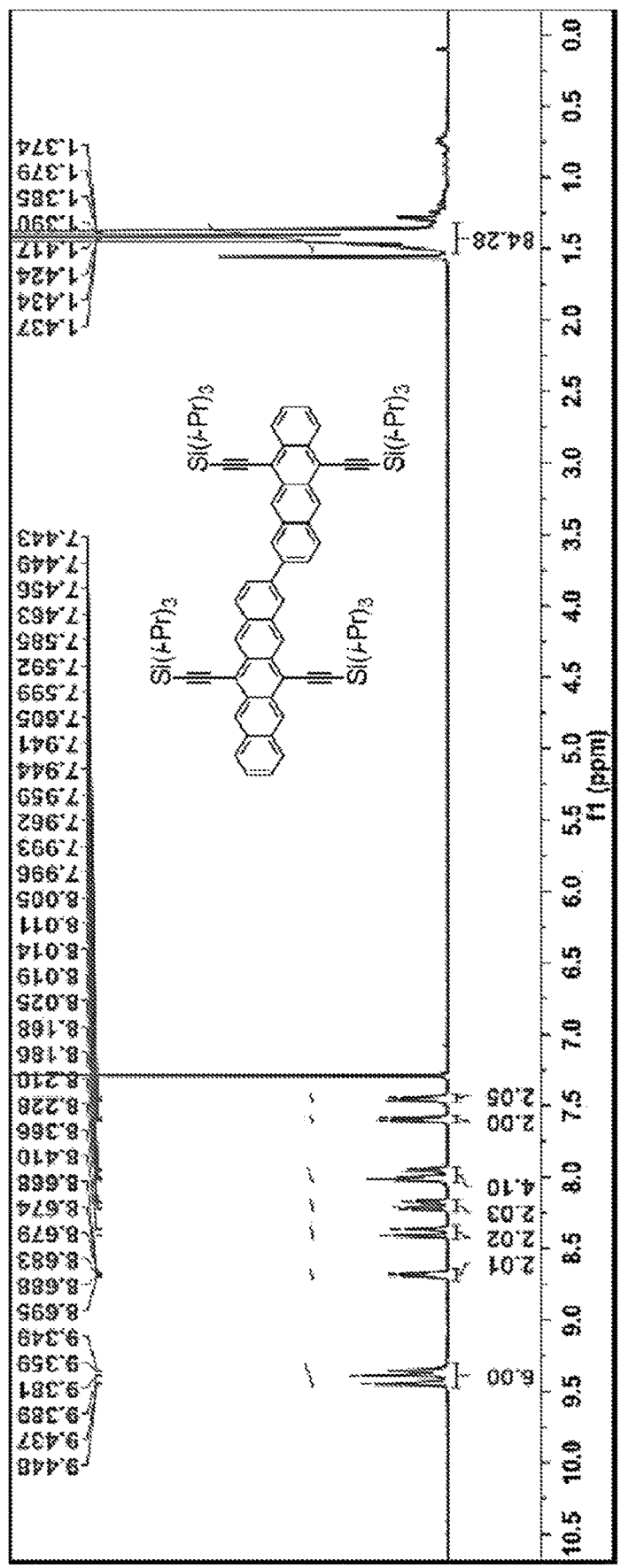
FIG. 26A shows $^1$H NMR of Pentacene-Tetracene Dimer PT of Example 11 characterized by $^1$H-NMR (500 MHz, CDCl$_3$, δ ppm): 9.45-9.35 (m, 6H), 8.69-8.67 (m, 2H), 8.41-8.37 (m, 2H), 8.23-8.17 (m, 2H), 8.03-7.94 (m, 4H), 7.61-7.59 (m, 2H), 7.46-7.44 (m, 2H) and 1.44-1.37 (m, 84H).
Figure 26B:
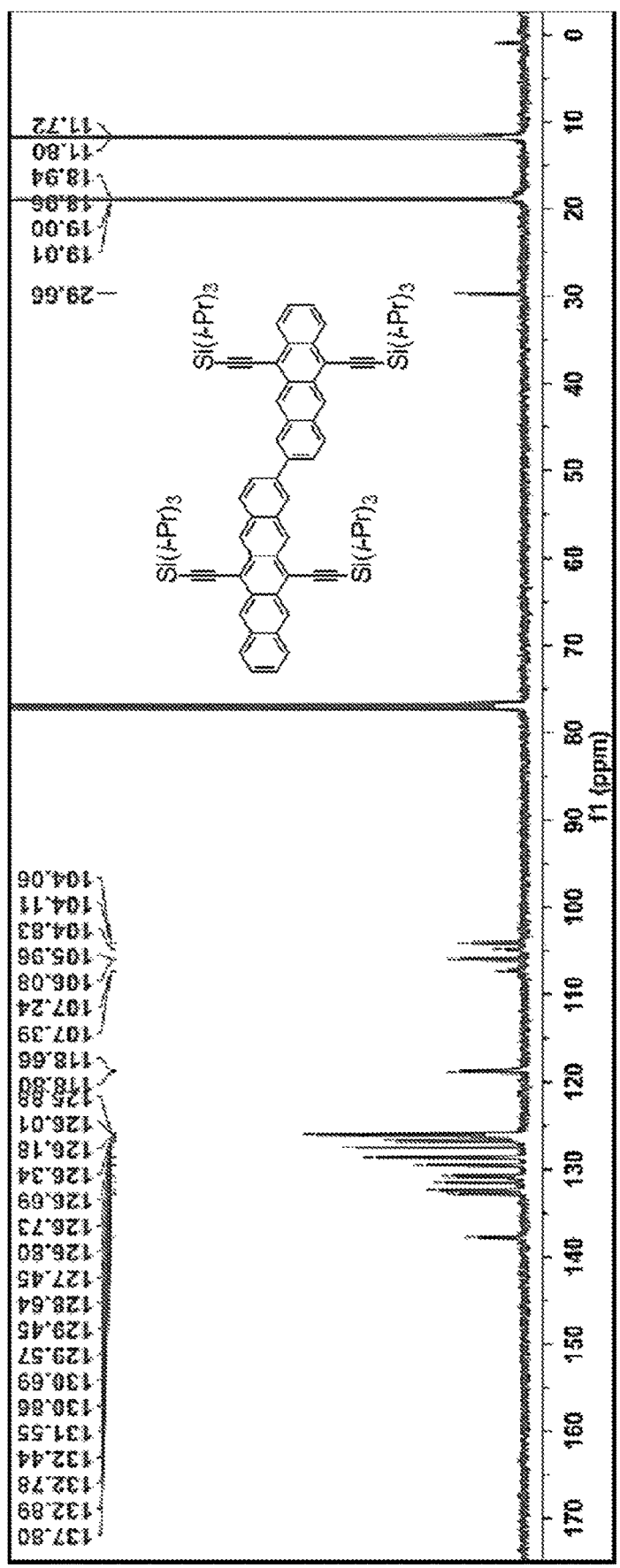
FIG. 26B shows $^{13}$C NMR of Pentacene-Tetracene Dimer PT of Example 11 characterized by $^{13}$C-NMR (125 MHz, CDCl$_3$, 50° C., δ ppm): 137.9, 137.8, 132.9, 132.8, 132.5, 132.4, 131.6, 130.9, 130.7, 129.6, 129.5, 128.6, 127.5, 126.8, 126.7, 126.69, 126.3, 126.2, 126.0, 125.9, 118.8, 118.7, 107.4, 107.2, 106.1, 105.96, 104.8, 104.1, 104.06, 29.7, 19.01, 19.00, 18.96, 18.94, 11.8 and 11.7.
Figure 27A:
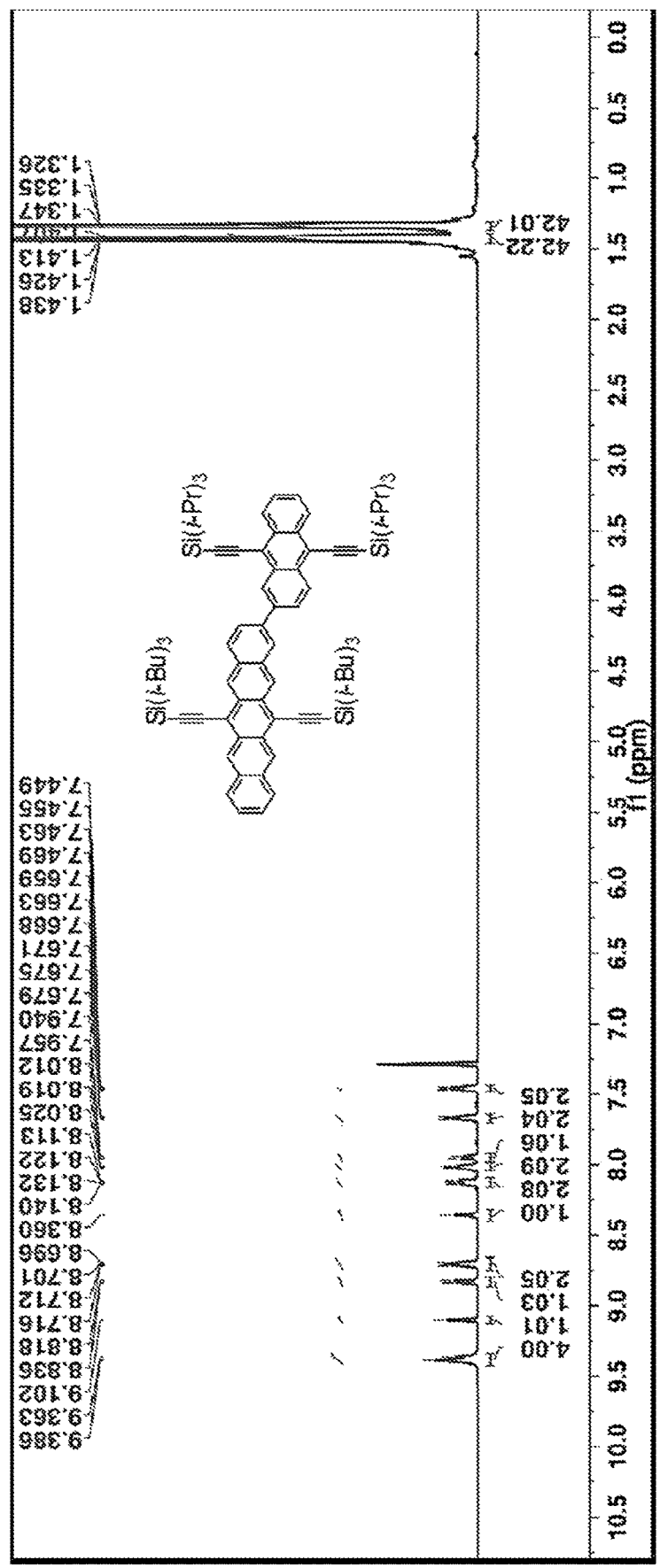
FIG. 27A shows $^1$H NMR of Pentacene-Anthracene Dimer PA of Example 12 characterized by $^1$H-NMR (500 MHz, CDCl$_3$, δ ppm): 9.39-9.36 (m, 4H), 9.10 (s, 1H), 8.84-8.82 (m, 1H), 8.72-8.69 (m, 2H), 8.36 (s, 1H), 8.14-8.11 (m, 2H), 8.03-8.01 (m, 2H), 7.96-7.94 (m, 1H), 7.68-7.66 (m, 2H), 7.47-7.45 (m, 2H), 1.44-1.41 (m, 42H) and 1.35-1.33 (m, 42H).
Figure 27B:
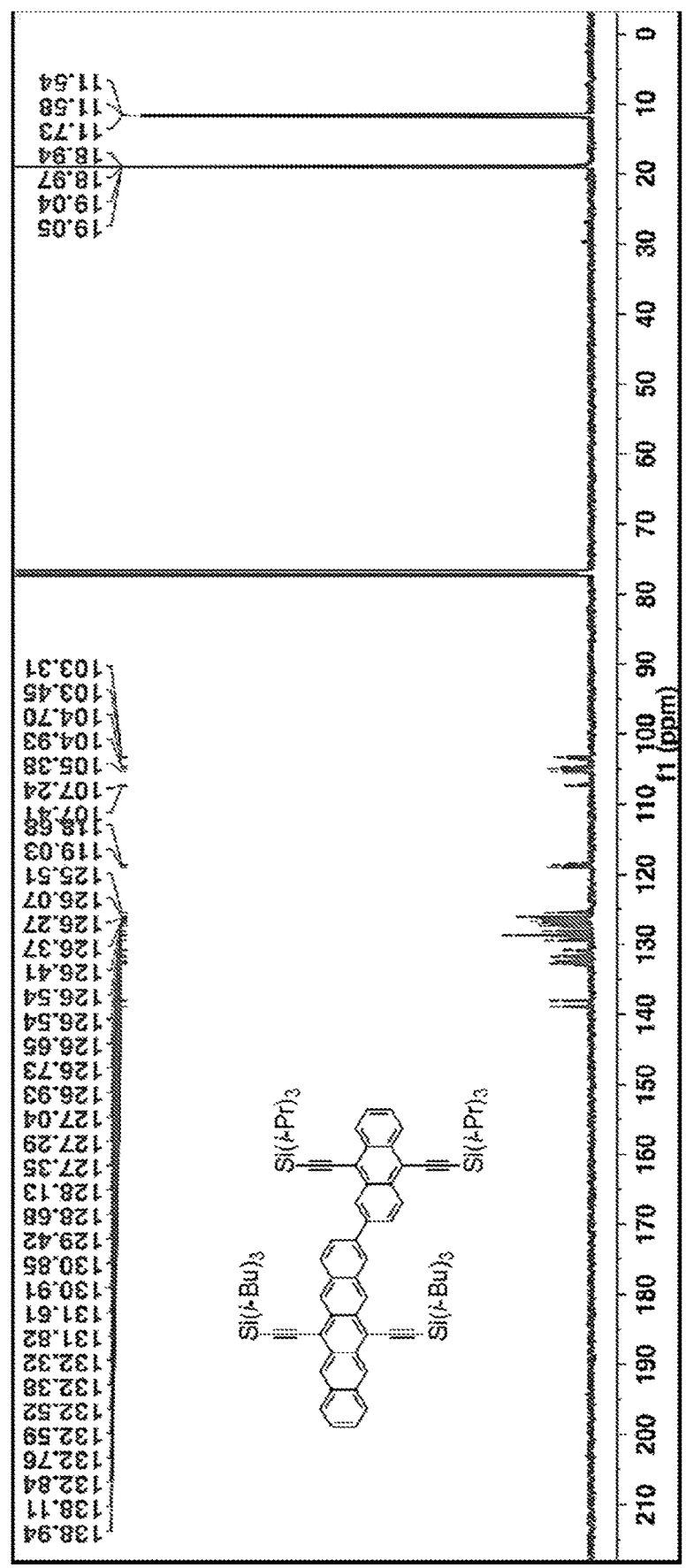
FIG. 27B shows $^{13}$C NMR of Pentacene-Anthracene Dimer PA of Example 12 characterized by $^{13}$C-NMR (125 MHz, CDCl$_3$, 50° C., δ ppm): 138.9, 138.1, 132.8, 132.7, 132.6, 132.5, 132.4, 132.3, 131.8, 131.6, 130.95, 130.9, 130.8, 130.7, 129.4, 128.7, 128.1, 127.4, 127.3, 127.0, 126.9, 126.7, 126.65, 126.54, 126.4, 126.37, 126.3, 126.1, 125.5, 119.0, 118.7, 118.5, 118.4, 107.4, 1-7.2, 105.4, 104.9, 104.7, 103.5, 103.3, 19.1, 19.0, 18.97, 18.94, 11.7, 11.6 and 11.5.
Figure 28A:
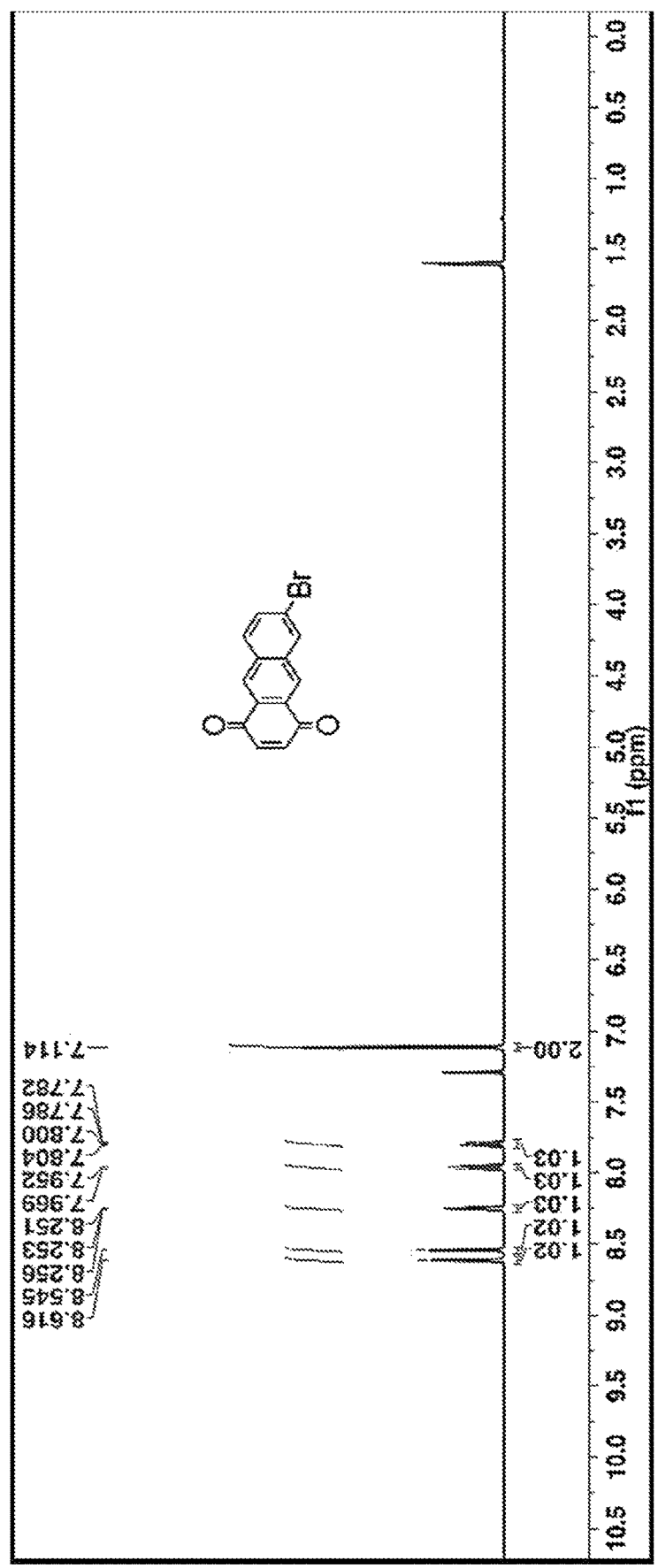
FIG. 28A shows $^1$H NMR of Bromo Anthraquinone 12 of Example 13 characterized by $^1$H-NMR (500 MHz, CDCl$_3$, δ ppm): 8.62 (s, 1H), 8.55 (s, 1H), 8.26-8.25 (m, 1H), 7.97-7.95 (m, 1H), 7.80-7.78 (m, 1H) and 7.11 (s, 2H).
Figure 28B:
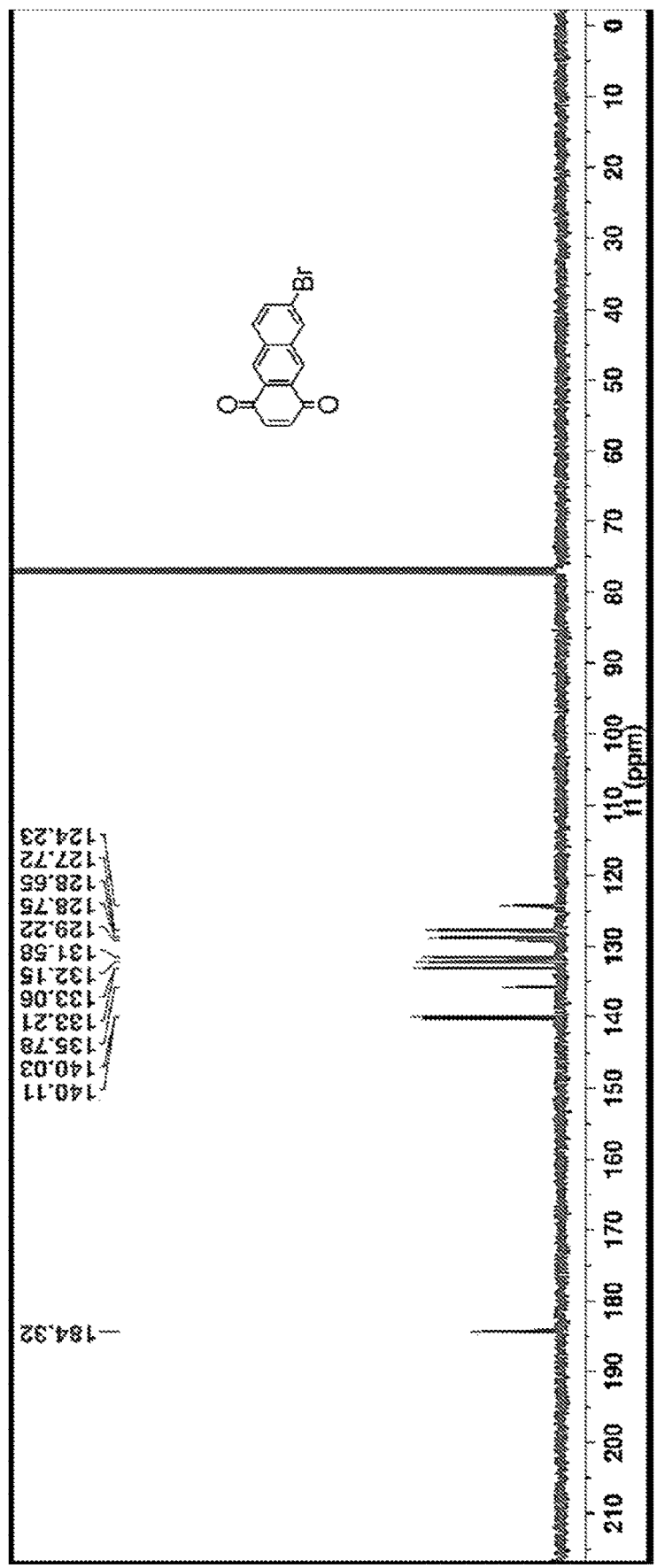
FIG. 28B shows $^{13}$C NMR of Bromo Anthraquinone 12 of Example 13 characterized by $^{13}$C-NMR (125 MHz, CDCl$_3$, δ ppm): 184.3, 140.1, 140.0, 135.8, 133.2, 133.1, 132.2, 131.6, 129.2, 128.8, 128.7, 127.7 and 124.2.
Figure 29A:
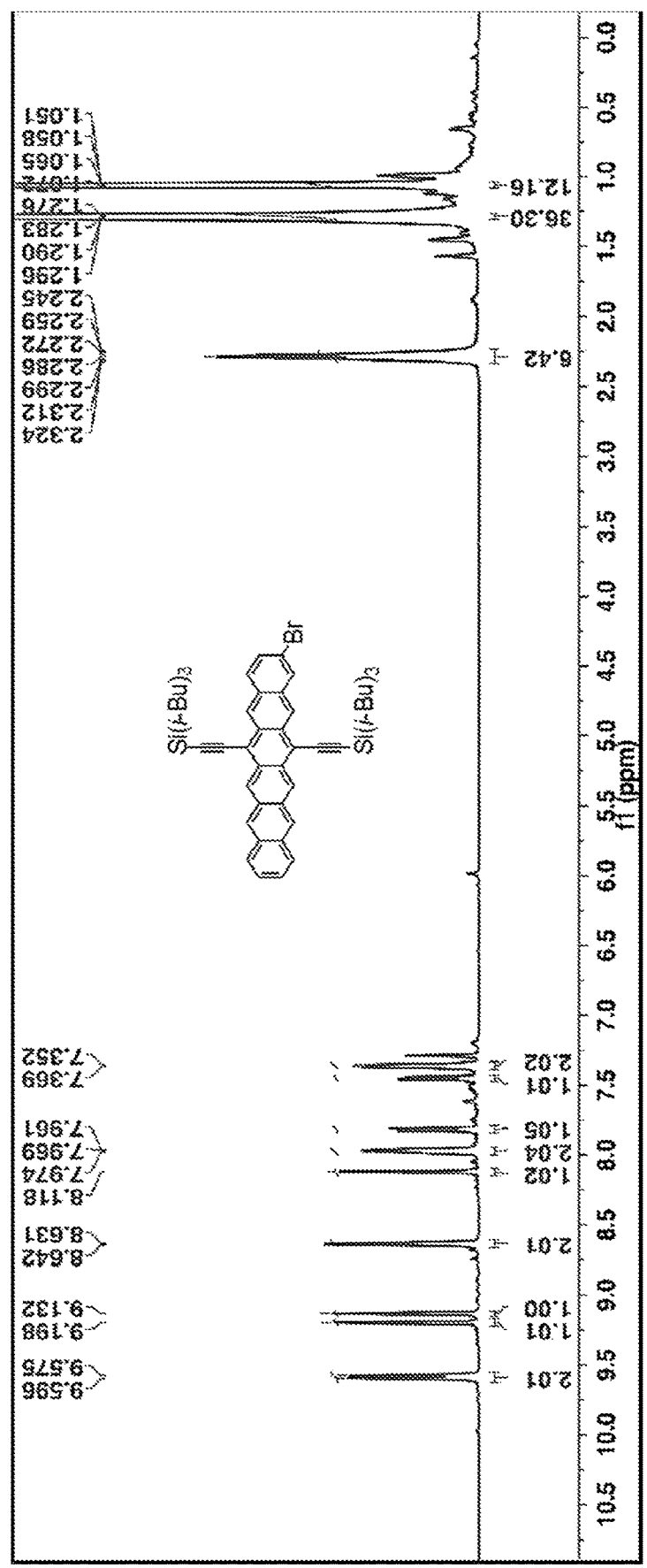
FIG. 29A shows $^1$H NMR of Bromo Hexacene 14 of Example 15 characterized by $^1$H-NMR (500 MHz, CDCl$_3$, δ ppm): 9.59-9.58 (m, 2H), 9.19 (s, 1H), 9.13 (s, 1H), 8.64-8.63 (m, 2H), 8.12 (s, 1H), 7.97-7.96 (m, 2H), 7.83-7.81 (m, 1H), 7.47-7.45 (m, 1H), 7.37-7.35 (m, 2H), 2.32-2.25 (m, 6H), 1.29-1.28 (36H) and 1.07-1.05 (m, 12H).
Figure 29B:
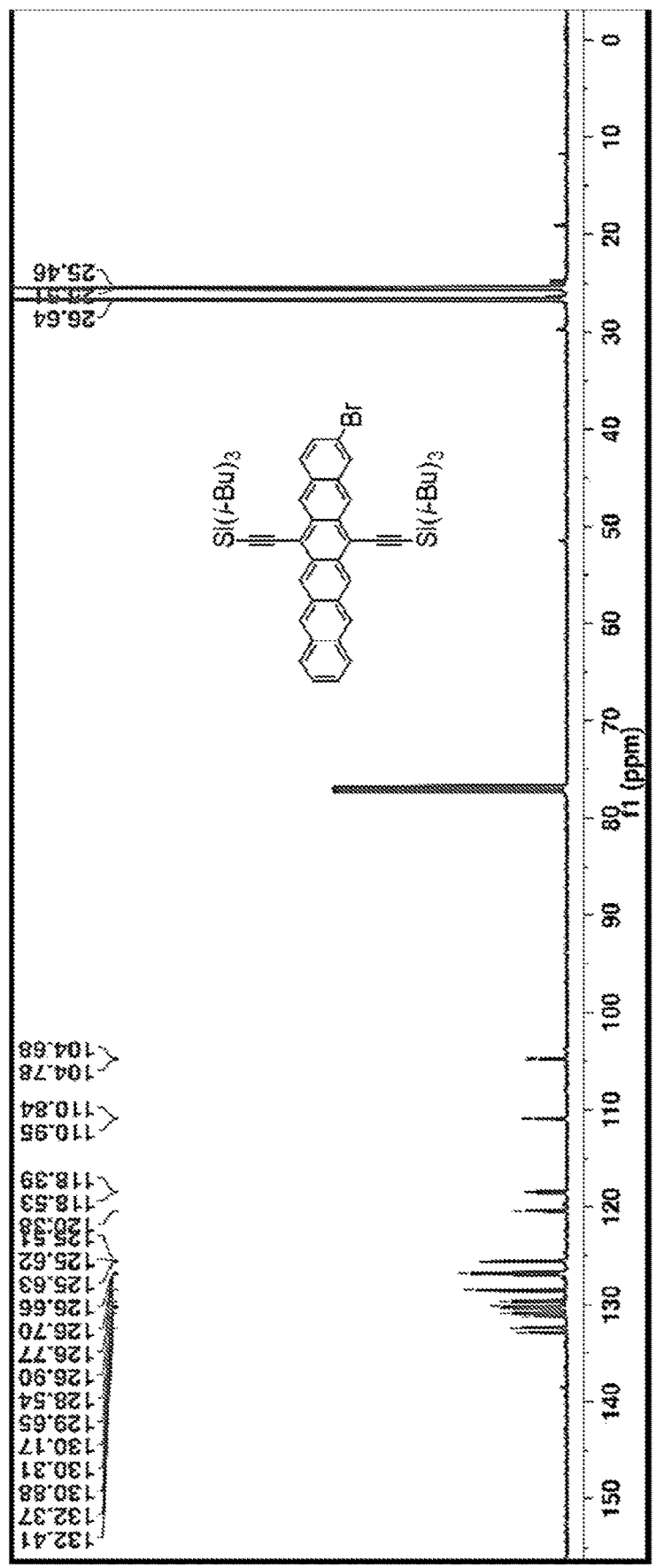
FIG. 29B shows $^{13}$C NMR of Bromo Hexacene 14 of Example 15 characterized by $^{13}$C-NMR (125 MHz, CDCl$_3$, δ ppm): 132.9, 132.4, 132.3, 131.2, 130.9, 130.8, 130.5, 130.4, 130.3, 130.2, 129.7, 128.5, 126.9, 126.8, 126.7, 126.6, 125.63, 125.62, 125.5, 120.4, 118.5, 118.4, 110.95, 110.8, 104.8, 104.7, 26.6, 25.5 and 25.4.
Figure 30A:
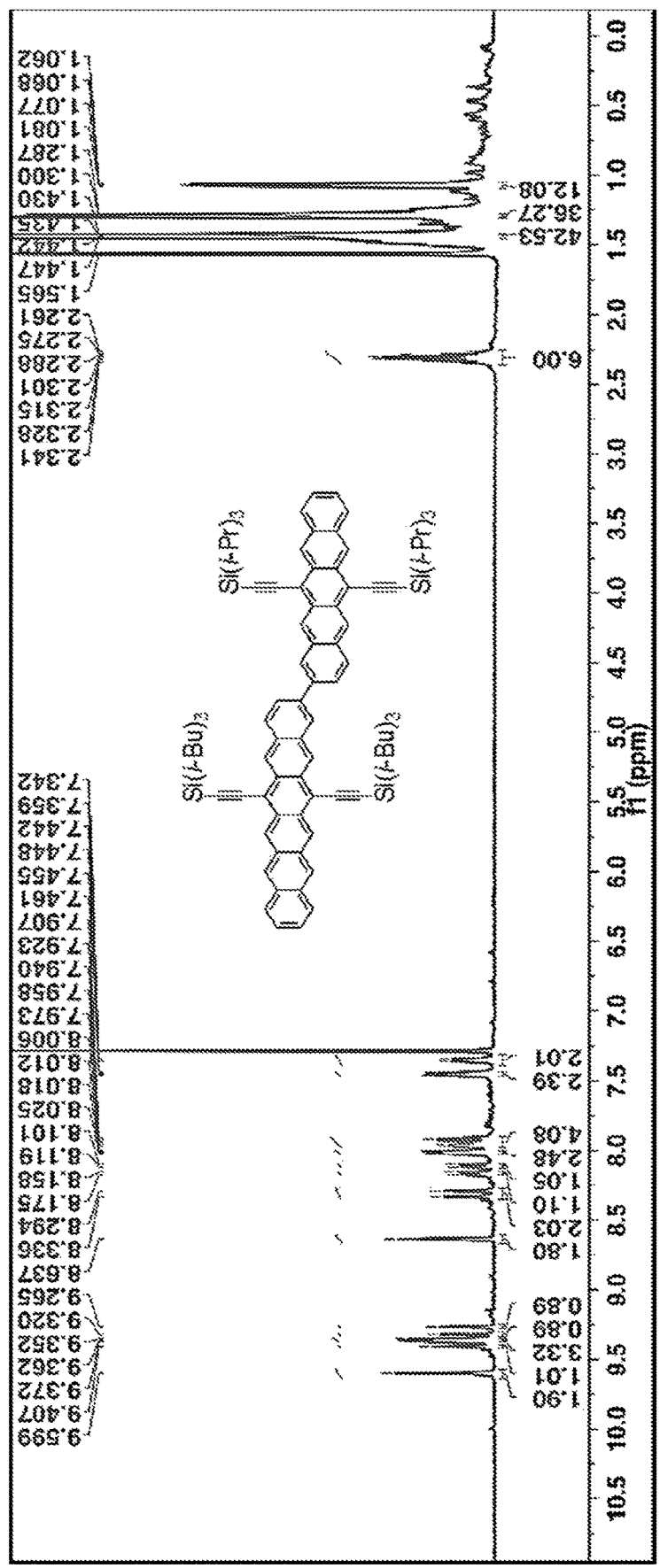
FIG. 30A shows $^1$H NMR of Pentacene-Hexacene Dimer PH of Example 16 characterized by $^1$H-NMR (500 MHz, CDCl$_3$, δ ppm): 9.59 (s, 2H), 9.41 (s, 1H), 9.37-9.35 (m, 3H), 9.32 (s, 1H), 9.27 (s, 1H), 8.64 (s, 2H), 8.34-8.29 (m, 2H), 8.18-8.16 (m, 1H), 8.12-8.10 (m, 1H), 8.03-8.01 (m, 2H), 7.97-7.91 (m, 4H), 7.46-7.44 (m, 2H), 7.36-7.34 (m, 2H), 2.34-2.26 (m, 6H), 1.45-1.43 (m, 42H), 1.30-1.29 (m, 36H) and 1.08-1.06 (m, 12H).
Figure 30B:
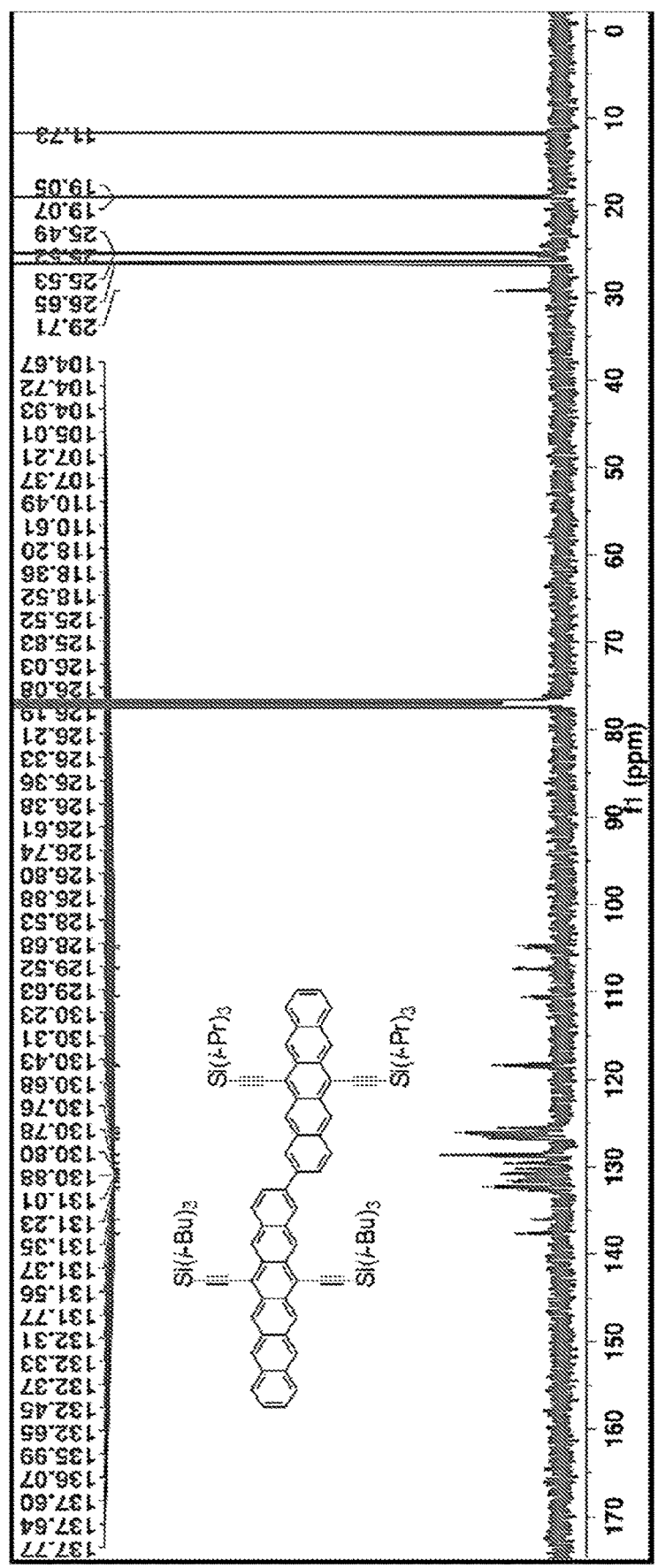
FIG. 30B shows $^{13}$C NMR of Pentacene-Hexacene Dimer PH of Example 16 characterized by $^{13}$C-NMR (125 MHz, CDCl$_3$, δ ppm): 137.8, 137.64, 137.60, 136.1, 135.9, 132.7, 132.5, 132.4, 132.33, 132.31, 131.8, 131.6, 131.4, 131.35, 131.2, 131.0, 130.9, 130.8, 130.78, 130.76, 130.7, 130.43, 130.3, 130.2, 129.6, 129.5, 128.9, 128.5, 126.9, 126.8, 126.7, 126.6, 126.4, 126.36, 126.33, 126.21, 126.19, 126.08, 126.0, 125.8, 125.5, 118.5, 118.4, 118.2, 110.6, 110.5, 107.4, 107.2, 105.0, 104.9, 104.72, 104.67, 29.7, 26.65, 25.53, 25.52, 25.49, 19.07, 19.05 and 11.73.

The steady state absorption spectra of the heterodimers show the characteristic features of both monomers (FIG. 13). A prominent low-energy singlet transition peak associated with TIPS-pentacene (S$_1$[P]) at ~660 nm and, respectively, its complement, with the anthracene peak (S$_1$[A]) at ~470 nm, the tetracene peak (S$_1$[T]) at ~550 nm, and the hexacene peak (S$_1$[H]) at ~750 nm was observed in PA, PT, and PH. Also a small redshift was observed in the dimers, relative to the monomer features. When coupling acenes at the 2 position, a high-energy feature in the ground state absorption was further observed. That feature, previously reported for 2,2' bipentacene (BP), is also observed in these compounds. It can be seen clearly in FIG. 13 for PA, but this peak in PT and PH has been omitted for clarity (see FIGS. 23A to 23C). UV-visible spectroscopy in chloroform in all heterodimers of FIGS. 23A to 23C revealed sets of peaks associated with each individual monomer. For example, peaks associated with TIBS-hexacene appear with an onset near 800 nm in PH, while peaks associated with TIPS-pentacene appear with an onset near 660 nm, and peaks associated with TIPS-anthracene appear near 460 nm. In addition to these features, a new set of high energy peaks were observed when dimerizing oligoacenes at the 2 position. These peaks have been reported before, and appear sensitive to the chromophores dimerized. For example, they appear near 540 nm in PH, near 480 nm in PT, and near 420 nm in PA. This high-energy feature is specific to directly coupled acenes at the position shown, and does not correspond to a peak in the parent monomers.

Figure 14:
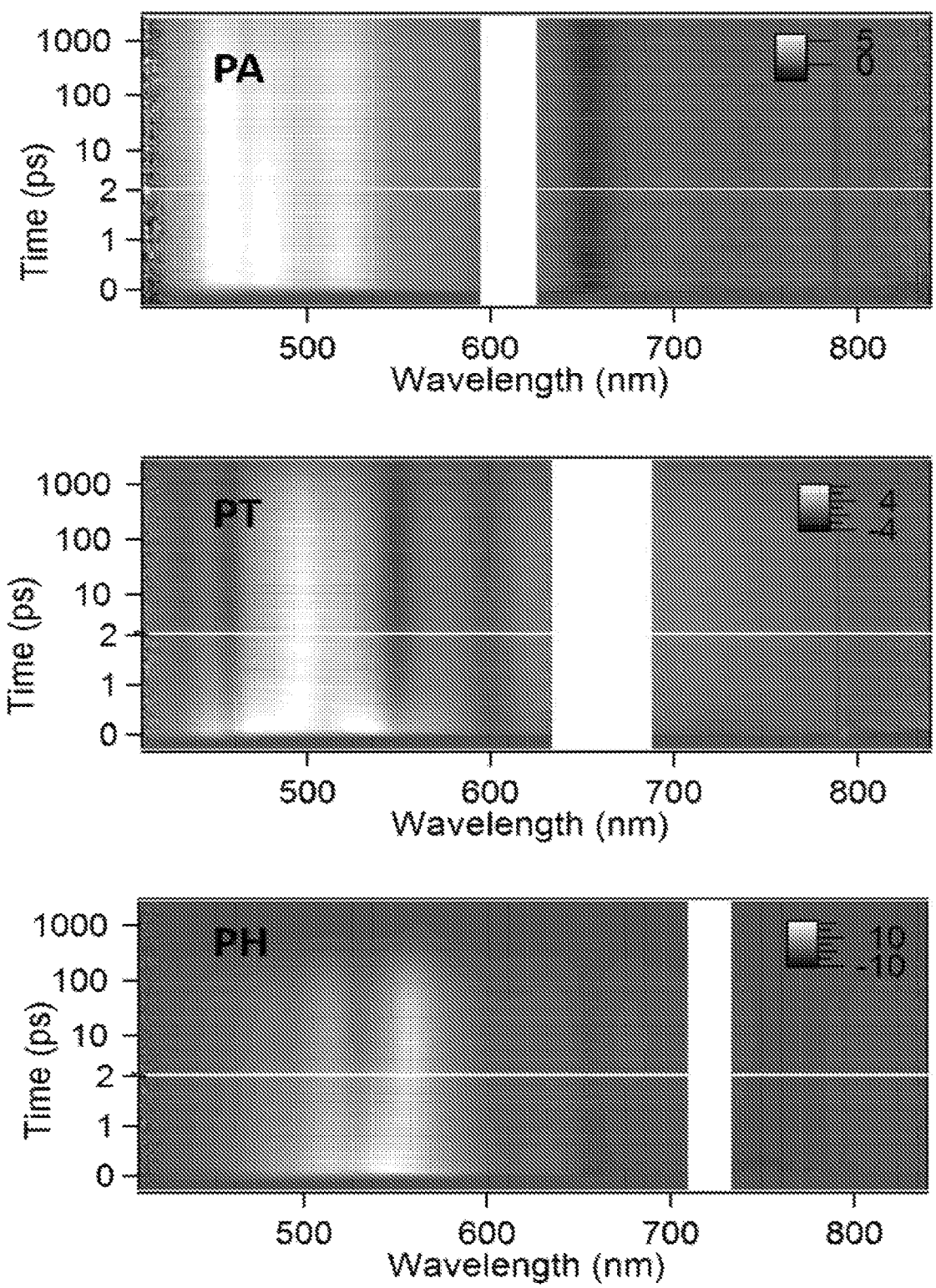
FIG. 14 shows transient absorption spectra of PA excited at 600 nm, PT excited at 660 nm and PH excited at 730 nm, at power ~0.1 mW in chloroform. In each case, warmer colors represent increased absorption after excitation, and cooler colors represent decreased absorption.

Transient Absorption Spectroscopy:

To observe and understand the exciton dynamics in these molecules, broadband transient absorption spectroscopy (TAS) may be used. Since the energetic requirements for iSF are probed, the chromophores are pumped at the lower singlet energy selectively (P transitions for PA, PT, and H transitions for PH) to determine if iSF occurs without significant excess excitation energy. FIG. 14 shows the resulting 2D plot of the spectral evolution of the transient absorption spectra as a function of time.

Figure 15:
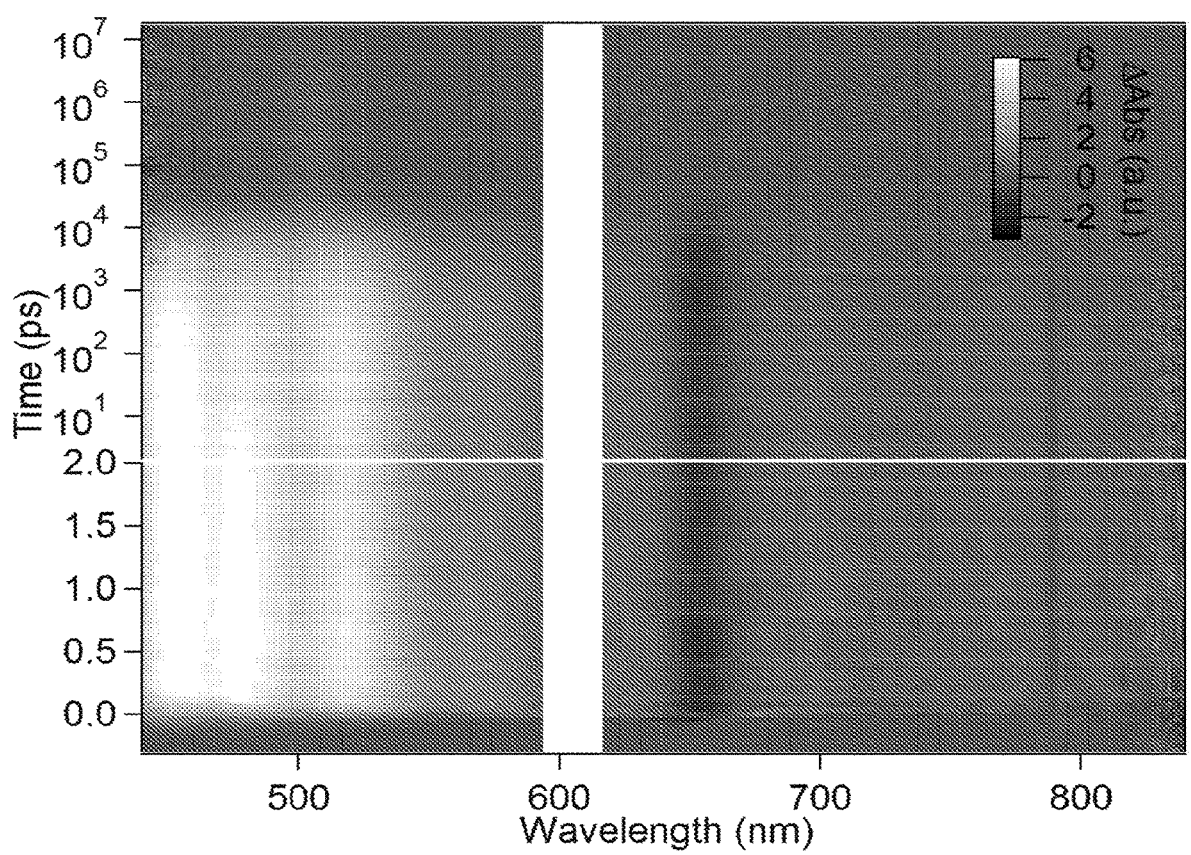
FIG. 15 shows a full 2D color plot obtained from transient absorption spectroscopy of PA in chloroform excited at 600 nm.

In the case of PA in FIG. 15, where iSF is expected to be significantly endothermic, no significant spectral changes of the singlet state features was observed. In fact, the photophysics of this heterodimer are similar to TIPS-pentacene, with a photoexcited singlet that decays with a ~11.5 ns time constant primarily through a radiative pathway (SI). The singlet lifetime is long enough to permit a small amount of triplet formation via intersystem crossing (ISC). By comparing the magnitude of the ground state bleach in the singlet and triplet manifold, a triplet yield of ~10% giving an ISC time constant of ~103.5 ns may be calculated.[40] The triplet relaxation dynamics (SI) are similar to TIPS-pentacene as well, with a decay time of 17.4 µs. This result verifies that, in the case where energetics are not appropriate for iSF, no additional decay pathways are present in these compounds beyond the typical monomer excited state deactivation.

Figure 16:
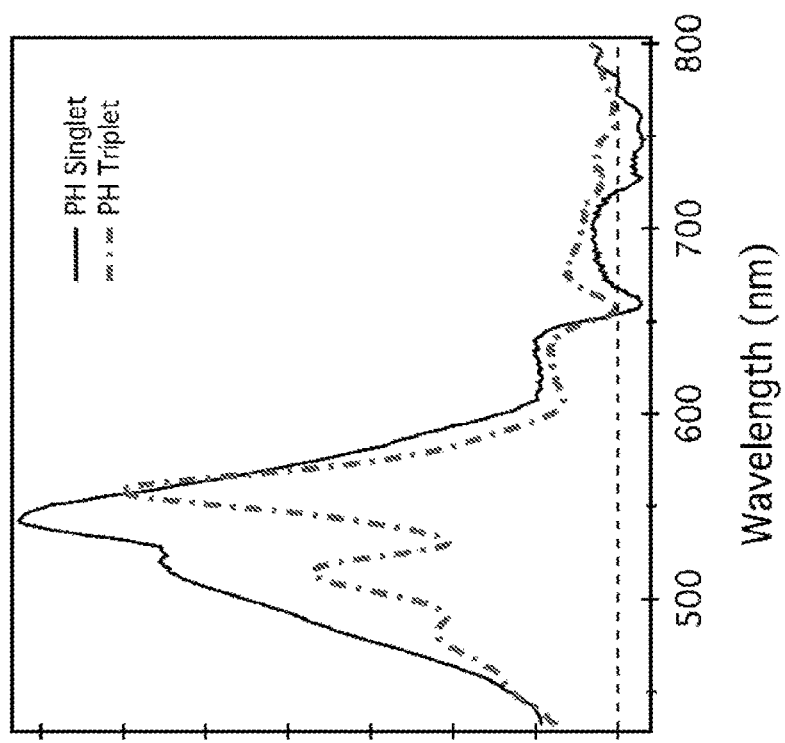
FIG. 16 shows (a) transient absorption spectroscopy of PH as a dilute solution in chloroform; (b) singlet and triplet spectra identified by global analysis (PH Upper singlet line at wavelengths ~425 nm to ~650 nm, which changes to the lower line at wavelengths ~650 nm to ~800 nm; and (c) single wavelength cuts at the peak of the triplet PIA (559 nm) which is not in a bell curve shape, rather a plateau spanning from about 0 ps to about $10^3$ ps, which is also nearly an isosbestic point, and at 670 nm, where the singlet PIA is 0, showing rise and decay of the triplet in a bell curve shape.
Figure 16:
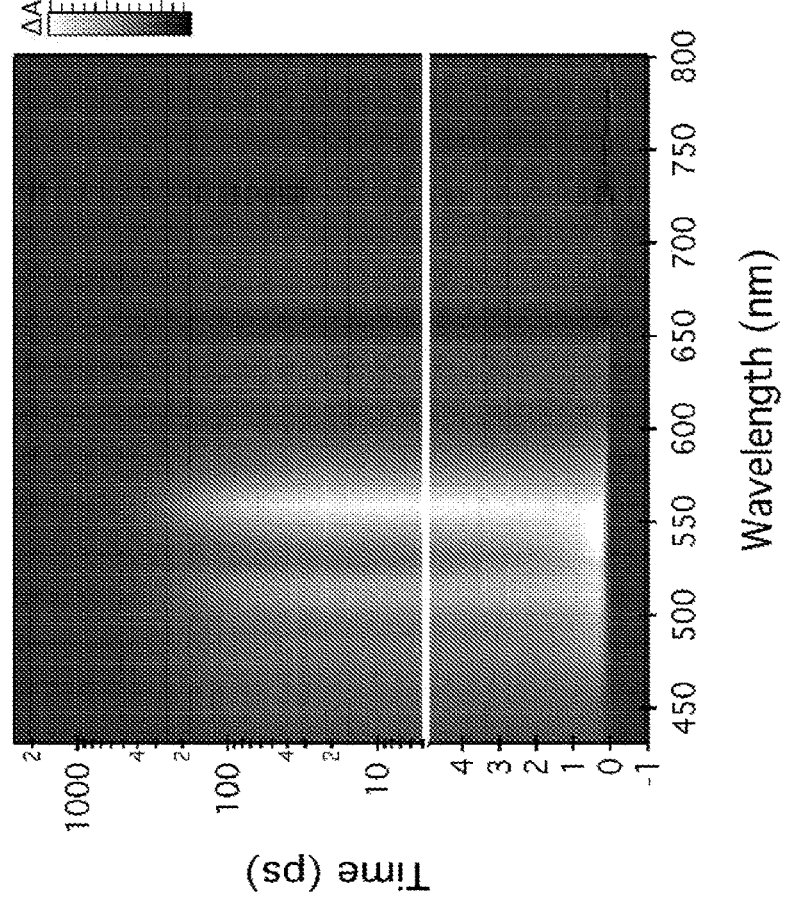
Figure 16:
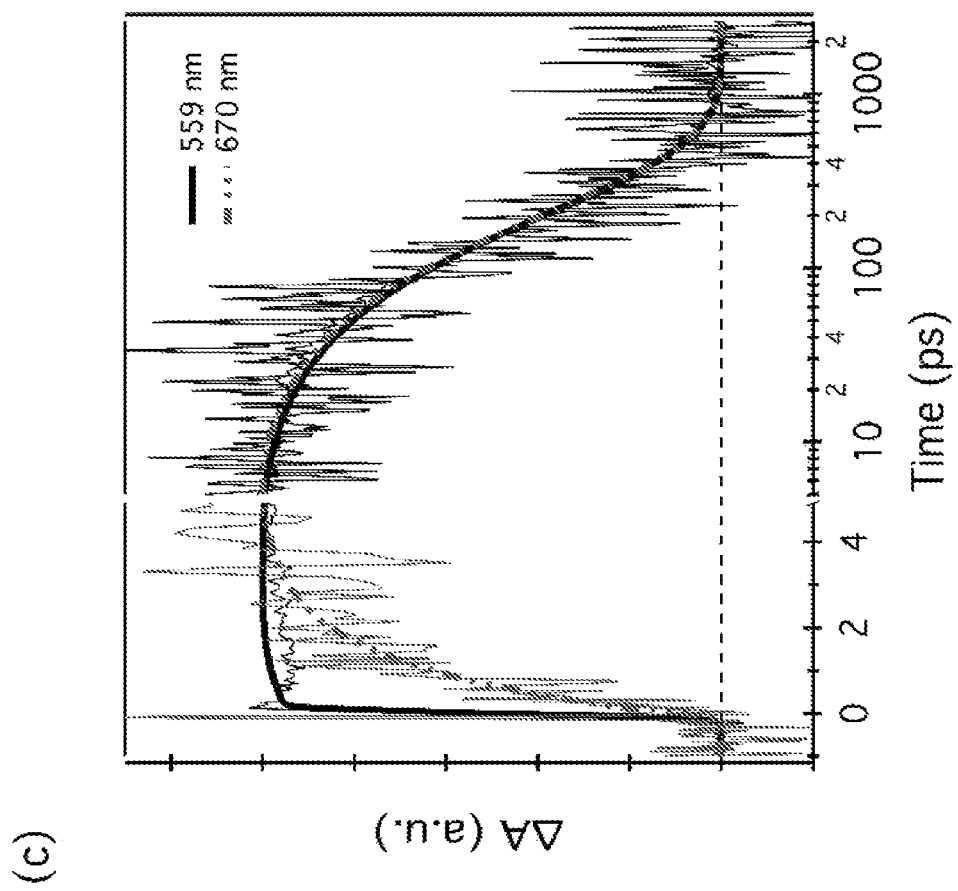

However, in FIG. 16, PT and PH singlet fission is roughly isoergic and exothermic, respectively. In these systems, TAS reveals dynamics similar to those observed in BP, where the photoexcited singlet rapidly decays into a triplet signal in dilute solution, consistent with iSF.[13] The triplet pair feature produced by iSF is dominated by the photoinduced absorption of the larger acene in each case, as the triplet absorption cross-section increases with increasing acene length[38,40,54] The triplet pair features ground-state bleach (GSB) characteristics of both monomers in magnitudes corresponding to the relative absorption heights in the linear spectra, as expected for a triplet pair where both monomers are bleached.

Measurements were taken as two scans on a dilute solution freshly prepared from pure solid PH and degassed with argon. The first and second scan were compared to ensure reproducibility. The similarity of the first and second scans indicate that the sample was stable enough under these conditions to produce reliable spectroscopic data. Indeed, the remarkable stability of this hexacene-containing compound under laser excitation may be in part due to the fast singlet excited state deactivation provided by singlet fission. Because the singlet exciton is involved in photodegradation reactions, this deactivation seems to result in fission compounds with enhanced stability relative to their monomeric counterparts.[45]

Notably, despite selectively pumping transitions associated with the hexacene monomer at 730 nm, where monomeric pentacene does not absorb, a clear signature of pentacene GSB is observed in the singlet as well as the triplet pair.

Figure 17:
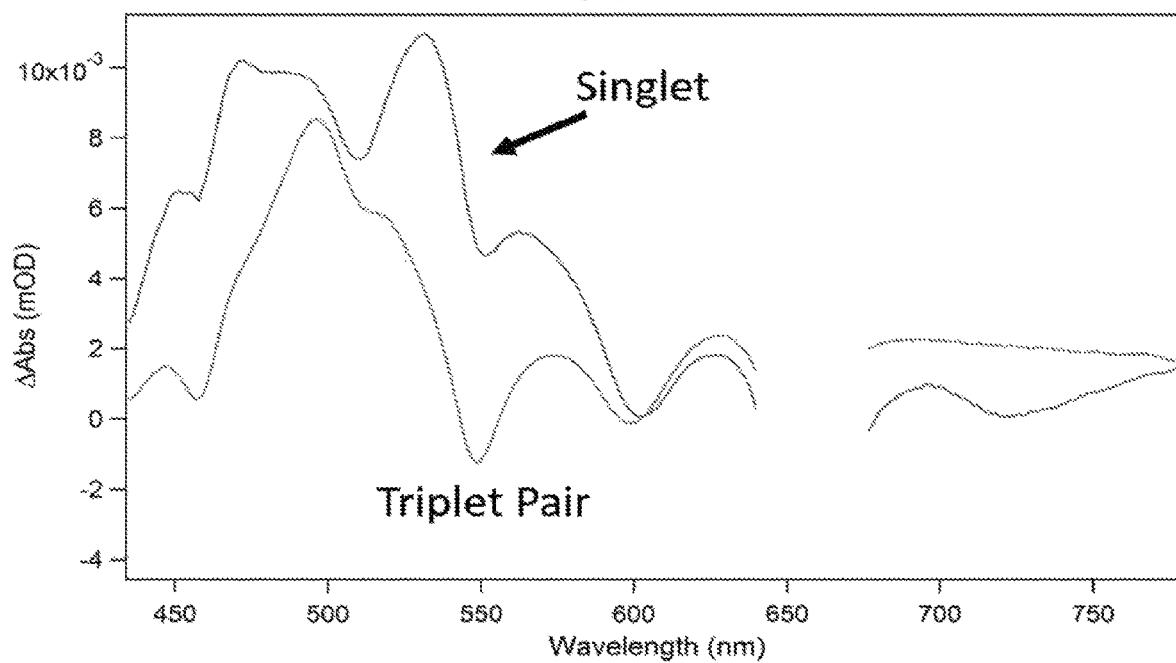
FIG. 17 shows singlet and triplet species for PT isolated from global analysis. Data are from transient absorption spectroscopy of PT dissolved as a dilute solution in chloroform and pumped at 660 nm. The line representing the PT Triplet Pair is the upper line at wavelength ~425 nm-~650 nm which turns into the lower line at wavelength ~600 nm-~650 nm, and the lower line at wavelength ~675 nm-~775 nm. The line representing the PT Singlet is the lower line at wavelength ~425 nm-~600 nm which turns into the upper line at wavelength ~600 nm-~650 nm, and the upper line at wavelength ~675 nm-~775 nm.

Similarly, global analysis isolates only two species for TAS data of PT probed in dilute solution, the singlet and triplet pair. (see, FIG. 17) Again, where the longer acene absorbs pumping occurs at 660 nm where the pentacene monomer absorbs and the tetracene monomer does not. However, even in the singlet exciton a clear GSB signal of both pentacene transitions (near 600 nm) as well as tetracene transitions (near 550 nm) is absorbed. While quantitative analysis is obscured by the large degree of overlap with PIA in this region, it appears that there is somewhat more bleach of the pentacene than tetracene in the singlet exciton. This may reflect a preferential localization of the singlet to some degree on the monomer with a lower singlet energy. Overall, the presence of GSB for both monomers in the singlet is consistent with a picture of SF from a delocalized singlet exciton as reported previously.[13,15]

The time constants for singlet fission ($\tau_{iSF}$) and triplet pair ($2\times T_1$) decay ($\tau_{2\times T}$) are shown in TABLE 1. Since there is no indication of a parasitic process that would compete with the singlet fission process, and the rates of SF are all orders of magnitude faster than fluorescence or internal conversion in PT and PH, the iSF process is quantitative. In other words, the rates of singlet decay and triplet formation are directly correlated, and the yields are determined only by the kinetic competition between iSF and the intrinsic decay processes (~10 ns).[10,13,38,40] is in stark contrast to the dynamics observed in PA. TABLE 1 shows the time constants for singlet fission ($\tau_{iSF}$) and triplet pair recombination ($\tau_{2\times T}$) for the pentacene-tetracene (PT) and pentacene-hexacene (PH) heterodimers, compared to bipentacene (BP, homodimer).

TABLE 1

| Compound* | $\tau_{ISC}$ (ps) | $\tau_T$ (ns) |
|---|---|---|
| PA | $1.0 \times 10^5$ | $1.74 \times 10^4$ |
| iSF Compound | $\tau_{iSF}$ (ps) | $\tau_{2 \times T}$ (ns) |
| PT | 0.83 | 1.75 |
| BP | 0.76 | 0.45 |
| PH | 1.2 | 0.21 |

*Compound PA: $S_1$ lifetime = 11.5 ns, ~ 10% T yield.

Figure 18:
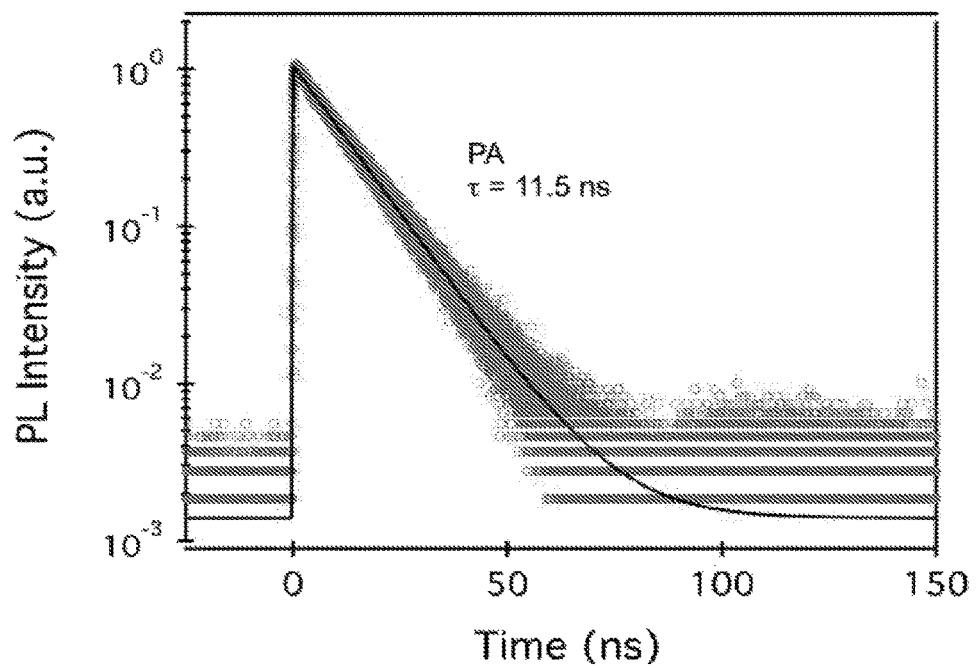
FIG. 18 shows that time correlated singlet photon counting can be used to monitor the long-lived, emissive singlet exciton observed in PA.

Time correlated single photon counting was used to probe the decay of the singlet exciton in PA. (see, FIG. 18) Notably, the 11.5 ns decay observed is in excellent agreement with the 11.3 ns lifetime for the singlet observed in transient absorption spectroscopy. Single photon counting was not successfully employed to probe singlet decay in PH or PT, as neither is appreciably fluorescent and the singlet lifetimes are much shorter than the time resolution of this technique.

Figure 19:
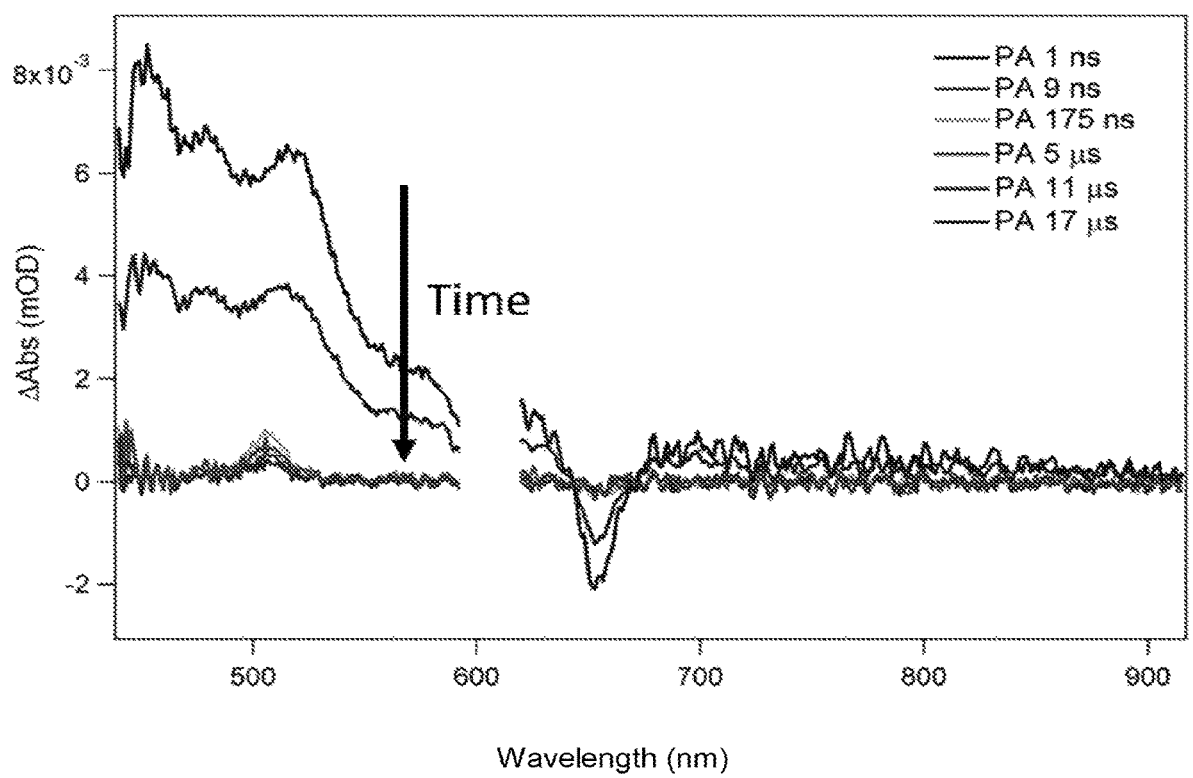
FIG. 19 shows spectral cuts taken at different times that reveal the decay of the singlet exciton in PA to yield a small population of triplets. The line for PA at 1 ns is above that of the line for PA at 9 ns (until around ~650 nm where the PA at 1 ns line dips below the PA at 9 ns line).

In FIG. 19, spectral line cuts reveal minimal spectral evolution of the photoexcited singlet in PA and its decay with an 11 ns time constant. Following the decay of the singlet, a very small triplet population remains, consistent with triplets formed via intersystem crossing on a slow timescale to create long-lived, individual triplets which subsequently decay with a ~20 µs lifetime, similar to the intrinsic lifetime of TIPS pentacene triplet excitons.

Beyond the kinetics, the heterodimers enable probing of the spatial dynamics of iSF since, due to asymmetry, the relative spectral weight of GSB in P and T will change when converting between different exciton states. Even though the absorption spectra of the heterodimers are qualitatively described as combinations of the absorption features due to the individual monomers, when the longer-wavelength absorption is pumped in any of the heterodimers both ground-state absorptions are bleached. The longer-wavelength absorption is bleached more thoroughly than the shorter-wavelength absorption. This asymmetry in bleaching is in contrast to quantitative bleaching of both chromophores in bipentacenes, and it arises from the greater portion of the excited singlet wavefunction residing on the monomer unit that is associated with the lower-energy excited state.[13,15] Averaging over vibrational and rotational degrees of freedom in the ensemble of molecules can thus lead to some partial bleaching (not quantitative, but non-zero) of the higher singlet-energy chromophore in the singlet.

Figure 20:
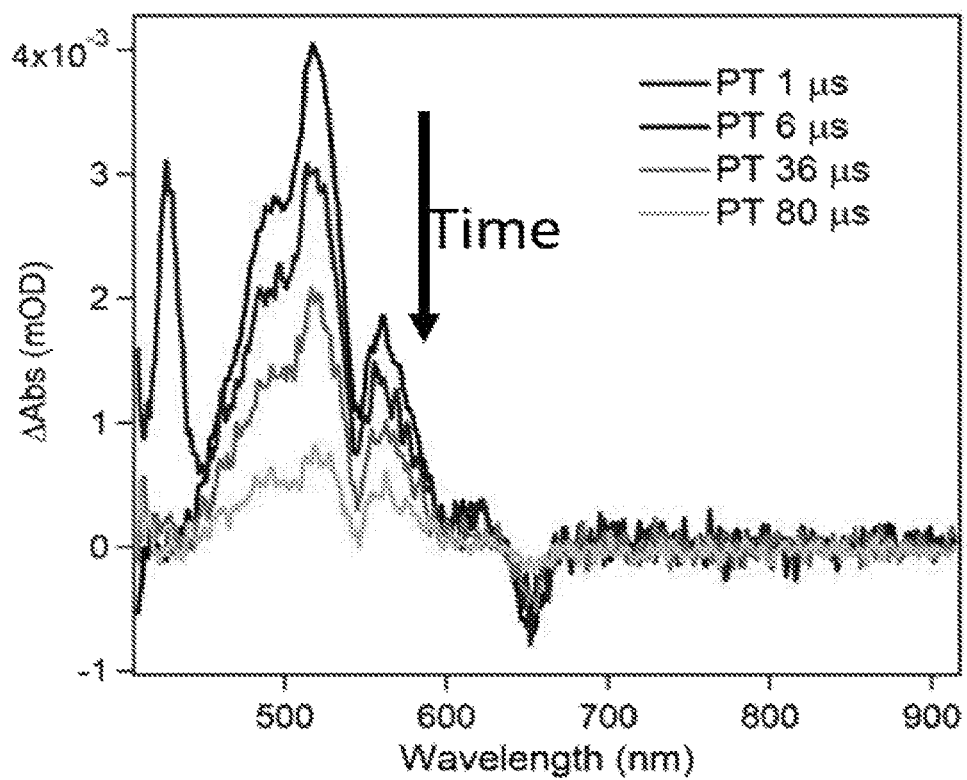
FIG. 20 shows a comparison of triplet transient absorption spectra obtained by photosensitization (single $T_1$) and singlet fission ($2 \times T_1$) in PT and PH.
Figure 20:
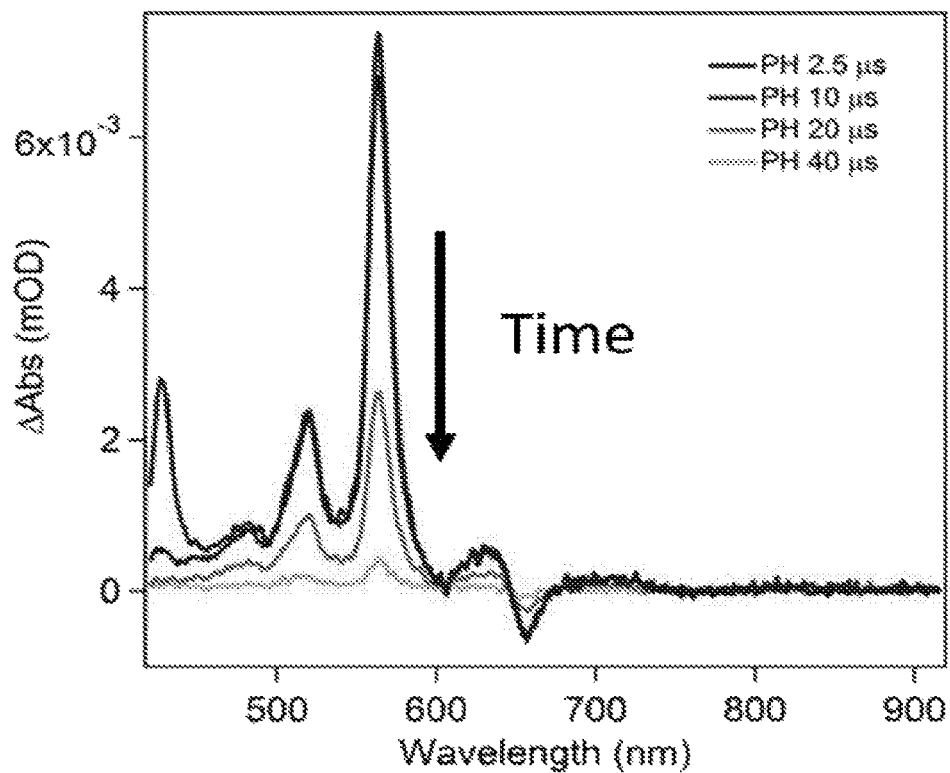

In order to characterize the triplet pair, singlet fission studies were compared with sensitization experiments, in which the triplet states are populated in the heterodimers via collisional transfer from a triplet donor (anthracene) in excess concentration (FIG. 20). Interestingly, in the case of the heterodimers, the anthracene can collide with and populate a triplet on either monomer. Given the pump energy employed in the sensitization experiments, individual molecules contain just one triplet exciton. Therefore, the spectra of individual triplets would appear significantly different from the triplet pair spectra produced by iSF. However, the ensemble contains a roughly even number of triplets on each monomer and can therefore be compared to iSF, which generates triplet pairs.

For triplet photosensitization, a solution of of ~20 mM anthracene in chloroform, along with a much smaller concentration of heterodimer (~50 µM) was excited by 360 nm pump light. This pump pulse primarily excites anthracene which, following intersystem crossing (ISC), results in anthracene triplets. Diffusional collisions subsequently transfer these triplets to the heterodimer. An optical probe pulse then interrogates the resulting triplet state.

The photoinduced absorption (PIA) spectra of the $T_1$ resulting from sensitization and $2\times T_1$ resulting from singlet fission are similar, but not identical. Modest spectral shifts of magnitude and/or wavelength of the PIA are found, consistent with reports of directly coupled pentacene dimers.[13,15] These shifts result from the strong correlation of the triplet pair when in close proximity, as demonstrated previously.[13] While these spectra are similar, the dynamics are significantly different. In general, the triplet pairs produced from iSF tend to decay on much shorter timescales than individual triplets. In the case of PT and PH, the lifetime of the $2 \times T_1$ is less than 2 ns, as opposed to tens of microseconds for their individual $T_1$.[38,40,54] The correlated triplet pair decay is apparent since both the pentacene and tetracene GSB signals decay at the same rate.

Figure 21:
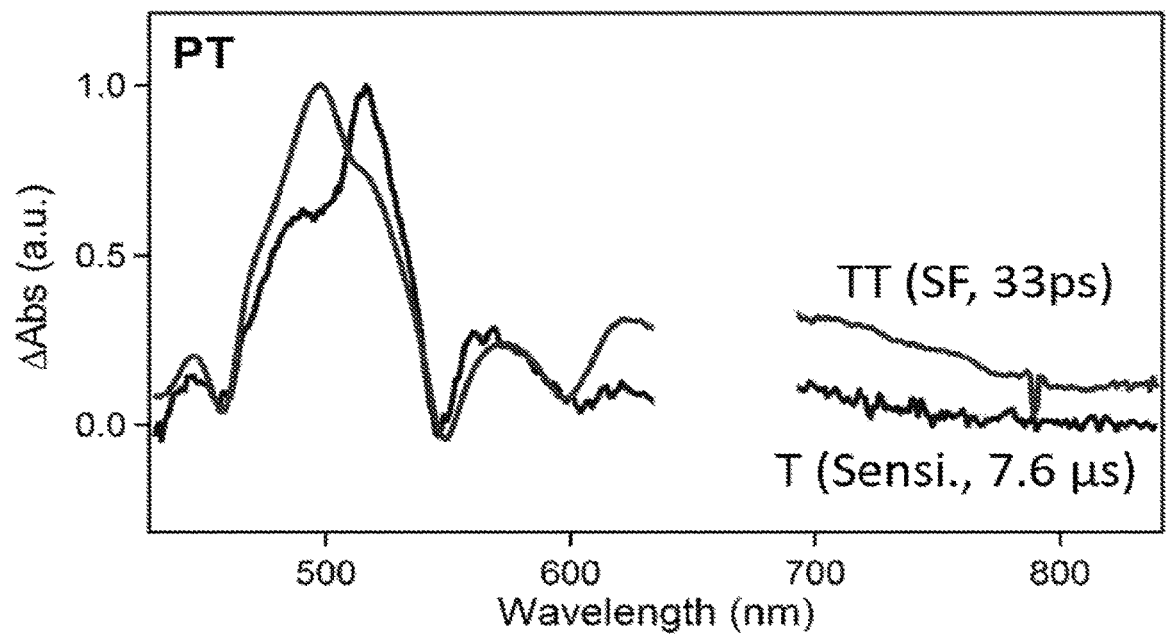
FIG. 21 shows spectral cuts from sensitization experiments of PT and PH heterodimers dissolved along with a significant excess of anthracene in chloroform. The signal at early times near 418 nm is due to anthracene triplet photoinduced absorption, and therefore it decays as triplets and are transferred to the heterodimer.
Figure 21:
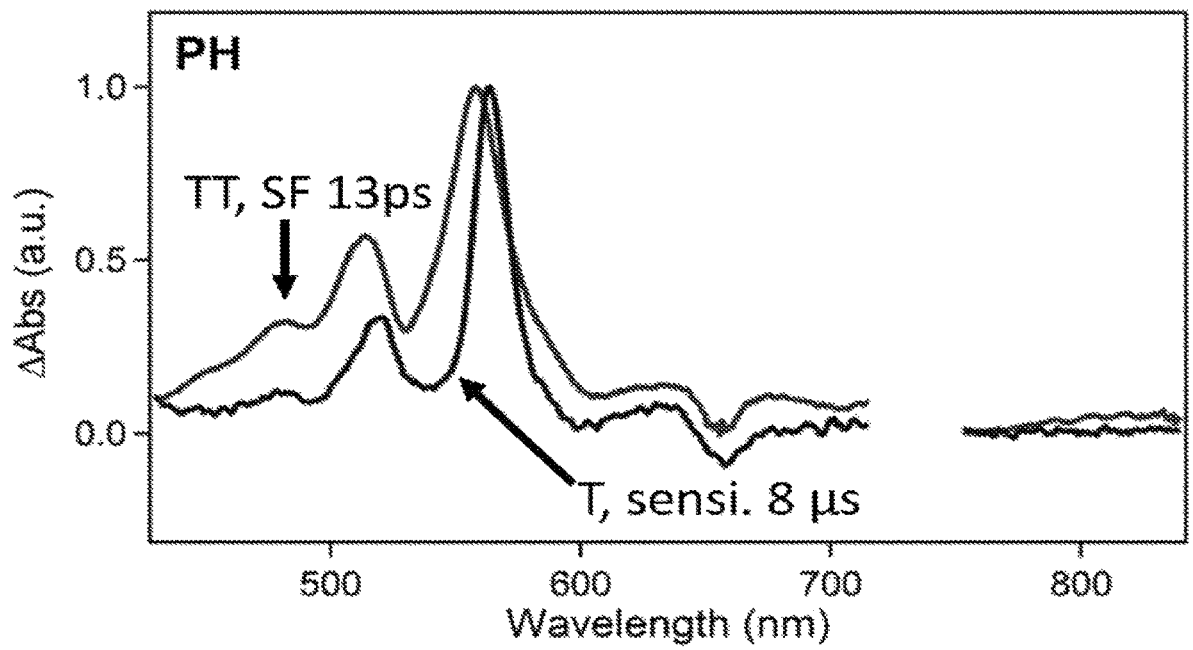

Data from sensitization of PH and PT in FIG. 21 shows a peak in the earliest time cut that is from the anthracene sensitizer triplet photoinduced absorption. This peak vanishes as triplets are transferred to the heterodimer. The minimal evolution of the spectrum after sensitization reveals an absence of triplet transfer within the heterodimers. If triplets were to transfer from pentacene (higher energy triplet) to hexacene (lower energy triplet), the PIA would shift in magnitude and absorption considerably and the pentacene GSB would recover much faster than the hexacene GSB. Similarly, in PT if the higher energy tetracene triplets were to transfer to pentacene, the tetracene bleach would recover faster than the pentacene bleach. None of this evidence for Dexter triplet transfer on a competitive timescale with intersystem crossing to the ground state is observed. Therefore, sensitization produces a static distribution of triplets, some on pentacene and some on hexacene. These populations decay independently. Since production of a tetracene, pentacene or hexacene triplet by diffusional collisions occurs with a similar probability, the resultant spectra can be approximately compared to the triplet pair (exactly half pentacene, half hexacene triplets) produced by fission. However, triplets on each monomer have different lifetimes, and so the spectrum shifts slightly over time as the relative population changes. Therefore, to most accurately compare to the triplet pair, a relatively early time cut is used before the relative populations shift significantly.

Figure 22:
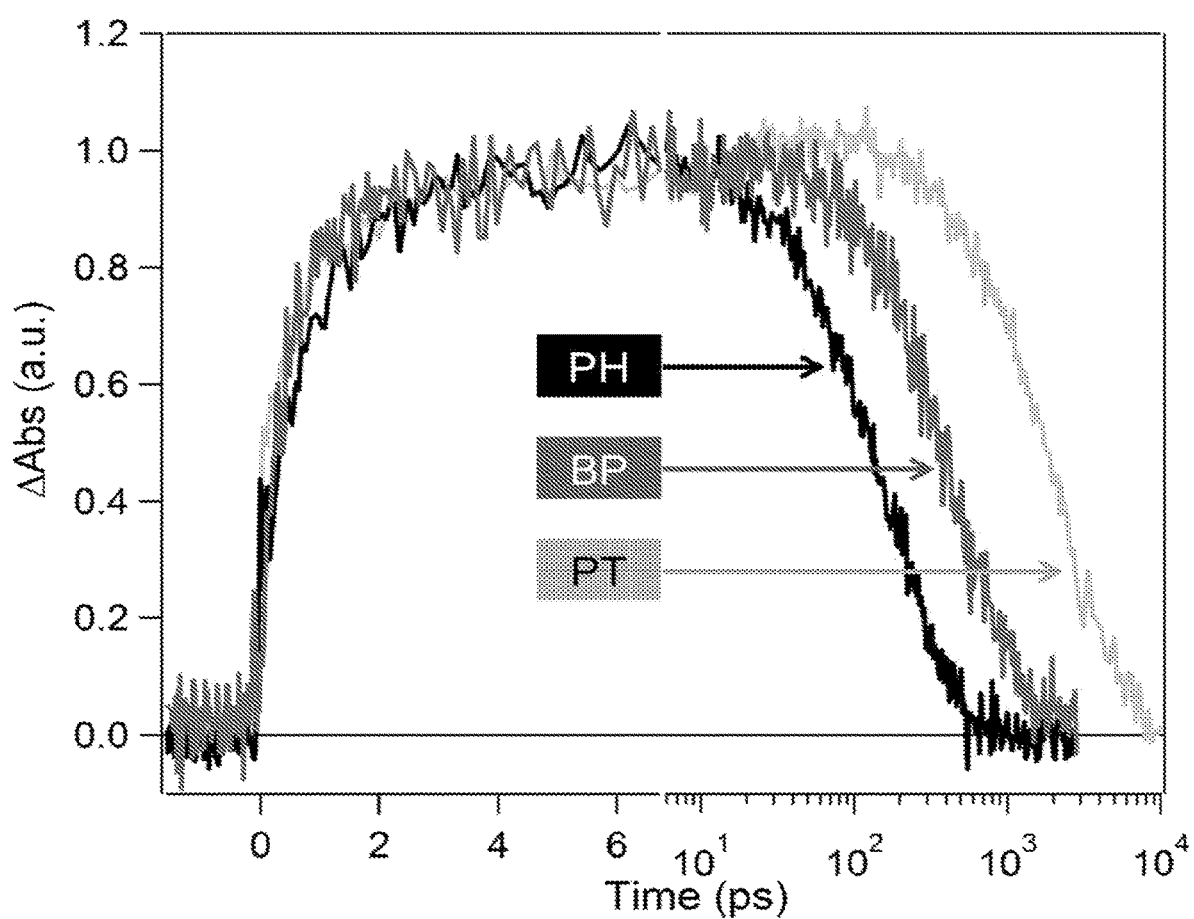
FIG. 22 shows rise and decay kinetic traces of the triplet pair in PH, BP, and PT, probed at the $\lambda_{max}$ of the triplet excited state absorption spectra (683, 712, 707 nm respectively).

While energetics have a dramatic impact on whether or not iSF will occur, the rates of iSF for PT, BP, and PH are surprisingly insensitive to the driving force, each being ~1 ps. In contrast, the recombination kinetics have a clear dependence on overall triplet pair energy. The lifetime of the triplet pair decreases following the trend, PT>BP>PH, in agreement with the trend of decreasing energy of the triplet state (FIG. 22). The triplet pair lifetime varies from 0.18 ns to 1.75 ns as the expected triplet pair energy decreases from ~1.8 eV to ~1.2 eV. In all cases, the triplet pair is significantly less emissive than the singlet, and these lifetimes are much shorter than the radiative lifetime of the monomers. Therefore, the decay in the directly linked acene series is primarily non-radiative and can be explained by invoking a simple energy gap argument for non-radiative decay processes, where the rate of such a multiphonon process is inversely proportionate to the number of photons needed, i.e. the energy above the ground state.[42-44]

Embodiments of the invention are directed to the synthesis and characterization of a series of pentacene-acene heterodimers. By systematically varying the singlet and triplet pair energies heterodimers comprising a pentacene unit covalently bonded to another acene are affected because the energies control the SF process, particularly where dimers undergo SF provided that the resulting triplet pair energy is similar or lower in energy than the singlet state. In these systems the singlet energy is determined by the lower energy chromophore, and the rate of SF is relatively independent of the driving force. However, triplet pair recombination in these heterodimers follows the energy gap law. PA, where iSF is significantly endothermic, undergoes typical, slow singlet state deactivation processes of internal conversion, fluorescence and a small amount of ISC. However, PT and PH, where iSF is energetically feasible, undergo iSF with ~1 ps time constant, as demonstrated by ultrafast transient absorption spectroscopy and triplet photosensitization experiments. Triplet pair recombination adheres to the energy gap law, but formation of the triplet pair appears to be insensitive to the driving force in iSF heterodimers. The ability to tune the energies of these materials provides an important process for third generation photovoltaics by designing new SF materials.

Applications

Embodiments of the invention are directed to a soluble bipentacene derivative compound, 22'BP, and similar materials that undergo ultrafast iSF. The Examples section below shows the synthesis scheme and characterizes the final compound as well as the compounds that were used in the synthesis. Since these materials do not rely on intermolecular coupling or packing interactions, they may inspire solution processing and be applicable to various types of optoelectronic devices. Non-limiting examples of optical, electro-optical, and electronic devices include, organic field effect transistors (OFET), organic thin film transistors (OTFT), organic light emitting diodes (OLED), organic light emitting transistors (OLET), organic photovoltaic devices (OPV), organic solar cells, laser diodes, Schottky diodes, photo-conductors, photo-detectors (sf photo-detectors), printable circuits, capacitors, sensors, and the like. The desired materials described here may be used in photodetectors with enhanced quantum yield.

In one embodiment, preferred simple, stable, and soluble quantitative singlet fission materials as described here may be applied to solar cells or photovoltaic devices and thereby overcome the Shockley-Queisser limit of efficiency. Since this invention removes the morphology requirement for singlet fission, the desired compounds or materials are more viable for application in bulk heterojunction, dye sensitized, or other types of solar cells.

The multiexcitonic materials according to the present invention may also be used in other optoelectronic thin-film technologies. For applications in modem microelectronics it is generally desirable to generate small structures or patterns to reduce cost (more devices/unit area), and power consumption. Patterning of thin layers comprising a material according to the present invention can be carried out for example by photolithography, electron beam lithography or laser patterning.

For use as thin layers in electronic or electro-optical devices the materials, compounds or formulations in, for example, solid, gas, or preferably a solution or liquid phase of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, letterpress printing, screen printing, doctor blade coating, roller printing, reverse-roller printing, offset lithography printing, flexographic printing, web printing, spray coating, brush coating or pad printing. Ink-jet printing is particularly preferred as it allows high resolution layers and devices to be prepared.

Selected formulations of the present invention may be applied to prefabricated device substrates by ink jet printing or microdispensing. Preferably industrial piezoelectric print heads such as but not limited to those supplied by APRION, HITACHI-KOKI, inkjet technology, ON TARGET TECHNOLOGY, PICOJET, SPECTRA, TRIDENT, and XAAR may be used to apply the desired material possessing quantitative intramolecular singlet fission in a layer to a substrate.

Additionally semi-industrial heads such as those manufactured by BROTHER, EPSON, KONICA, SEIKO INSTRUMENTS, TOSHIBA TEC or single nozzle microdispensers such as those produced by MICRODROP and MICROFAB may be used.

The materials or formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The materials according to the present invention are useful as charge transport, semiconducting, electrically conducting, photoconducting or light emitting materials in optical, electrooptical, electronic, electroluminescent or photoluminescent components or devices. In these devices, the materials of the present invention are typically applied as thin layers or films.

Thus, the present invention also provides the use of the semiconducting materials, compounds, polymers, formulations or layers in an electronic device. The formulation may be used as a high mobility semiconducting material in various devices and apparatus. For example, the formulation may be used in the form of a semiconducting layer or film. Accordingly, in another aspect, the present invention provides a semiconducting layer for use in an electronic device, the layer comprising a polymer, polymer blend or formulation according to the invention. The layer or film may be less than about 30 microns. For various electronic device applications, the thickness may be less than about 1 micron. The layer may be deposited, for example on a part of an electronic device, by any of the aforementioned solution coating or printing techniques.

The invention additionally provides an electronic, optical, or electro-optical component or device comprising a singlet fission material, compound, oligomer, polymer, polymer blend, formulation or organic semiconducting layer according to the present invention, where the singlet fission material, compound, oligomer, or polymer is preferably soluble and stable. Non-limiting examples of devices include organic field effect transistors (OFETs), organic thin film transistors (OTFTs), integrated circuits (ICs), logic circuits, capacitors, radio frequency identification tags (RFID tags), organic light emitting diodes (OLEDs), organic light emitting transistors (OLETs), organic photovoltaic devices (OPVs), solar cells, laser diodes, photoconductors, photodetectors, photocatalytic devices, electrophotographic devices, electrophotographic recording devices, organic memory devices, sensor devices, charge injection layers, Schottky diodes, planarising layers, antistatic films, conducting substrates and conducting patterns.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps. Unless the context clearly indicates otherwise, as used herein plural forms of the terms herein are to be construed as including the singular form and vice versa. Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

EXAMPLES

The following Examples of the invention are provided only to further illustrate the invention, and are not intended to limit its scope.

Example 1

General Synthetic Details and Preparation of Compound 1

All commercially obtained reagents and solvents were purchased from Alfa Aesar®, Sigma-Aldrich °, Acros Organics®, TCI America®, Mallinckrodt®, and Oakwood Products®, and used as received without further purification, unless otherwise noted.

Unless stated otherwise, reactions were conducted in oven-dried glassware under argon atmosphere. $^1$H-NMR and $^{13}$C-NMR spectra were recorded on Bruker 400 MHz (100 MHz for $^{13}$C) and on 500 MHz (125 MHz for $^{13}$C) spectrometers. Data from the $^1$H-NMR and $^{13}$C spectroscopy are reported as chemical shift (δ ppm) with the corresponding integration values. Coupling constants (J) are reported in hertz (Hz). Standard abbreviations indicating multiplicity were used as follows: s (singlet), b (broad), d (doublet), t (triplet), q (quartet), m (multiplet) and virt (virtual).

The mass spectral data for the compounds were obtained from XEVO G2-XS Waters® equipped with a QTOF detector with multiple inlet and ionization capabilities including electrospray ionization (ESI), atmospheric pressure chemical ionization (APCI), and atmospheric solids analysis probe (ASAP). The base peaks were usually obtained as $[M]^+$ or $[M+H]^+$ ions.

Absorption spectra were obtained on a Shimadzu UV 1800 UV-Vis spectrophotometer. Anhydrous solvents were obtained from a Schlenk manifold with purification columns packed with activated alumina and supported copper catalyst (Glass Contour, Irvine, Calif., USA). All reactions were carried out under argon unless otherwise noted. The TGA analysis was carried out in q500-2210 TA instrument. Differential Scanning calorimetry (DSC) was performed on a TA Instruments DSC Q2000 fitted with a RCS90 refrigerated cooling system to determine the glass transition temperatures. DSC measurements were taken at a sampling rate of 10° C./min in the temperature range of 0° C. to 140° C.

MALDI measurements were carried out in Bruker UltrafleXtreme MALDI-TOF/TOF instrument. Samples were diluted in 0.5 mL of dichloromethane. 1 μL of sample was spotted onto MALDI target and 1 ul of matrix was added (Dithranol, α-Cyano-4-hydroxycinnamic acid). Samples were analyzed on with various different methods such as different laser settings, detector settings, negative/positive ion mode.

Anhydrous solvents were obtained from a Schlenk manifold with purification columns packed with activated alumina and supported copper catalyst (Glass Contour, Irvine, Calif.). All reactions were carried out under argon unless otherwise noted.

Gel permeation chromatography (GPC) analyses were carried out using an Agilent PL-GPC 50 integrated system (2×PLgel Mini-MIX C columns, 5 micron, 4.6 mm ID) equipped with UV and refractive index detectors. The GPC columns were eluted at a rate of 1.0 mL/min with 1,2,4-trichlorobenzene (150° C.) and were calibrated relative to monodisperse polyethylene standards.

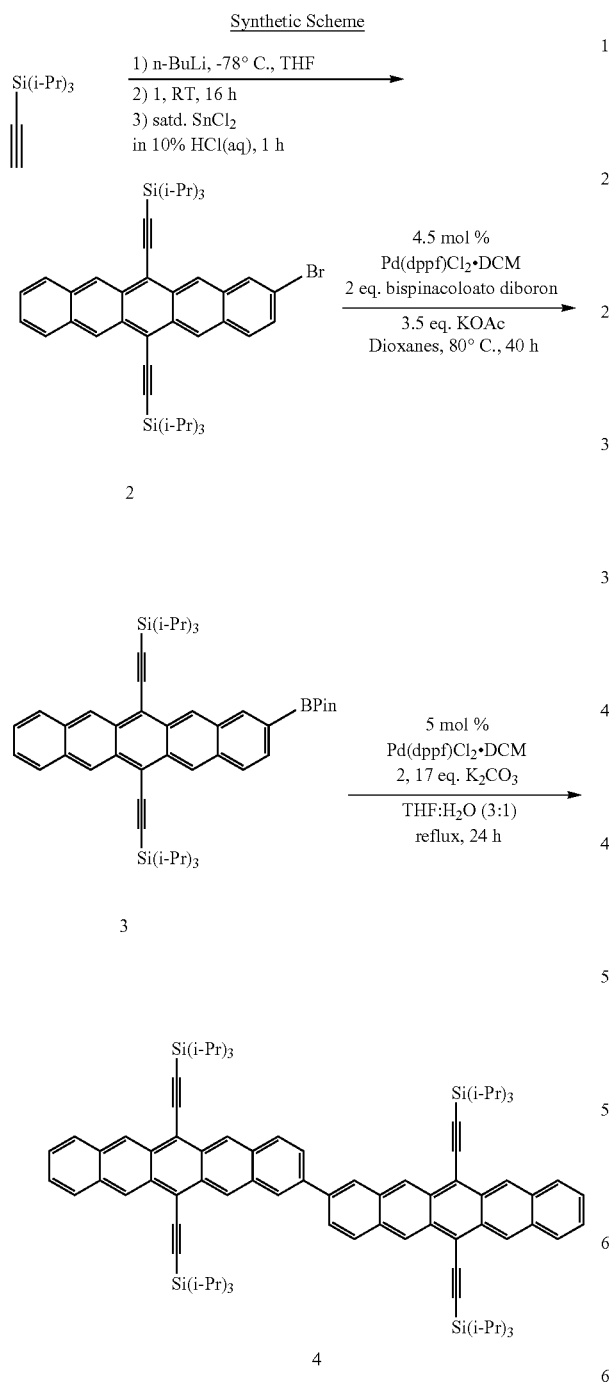

Methods:

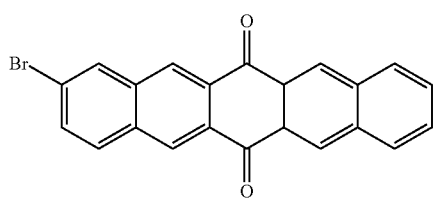

Compound 1 was synthesized according to a previously published procedure.[55]

Example 2

Preparation of Compound 2

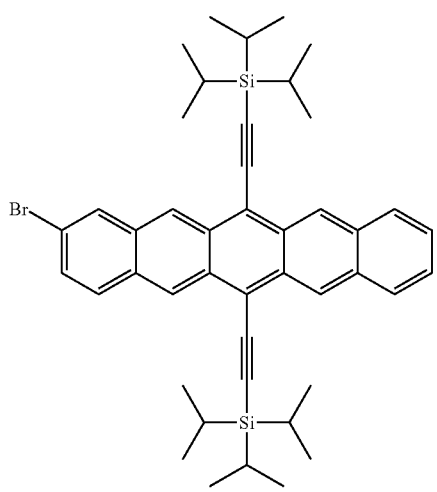

Compound 2: To a 200 mL Schlenk flask was added degassed triisopropylsilyl acetylene (7.84 mL, 35 mmol) in 25 mL of THF. This solution was cooled to −78° C. and n-butyllithium (13.6 mL, 34 mmol, 2.5 M in hexanes) was added dropwise and the resulting solution was allowed to stir at −78° C. for 1 h. To this solution, 2 (3.92 g, 10 mmol) was added as a solid under positive argon flow. The solution was allowed to warm to room temperature and stirred overnight (16 hours), or until solid pentacene quinone was no longer present by TLC. To this clear, deep yellow solution was added 50 mL of a saturated solution of tin (II) chloride dihydrate in 10% aqueous HCl solution. The resulting solution turned deep blue and was allowed to stir 1 hour at room temperature in the dark. This solution was passed over a thick pad of silica gel in a Buchner funnel, eluting with dichloromethane. The filtrate was extracted between 250 mL of dichlorometane and 250 mL of water twice. The organic layer was dried by passage over sodium sulfate and solvent was removed in vacuo. The resulting blue solid was purified by column chromatography on silica gel (100% hexanes) to provide 2 as a deep blue solid (4.7 g, 65%).

Characteristics:

$^1$H NMR (500 MHz, CDCl$_3$, ppm): δ 1.35-1.44 (m, 42H), 7.40-7.46 (m, 3H), 7.84 (d, J=9 Hz, 1H), 7.95-8.00 (m, 2H), 8.12 (s, 1H), 9.19 (s, 1H), 9.26 (s, 1H), 9.29 (s, 1H), 9.31 (s, 1H).

$^{13}$C NMR (500 MHz, CDCl$_3$, ppm): δ 11.68, 19.00, 104.39, 104.45, 107.57, 107.66, 118.50, 118.67, 120.31, 125.47, 126.19, 126.23, 126.37, 126.40, 126.89, 128.68, 129.54, 130.18, 130.24, 130.42, 130.55, 130.67, 130.82, 130.90, 132.41, 132.49, 132.63.

MS (MALDI) m/z calcd for C$_{44}$H$_{53}$BrSi$_2$: 718.28. Found (isotopic pattern) 717.19, 719.22.

Example 3

Preparation of Compound 3

3

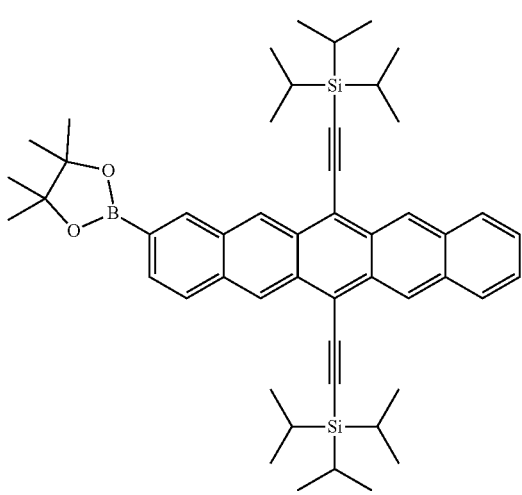

Compound 3: To a 100 mL round bottomed flask was added 2 (4.0 g, 5.57 mmol), Pd(dppf)Cl$_2$.DCM (203 mg, 0.25 mmol), KOAc (1.91 g, 19.5 mmol), and bis(pinacolato)diboron (2.82 g, 11.1 mmol). Sequential vacuum and argon were used to degas these solids, and then degassed 1,4 dioxane (70 mL) was added. The mixture was stirred at 80° C. for 40 hours in the dark. Solvent was removed in vacuo, and the solid product was extracted between 250 mL dichloromethane, 250 mL water twice. The organic layer was dried over sodium sulfate and solvent was removed in vacuo. Purification by column chromatography on silica gel (hexanes/dichloromethane) yielded 3 as a deep blue solid (2.08 g, 49%).

Characteristics:

$^1$H NMR (500 MHz, CDCl$_3$, ppm): δ 1.38-1.46 (m, 42H), 1.48 (s, 12H), 7.43-7.46 (m, 2H), 7.95 (d, J=11.5 Hz), 7.98-8.02 (m, 2H), 8.55 (s, 1H), 9.30 (s, 1H), 9.34 (s, 1H), 9.36 (s, 1H), 9.37 (s, 1H).

$^{13}$C NMR (500 MHz, CDCl$_3$, ppm): δ 11.84, 19.15, 19.20, 25.11, 84.22, 104.71, 104.82, 107.34, 107.61, 118.45, 118.97, 126.15, 126.18, 126.21, 126.43, 126.58, 127.67, 127.76, 128.80, 128.82, 129.75, 130.71, 130.89, 130.92, 131.25, 131.93, 132.41, 132.49, 133.17, 138.08

MS (MALDI) m/z calcd for C$_{50}$H$_{65}$BO$_2$Si$_2$: 764.46. Found 764.94.

Example 4

Preparation of Compound 4: 22'BP

4

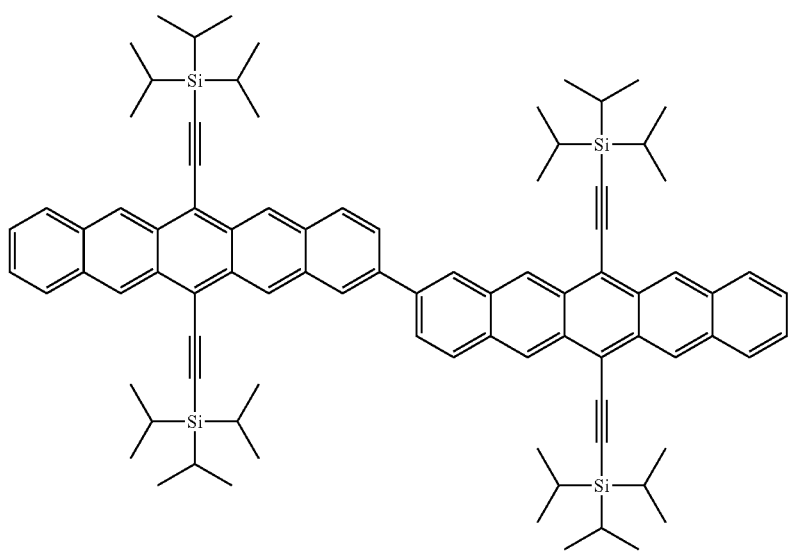

Compound 4 (22'BP): To a 20 mL sealed tube was added Compound 2 (72 mg, 0.1 mmol) (Example 2), Compound 3 (76 mg, 0.1 mmol) (Example 3), Pd(dppf)Cl$_2$.DCM (4 mg, 0.005 mmol), and K$_2$CO$_3$ (240 mg, 1.7 mmol) Sequential vacuum and argon were used to degas the tube containing these solids, and then degassed H$_2$O (1 mL) and THF (3 mL) were added. The resulting solution was stirred in the dark at 70° C. for 24 hours. The solution was then poured into a separatory funnel and extracted twice between 30 mL dichloromethane and 30 mL H$_2$O. The organic layer was dried over NaSO$_4$ and solvent removed in vacuo. Column chromatography on silica gel (hexanes/dichloromethane) yielded 4 as a deep purple solid (77 mg, 60% yield). Characteristics:

$^1$H NMR (500 MHz, CDCl$_3$, ppm): δ 1.37-1.49 (m, 84H), 7.41-7.45 (m, 4H), 7.91-7.95 (m, 2H), 7.97-8.01 (m, 4H), 8.15 (d, J=9 Hz, 2H), 8.35 (s, 2H), 9.32 (s, 1H), 9.33 (s, 1H), 9.36 (s, 1H), 9.42 (s, 1H).

$^{13}$C NMR (500 MHz, CDCl$_3$, ppm): δ 11.72, 19.03, 19.05, 77.20, 104.65, 104.72, 107.23, 107.38, 118.37, 118.51, 125.97, 126.07, 126.16, 126.22, 126.36, 126.83, 128.68, 129.63, 130.66, 130.78, 130.88, 131.04, 131.57, 132.33, 132.37, 132.46, 137.69.

MS (MALDI) m/z calcd for C$_{88}$H$_{106}$Si$_4$: 1275.74. Found: 1275.90.

$^1$H and $^{13}$C nuclear magnetic resonance spectra were recorded at 300K on BRUKER DRX400 (400 MHz) or BRUKER DRX500 (500 MHz) FT NMR spectrometers. High-resolution mass spectra were recorded on a JEOL JMSHX110A/110A tandem mass spectrometer mass spectrometer. UV-Vis absorption spectra were taken on a SHIMADZU UV-1800 spectrophotometer.

Transient Absorption Spectroscopy:

All data shown were from dilute solutions using chloroform as a solvent, except for FIG. 4 in which para-xylene was used for direct comparison to pulse radiolysis data. Similar carrier dynamics were observed in a range of solvents, including 1,2 chlorobenzene and para-xylene. Transient absorption spectroscopy was conducted using a commercial 1 kHZ amplified Ti:Sapphire laser system (SpectraPhysics |800 nm|100 fs|3.5 mJ|1 kHz), and a commercial optical parametric amplifier (Light Conversion) was used to generate excitation light. Supercontinuum probe light was generated by focusing the 800 nm fundamental output or a portion thereof from the amplifier into a sapphire disc and is overlapped in space and time with a resonantly tuned excitation pulse. The probe light was split into signal and reference beams, which were detected on a shot-by-shot basis by a fibre-coupled silicon (visible) or InGaAs (infrared) diode and was achieved with 1024 element multichannel detectors and fast digitizers. The pump-probe delay was controlled by a mechanical delay stage (Newport).

Figure 5:
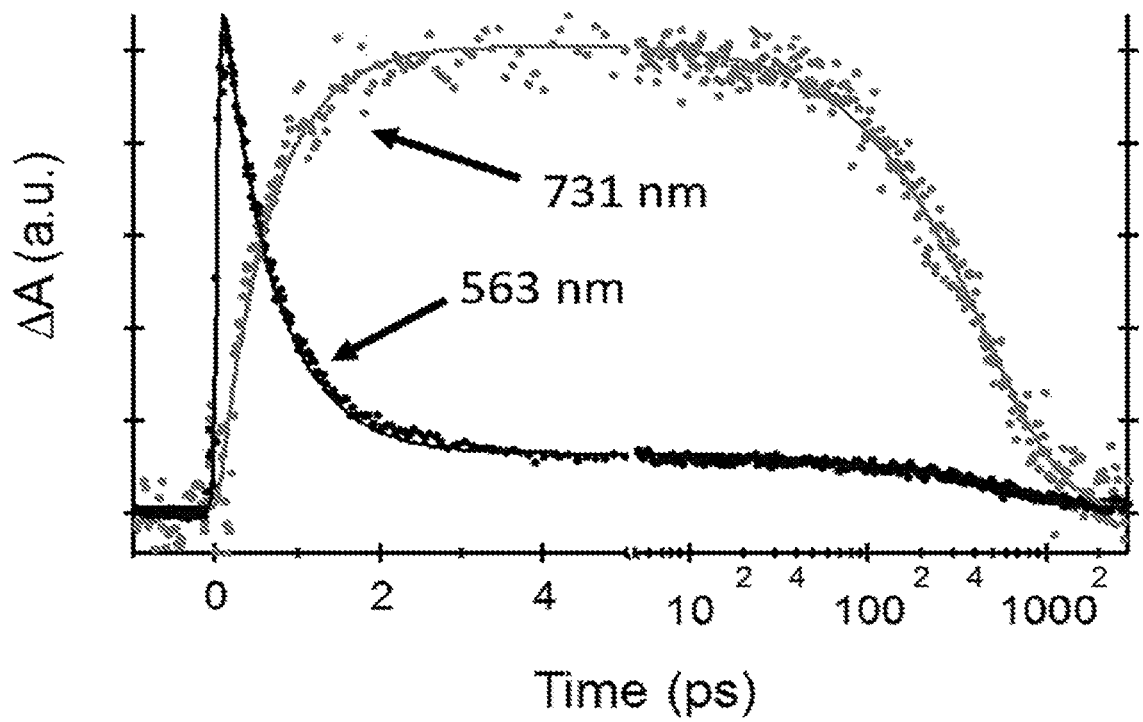
FIG. 5 shows two exponential fit of two kinetic traces from raw data using two "globally" constrained rate constants.

Global and Target Analysis:

Global (singular value decomposition-based) and target (differential equation-based) analyses were accomplished using the Glotaran software package (hypertext transfer protocol://glotaran.org). The advantage of these methods was that they treat the full (~800 kinetic trances) data set in aggregate, yielding much more accurate fits of the rate constants and deconvoluted "spectra" which track the distribution of the rate constants as a function of wavelength. A simple sequential decay model (S$_1$→T$_1$→S$_0$) was found sufficient to accurately reproduce the data set when pumping close to the band edge and the exciton dynamics for PH and PT. Similar results can be accomplished using global (constrained) fits of real data slices rather than singular vectors. The results of global fitting at two raw kinetic traces is show in FIG. 5 (with residuals) in which only two decay rates are used for the entire data set. This treatment accurately reproduced the correlated singlet decay and triplet rise, with time constants matching well with those extracted from the full data set analysis.

Example 5

Further Analyses of Compound 4

Calculation of PL Quantum Yield

The photoluminescence quantum yield of 22'BP was measured relative to a dilute solution of rhodamine 610 (R6B) in ethanol, which has a published quantum yield of 0.5.[56] A high repetition rate (5 MHz) picosecond pulsed laser was used for photoexcitation at 488 nm. Emission was detected with a JY HORIBA iHR320 spectrometer and liquid nitrogen cooled back-illuminated deep depleted CCD camera, with enhanced NIR sensitivity. A 530 nm long pass filter was used to reject the excitation light (Semrock). The PL quantum yield was calculated using the integrated PL spectrum, according to published methods, where I is the integrated PL intensity (corrected for grating and detector response functions), n are the solvent indices of refraction, and OD are the optical densities of the solutions (in 1 mm path length cuvettes) at the excitation wavelength.[57]

$$QY = QYR\ (I/IR)\ (ODR/OD)\ n^2/nR^2$$

$$= 0.5^*(123071/5.462421e+06)^*(0.005/0.149)^*(1.361/1.5241)^2$$

$$= 0.00030135$$

$$= 0.030\%$$

Computational Methods:

Calculations were done using Density Functional Theory (DFT) and Time Dependent DFT (TDDFT) with the B3LYP functional and the 6-31G** basis set. The molecular input file was generated on the Maestro molecular dynamics program, and the geometry was optimized through the Jaguar computational software. To simplify the computation, trimethylsilyl groups were drawn in place of TIPS groups, which do not contribute electron density to the system.

The exothermicity of the singlet fission process was defined as E(S$_1$)–2E(T$_1$) under conditions of weak interchromophore coupling. The final state was better approximated, however, by the energy of the quintet state of the dimer, or E(Q$_1$), in that the quintet state more closely described the energetics of a two-triplet state. For this computational study, the exothermicity of pentacene dimer fission was calculated both from E(S$_1$)–E(Q$_1$).

Static DFT was used to calculate $ of 4.62 eV. Relative to the $, static DFT also yielded Q$_1$ of 1.26 eV. TDDFT calculations were used to compute the energy of S$_1$, which was 1.52 eV above S$_0$. E(S$_1$)–E(Q$_1$) was found to be 0.26 eV exothermic, which is in close agreement with the 0.3 eV fission exothermicity previously suggested for a similar dimer with no solubilizing chains.[50]

Single Crystal X-Ray Diffraction:

Single crystal x-ray diffraction data of 22' BP was collected on an AGILENT SuperNova diffractometer using mirror-monochromated Cu Kα radiation. The crystals were mounted using a MiTeGen MicroMount cooled to 100 K with an Oxford-Diffraction Cryojet system. Data reduction was performed in CrysAlis.[58] Empirical correction and scaling was performed using ABSPACK, and face-indexed absorption correction was performed by analytical numeric methods.[59] Structure was solved using Superflip or ShelXS and refined by full-matrix least-squares against $F^2$ using ShelXL with the aid of Olex2.[60-61]

Single crystals of 22'BP were grown by slow evaporation of dichloromethane solution at room temperature for 1 week. A suitable crystal (0.50×0.06×0.03 mm) was selected and mounted with the aid of STP oil treatment and cooled to 100 K on the diffractometer. Complete data (99.2%) were collected. 21545 reflections were collected (7221 unique, 5193 observed) with R(int)=5.6% and R(sigma)=6.5% after absorption correction ($T_{max}$=0.969 and $T_{min}$=0.790).

The structure was solved in P-1, and all non-H atoms were freely refined. Hydrogen atoms were placed in calculated positions and refined with riding coordinates and ADPs. The final refinement (7221 data, 427 parameters, 0 restraints) converged with $R_1$ ($F_o$>4σ($F_o$))=6.3%, $wR_2$=17.8%, S=1.035. The largest Fourier features were 0.74 and −0.30 e⁻Å³.

TABLE 2 shows selected crystallographic data for 22'BP.

TABLE 2

| Parameter | 22'BP |
| --- | --- |
| Formula | $C_{88}H_{106}Si_4$ |
| MW | 1276.08 |
| Lattice type | Triclinic |
| Space group | P-1 |
| a (Å) | 8.6287(3) |
| b (Å) | 14.5001(6) |
| c (Å) | 16.3117(8) |
| α (°) | 70.296(4) |
| β (°) | 79.485(3) |
| γ (°) | 77.514(3) |
| V (Å³) | 1862.55(14) |
| Z value | 1 |
| $D_{calc}$ (g cm⁻³) | 1.138 |
| T (K) | 100 |
| GOF on $F^2$ | 1.035 |
| $R_1$ [$F^2$ > 4σ ($F^2$)] | 0.0626 |
| $wR_2$ (all data) | 0.1785 |

Example 6

Synthesis of Tetracene-Pentacene Derivatives: Pentacene-Tetracene (PT) and Pentacene-Anthracene (PA)

Figure 72:
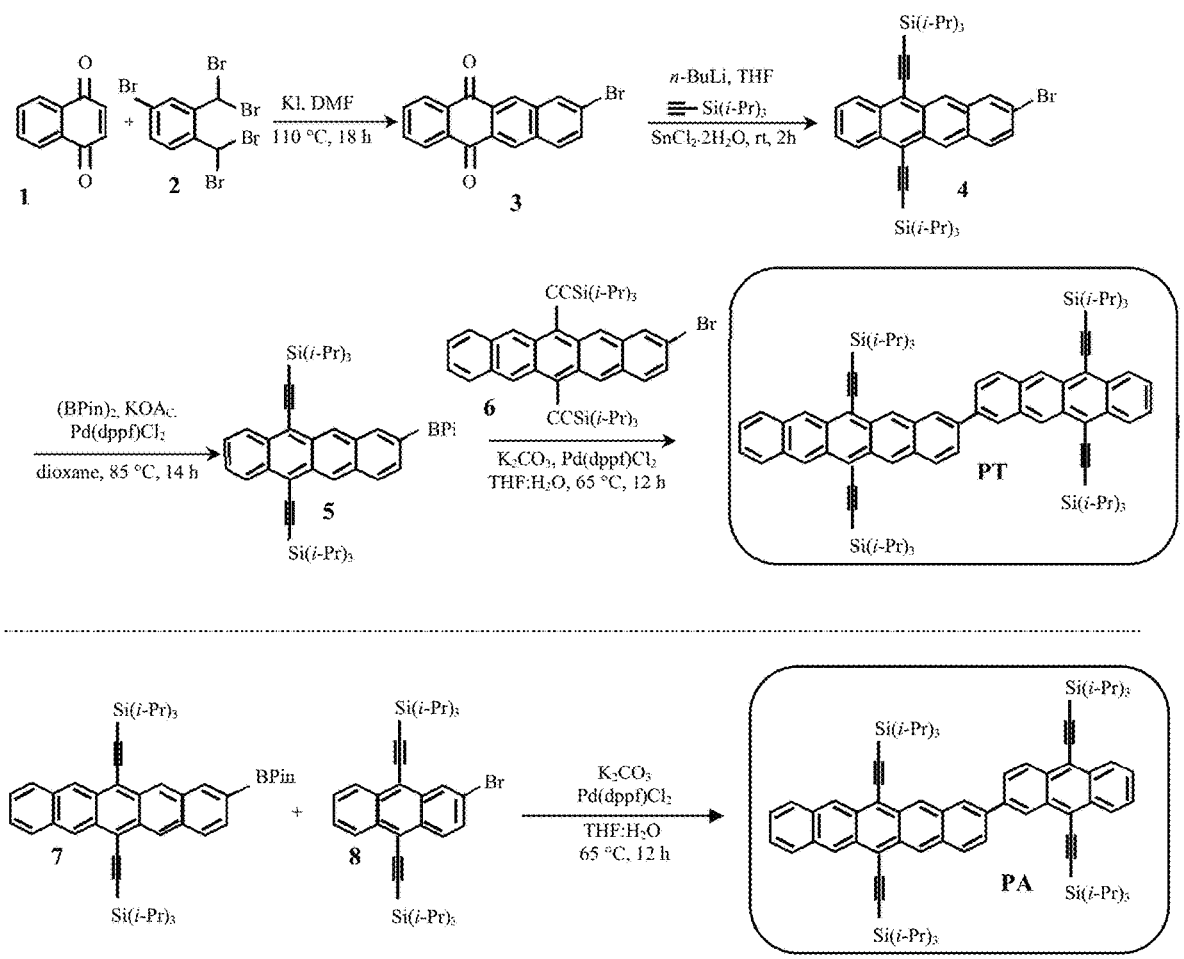
FIG. 72. shows exemplary methods of synthesizing tetracene-pentacene derivatives; pentacene-tetracene (PT) and pentacene-anthracene (PA).

FIG. 72 shows exemplary methods of synthesizing tetracene-pentacene derivatives; pentacene-tetracene (PT) and pentacene-anthracene (PA).

Example 7

Synthesis of Hexacene-Pentacene Derivatives-Pentacene-Hexacene (PH)

Figure 73:
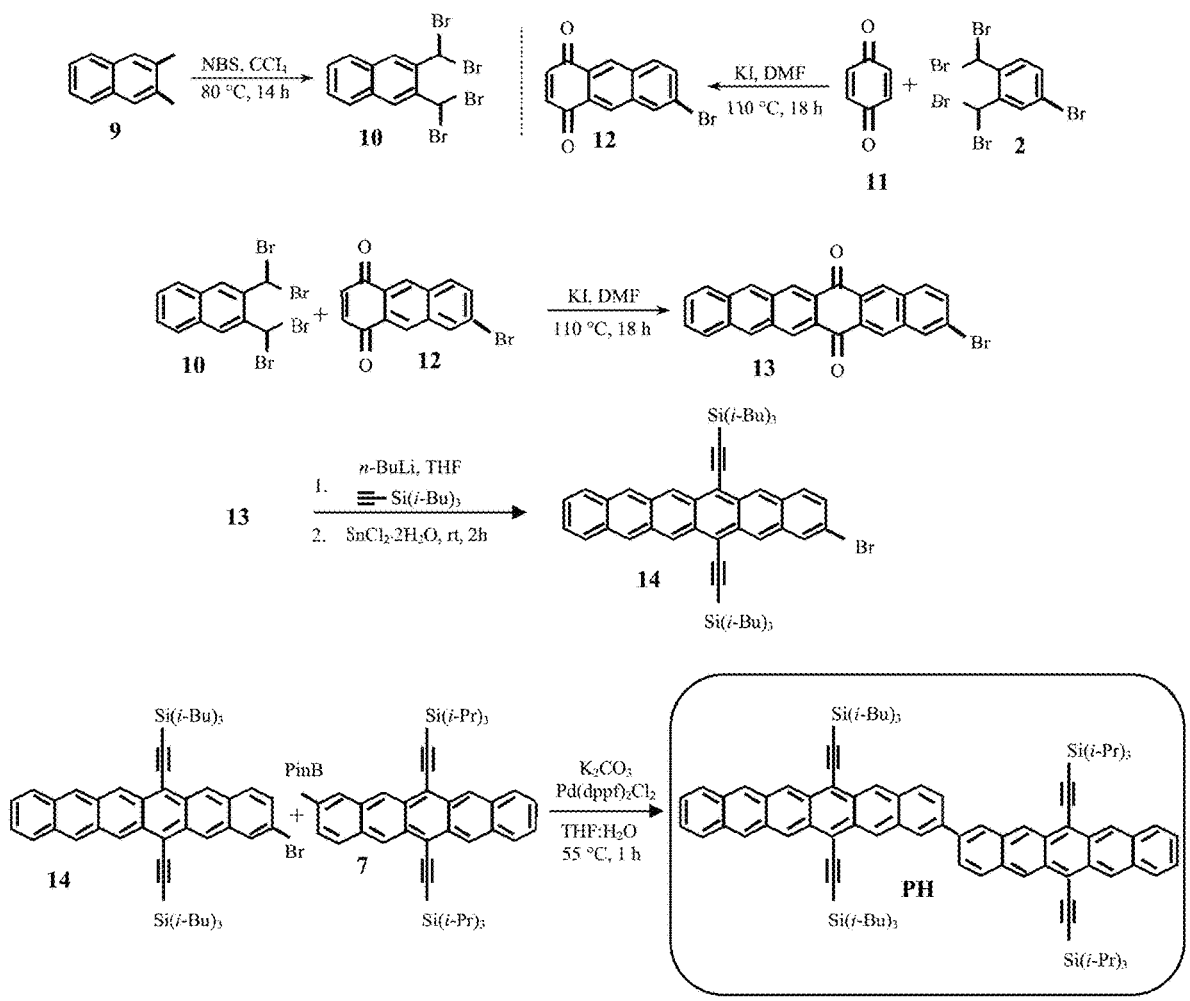
FIG. 73 shows a method of synthesizing hexacene-pentacene derivatives-pentacene-hexacene (PH).

FIG. 73 shows a method of synthesizing hexacene-pentacene derivatives-pentacene-hexacene (PH).

The bromo pentacene 6, Bpin pentacene 7 and Bromo anthracene 8 were synthesized according to a procedures reported in the literature.[13,62]

Example 8

Figure 74:
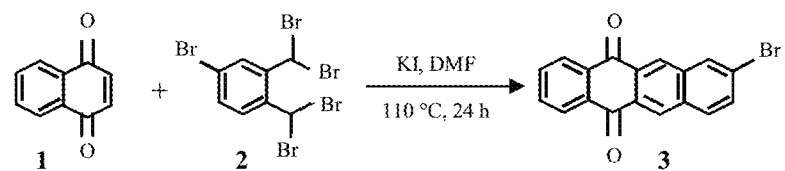
FIG. 74 shows a method of synthesizing bromo-tetracene-quinone.

Synthesis of Bromo-Tetracenequinone 3 (FIG. 74)

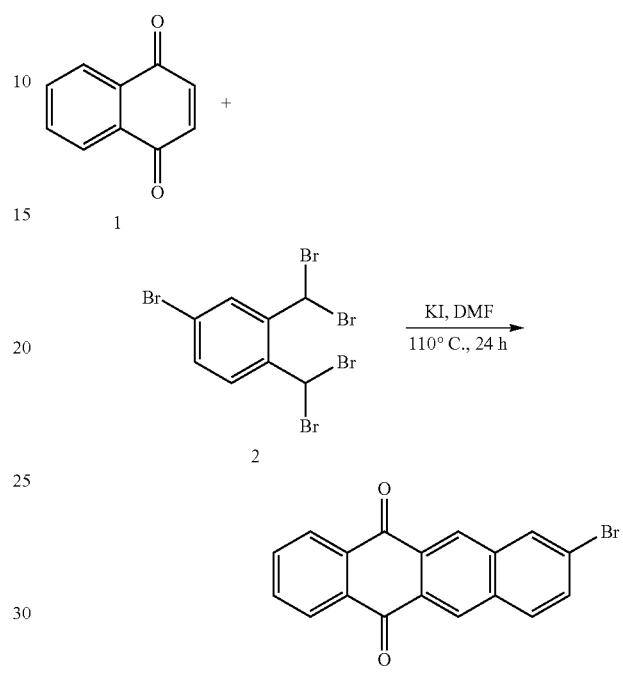

To a 250 mL flask, 1 (1.6 g, 10.0 mmol, 1.0 equiv.), 2 (5.0 g 10.0 mmol, 1.0 equiv.) and potassium iodide (6.5 g, 40 mmol. 4.0 equiv.) were added. Sequential vacuum and argon were used to remove oxygen, at which point dry and degassed DMF (120 mL) was added and the mixture was heated at 110° C. for 18 h. After the reaction, the mixture was cooled to room temperature, poured into 200 mL of methanol and filtered. The solid was then washed with DI water (100 mL), methanol (50 mL) and chloroform (50 mL) to yield 1.8 g (53% yield) of shiny, golden solid.

Due to the minimal solubility of the product, no characterization was undertaken and the product was carried forward to the next step.

Example 9

Synthesis of Bromo-Tips-Tetracene 4

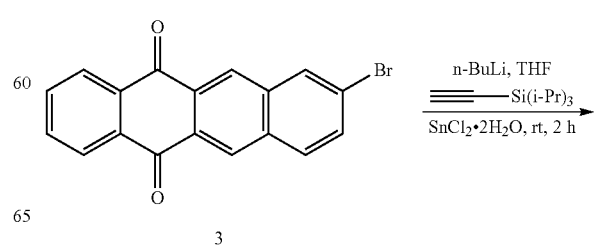

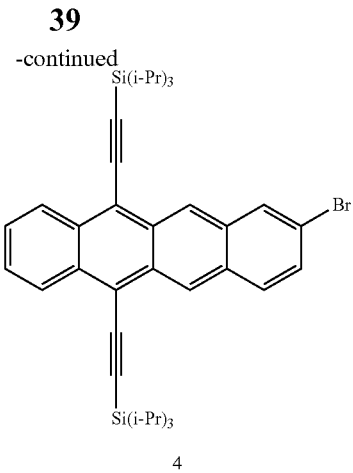

4

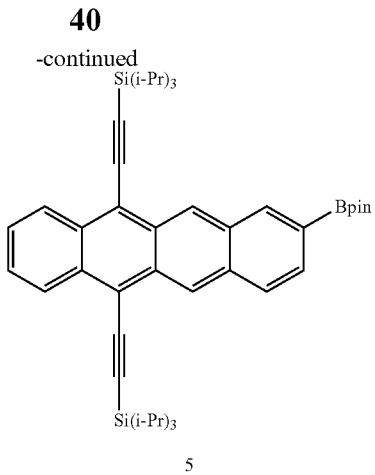

5

To a 50 mL schlenk flask, triisopropylsilylacetylene (3.6 mL, 16 mmol, 3.0 equiv.) and dry THF (20 mL) were added under argon. At −78° C., 2.5 M n-butyl lithium in hexanes (6.0 mL, 15 mmol, 2.8 equiv.) was added. The mixture was warmed to 0° C. and stirred for 45 min, at which point tetracenequinone 3 (1.6 g, 5.4 mmol, 1.0 equiv.) was added and the mixture was stirred at room temperature for 16 h. To the clear brown mixture, an excess of 10% aq. HCl solution and saturated with $SnCl_2 \cdot 2H_2O$, was added, turning the solution deep red. After 30 minutes stirring at room temperature, this mixture was partitioned between water (150 mL) and DCM (100 mL). The aqueous layer was extracted with DCM (2×80 mL). The combined organic phase was dried over $Na_2SO_4$, filtered and concentrated under reduced pressure. The crude product was purified by column chromatography over silica (100% hexanes to isolate 1.6 g of product as deep red solid (50% yield).

Characteristics:

$^1$H-NMR (500 MHz, CDCl$_3$, δ ppm): 9.29 (s, 1H), 9.22 (s, 1H), 8.66-8.63 (m, 2H), 8.19 (s, 1H), 7.91-7.89 (m, 1H), 7.60-7.57 (m, 2H), 7.53-7.51 (m, 1H) and 1.40-1.33 (m, 42H)

$^{13}$C-NMR (125 MHz, CDCl$_3$, δ ppm): 133.0, 132.8, 132.6, 130.7, 130.4, 130.3, 130.2, 130.1, 129.5, 127.4, 127.4, 127.1, 126.9, 126.8, 125.5, 120.3, 118.9, 118.7, 106.3, 106.2, 103.67, 103.65, 18.98, 18.96 and 11.6.

MS (ESI): Calculated: 667.2788; Observed: 667.2791.

Example 10

Synthesis of Bpin-Tips-Tetracene 5

To a 20 mL sealed tube was added Bromo tetracene derivative 4 (1.0 g, 1.5 mmol, 1.0 equiv.), bis(pinacolato) diboron (0.58 g, 2.3 mmol, 1.5 equiv.), Pd(dppf)Cl$_2$.DCM (61 mg, 0.07 mmol, 0.05 equiv.) and KOAc (0.52 g, 5.3 mmol, 3.5 equiv.). This tube was degassed by sequential vacuum and argon, followed by the addition of dry and degassed dioxane (7 mL). The mixture was heated to 85° C. and maintained for 14 h in the dark. The reaction mixture was partitioned between water (50 ML) and DCM (50 mL). The aqueous layer was extracted with DCM (50 mL). The combined organic phase was dried over $Na_2SO_4$, filtered and solvent removed under reduced pressure. The crude reaction mixture was purified by silica column chromatography using a mixture of hexanes and DCM as eluent to yield 320 mg (30% yield) of bright red product.

Characteristics:

$^1$H-NMR (500 MHz, CDCl$_3$, δ ppm): 9.44 (s, 1H), 9.39 (s, 1H), 8.76-8.72 (m, 2H), 8.66 (s, 1H), 8.09-8.07 (m, 1H), 7.89-7.87 (m, 1H), 7.64-7.62 (m, 2H), 1.49 (s, 12H) and 1.43-1.37 (m, 42H).

$^{13}$C-NMR (125 MHz, CDCl$_3$, δ ppm): 137.8, 133.1, 132.9, 132.8, 131.7, 130.96, 130.4, 129.8, 127.6, 127.5, 127.4, 126.9, 126.7, 126.1, 119.1, 118.6, 106.2, 105.9, 103.9, 103.8, 84.1, 24.9, 19.1, 19.0 and 11.7

MS (ESI): Calculated: 714.4465; Observed: 714.4460.

Example 11

Synthesis of Pentacene-Tetracene Dimer PT

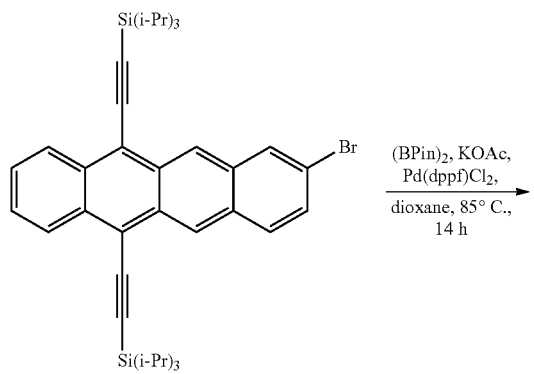

4

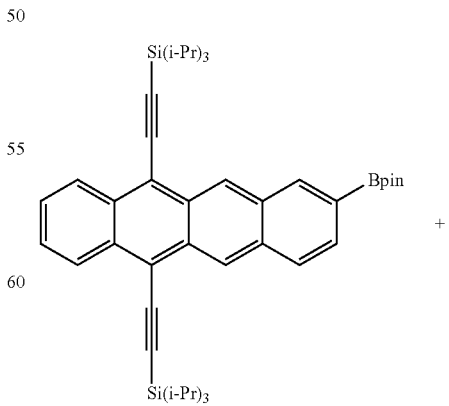

5

Example 12

Synthesis of Pentacene-Anthracene Dimer PA

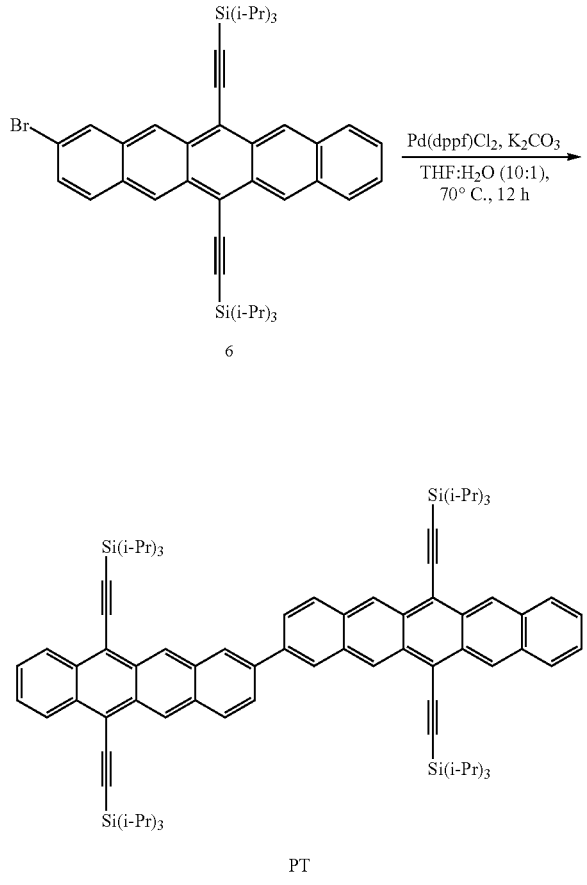

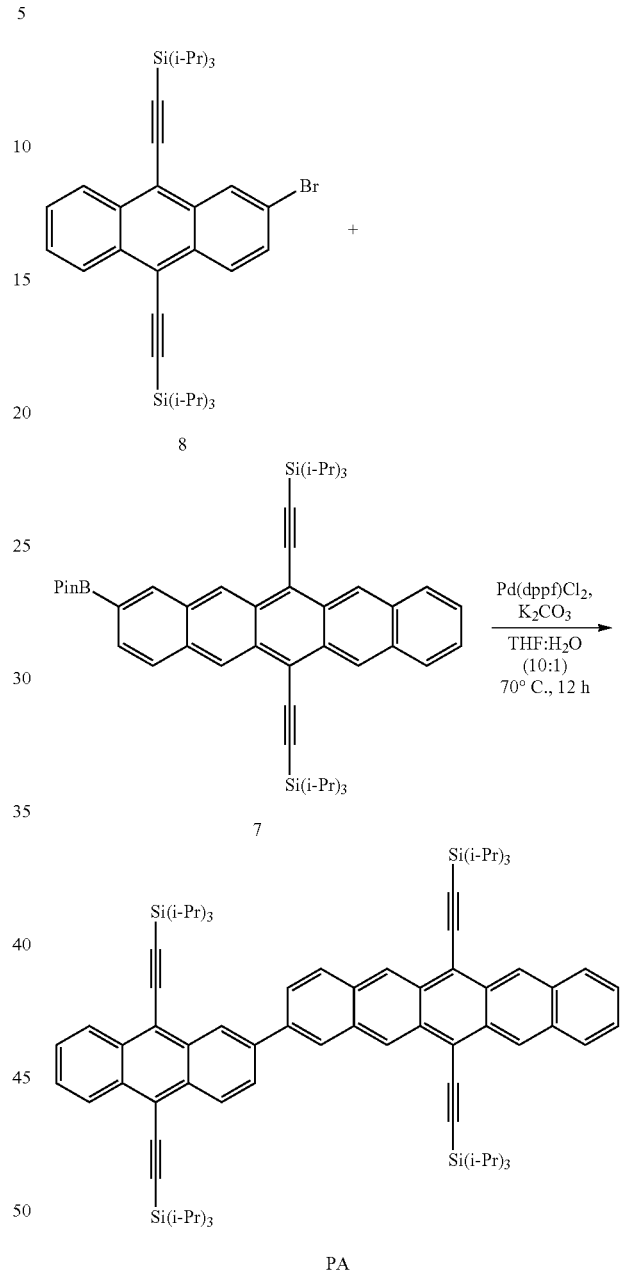

To a sealed tube was added bromo pentacene derivative 6 (100 mg, 0.12 mmol, 1 equiv.), Bpin-tetracene derivative 5 (96 mg, 0.14 mmol, 1.2 equiv.), Pd(dppf)Cl$_2$DCM (9.8 mg, 0.01 mmol, 0.1 equiv.), and K$_2$CO$_3$ (282 mg, 2.04 mmol, 17 equiv.). Sequential vacuum and argon were used to degas the solids, followed by the addition of degassed THF (10 mL) and degassed water (1 mL). The mixture was heated to 70° C. and maintained for 12 h in the dark. The crude reaction mixture was concentrated and purified by chromatography on silica gel (DCM:Hexanes) to yield 55 mg of dark reddish brown solid (37% yield).

Characteristics:

$^1$H-NMR (500 MHz, CDCl$_3$, δ ppm): 9.45-9.35 (m, 6H), 8.69-8.67 (m, 2H), 8.41-8.37 (m, 2H), 8.23-8.17 (m, 2H), 8.03-7.94 (m, 4H), 7.61-7.59 (m, 2H), 7.46-7.44 (m, 2H) and 1.44-1.37 (m, 84H).

$^{13}$C-NMR (125 MHz, CDCl$_3$, 50° C., δ ppm): 137.9, 137.8, 132.9, 132.8, 132.5, 132.4, 131.6, 130.9, 130.7, 129.6, 129.5, 128.6, 127.5, 126.8, 126.7, 126.69, 126.3, 126.2, 126.0, 125.9, 118.8, 118.7, 107.4, 107.2, 106.1, 105.96, 104.8, 104.1, 104.06, 29.7, 19.01, 19.00, 18.96, 18.94, 11.8 and 11.7.

MS (ESI): Calculated: 1224.7215; Observed: 1224.7212.

To a sealed tube was added bromo anthracene derivative 8 (129 mg, 0.18 mmol, 1.2 equiv.), Bpin-pentacene derivative 7 (100 mg, 0.15 mmol, 1.0 equiv.), Pd(dppf)Cl$_2$DCM (12.2 mg, 0.015 mmol, 0.1 equiv.), and K$_2$CO$_3$ (352 mg, 2.55 mmol, 17 equiv.). Sequential vacuum and argon were used to degas the solids, followed by the addition of degassed THF (45 mL) and degassed water (5 mL). The mixture was heated to 70° C. and maintained for 12 h in the dark. The crude reaction mixture was concentrated and purified by chromatography on silica gel (DCM:Hexanes) to yield 120 mg of green solid (68% yield).

Characteristics:

$^1$H-NMR (500 MHz, CDCl$_3$, δ ppm): 9.39-9.36 (m, 4H), 9.10 (s, 1H), 8.84-8.82 (m, 1H), 8.72-8.69 (m, 2H), 8.36 (s, 1H), 8.14-8.11 (m, 2H), 8.03-8.01 (m, 2H), 7.96-7.94 (m, 1H), 7.68-7.66 (m, 2H), 7.47-7.45 (m, 2H), 1.44-1.41 (m, 42H) and 1.35-1.33 (m, 42H).

$^{13}$C-NMR (125 MHz, CDCl$_3$, 50° C., δ ppm): 138.9, 138.1, 132.8, 132.7, 132.6, 132.5, 132.4, 132.3, 131.8, 131.6, 130.95, 130.9, 130.8, 130.7, 129.4, 128.7, 128.1, 127.4, 127.3, 127.0, 126.9, 126.7, 126.65, 126.54, 126.4, 126.37, 126.3, 126.1, 125.5, 119.0, 118.7, 118.5, 118.4, 107.4, 1-7.2, 105.4, 104.9, 104.7, 103.5, 103.3, 19.1, 19.0, 18.97, 18.94, 11.7, 11.6 and 11.5.

MS (ESI): Calculated: 1174.7059; Observed: 1174.7051.

Example 13

Synthesis of Bromo Anthraquinone 12

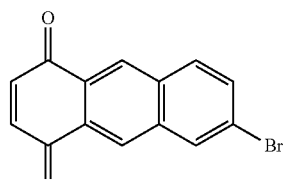

To a 250 mL round bottom flask was added benzoquinone 11 (30.2 g, 280 mmol, 7 equiv.), bromo derivative 2 (20.0 g, 40 mmol, 1.0 equiv.) and KI (26.5 g, 160 mmol, 4.0 equiv.). Sequential vacuum and argon were used to degas the solids, at which point dry and degassed DMF (360 mL) was added and the reaction was stirred at 110° C. for 18 h. The mixture was cooled and poured into 1:1 water methanol mixture (400 mL). The resulting precipitate was filtered, then placed in a separatory funnel where it was separated between 1 L of DCM and 1 L of water. The solvent was removed in vacuo and loaded onto a silica gel column, where elution with DCM:hexanes yielded 4.8 g of yellowish orange powder product (42% yield).

Characteristics:

$^1$H-NMR (500 MHz, CDCl3, δ ppm): 8.62 (s, 1H), 8.55 (s, 1H), 8.26-8.25 (m, 1H), 7.97-7.95 (m, 1H), 7.80-7.78 (m, 1H) and 7.11 (s, 2H).

$^{13}$C-NMR (125 MHz, CDCl3, δ ppm): 184.3, 140.1, 140.0, 135.8, 133.2, 133.1, 132.2, 131.6, 129.2, 128.8, 128.7, 127.7, 124.2.

MS (ESI): Calculated: 286.9708; Observed: 286.9699.

Example 14

Synthesis of Bromo Hexacenequinone 13

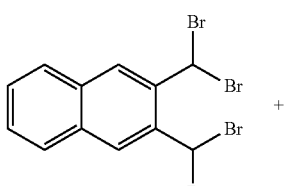

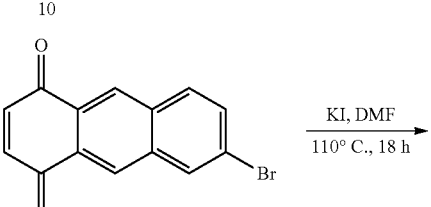

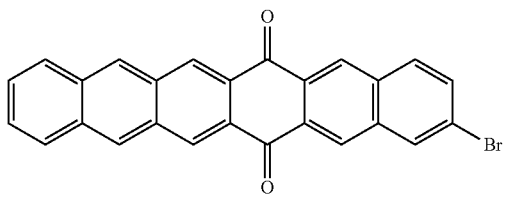

To a 250 mL RBF were added naphthalene tetrabromide 10 (2.13 g, 4.5 mmol, 1.0 equiv.), 6-bromoanthracene-1,4-dione 12 (1.3 g, 4.5 mmol), and KI (3.0 g, 18 mmol, 4.0 equiv.). Sequential vacuum and argon were used to remove oxygen followed by the addition of dry and degassed DMF (100 mL). The mixture was heated at 110° C. for 18 h after which it was cooled to room temperature, poured into DI water (100 mL) and filtered. The solid was washed with methanol (50 mL), dichloromethane (150 mL), water (50 mL) until the filtrate was clear to yield 400 mg of brown solid product (20% yield).

No characterization was carried out due to limited solubility of the product.

Example 15

Synthesis of Bromo Hexacene 14

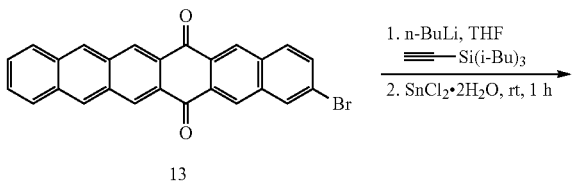

-continued

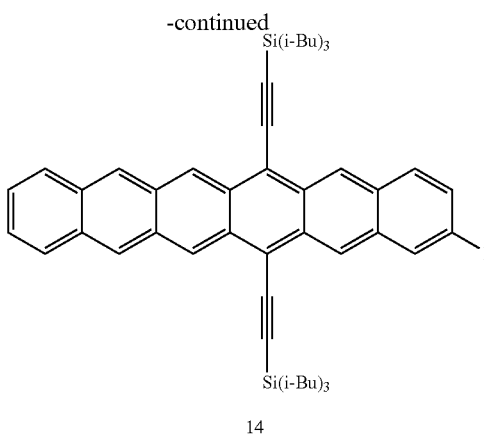

14

To a 250 mL schlenk flask was added tri-isobutylsilylacetylene (1.7 g, 5 equiv.) and hexanes (25 mL). The mixture was cooled to 0° C. under argon and 2.5 Mn-butyl lithium solution in hexanes (2.9 mL, 7.15 mmol, 4.8 equiv.) were added and the mixture was stirred one hour. To this solution bromo hexacenequinone 13 (650 mg, mmol, 1.0 equiv.) was added as well as dry, degassed hexanes (70 mL) and THF (10 mL). This solution was stirred at room temperature overnight and the solvent was then removed in vacuo. The crude reaction mixture was purified in a silica plug first eluting with hexanes to remove excess acetylene followed by DCM to obtain bromo-hexacene diol product.

The bromo-hexacene diol was dissolved in dry and degassed THF (20 mL) to which a solution of excess $SnCl_2.2H_2O$ in 10 mL of 10% aq.HCl was added at room temperature and stirred in the dark until TLC indicated completion of the reduction (~1 h). Extraction between DCM and water (50 mL each) followed by drying of the organic phase over $NaSO_4$ and removal of solvent in vacuo gave a crude green solid which was purified by column chromatography to yield 236 mg of green powder (19% yield).

Characteristics:

$^1$H-NMR (500 MHz, $CDCl_3$, δ ppm): 9.59-9.58 (m, 2H), 9.19 (s, 1H), 9.13 (s, 1H), 8.64-8.63 (m, 2H), 8.12 (s, 1H), 7.97-7.96 (m, 2H), 7.83-7.81 (m, 1H), 7.47-7.45 (m, 1H), 7.37-7.35 (m, 2H), 2.32-2.25 (m, 6H), 1.29-1.28 (36H) and 1.07-1.05 (m, 12H).

$^{13}$C-NMR (125 MHz, $CDCl_3$, δ ppm): 132.9, 132.4, 132.3, 131.2, 130.9, 130.8, 130.5, 130.4, 130.3, 130.2, 129.7, 128.5, 126.9, 126.8, 126.7, 126.6, 125.63, 125.62, 125.5, 120.4, 118.5, 118.4, 110.95, 110.8, 104.8, 104.7, 26.6, 25.5 and 25.4.

MS (ASAP): Calculated: 851.4043; Observed: 851.4044.

Example 16

Synthesis of Pentacene-Hexacene Dimer PH

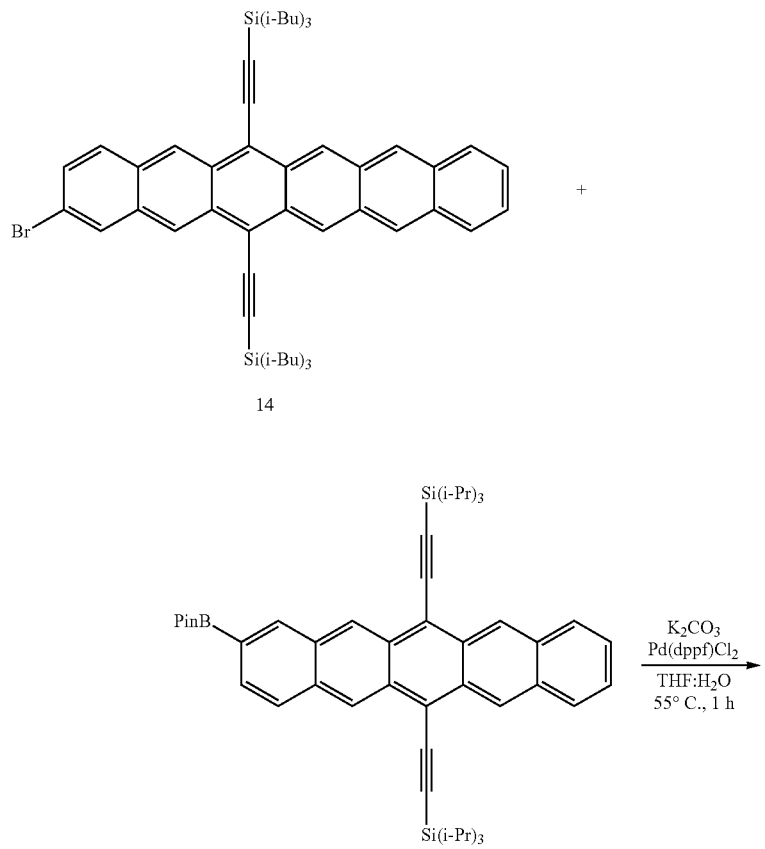

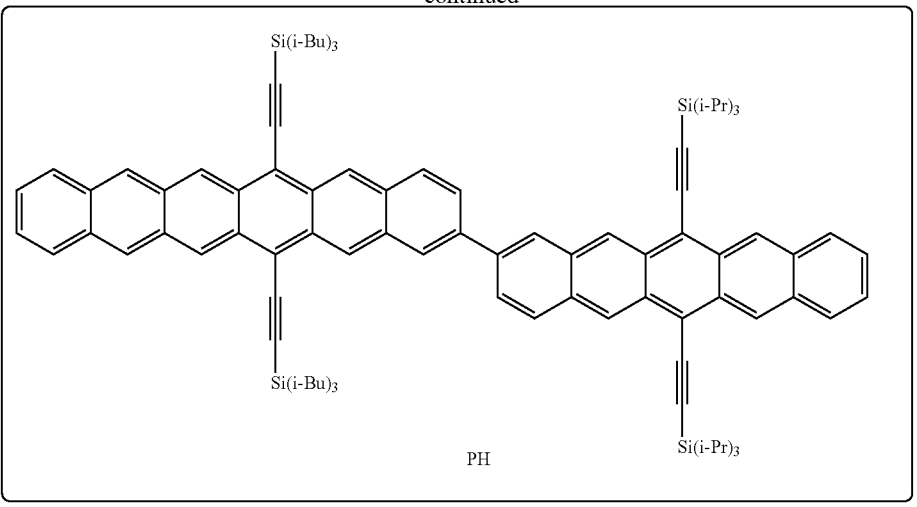

To a dry round bottomed flask was added bromohexacene derivative 14 (30 mg, 0.035 mmol, 1.0 equiv), Bpin pentacene derivative 7 (32 mg, 0.042 mmol, 1.2 equiv.) $K_2CO_3$ (83 mg, 0.6 mmol, 17 equiv.) and Pd(dppf)$Cl_2$.DCM (2.9 mg, 0.0035 mmol, 0.1 equiv.). Sequential vacuum and argon were used to degas the mixture followed by the addition of degassed THF and $H_2O$ (9:1 ratio, 20 mL). The mixture was heated to 55° C. and maintained for 1.5 h in the dark. The reaction was cooled to room temperature, concentrated and the crude was purified using by silica chromatography using mixtures of hexanes/DCM as an eluent to obtain the product as a purple solid (30 mg, 60%).

The column was run quickly and using $N_2$ pressure instead of air. The solvent was evaporated under dark and stored under argon and in dark. The spectroscopic measurements were undertaken shortly after purification, and repeated twice to ensure reproducibility. The product decomposed over 2 months, as evidenced from its green color even when stored under argon and away from light.

Characteristics:

$^1$H-NMR (500 MHz, CDCl$_3$, δ ppm): 9.59 (s, 2H), 9.41 (s, 1H), 9.37-9.35 (m, 3H), 9.32 (s, 1H), 9.27 (s, 1H), 8.64 (s, 2H), 8.34-8.29 (m, 2H), 8.18-8.16 (m, 1H), 8.12-8.10 (m, 1H), 8.03-8.01 (m, 2H), 7.97-7.91 (m, 4H), 7.46-7.44 (m, 2H), 7.36-7.34 (m, 2H), 2.34-2.26 (m, 6H), 1.45-1.43 (m, 42H), 1.30-1.29 (m, 36H) and 1.08-1.06 (m, 12H).

$^{13}$C-NMR (125 MHz, CDCl$_3$, δ ppm): 137.8, 137.64, 137.60, 136.1, 135.9, 132.7, 132.5, 132.4, 132.33, 132.31, 131.8, 131.6, 131.4, 131.35, 131.2, 131.0, 130.9, 130.8, 130.78, 130.76, 130.7, 130.43, 130.3, 130.2, 129.6, 129.5, 128.9, 128.5, 126.9, 126.8, 126.7, 126.6, 126.4, 126.36, 126.33, 126.21, 126.19, 126.08, 126.0, 125.8, 125.5, 118.5, 118.4, 118.2, 110.6, 110.5, 107.4, 107.2, 105.0, 104.9, 104.72, 104.67, 29.7, 26.65, 25.53, 25.52, 25.49, 19.07, 19.05 and 11.73.

MS (APCI): Calculated: 1408.8441; Observed: 1408.8467.

Example 17

Synthesis of Oligo-Poly(2,[9/10]-Pentacene)S

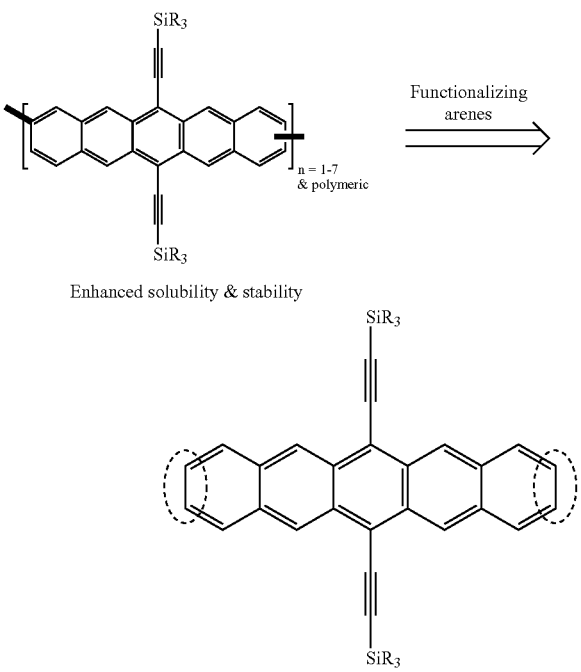

Shown in Scheme 2, coupling occurred at the 2,[9/10] positions, which for retention of the solubilizing/stabilizing functionalities at the 6 and 13 positions on every monomer unit in the oligomer. This strategy overcame previous limitations, finally allowing for synthesis and characterization of well-defined conjugated oligomers of pentacenes (n=1-7), in addition to a soluble homopolymer of pentacene by step-growth polymerization. The SiR$_3$ groups enhanced solubility and stability.

The building blocks shown in Scheme 3 (FIG. 75) were designed to access well-defined pentacene oligomers and polypentacene, which are synthesized in multi-gram scales, and are soluble and stable. All materials stem from the primary pentacenes 1A and 1A2,[82] which are borylated to 1B and 1B2 under mild conditions. Using these four primary building blocks, the secondary and tertiary building blocks are synthesized in good yields. Subsequent palladium-catalyzed cross-couplings in the combinations shown in Scheme 3 yield the oligopentacenes of interest.

However, NMR spectroscopic characterization of oligomers >4Pc was hampered by peak broadening which was prevalent even at elevated temperature (1H-NMR at 50° C.). This peak broadening is the result of several factors such as the presence of regioisomers, similar location of aromatic protons on adjacent pentacenes and decreasing symmetry in higher oligomers.[105] In order to definitively assign the identity of the oligomers 4-7Pc, 1H-NMR was corroborated by MALDI mass spectrometry.

Scheme 5

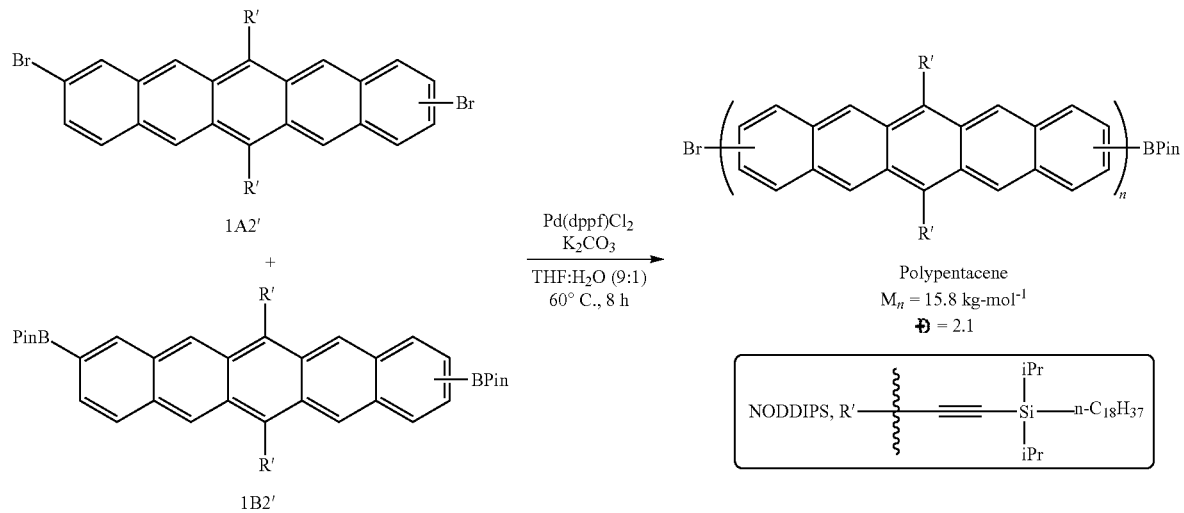

Initial attempts to synthesize oligopentacenes contained triisopropylsilylethynyl groups (TIPS) as the solubilizing unit. Unfortunately, TIPS was not sufficiently solubilizing for pentacene oligomers with more than three repeat units. To overcome this problem, n-octyl-diisopropylsilylethynyl (NODIPS), which Anthony and co-workers had previously demonstrated as a better solubilizing group for pentacenes was used.[93] The synthesis of the pentacene core has been well-established in the literature and is detailed in the supporting information.[46,55,94-104] The oligopentacenes exhibit excellent solubility in solvents such as THF and chlorinated solvents (DCM and chloroform).

Figure 75:
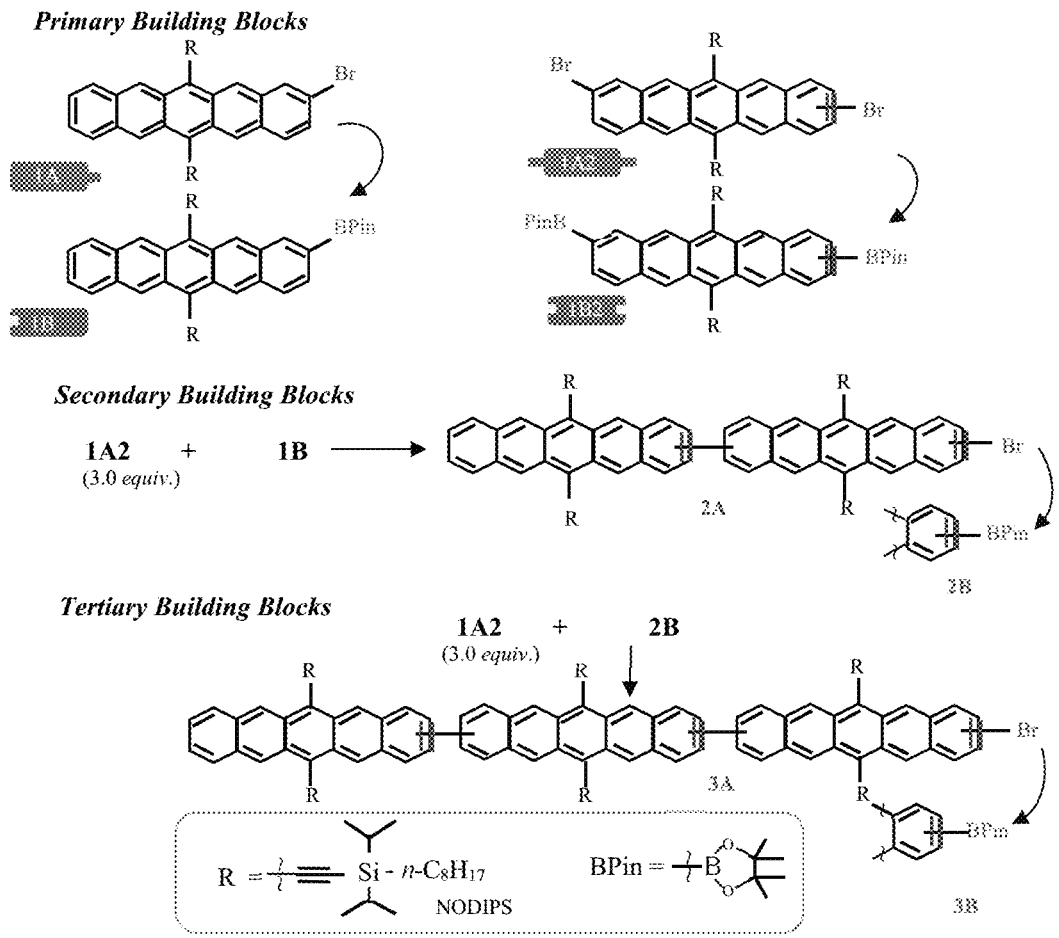
FIG. 75 shows building blocks for oligopentacenes and an oligopentacene synthesis approach.
Figure 75:
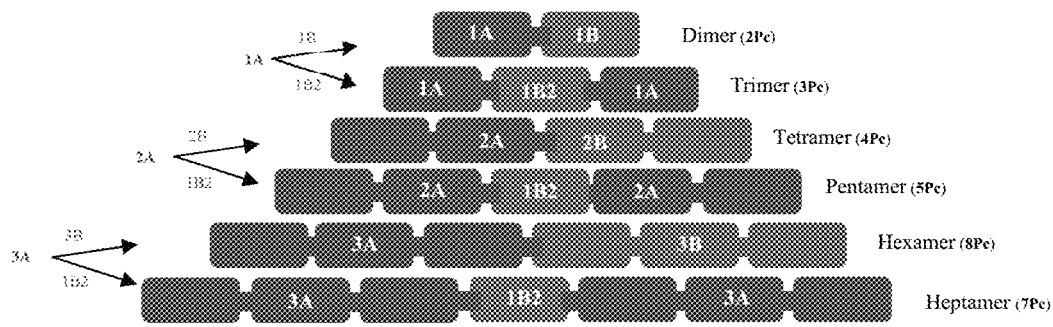
Figure 75:
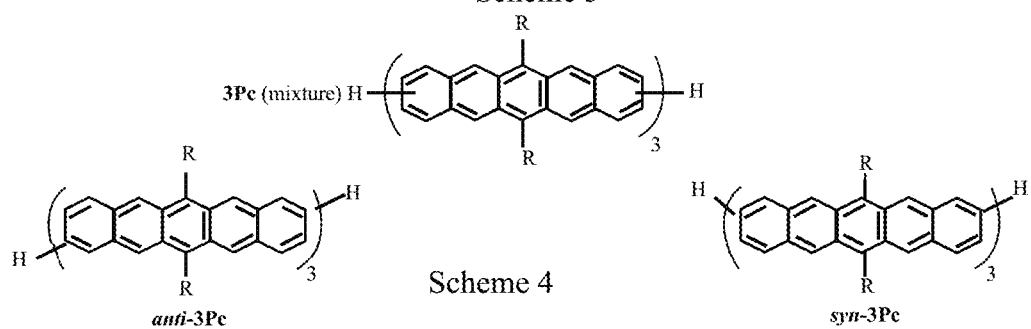

While this synthetic strategy is modular in nature and allows synthesis of higher oligomers, the products are regioisomeric mixtures because 1A2 is a mixture of 2,9-dibromopentacene (anti) and 2,10-dibromopentacene (syn) derivatives.[105] The effect of this regioisomerism on the properties of the resultant oligomers were explored. The two regioisomers of the trimer, syn-3Pc and anti-3Pc (Scheme 4; FIG. 75), were synthesized using Bao and coworker's selective crystallization strategy for regiopure syn and anti-dibromopentacenequinone.[106] The properties of these regiopure trimers were compared. Beyond trimers, exhaustive exploration of possible regioisomers was precluded by the exponentially increasing number of regioisomers, as well as the many steps and difficulties in acquiring large quantities of regiopure dibromoquinone starting material.

The oligomers up to 3Pc were readily characterized by NMR spectroscopy and high-resolution mass spectrometry.

Figure 76:
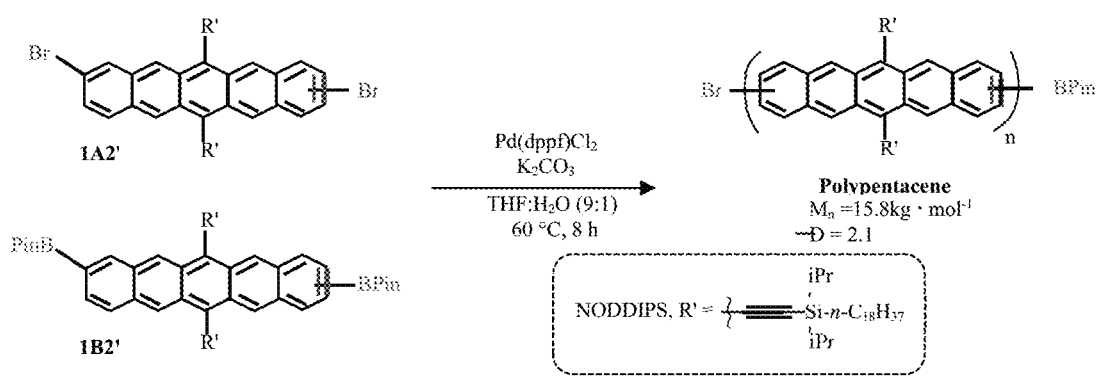
FIG. 76 shows a method of synthesizing a pentacene homopolymer.

An effort to obtain polypentacene was carried out by step-growth polymerization of 1A2 and 1B2. The initial attempt on polymerization at 65° C. for 3 days resulted in an insoluble black solid. Reduction of the temperature or reaction time only resulted in oligomers of pentacenes as determined by mass spectrometry. This result indicated that the NODIPS chain is insufficient to produce soluble polypentacenes. Therefore the C-8 chain in NODIPS was substituted with a C-18 chain to create the stronger solubilizing group, n-octadecyl-diisopropylsilylethynyl (NODDIPS). The polymerization was carried out between 1A2' and 1B2' at 60° C. to obtain a pentacene homopolymer (Scheme 5; FIG. 76). The reaction time was limited to 8 h to access soluble polymers. The reaction mixture was precipitated into methanol and the solid was purified by Soxhlet extraction, consecutively with hexanes, chloroform and chlorobenzene. The molecular weight of the polypentacene from the chlorobenzene fraction was determined by gel permeation chromatography (GPC) using hot 1,2,4-trichlorochlorobenzene (150° C.) as the eluent against polyethylene standards. The polypentacene was found to have a number average molecular weight (Mn) of ~15.8 kg·mol$^{-1}$ with Đ=2.1.

Example 18

Synthesis of Building Blocks for Oligopentacenes

Figure 77:
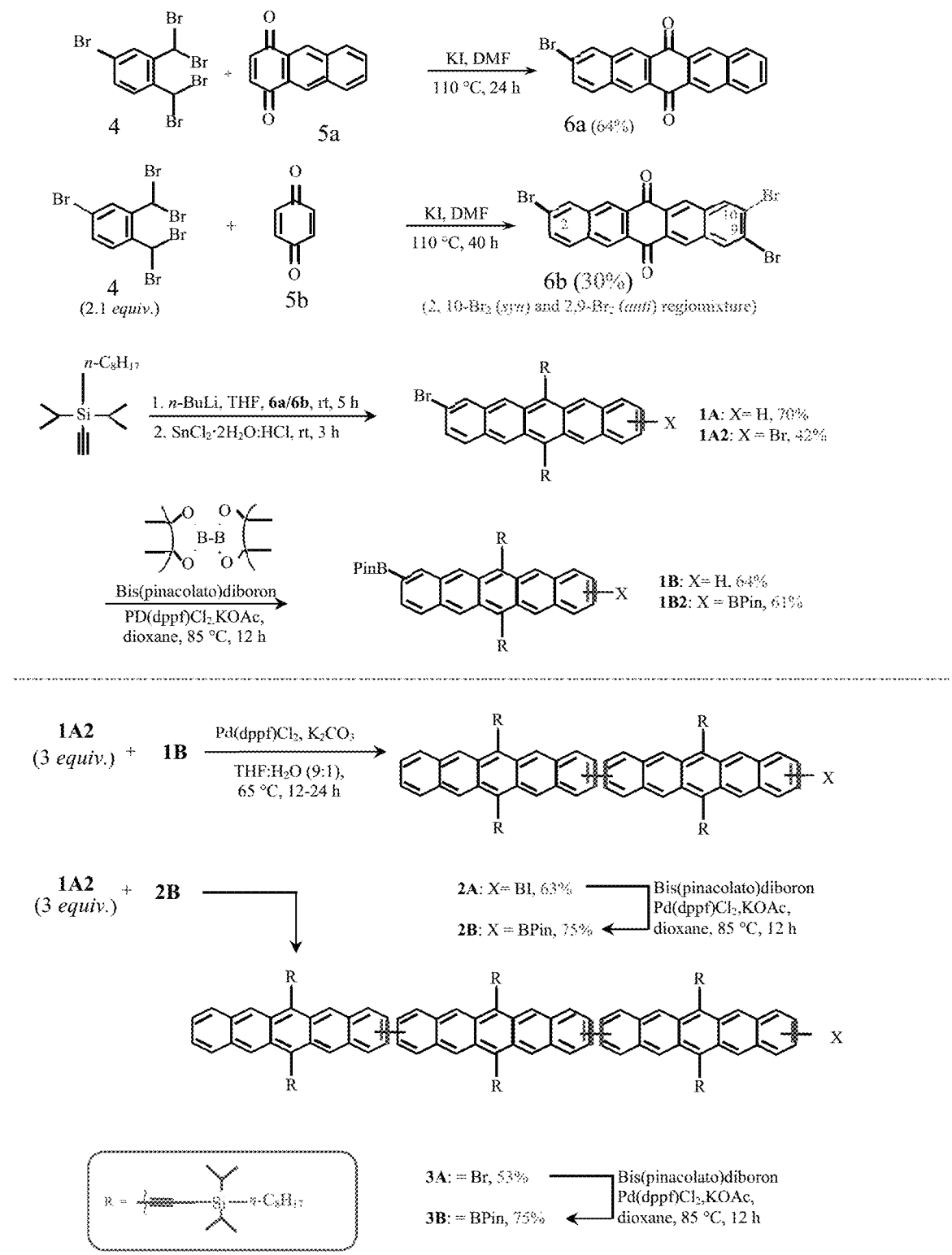
FIG. 77 shows a method of synthesizing Compounds 6a and 6b.

Compounds 6a and 6b were synthesized according to a procedure reported in the literature.[55,82] (FIG. 77)

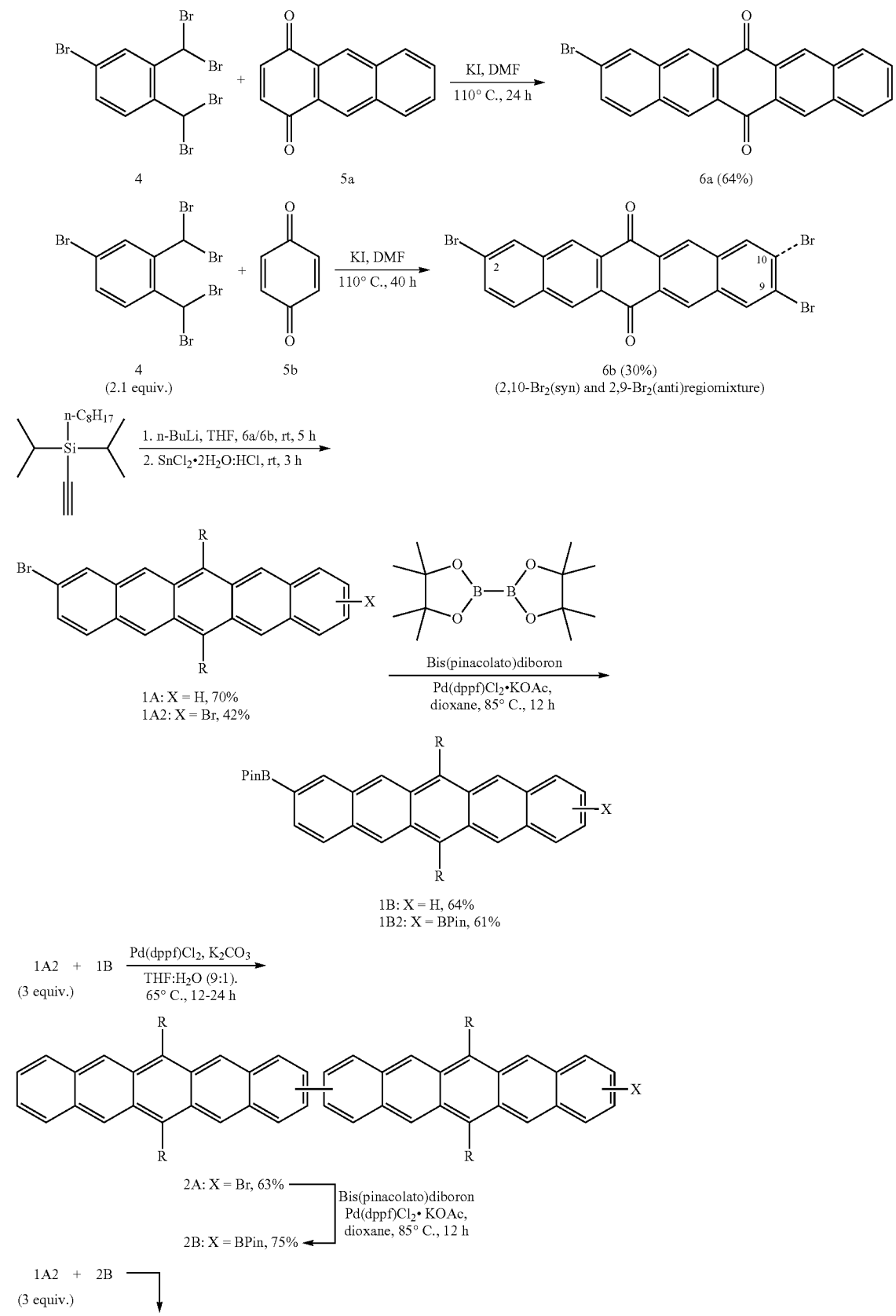

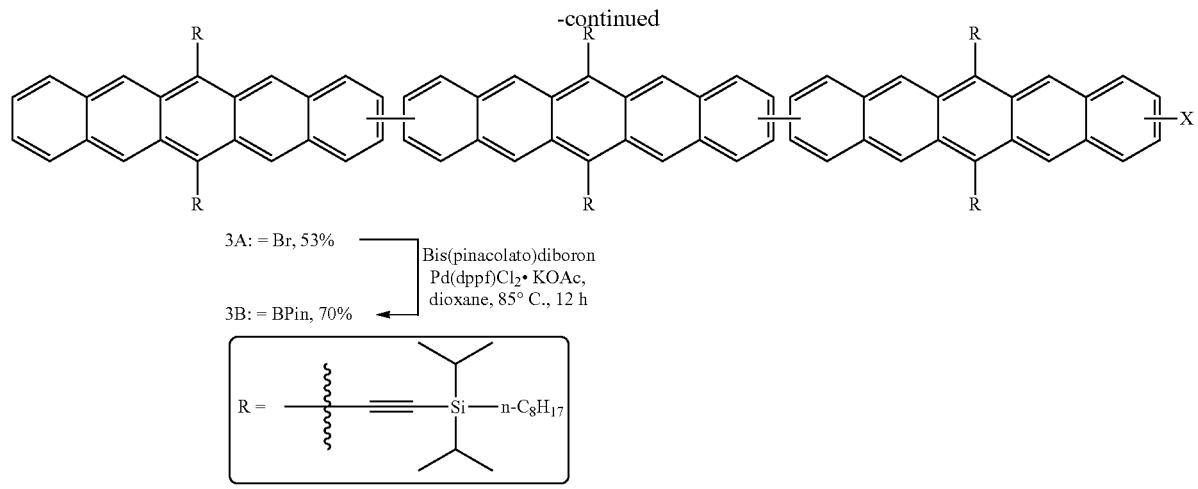

3A: = Br, 53%
3B: = BPin, 70%

Bis(pinacolato)diboron
Pd(dppf)Cl$_2$• KOAc,
dioxane, 85° C., 12 h

R = —C≡C—Si(iPr)$_2$—n-C$_8$H$_{17}$

Example 19

Synthesis of Oligopentacenes

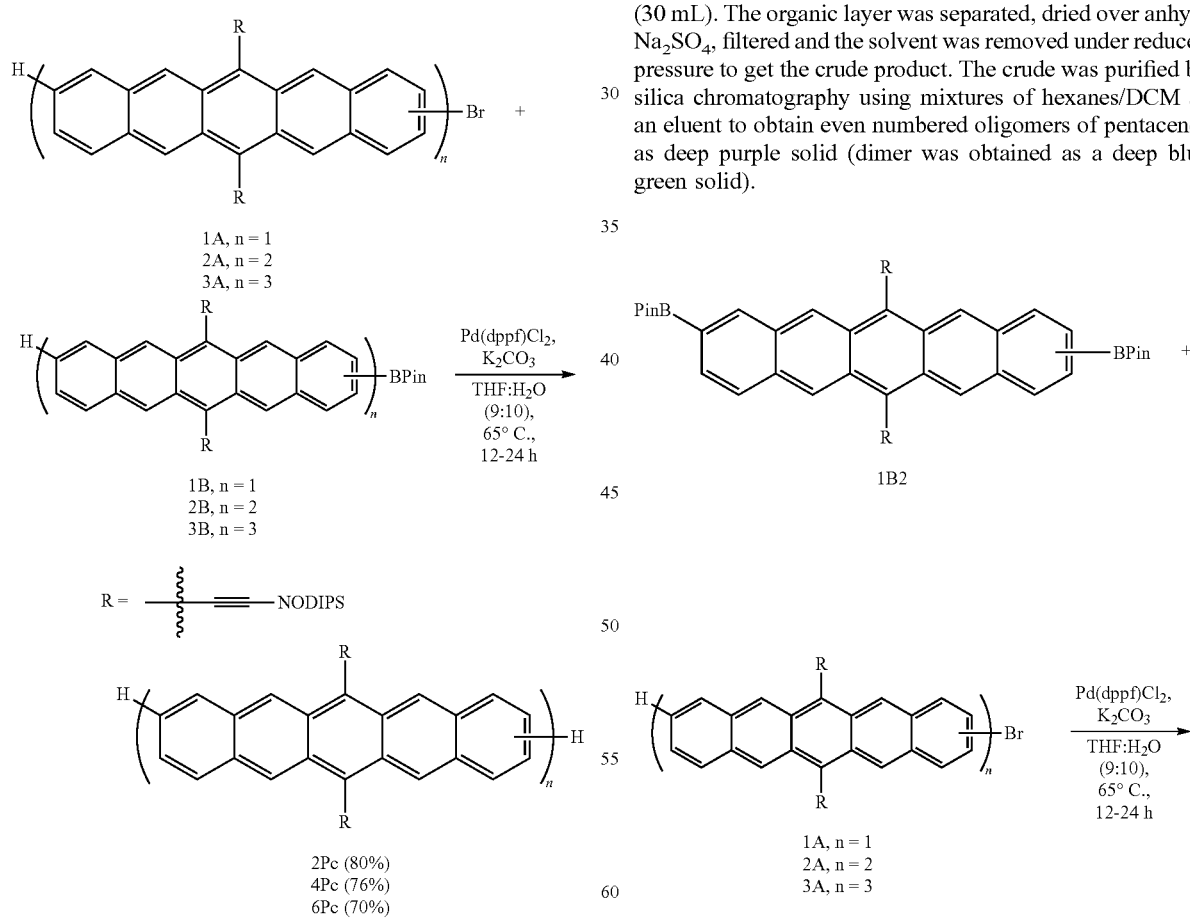

1A, n = 1
2A, n = 2
3A, n = 3

1B, n = 1
2B, n = 2
3B, n = 3

R = —C≡C—NODIPS

2Pc (80%)
4Pc (76%)
6Pc (70%)

1A, n = 1
2A, n = 2
3A, n = 3

R = —C≡C—NODIPS

Even numbered oligopentacenes: A mixture of bromopentacene derivative 1A/2A/3A (100 mg, 1.0 equiv.), BPin-pentacene derivative 1B/2B/3B (1.2 equiv.), Pd(dppf)Cl$_2$.DCM (4 mg, 5 mol %), and K$_2$CO$_3$ (5 equiv.) in a dry round bottom flask was subjected to sequential vacuum and argon to degas the mixture followed by the addition of degassed H$_2$O (2 mL) and THF (18 mL). The resulting solution was heated to 65° C. and maintained for 24 h in dark. After the reaction, the solution was poured into a separatory funnel containing chloroform (30 mL) and water (30 mL). The organic layer was separated, dried over anhyd. Na$_2$SO$_4$, filtered and the solvent was removed under reduced pressure to get the crude product. The crude was purified by silica chromatography using mixtures of hexanes/DCM as an eluent to obtain even numbered oligomers of pentacenes as deep purple solid (dimer was obtained as a deep blue green solid).

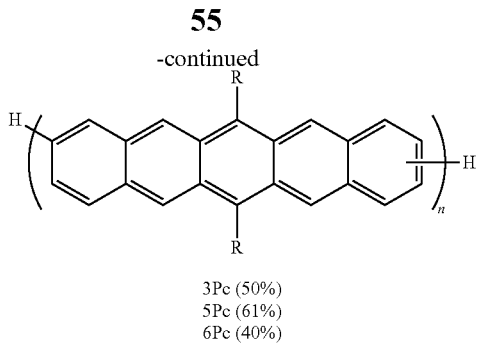

3Pc (50%)
5Pc (61%)
6Pc (40%)

Odd numbered oligopentacenes: Similar procedure followed for the synthesis of odd numbered oligopentacenes except the 2.3 equiv. of bromo derivatives of pentacenes 1A/2A/3A were used.

Proton NMR ($^1$H-NMR), carbon-13 NMR ($^{13}$C-NMR), and mass spectra for the prepared oligoacenes may be found at FIGS. 38-58.

Characteristics:

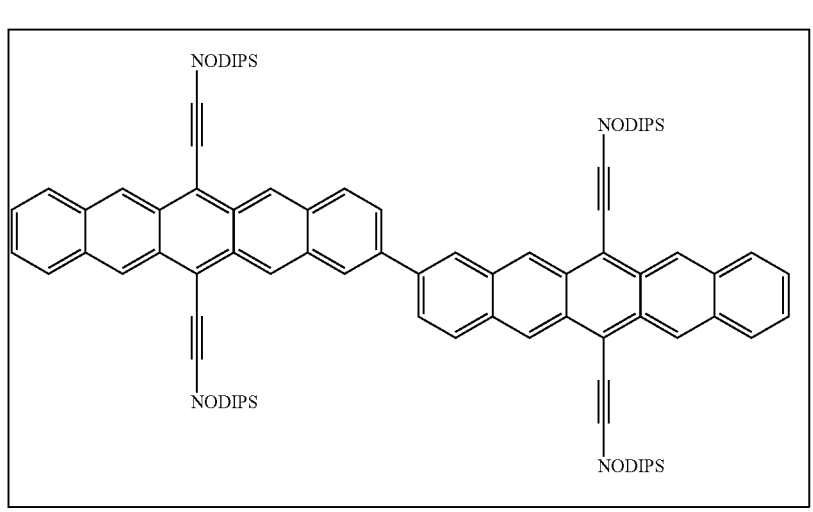

2Pc $^1$H-NMR (500 MHz, CDCl$_3$, δ ppm): 9.43-9.35 (m, 8H), 8.39 (s, 2H), 8.20-8.18 (m, 2H), 8.05-8.03 (m, 4H), 7.97-7.97 (m, 2H), 4.47-7.45 (m, 4H), 1.87-1.79 (m, 8H), 1.87-1.79 (m, 8H), 1.60-1.54 (m, 8H), 1.44-1.38 (m, 66H), 1.32-1.21 (m, 22H), 1.04-1.00 (m, 8H), 0.89-0.87 (m, 6H) and 0.79-0.78 (m, 6H).

$^{13}$C-NMR (125 MHz, CDCl$_3$, δ ppm): 137.6, 132.5, 132.4, 132.35, 131.6, 131.0, 130.9, 130.8, 130.7, 129.6, 128.7, 126.9, 126.4, 126.2, 126.1, 125.9, 118.5, 118.4, 107.7, 107.5, 104.6, 104.5, 34.1, 34.05, 32.0, 31.9, 29.6, 29.5, 29.4, 29.39, 25.1, 24.99, 22.7, 22.6, 18.8, 18.75, 18.5, 18.48, 14.1, 14.0, 12.2, 10.5 and 10.5.

MS (ESI): Calculated [M]$^+$: 1555.0461; Observed: 1555.0502.

Characteristics:

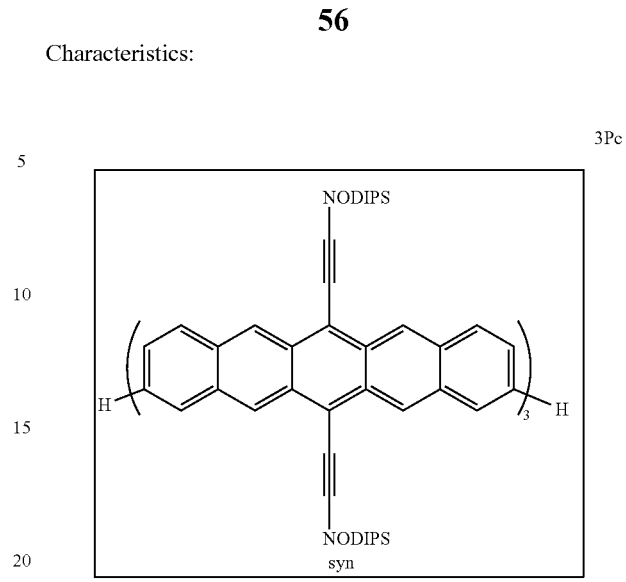

3Pc $^1$H-NMR (500 MHz, CDCl$_3$, δ ppm): 9.41-9.33 (m, 12H), 8.35-8.32 (m, 4H), 8.19-8.18 (m, 4H), 8.03-8.00 (m, 4H), 7.96-7.94 (m, 4H), 7.45-7.40 (m, 4H), 1.87-1.81 (m, 12H), 1.62-1.55 (m, 12H), 1.49-1.39 (m, 105H), 1.31-1.29 (m, 22H), 1.05-1.01 (m, 12H), 0.92-0.87 (m, 12H), 0.79-0.77 (m, 8H) and 0.70-0.68 (m, 3H).

$^{13}$C-NMR (125 MHz, CDCl$_3$, δ ppm): 137.5, 137.4, 132.5, 132.4, 132.36, 132.3, 131.6, 131.5, 131.1, 131.0, 130.9, 130.86, 130.7, 130.6, 129.6, 128.7, 126.9, 126.85, 126.3, 126.2, 126.1, 125.83, 125.80, 118.7, 118.5, 118.3, 107.8, 107.6, 107.5, 104.7, 104.6, 104.54, 104.51, 34.2, 34.1, 34.08, 34.06, 32.0, 31.9, 31.87, 31.6, 29.6, 29.56, 29.54, 29.51, 29.49, 29.44, 29.41, 29.39, 26.2, 25.1, 25.06, 25.0, 24.99, 24.8, 22.7, 22.67, 22.63, 22.59, 18.84, 18.83, 18.79, 18.76, 18.55, 18.52, 18.49, 14.14, 14.12, 14.05, 14.03, 13.95, 12.26, 12.25, 12.22, 10.56, 10.52 and 10.51.

MALDI: Calculated: 2331.57; Observed: 2332.54.

Characteristics:

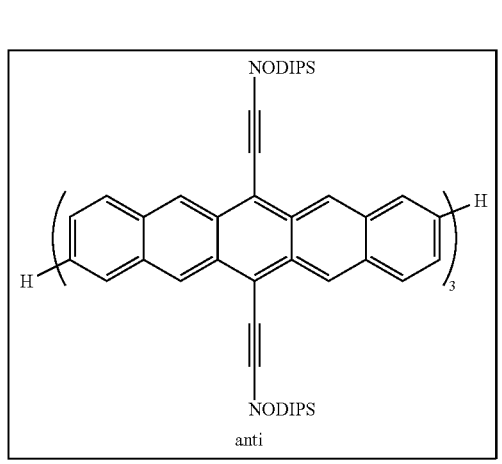
3Pc
anti

¹H-NMR (400 MHz, CDCl₃, δ ppm): 9.42-9.33 (m, 12H), 8.37 (m, 4H), 8.21-8.17 (m, 4H), 8.04-7.95 (m, 8H), 7.46-7.41 (m, 4H), 1.88-1.79 (m, 12H), 1.62-1.54 (m, 13H), 1.47-1.38 (m, 98H), 1.32-1.19 (m, 31H), 1.08-1.00 (m, 14H), 0.89-0.86 (m, 6H) and 0.81-0.76 (m, 12H).

¹³C-NMR (125 MHz, CDCl₃, δ ppm): 136.5, 136.48, 136.45, 132.3, 132.23, 132.21, 132.19, 131.7, 131.6, 131.5, 130.9, 130.92, 130.88, 130.85, 130.7, 130.6, 129.4, 128.57, 128.54, 126.9, 126.86, 126.3, 126.2, 125.9, 125.8, 125.5, 125.4, 125.3, 118.4, 118.3, 107.4, 107.36, 107.29, 104.7, 104.6, 34.18, 34.14, 34.1, 32.0, 31.96, 31.95, 29.58, 29.56, 29.52, 29.45, 29.43, 29.42, 25.1, 25.07, 25.0, 22.7, 22.66, 22.64, 18.9, 18.85, 18.8, 18.6, 18.56, 18.53, 14.1, 14.06, 14.0, 12.32, 12.28, 12.25, 10.62, 10.57 and 10.55.

MALDI: Calculated: 2331.57; Observed: 2332.46.

Characteristics:

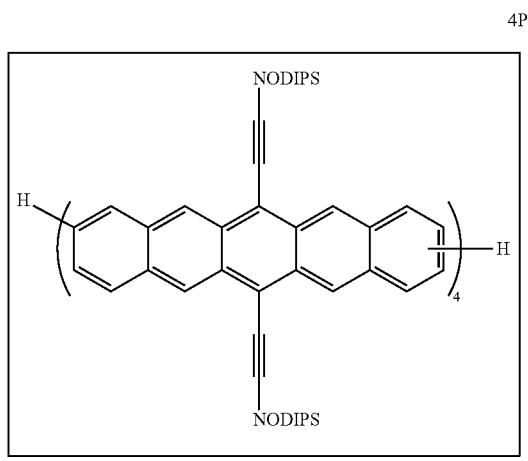
4Pc

¹H-NMR (500 MHz, 50° C., CDCl₃, δ ppm): 9.44-9.34 (m, 16H), 8.38 (s, 6H), 8.18 (s, 6H), 8.01-7.97 (m, 10H), 7.44 (s, 4H), 1.87-1.83 (m, 18H), 1.62-1.21 (m, 200H) and 0.89-0.79 (m, 30H).

MALDI: Calculated: 3108.08; Observed: 3109.14.

Characteristics:

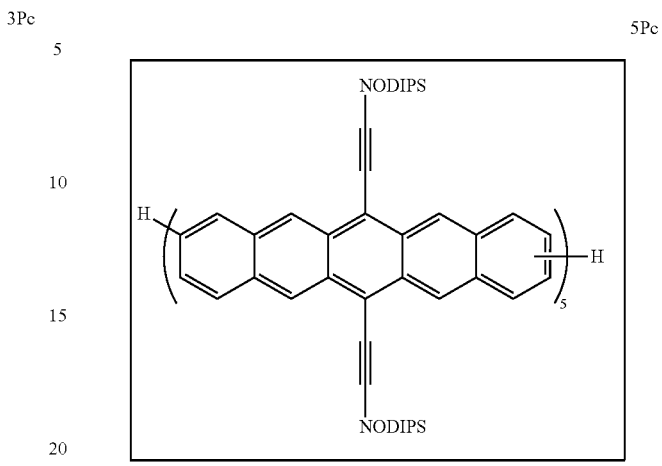
5Pc

¹³C-NMR ((500 MHz, 50° C., CDCl₃, δ ppm): 9.38-9.34 (s, 20H), 8.39 (s, 8H), 8.18 (s, 8H), 7.97 (s, 12H), 7.44-7.42 (m, 4H), 1.87 (m, 21H), 1.61-1.03 (m, 258H) and 0.89-0.78 (m, 31H).

MALDI: Calculated: 3884.60; Observed: 3886.72.

Characteristics:

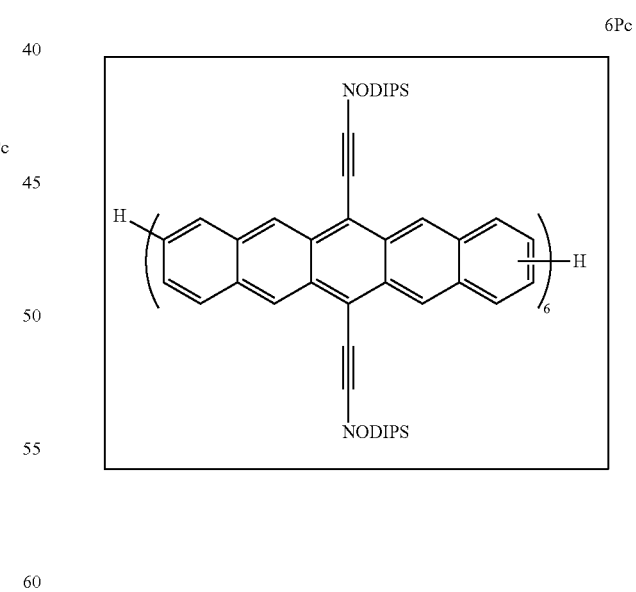
6Pc

¹H-NMR (500 MHz, 50° C., CDCl₃, δ ppm): 9.34 (bs, 24H), 8.39-7.97 (m, 38H) and 1.89-0.71 (m, 372H, water peak overlap)

MALDI: Calculated: 46661.10; Observed: 4663.05.

Characteristics:

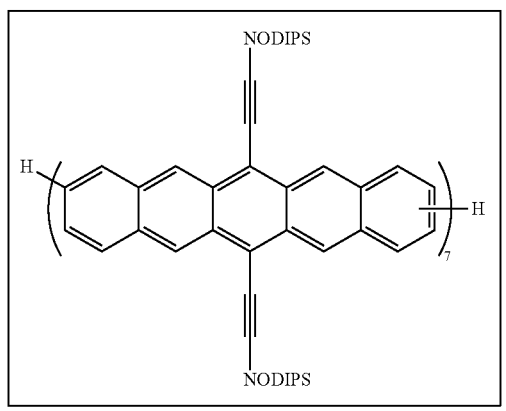

$^1$H-NMR (500 MHz, 50° C., CDCl$_3$, δ ppm): 9.44-9.35 (m, 28H), 8.40 (s, 10H), 8.19-7.98 (m, 34H) and 1.88-0.78 (m, 434H, water peak overlap)

MALDI: Calculated: 5437.64; Observed: 5440.72.

Example 20

General Protocol for Synthesis of Regiopure Dibromo Pentacenes 1A2

Figure 78:
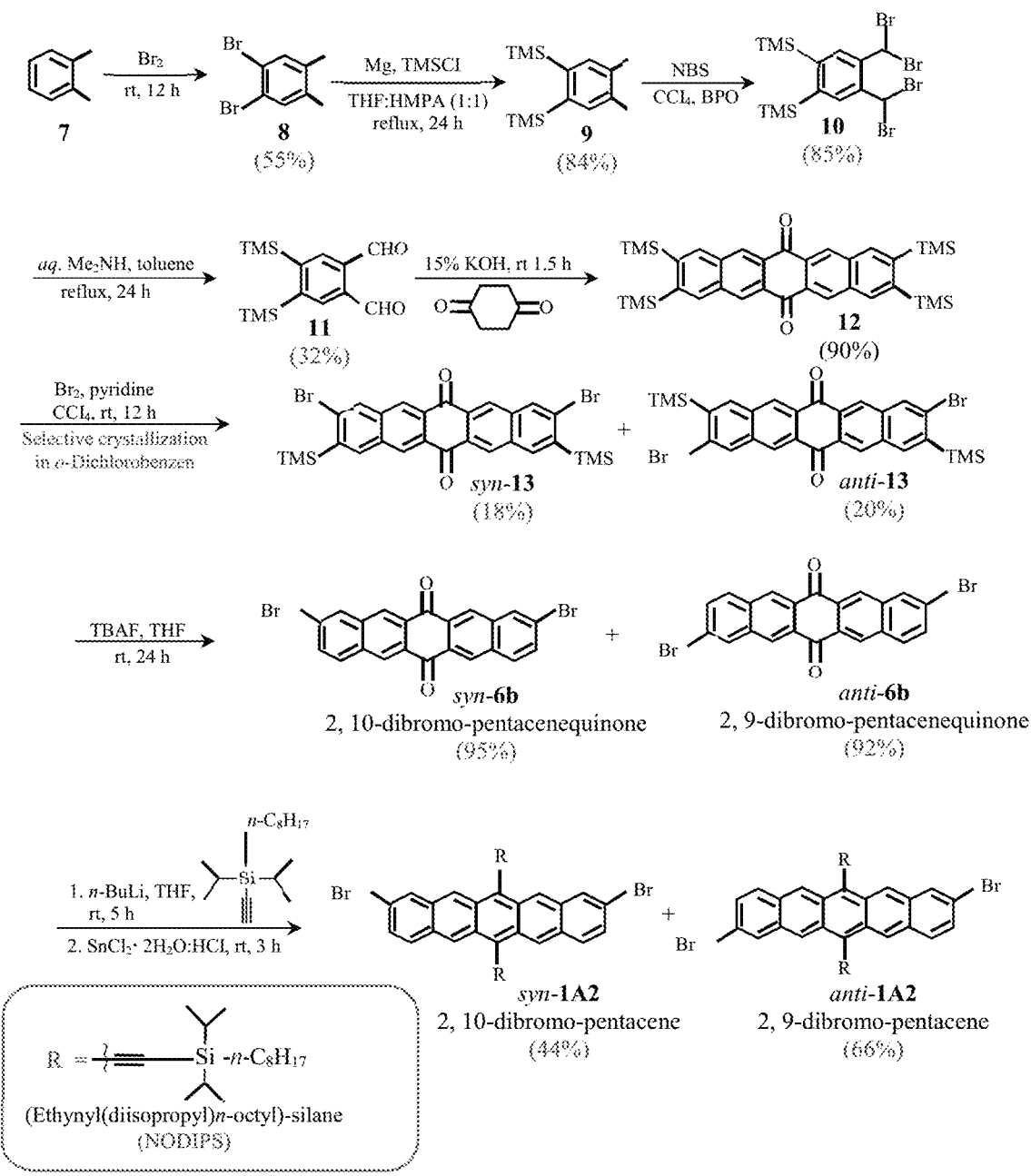
FIG. 78 shows a method of synthesizing the regiopure dibromoquinones syn-6b and anti-6b.

The regiopure dibromoquinones syn-6b and anti-6b were synthesized according to a procedure reported in the literature.[106,110] (FIG. 78)

Example 21

Synthesis of Bis(Trimethylsilyl)-O-Xylene

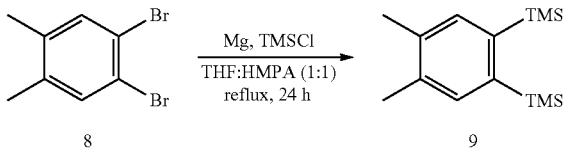

To a mixture of magnesium (5.52 g, 0.23 mol) and trimethylsilyl chloride (77 mL, 0.61 mol) in THF:HMPA (1:1, 200 mL) at 40° C. added 1 mL of dibromoethane (catalytic) followed by the addition of dibromoxylene 8 (20 g, 0.08 mol) in THF (15 mL) slowly over 15 mins. The resulting mixture was heated to reflux and maintained for 24 h. After the reaction, the mixture was cooled to rt, diluted with hexanes (300 mL) and filtered through celite carefully to remove magnesium chloride and excess magnesium. The solution was cooled to 0° C. and diluted with water (200 mL), stirred and the layers were separated. The aqueous layer was extracted with hexanes (2×100 mL) and the combined layer was dried over sodium sulfate, filtered and concentrated to get the crude. The crude was purified in column chromatography using hexanes as eluent.

Characteristics:

$^1$H-NMR (400 MHz, CDCl3, δ ppm): 7.52 (s, 2H), 2.35 (s, 6H) and (s, 18H).

$^{13}$C-NMR (100 MHz, CDCl3, δ ppm): 143.0, 137.1, 136.1, 19.7 and 2.1.

Example 22

Synthesis of N-Octyl(Diisopropyl)Silylacetylene (NODIPS)

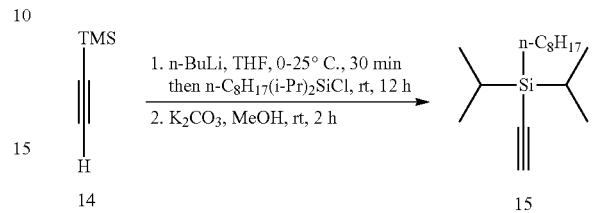

To a solution of TMS-acetylene 14 (7.43 g, 75.6 mmol) in dry THF (400 mL) at 0° C. under N$_2$ atmosphere n-BuLi (2.5 M in hexanes, 30.2 mL, 75.6 mmol) was added. The solution was warmed to rt and stirred for further 30 mins. A solution of n-octyl(diisopropyl)chlorosilane (21.8 g, 83.2 mmol) in THF (50 mL) was slowly added over 10 mins and the resulting solution was stirred at rt for 12 h. The reaction was diluted with water (200 mL), extracted with hexanes (3×75 mL) and the combined organic layer was dried, filtered and concentrated to get the crude. The crude was directly taken to next step.

To a mixture of crude product in methanol (500 mL) added K$_2$CO$_3$ (12.4 g, 89.8 mmol) and the mixture was stirred at rt for 2 h. After the reaction, the mixture was diluted with ice cold water (200 mL), extracted with hexanes (3×75 mL) and the combined organic layer was dried, filtered and concentrated to get the crude product. The crude was purified by silica gel column chromatography using hexanes as eluent.

Characteristics:

Yield: 86% colorless oil.

$^1$H-NMR (500 MHz, CDCl$_3$, δ ppm): 2.37 (s, 1H), 1.46-1.27 (m, 13H), 1.10-1.06 (m, 13H), 0.92-0.91 (m, 3H) and 0.67-0.64 (m, 2H).

$^{13}$C-NMR (125 MHz, CDCl$_3$, δ ppm): 94.5, 86.4, 33.8, 31.9, 29.3, 29.2, 24.3, 22.7, 18.1, 17.9, 14.1, 11.5 and 9.9.

Example 23

Synthesis of N-Octadecyl(Diisopropyl)Silylacetylene (NODDIPS)

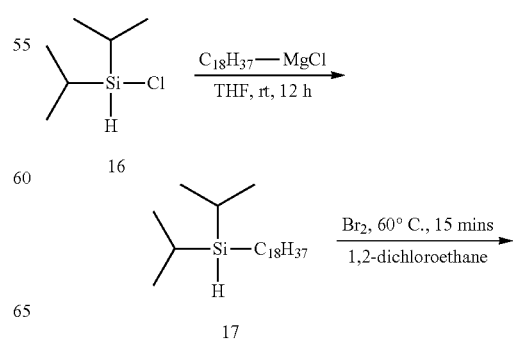

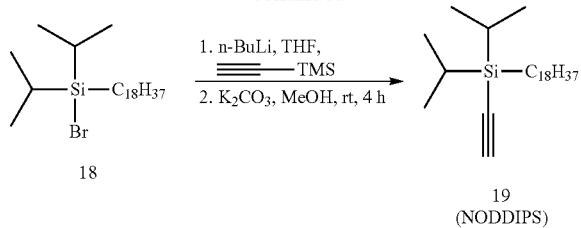

To a solution of diisopropylchlorosilane 16 (10.0 g, 66.3 mmol) in dry THF (80 mL) at 0° C. under N₂ atmosphere octadecylmagnesium chloride (0.5 M in THF, 121 mL, 60.3 mmol) was added slowly over 45 mins. The solution was warmed to rt and stirred for further 12 h. The reaction was diluted with water (200 mL), extracted with hexanes (3×75 mL) and the combined organic layer was dried, filtered and concentrated to get the crude. The crude was purified by column chromatography using hexanes.
Characteristics:
$^1$H-NMR (400 MHz, CDCl₃, δ ppm): 3.46-3.43 (m, 1H), 1.33-1.29 (m, 34H), 1.07-1.04 (m, 14H) and 0.92 (t, 3H).

The silane derivative 17 from the above reaction in 1,2-dichloroethane at 0° C. was titrated with Br₂ until the color of the bromine persisted. The reaction mixture was heated to 60° C. and maintained for 15 mins. The reaction mixture was concentrated and the crude was taken to the next step without further purification.

The product 17 contained quenched octadecane (45%, characterized by $^1$H-NMR using the methyl group as a handle). This impurity was carried all the way through NODDIPS19. This impurity was removed at the later stage where excess NODDIPS is removed at the pentacene-diol stage prior to SnCl₂ reduction to get the desired pentacene.

The conversion of 18 to 19 was achieved using the synthetic protocol described for the synthesis of NODIPS.
Characteristics:
$^1$H-NMR (400 MHz, CDCl₃, δ ppm): 2.37 (s, 1H), 1.34-1.29 (m, 34H), 1.11-1.04 (m, 14H) and 0.91 (t, 3H)

Example 24

Synthesis of Bromo Derivatives of Pentacenes

To a solution of (n-octyl-diisopropylsily)acetylene/(n-octadecyl-diisopropylsilyl)acetylene (3.5 equiv.) in dry and degassed THF (40 mL) in 200 mL Schlenk flask at 0° C. added n-butyl lithium (3.4 equiv., 2.5 M in hexanes). This solution was allowed to stir at 0° C. for 1 h followed by the addition of quinone 6a-b (4.0 g, 1.0 equiv.) under positive argon flow. The solution was warmed to rt and stirred for further 5 h. The reaction was diluted with water (50 mL) and extracted with ethyl acetate (2×50 mL). The combined organic layer was washed with brine (30 mL), dried over sodium sulfate, filtered and concentrated to get the crude. The crude was purified in column chromatography using hexanes as eluent first to recover excess silylacetylene (NODIPS) and then with DCM to obtain intermediate diol product.

To a solution of diol in THF (40 mL) at 0° C. added a solution of tin (II) chloride dihydrate (10 equiv.) in 10% aqueous HCl solution (20 mL) during which the solution turned deep blue. The resulting mixture was stirred at rt for 3 h under dark and diluted with water (50 mL). The mixture was extracted with hexanes (2×50 mL). The combined organic layer was washed with brine (30 mL), dried over sodium sulfate, filtered and concentrated to get the crude. The crude was purified in column chromatography using hexanes as eluent to obtain the product.
Characteristics:

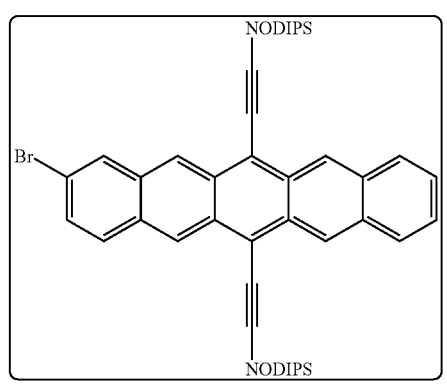

Yield=70%; Blue paste.
$^1$H-NMR (400 MHz, CDCl₃, δ ppm): 9.39-9.38 (m, 2H), 9.35 (s, 1H), 9.28 (s, 1H), 8.25 (s, 1H), 8.10-8.08 (m, 2H), 7.95-7.93 (m, 1H), 7.54-7.51 ((m, 3H), 1.90-1.81 (m, 4H), 1.64-1.57 (m, 4H), 1.49-1.33 (m, 44H), 1.07-1.02 (m, 4H) and 0.96-0.92 (m, 6H).
$^{13}$C-NMR (100 MHz, CDCl₃, δ ppm): 132.7, 132.6, 132.5, 130.9, 130.87, 130.7, 130.6, 130.4, 130.3, 130.27, 125.6, 128.7, 126.9, 126.5, 126.4, 126.2, 126.2, 125.5, 120.4, 118.7, 118.6, 107.98, 104.4, 34.1, 34.09, 32.1, 29.6, 29.58, 29.49, 29.46, 25.1, 25.0, 22.8, 18.8, 18.5, 14.2, 12.3 and 10.5.
MS (ESI): Calculated [M]$^+$: 856.4434; Observed: 856.4423.
Characteristics:

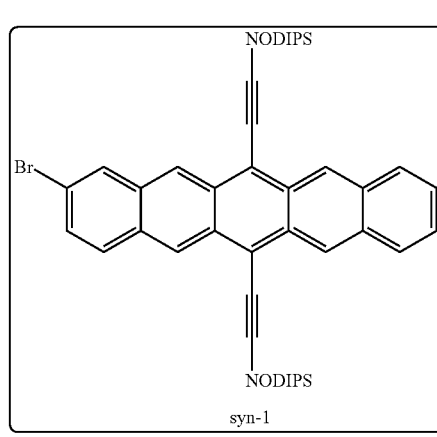

Yield=44%; Blue paste solidifies over time.
$^1$H-NMR (400 MHz, CDCl₃, δ ppm): 9.27 (s, 2H), 9.21 (s, 2H), 8.18 (s, 2H), 7.89-7.88-9.27 (m, 2H), 7.50-7.47-9.27 (m, 2H), 1.83-1.73 (m, 4H), 1.58-1.49 (m, 4H), 1.41-1.27 (m, 44H), 1.01-0.96 (m, 4H) and 0.88-0.85 (m, 6H).
$^{13}$C-NMR (125 MHz, CDCl₃, δ ppm): 132.8, 131.0, 130.5, 130.4, 130.35, 130.2, 129.8, 129.7, 126.95, 125.5, 120.6, 118.9, 118.6, 108.4, 108.2, 104.1, 103.98, 34.1, 34.09, 34.06, 32.0, 29.6, 28.59, 29.55, 29.49, 29.46, 29.43, 25.1, 25.04, 25.0, 22.8, 22.7, 18.8, 18.77, 18.5, 18.49, 14.2, 12.2, 10.5 and 10.45.

MS (ASAP): Calculated [M+H]: 935.3618; Observed: 935.3606.

Characteristics:

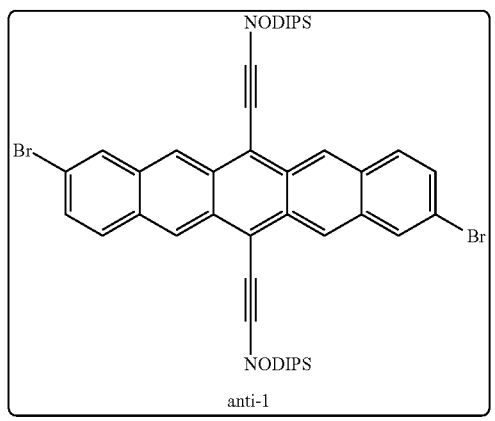

Yield=44%; Blue paste solidifies over time.

$^1$H-NMR (400 MHz, CDCl$_3$, δ ppm): 9.27 (s, 2H), 9.21 (s, 2H), 8.18 (s, 2H), 7.89-7.88-9.27 (m, 2H), 7.50-7.47-9.27 (m, 2H), 1.83-1.73 (m, 4H), 1.58-1.49 (m, 4H), 1.41-1.27 (m, 44H), 1.01-0.96 (m, 4H) and 0.88-0.85 (m, 6H).

$^{13}$C-NMR (125 MHz, CDCl$_3$, δ ppm): 132.8, 131.0, 130.5, 130.4, 130.35, 130.2, 129.8, 129.7, 126.95, 125.5, 120.6, 118.9, 118.6, 108.4, 108.2, 104.1, 103.98, 34.1, 34.09, 34.06, 32.0, 29.6, 28.59, 29.55, 29.49, 29.46, 29.43, 25.1, 25.04, 25.0, 22.8, 22.7, 18.8, 18.77, 18.5, 18.49, 14.2, 12.2, 10.5 and 10.45.

MS (ASAP): Calculated [M+H]: 935.3618; Observed: 935.3606.

Characteristics:

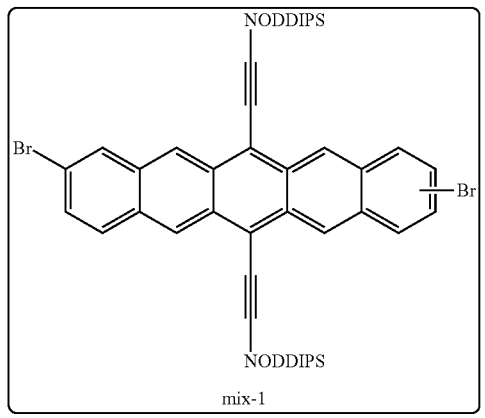

Yield=30%; Blue paste solidifies over time.

$^1$H-NMR (500 MHz, CDCl$_3$, δ ppm): 9.27-9.25 (m, 2H), 9.19-9.18 (m, 2H), 8.16 (m, 2H), 7.87-7.86 (m, 2H), 7.48-7.46 (m, 2H), 1.78-1.73 (m, 4H), 1.53-1.51 (m, 4H), 1.36-1.19 (m, 88H) and 0.89 (t, 6H).

$^{13}$C-NMR (125 MHz, CDCl$_3$, δ ppm): 132.8, 132.7, 131.0, 130.8, 130.7, 130.5, 130.4, 130.38, 130.34, 130.2, 129.74, 129.71, 126.96, 126.91, 125.6, 125.5, 120.6, 120.5, 118.9, 118.8, 118.6, 108.4, 108.3, 108.2, 34.1, 34.0, 33.9, 31.9, 29.8, 29.73, 29.70, 29.6, 29.56, 29.52, 29.40, 25.0, 24.98, 24.94, 22.7, 18.8, 18.73, 18.71, 18.5, 18.45, 18.43, 14.2, 12.1 and 10.4.

MS (ASAP): Calculated [M+H]: 1214.6669; Observed: 1214.6671.

Example 25

Comparison of NMR Spectrum of Mixture, Syn and Anti Isomers of 1A2

Figure 31:
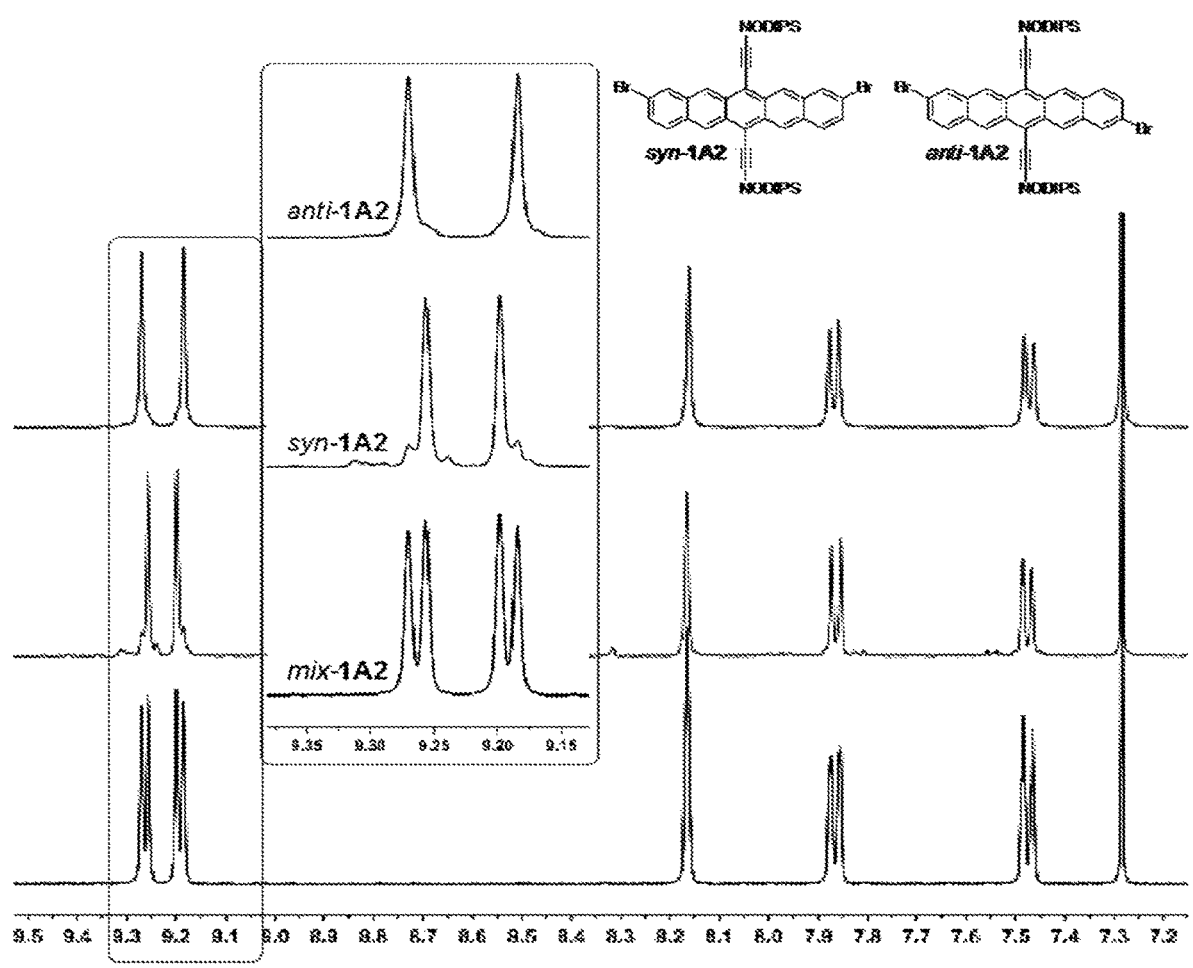
FIG. 31 shows the NMR spectrum of mix-1A2 (bottom, blue), syn-1A2 (middle, green) and anti-1A2 (top, red) isomers. The aliphatic regions are omitted for clarity.
Figure 32B:
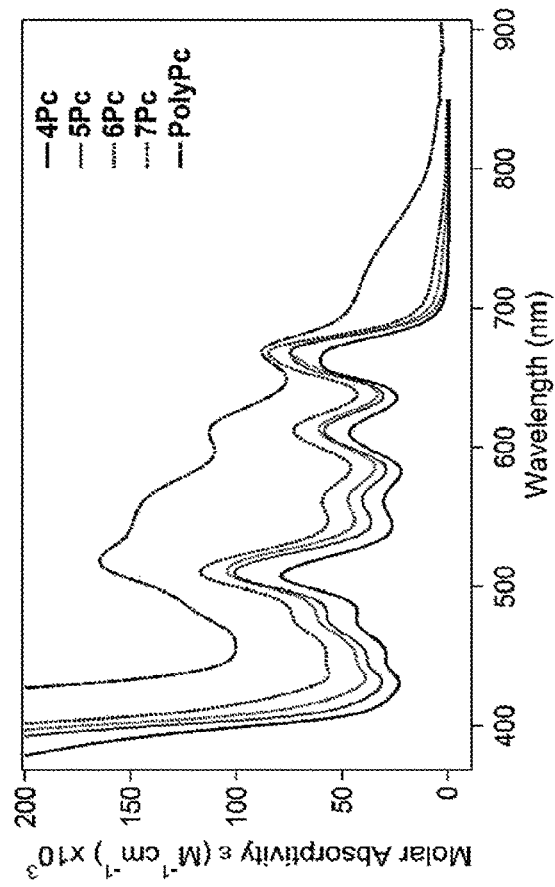
FIGS. 32A to 32D shows UV-vis spectra.
Figure 32A:
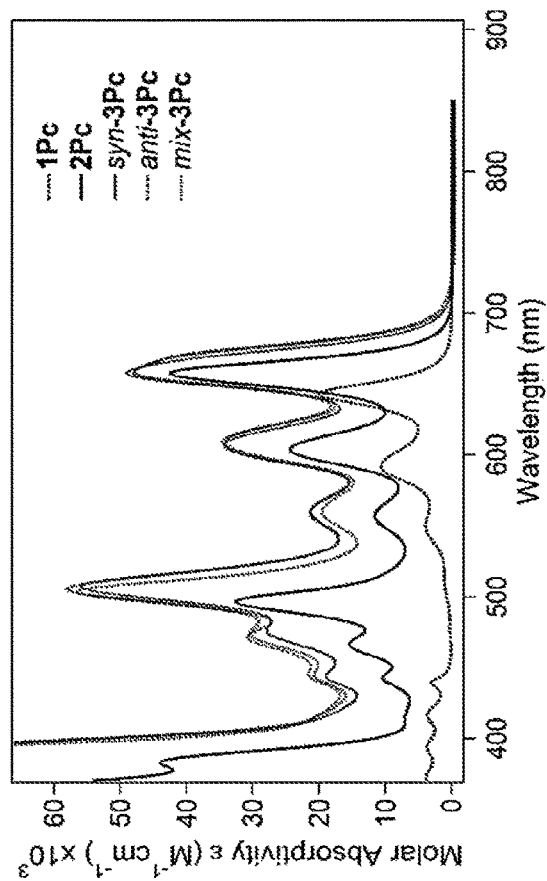
Figure 32D:
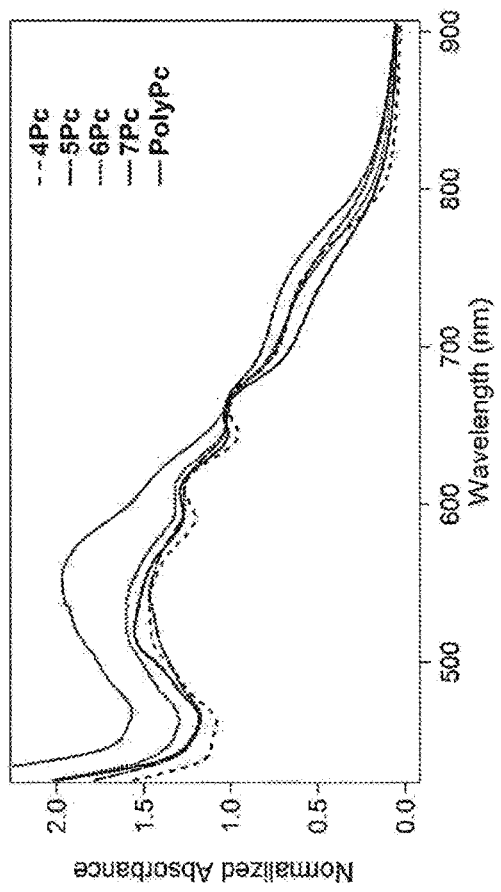
Figure 32C:
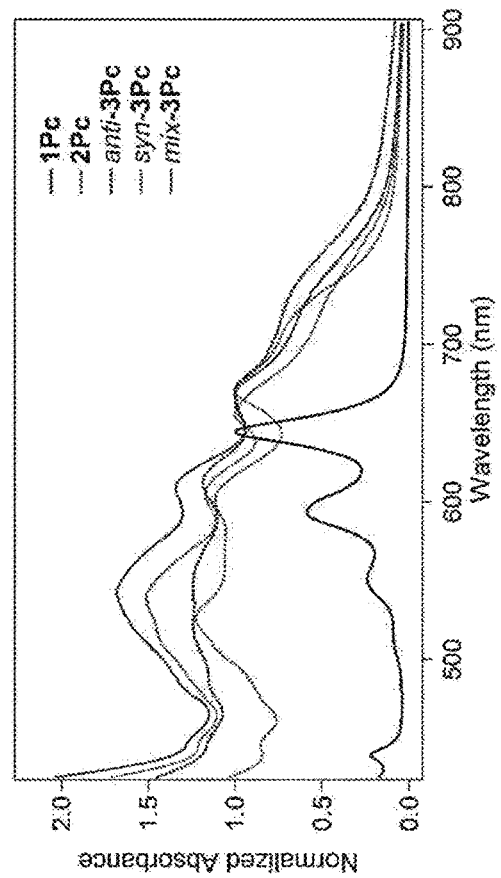
Figure 33A:
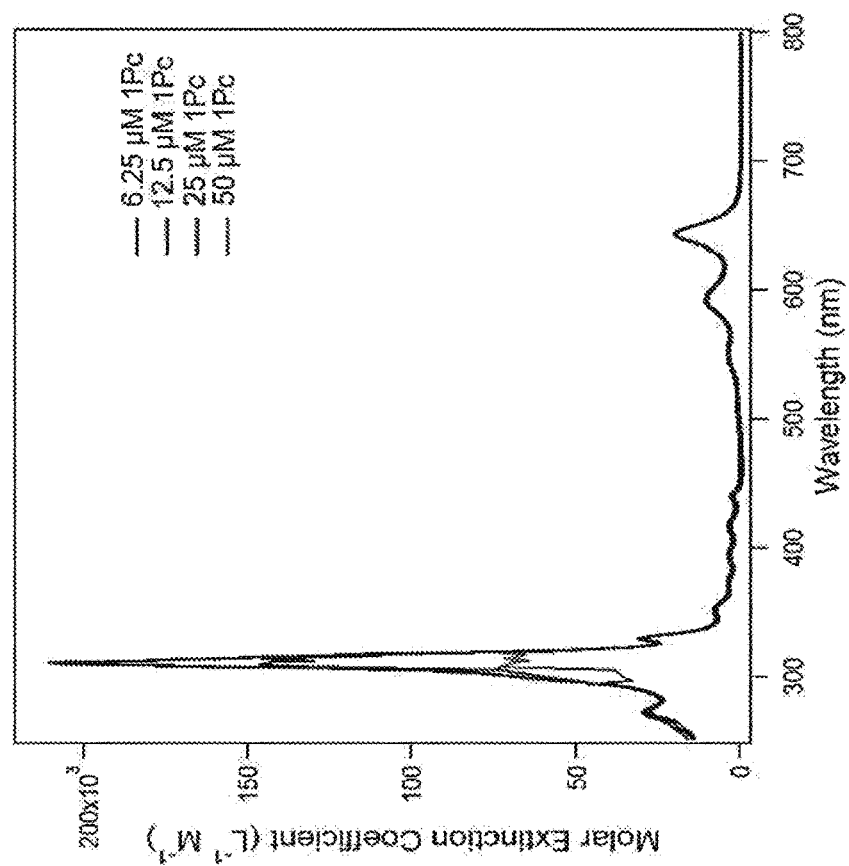
FIGS. 33A to 33E show steady state absorption in chloroform for the oligomers.
Figure 33A:
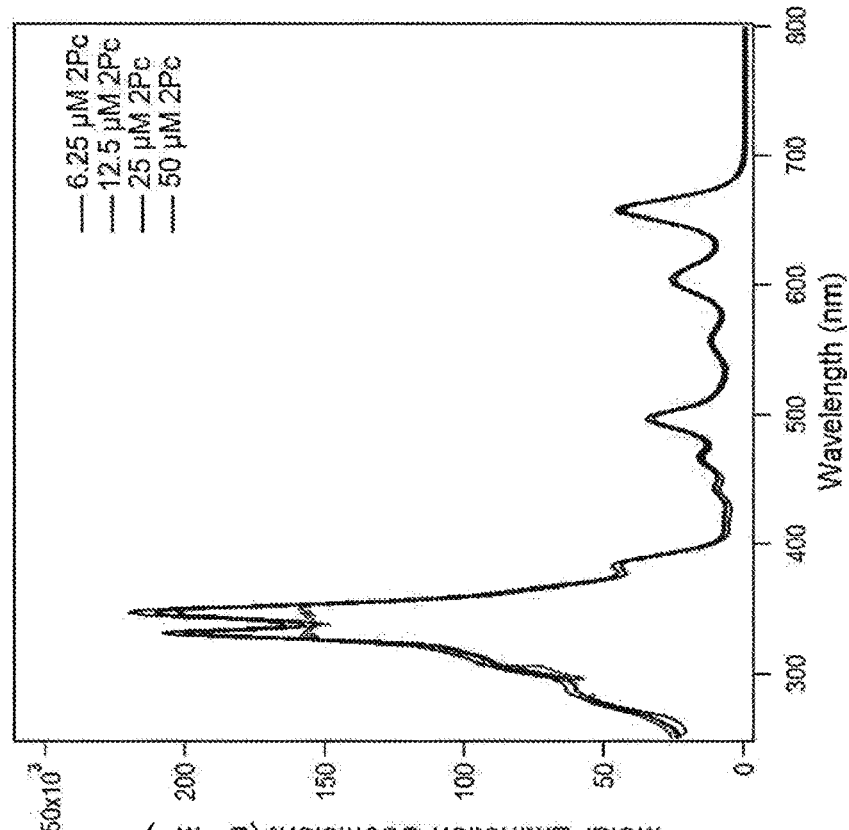
Figure 33B:
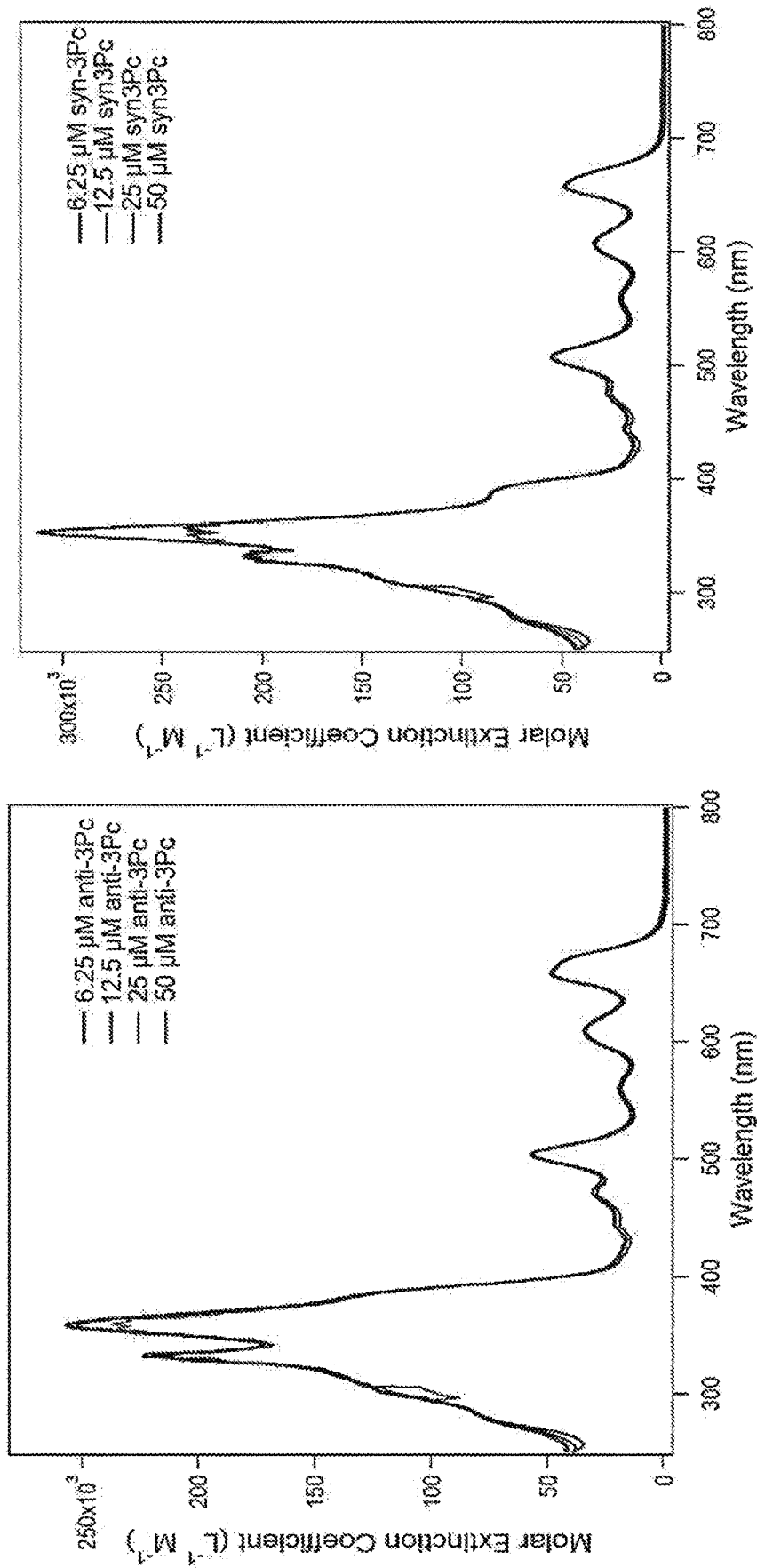
Figure 33C:
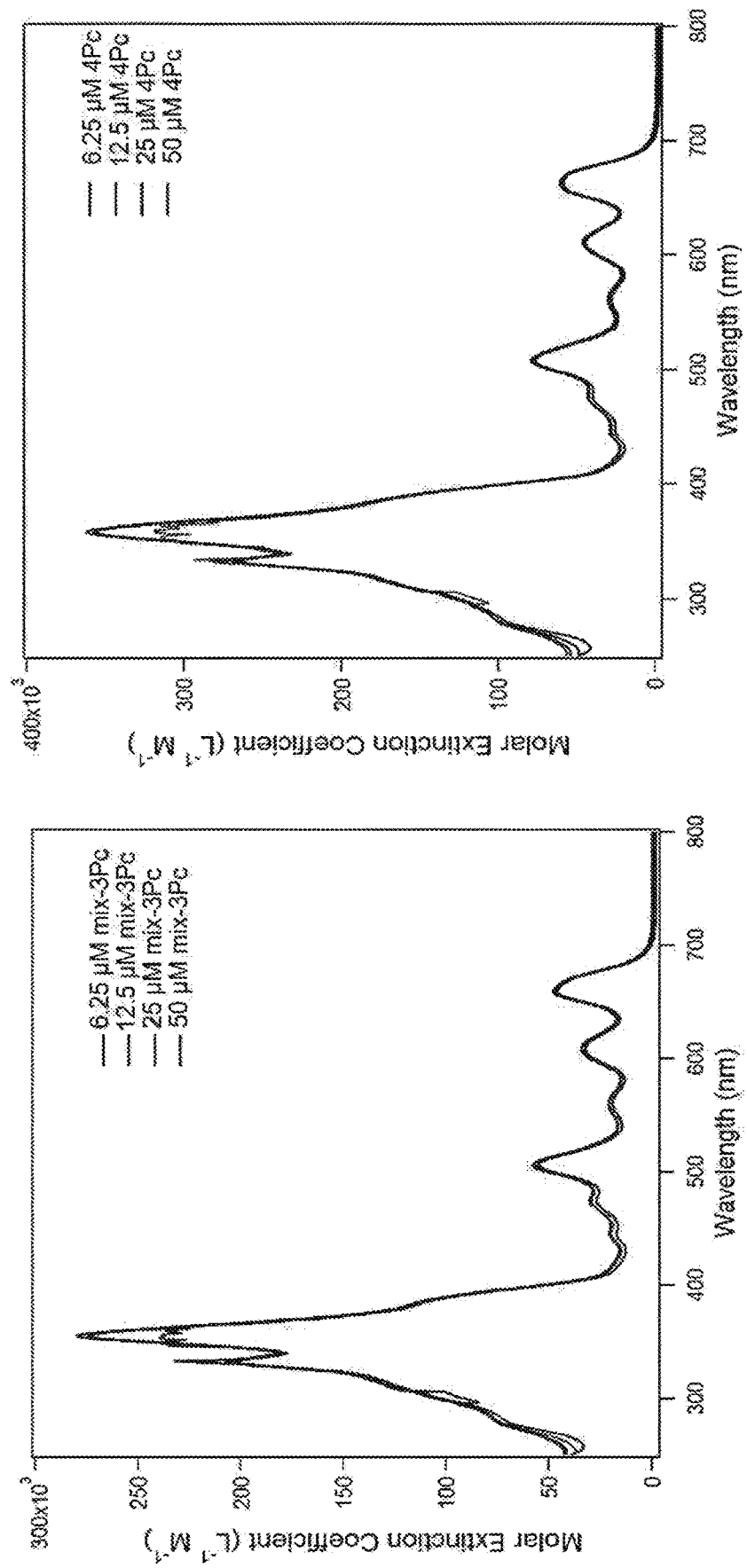
Figure 33D:
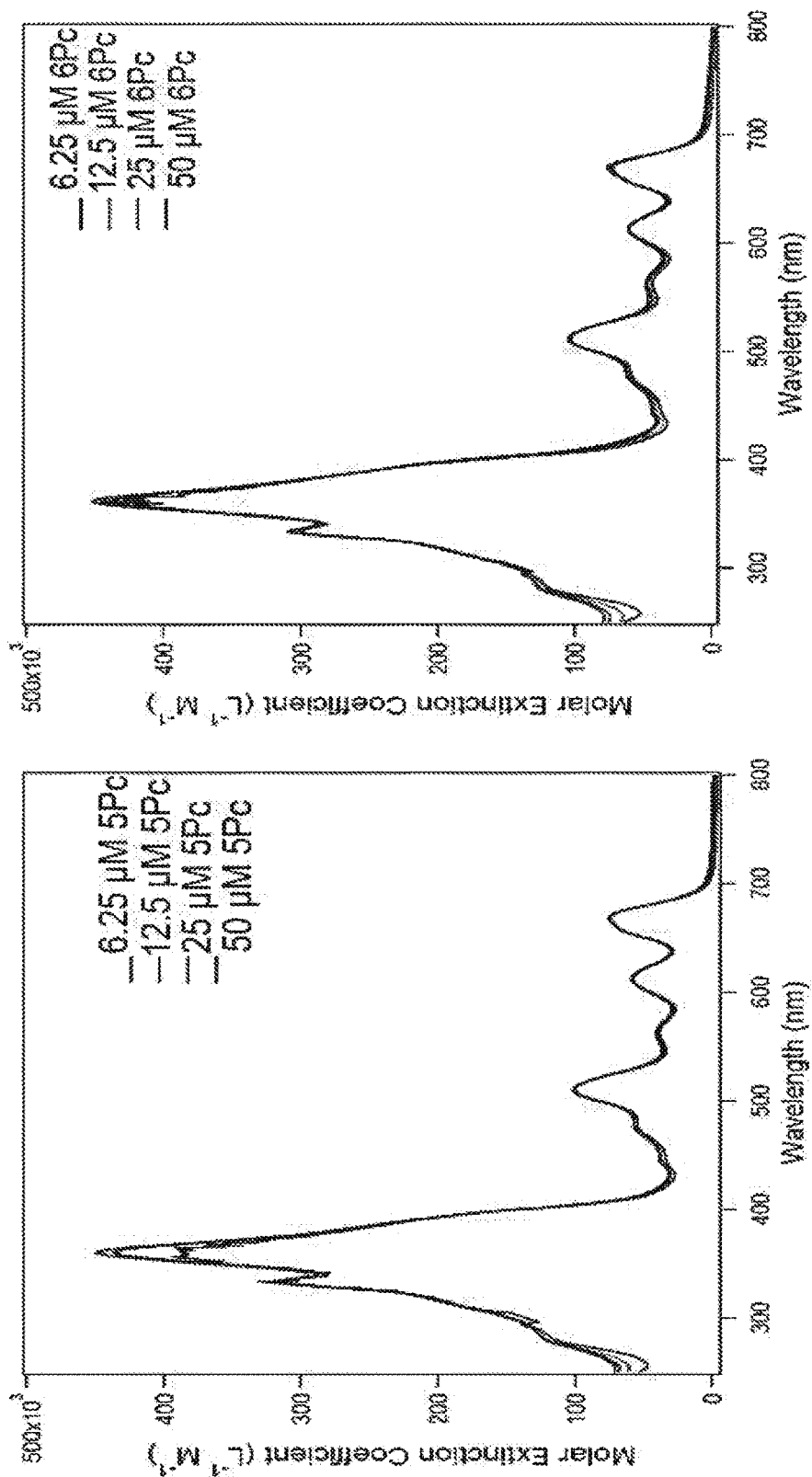
Figure 33E:
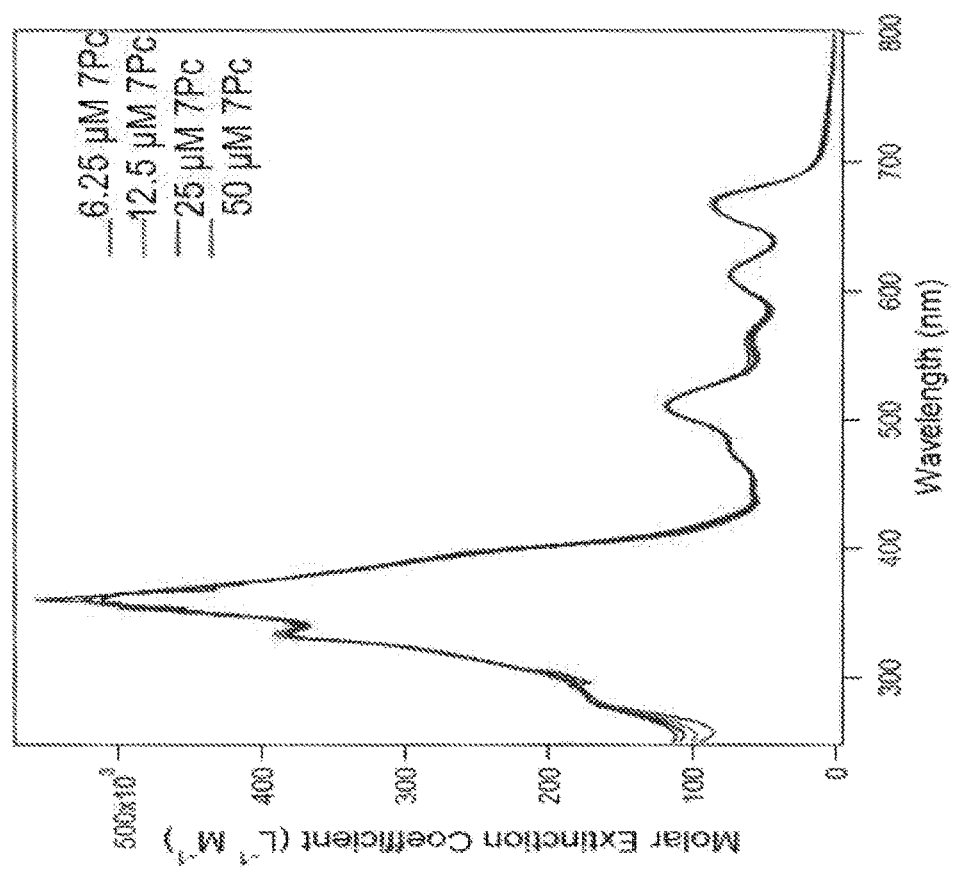
Figure 38A:
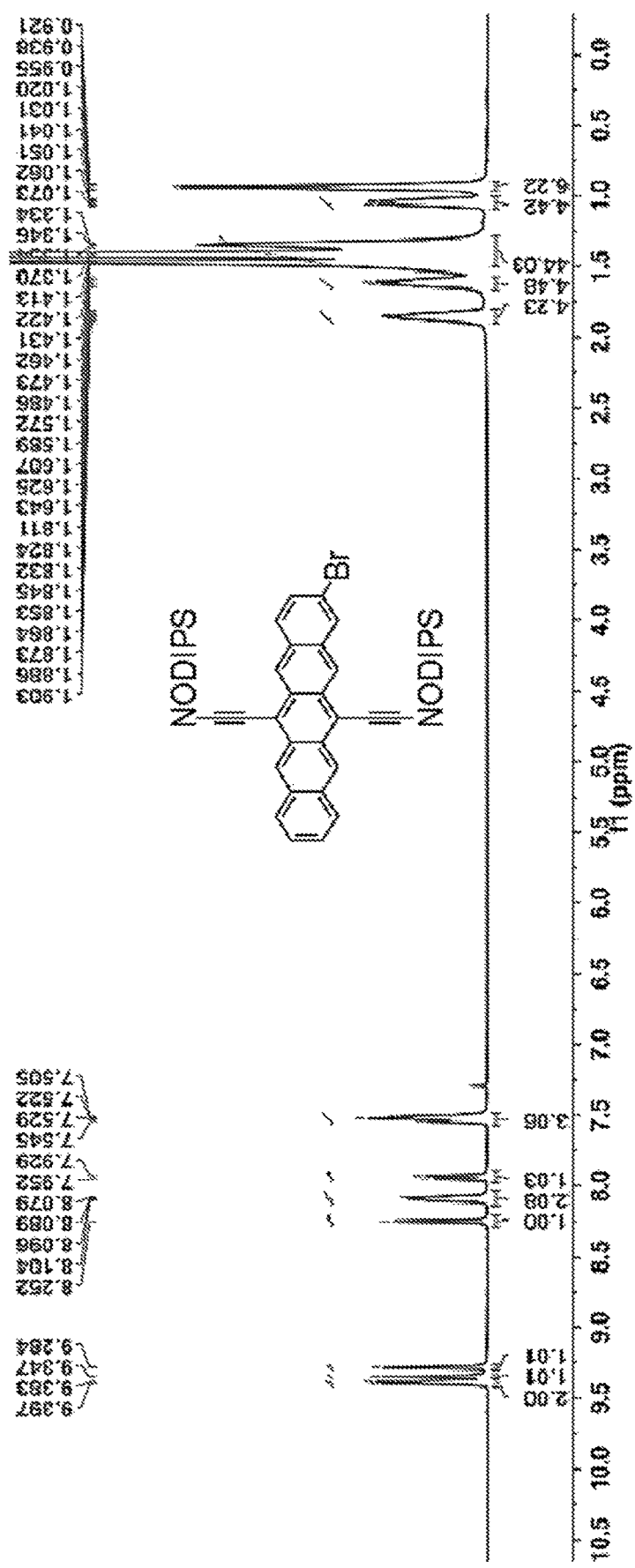
FIG. 38A shows $^1$H NMR absorption spectrum for primary pentacene 1A at its optimum geometry characterized by $^1$H-NMR (400 MHz, CDCl$_3$, δ ppm): 9.39-9.38 (m, 2H), 9.35 (s, 1H), 9.28 (s, 1H), 8.25 (s, 1H), 8.10-8.08 (m, 2H), 7.95-7.93 (m, 1H), 7.54-7.51 ((m, 3H), 1.90-1.81 (m, 4H), 1.64-1.57 (m, 4H), 1.49-1.33 (m, 44H), 1.07-1.02 (m, 4H) and 0.96-0.92 (m, 6H).
Figure 38B:
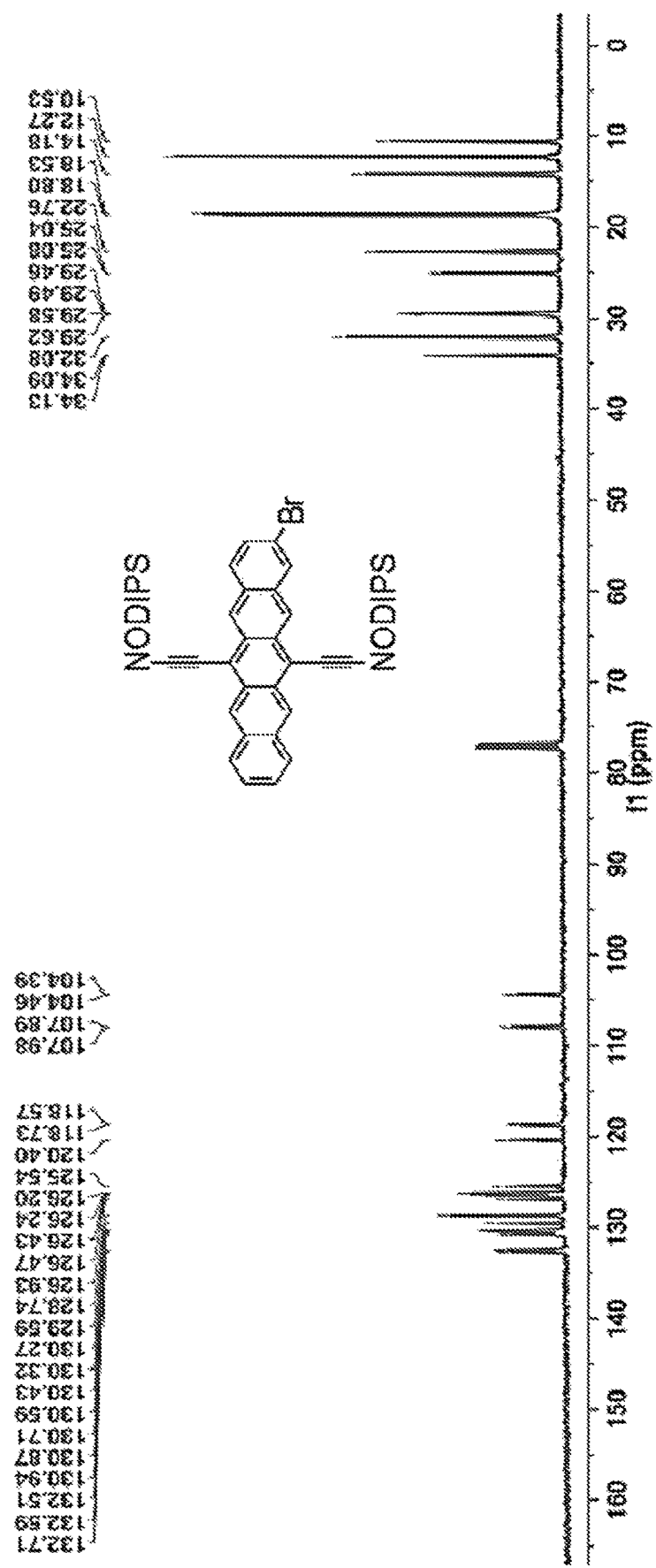
FIG. 38B shows $^{13}$C NMR absorption spectrum for primary pentacene 1A at its optimum geometry characterized by $^{13}$C-NMR (100 MHz, CDCl$_3$, δ ppm): 132.7, 132.6, 132.5, 130.9, 130.87, 130.7, 130.6, 130.4, 130.3, 130.27, 125.6, 128.7, 126.9, 126.5, 126.4, 126.2, 126.2, 125.5, 120.4, 118.7, 118.6, 107.98, 104.4, 34.1, 34.09, 32.1, 29.6, 29.58, 29.49, 29.46, 25.1, 25.0, 22.8, 18.8, 18.5, 14.2, 12.3 and 10.5.
Figure 39A:
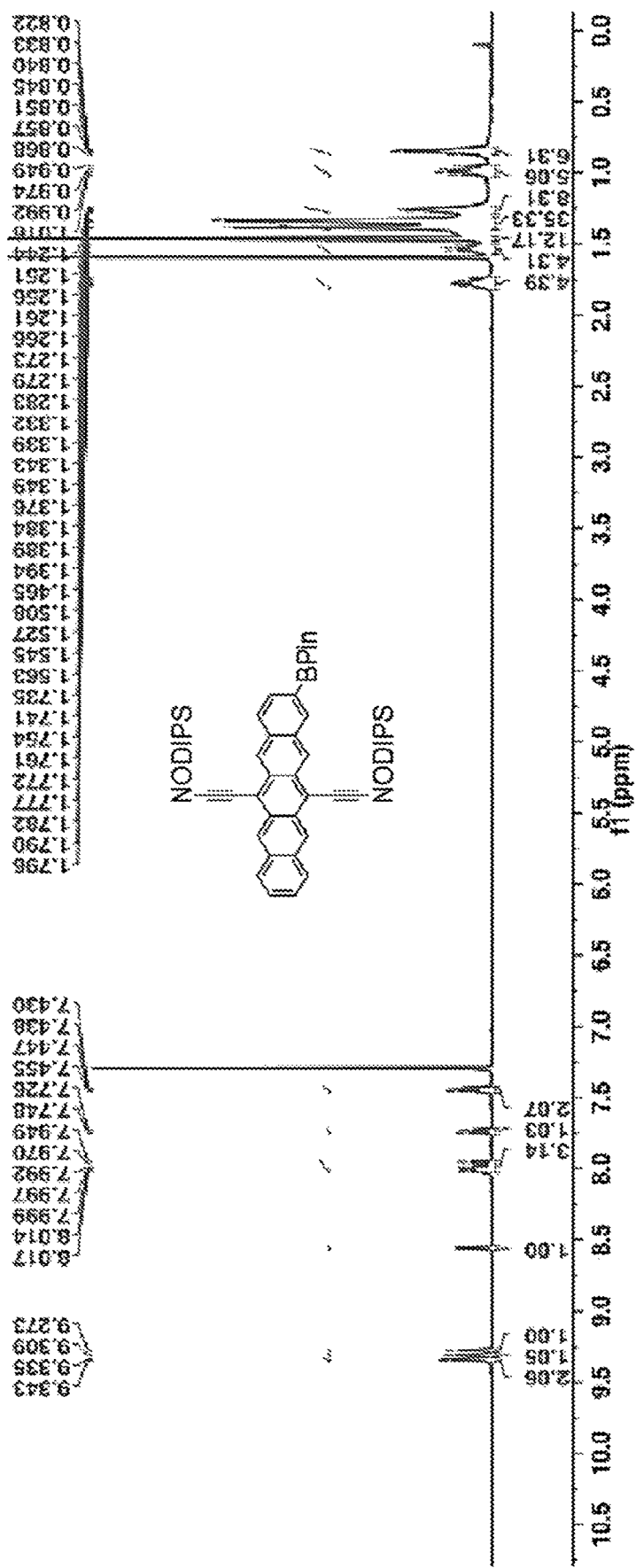
FIG. 39A shows $^1$H NMR absorption spectrum for primary pentacene 1B at its optimum geometry characterized by $^1$H-NMR (500 MHz, CDCl$_3$, δ ppm): 9.34-9.33 (m, 2H), 9.31 (s, 1H), 9.27 (s, 1H), 8.56 (s, 1H), 8.02-7.95 (m, 3H), 7.75-7.73 (m, 1H), 7.46-7.43 (m, 2H), 1.79-1.74 (m, 4H), 1.56-1.51 (m, 4H), 1.47 (s, 12H), 1.39-1.33 (m, 35H), 1.28-1.24 (m, 8H), 1.02-0.95 (m, 5H) and 0.87-0.82 (m, 6H).
Figure 39B:
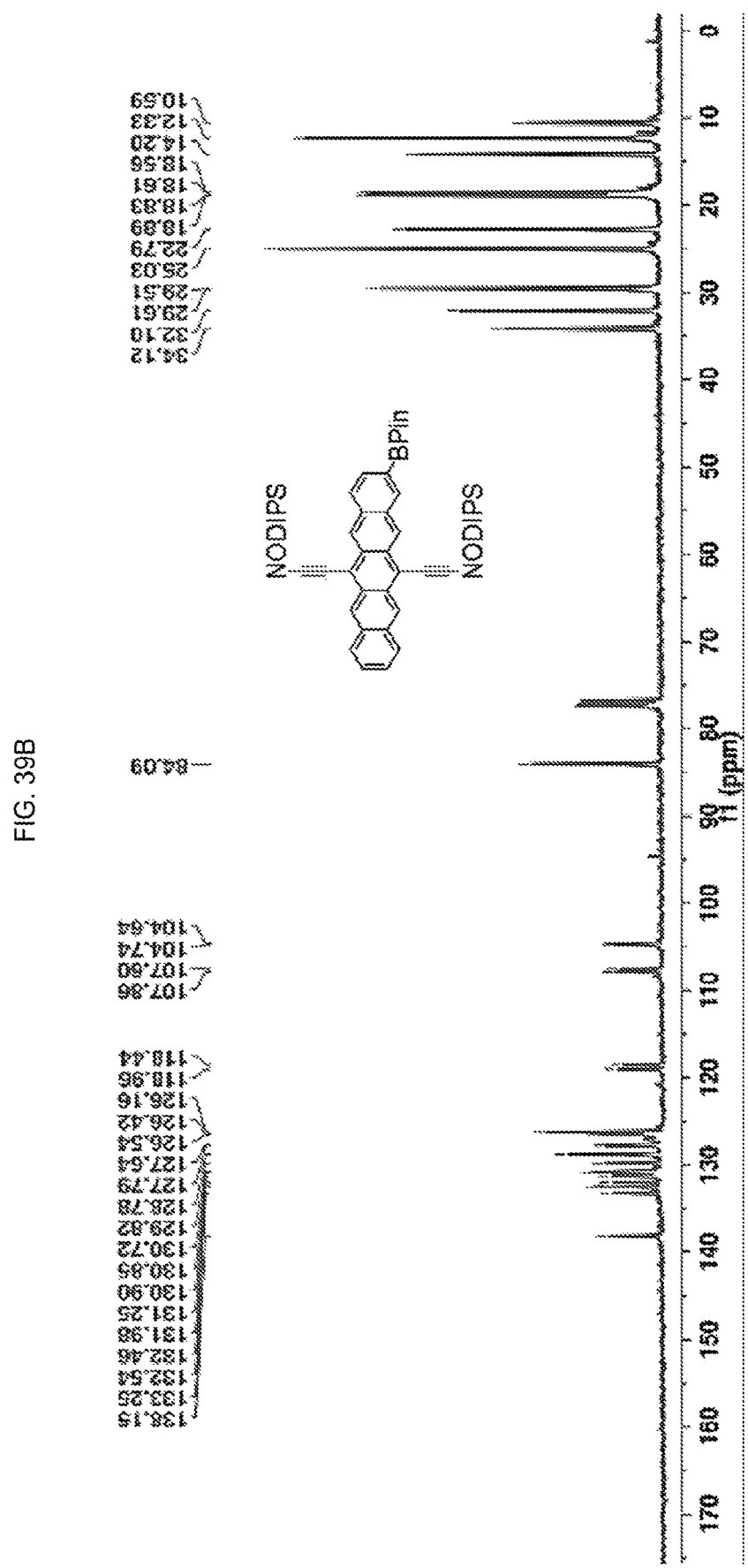
FIG. 39B shows $^{13}$C NMR absorption spectrum for primary pentacene 1B at its optimum geometry characterized by $^{13}$C-NMR (125 MHz, CDCl$_3$, δ ppm): 138.2, 133.3, 132.5, 132.46, 131.98, 131.3, 130.9, 130.85, 130.7, 129.8, 128.8, 127.8, 127.6, 126.5, 126.4, 126.2, 118.96, 118.4, 107.9, 107.6, 104.7, 104.6, 84.1, 34.1, 32.1, 29.6, 29.5, 25.0, 22.8, 18.9, 18.8, 18.6, 18.56, 14.2, 12.3 and 10.6.
Figure 40A:
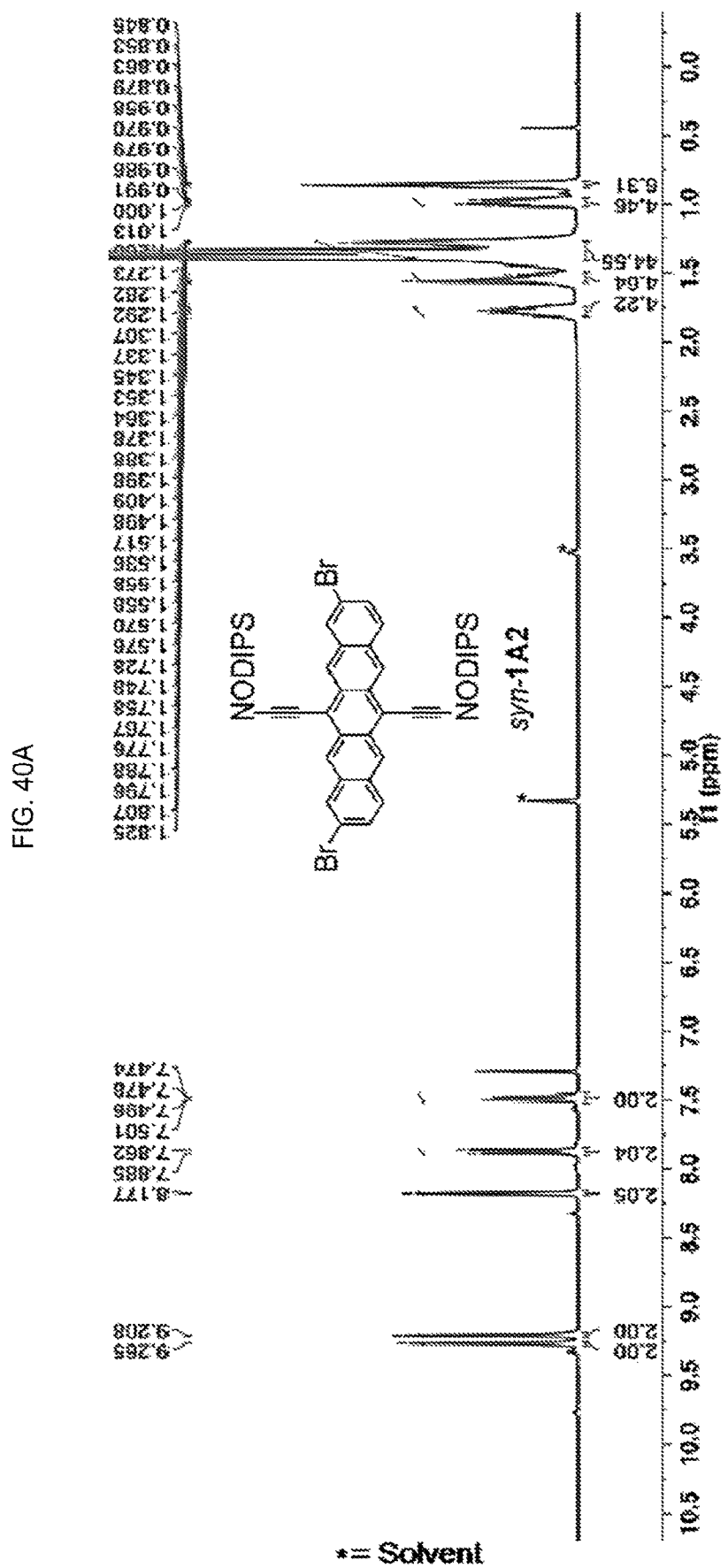
FIG. 40A shows $^1$H NMR absorption spectrum for primary pentacenesyn-1A2 at its optimum geometry characterized by $^1$H-NMR (400 MHz, CDCl$_3$, δ ppm): 9.27 (s, 2H), 9.21 (s, 2H), 8.18 (s, 2H), 7.89-7.88-9.27 (m, 2H), 7.50-7.47-9.27 (m, 2H), 1.83-1.73 (m, 4H), 1.58-1.49 (m, 4H), 1.41-1.27 (m, 44H), 1.01-0.96 (m, 4H) and 0.88-0.85 (m, 6H).
Figure 40B:
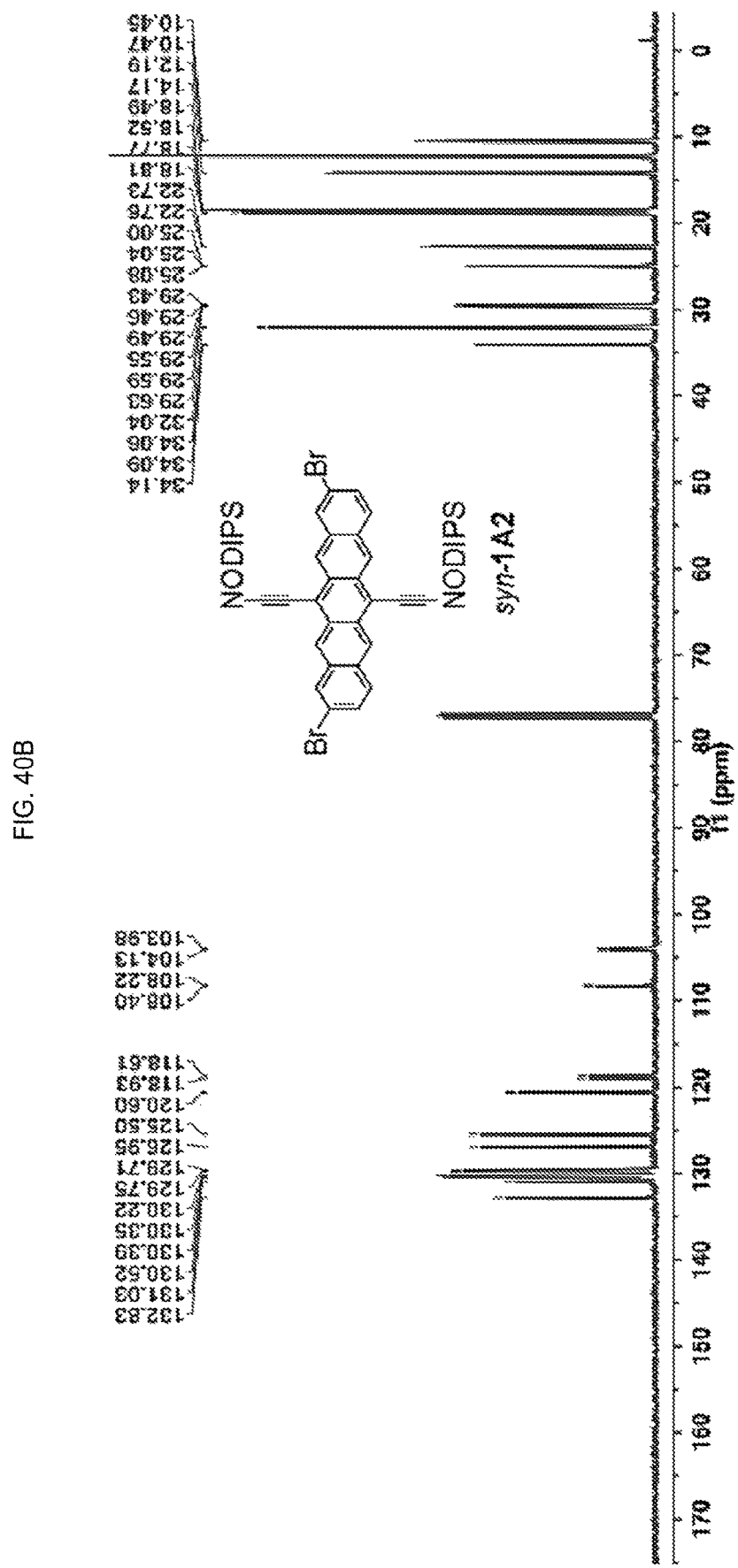
FIG. 40B shows $^{13}$C NMR absorption spectrum for primary pentacenesyn-1A2 at its optimum geometry characterized by $^{13}$C-NMR (125 MHz, CDCl$_3$, δ ppm): 132.8, 131.0, 130.5, 130.4, 130.35, 130.2, 129.8, 129.7, 126.95, 125.5, 120.6, 118.9, 118.6, 108.4, 108.2, 104.1, 103.98, 34.1, 34.09, 34.06, 32.0, 29.6, 28.59, 29.55, 29.49, 29.46, 29.43, 25.1, 25.04, 25.0, 22.8, 22.7, 18.8, 18.77, 18.5, 18.49, 14.2, 12.2, 10.5 and 10.45.
Figure 41A:
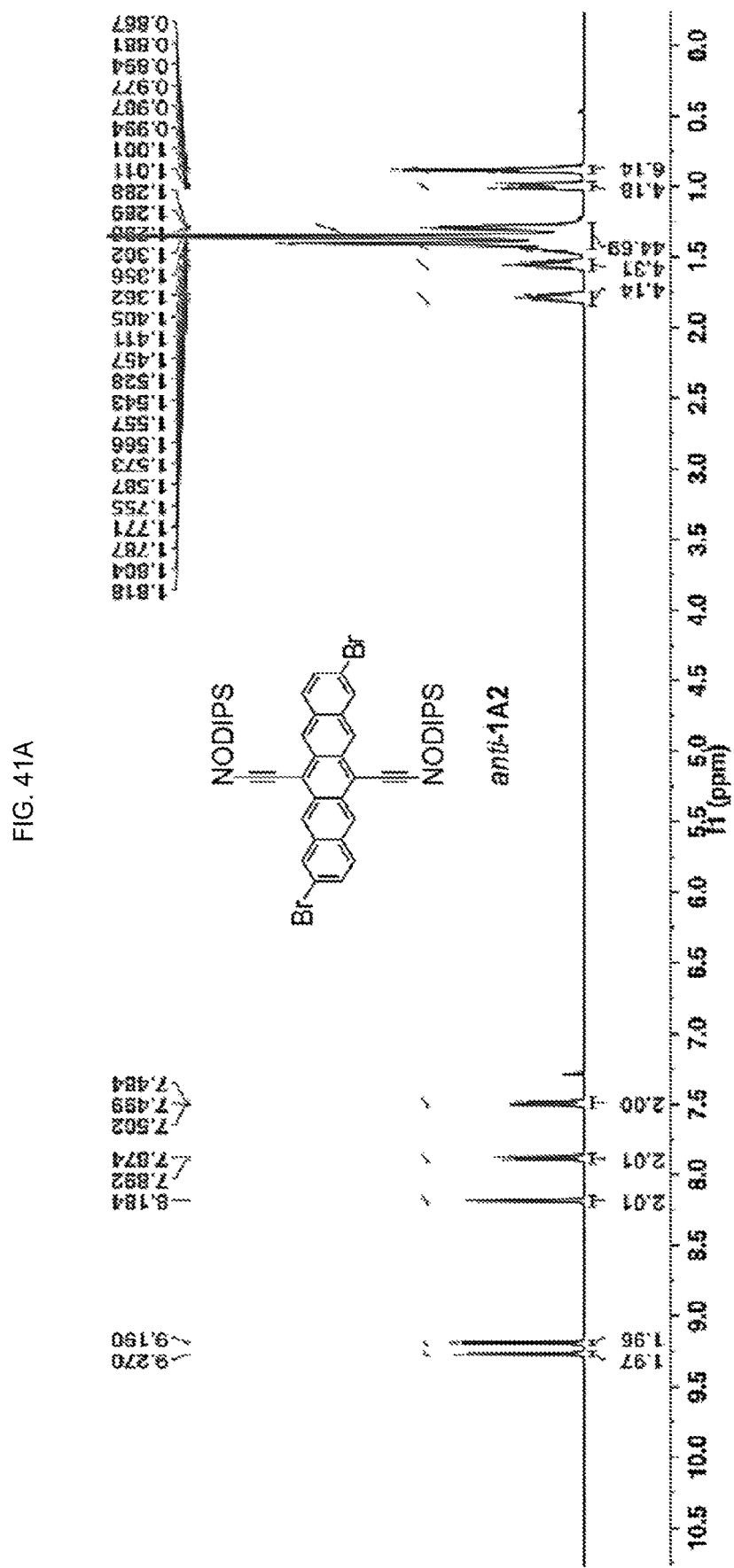
FIG. 41A shows $^1$H NMR absorption spectrum for primary pentaceneanti-1A2 at its optimum geometry characterized by $^1$H-NMR (500 MHz, CDCl$_3$, δ ppm): 9.27 (s, 2H), 9.19 (s, 2H), 8.18 (s, 2H), 7.89-7.87 (m, 2H), 7.50-7.48 (m, 2H), 1.82-1.76 (m, 4H), 1.59-1.53 (m, 4H), 1.46-1.29 (m, 44H), 1.01-0.98 (m, 4H) and 0.89-0.88 (m, 6H).
Figure 41B:
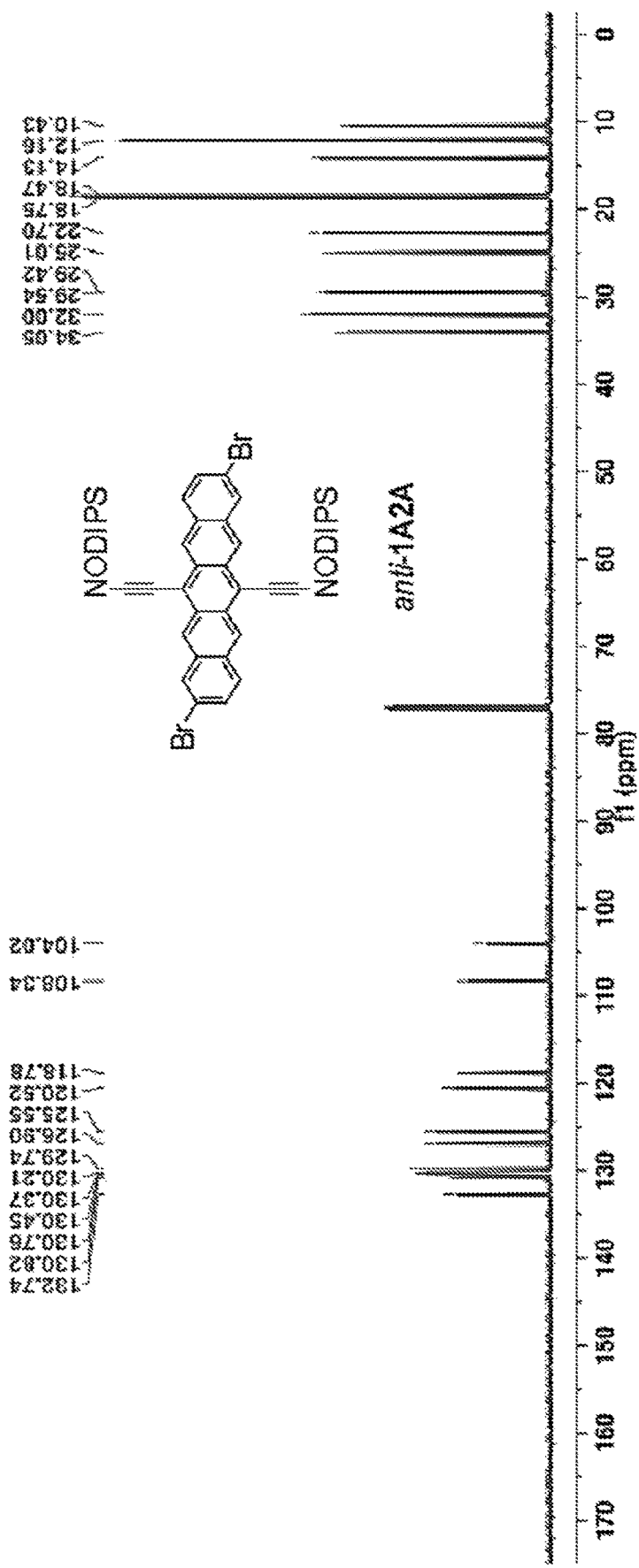
FIG. 41B shows $^{13}$C NMR absorption spectrum for primary pentaceneanti-1A2 at its optimum geometry characterized by $^{13}$C-NMR (125 MHz, CDCl$_3$, δ ppm): 132.7, 130.8, 130.76, 130.5, 130.4, 130.2, 129.7, 126.9, 125.6, 120.5, 118.8, 108.3, 104.0, 34.0, 32.0, 29.4, 25.0, 22.7, 18.8, 18.5, 14.1, 12.2 and 10.4.
Figure 42A:
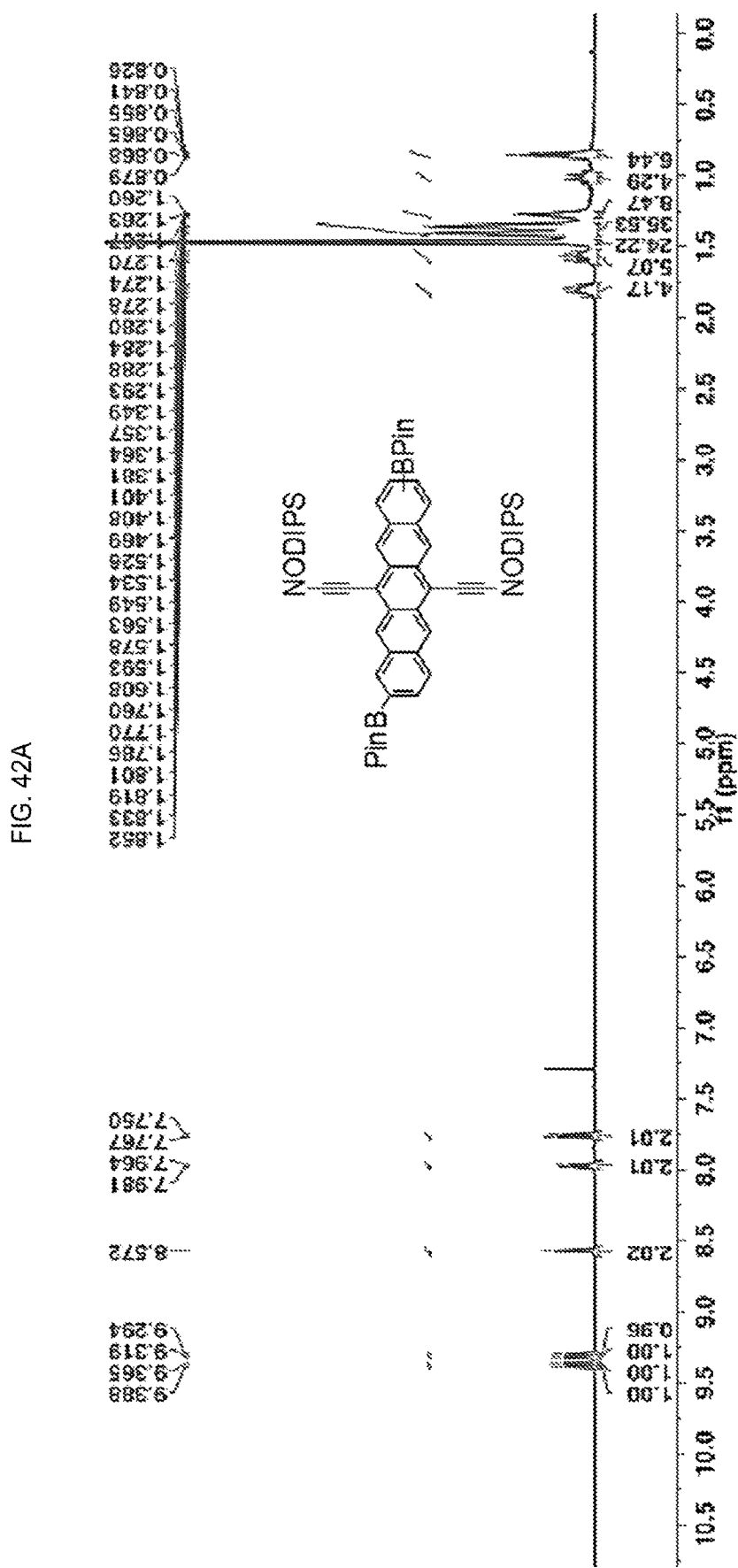
FIG. 42A shows $^1$H NMR absorption spectrum for primary pentacene 1B2 at its optimum geometry characterized by $^1$H-NMR (500 MHz, CDCl$_3$, δ ppm): 9.39 (s, 1H), 9.37 (s, 1H), 9.32 (s, 1H), 9.29 (s, 1H), 8.57 (s, 2H), 7.98-7.96 (m, 2H), 7.77-7.75 (m, 2H), 1.85-1.76 (m, 4H), 1.61-1.53 (m, 5H), 1.47 (s, 24H), 1.41-1.35 (m, 35H), 1.29-1.26 (m, 8H), 1.03-0.99 (m, 4H) and 0.88-0.83 (m, 6H).
Figure 42B:
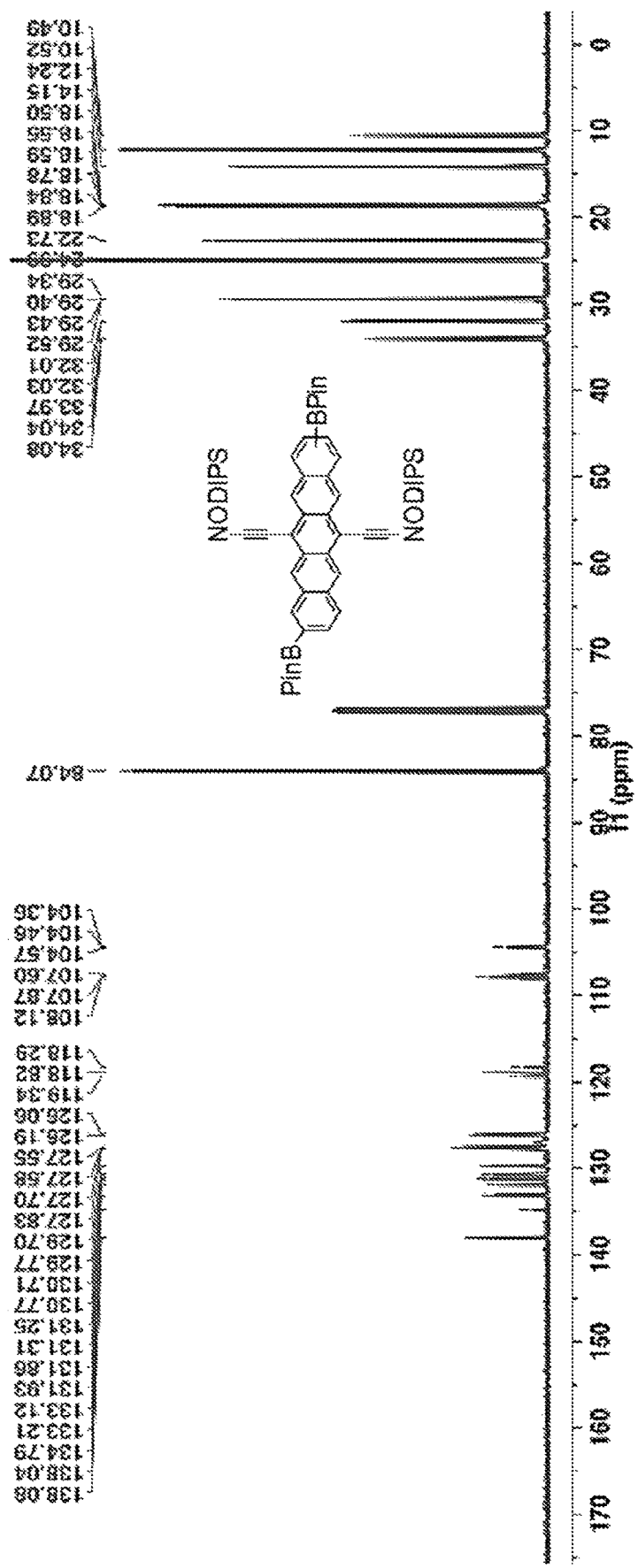
FIG. 42B shows $^{13}$C NMR absorption spectrum for primary pentacene 1B2 at its optimum geometry characterized by $^{13}$C-NMR (125 MHz, CDCl$_3$, δ ppm): 138.1, 138.0, 134.8, 133.2, 133.1, 131.9, 131.86, 131.3, 131.2, 130.8, 130.7, 129.8, 129.7, 127.8, 127.7, 127.6, 127.55, 126.2, 126.1, 119.3, 118.8, 118.3, 108.1, 107.9, 107.6, 104.6, 104.5, 104.4, 84.1, 34.1, 34.0, 33.97, 32.0, 32.01, 29.5, 29.4, 29.40, 29.3, 24.99, 22.7, 18.9, 18.8, 18.78, 18.6, 18.55, 18.5, 14.2, 12.2, 10.5 and 10.49.
Figure 43A:
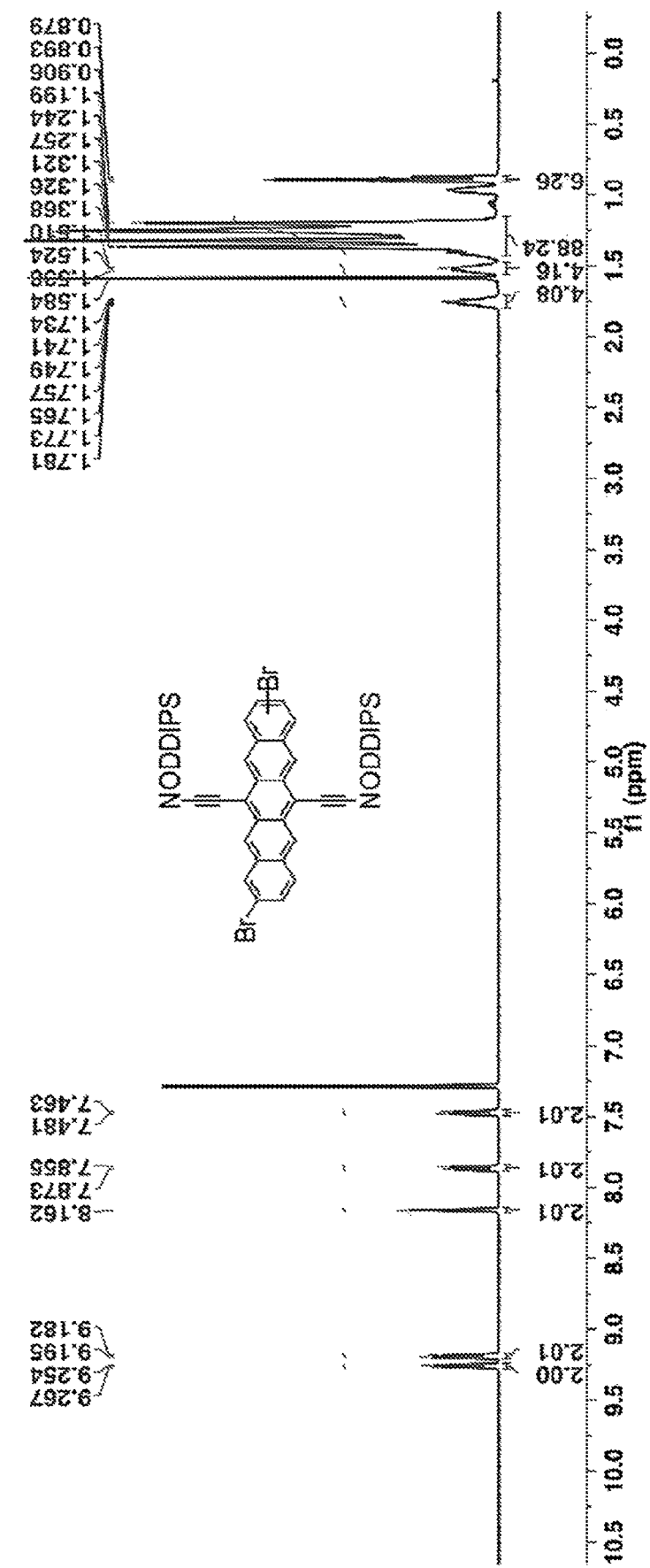
FIG. 43A shows $^1$H NMR absorption spectrum for primary pentacene mix-1A2' at its optimum geometry characterized by $^1$H-NMR (500 MHz, CDCl$_3$, δ ppm): 9.27-9.25 (m, 2H), 9.19-9.18 (m, 2H), 8.16 (m, 2H), 7.87-7.86 (m, 2H), 7.48-7.46 (m, 2H), 1.78-1.73 (m, 4H), 1.53-1.51 (m, 4H), 1.36-1.19 (m, 88H) and 0.89 (t, 6H).
Figure 43B:
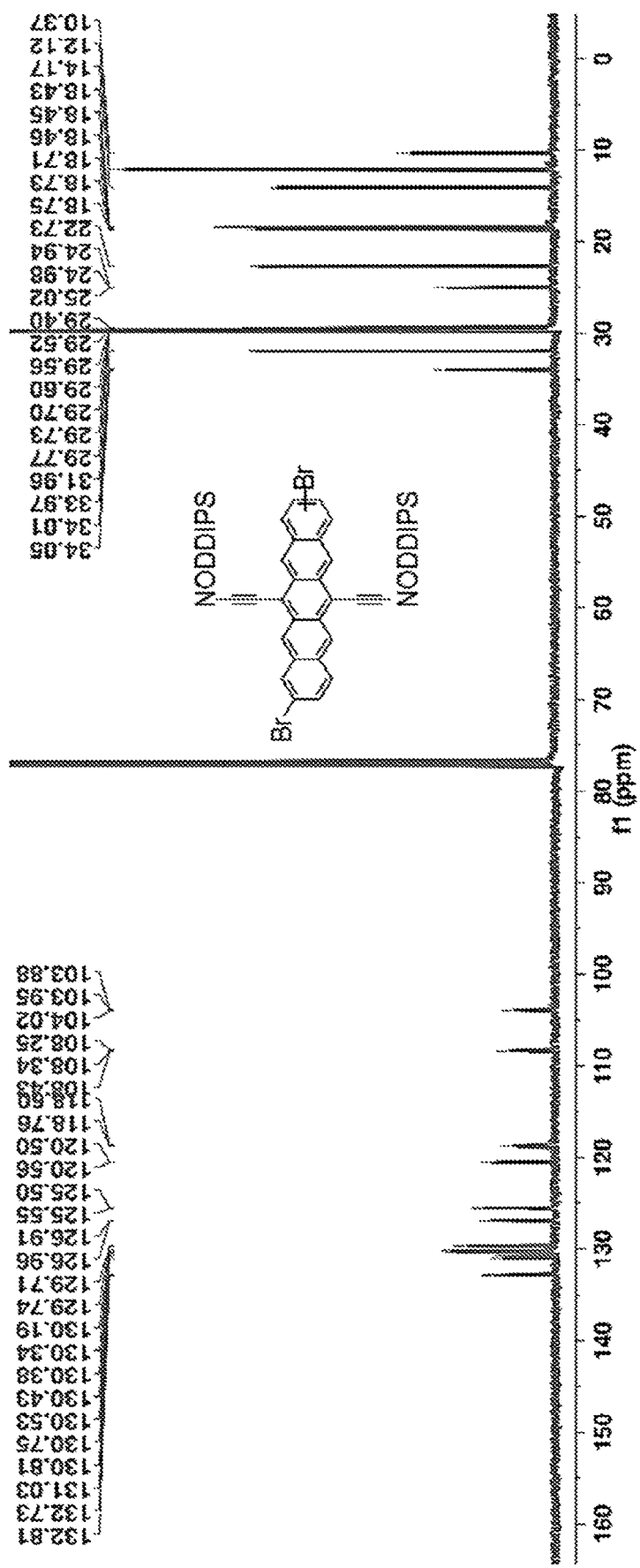
FIG. 43B shows $^{13}$C NMR absorption spectrum for primary pentacene mix-1A2' at its optimum geometry characterized by $^{13}$C-NMR (125 MHz, CDCl$_3$, δ ppm): 132.8, 132.7, 131.0, 130.8, 130.7, 130.5, 130.4, 130.38, 130.34, 130.2, 129.74, 129.71, 126.96, 126.91, 125.6, 125.5, 120.6, 120.5, 118.9, 118.8, 118.6, 108.4, 108.3, 108.2, 34.1, 34.0, 33.9, 31.9, 29.8, 29.73, 29.70, 29.6, 29.56, 29.52, 29.40, 25.0, 24.98, 24.94, 22.7, 18.8, 18.73, 18.71, 18.5, 18.45, 18.43, 14.2, 12.1 and 10.4.
Figure 44A:
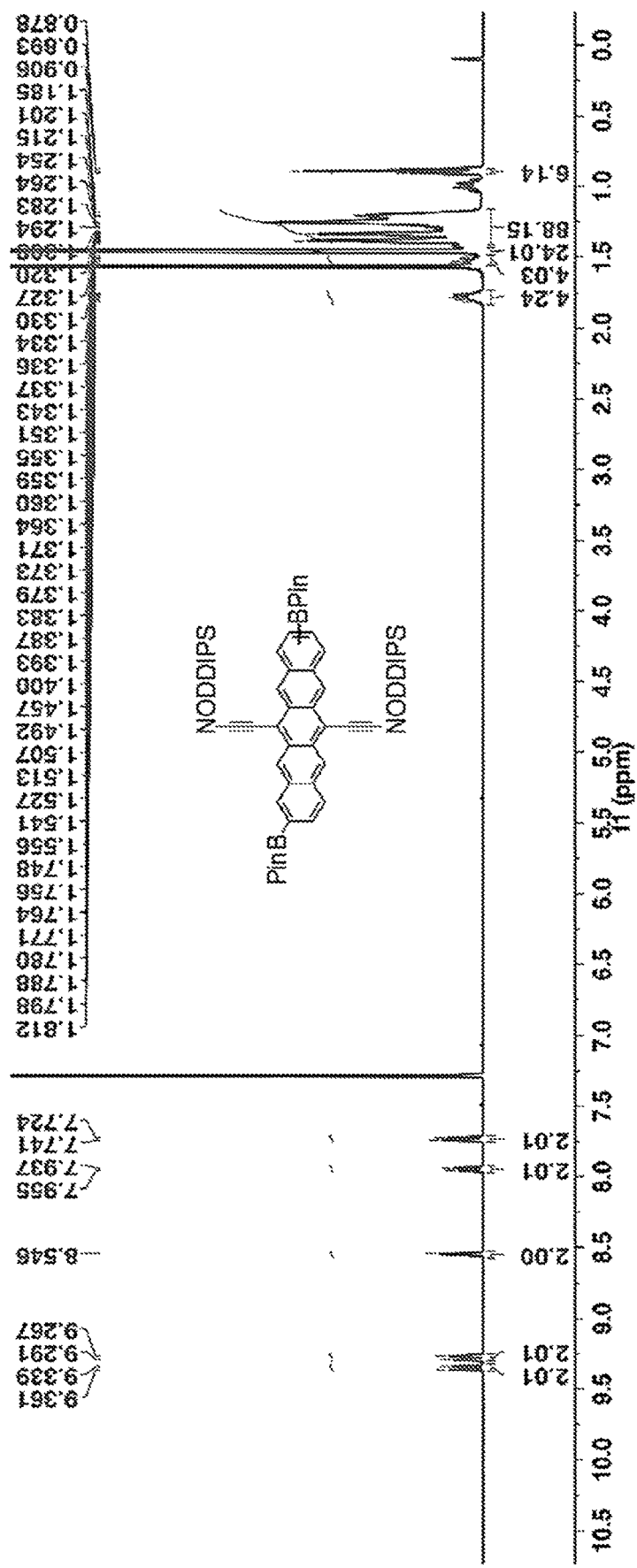
FIG. 44A shows $^1$H NMR absorption spectrum for primary pentacene mix-1B2' at its optimum geometry characterized by $^1$H-NMR (500 MHz, CDCl$_3$, δ ppm): 9.36-9.34 (m, 2H), 9.29-9.27 (m, 2H), 8.55 (s, 2H), 7.96-7.94 (m, 2H), 7.74-7.72 (m, 2H), 1.81-1.75 (m, 4H), 1.56-1.49 (m, 4H), 1.46 (s, 24H), 1.40-1.19 (m, 88H) and 0.89 (t, 6H).
Figure 44B:
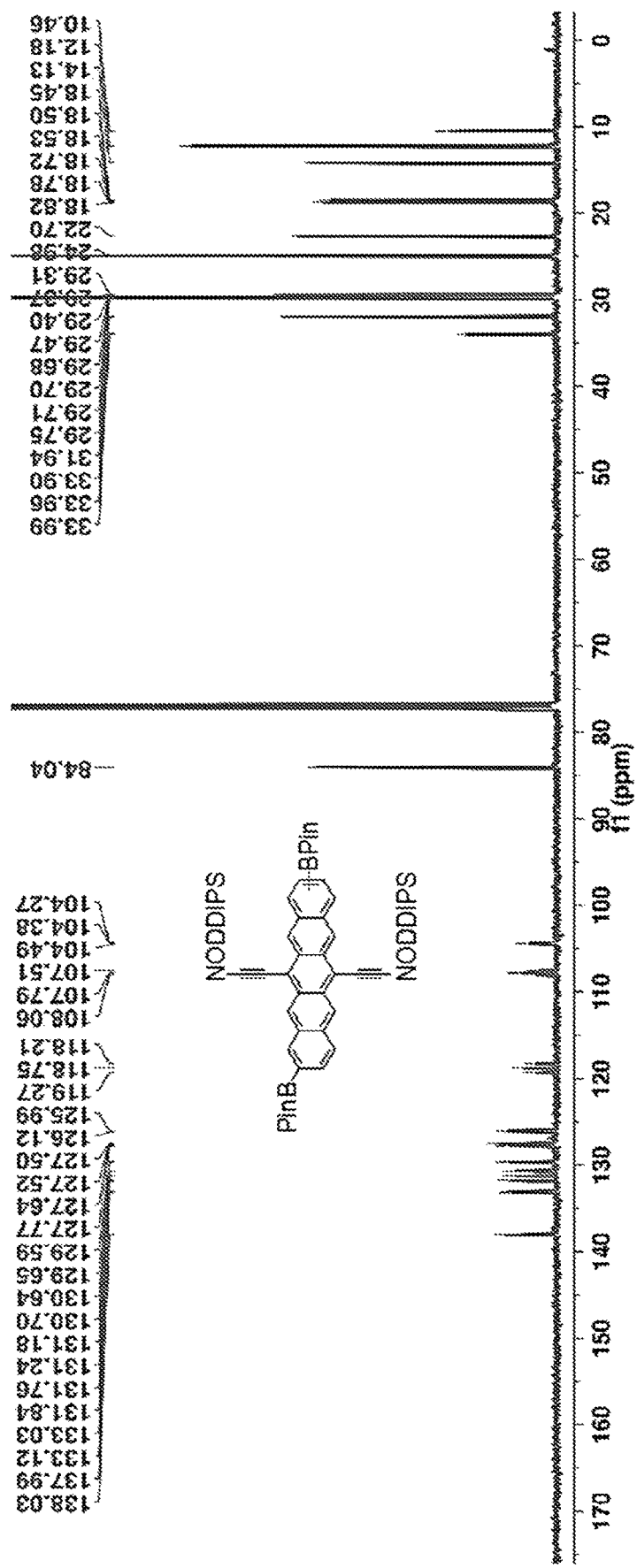
FIG. 44B shows $^{13}$C NMR absorption spectrum for primary pentacene mix-1B2' at its optimum geometry characterized by $^{13}$C-NMR (125 MHz, CDCl$_3$, δ ppm): 138.0, 137.9, 133.1, 133.0, 131.8, 131.7, 131.2, 131.1, 130.7, 130.6, 129.7, 129.6, 127.8, 127.6, 127.52, 127.50, 126.1, 125.99, 119.3, 118.8, 118.2, 108.1, 107.8, 107.5, 104.5, 104.4, 104.3, 84.0, 33.99, 33.96, 33.90, 31.9, 29.8, 29.71, 29.70, 29.7, 29.5, 29.4, 29.37, 29.31, 24.9, 22.7, 18.8, 18.78, 18.72, 18.5, 18.5, 18.45, 14.1, 12.2 and 10.5.
Figure 45A:
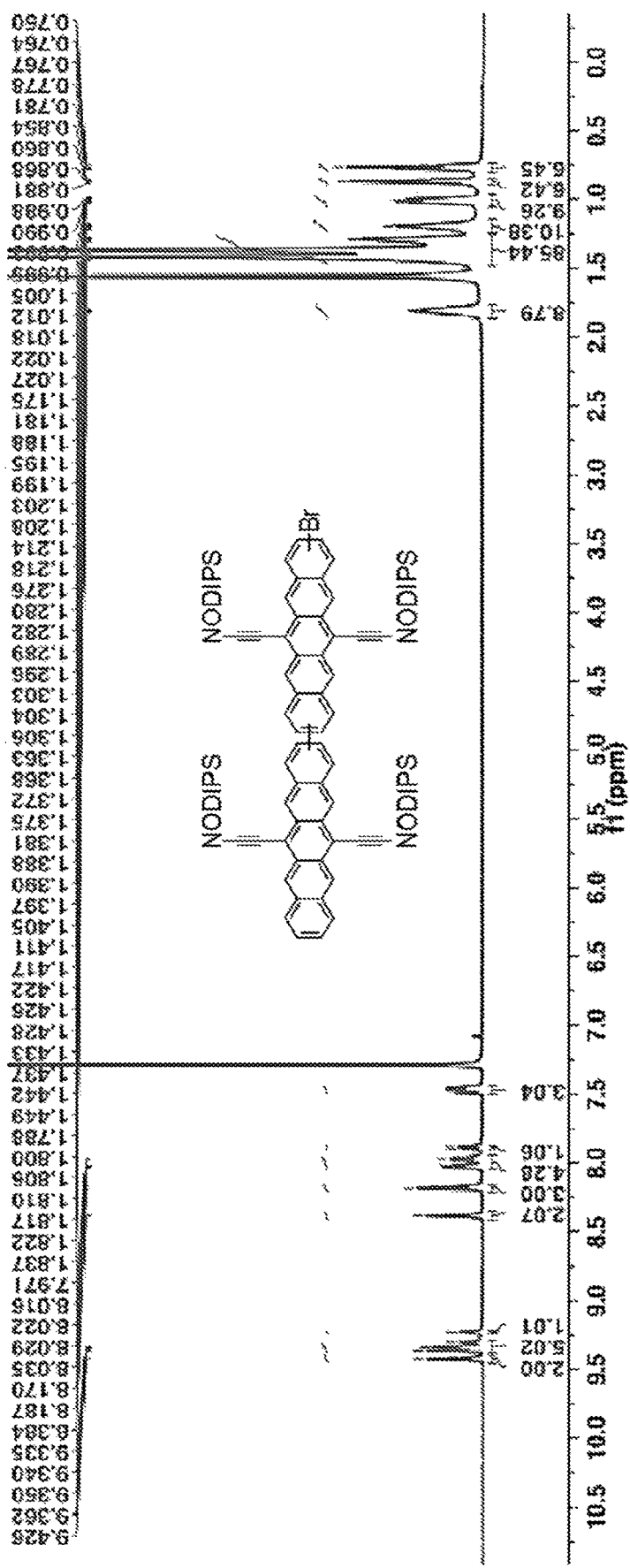
FIG. 45A shows $^1$H NMR absorption spectrum for pentacene 2A at its optimum geometry characterized by $^1$H-NMR (500 MHz, CDCl$_3$, δ ppm): 9.43-9.41 (m, 2H), 9.36-9.30 (m, 5H), 9.23-9.22 (m, 1H), 8.38 (s, 2H), 8.19-8.17 (m, 3H), 8.04-7.95 (m, 4H), 7.89-7.88 (m, 1H), 7.49-7.45 (m, 3H), 1.84-1.78 (m, 8H), 1.45-1.28 (m, 85H), 1.22-1.18 (m, 10H), 1.03-0.99 (m, 9H), 0.88-0.85 (m, 6H) and 0.78-0.75 (m, 6H).
Figure 45B:
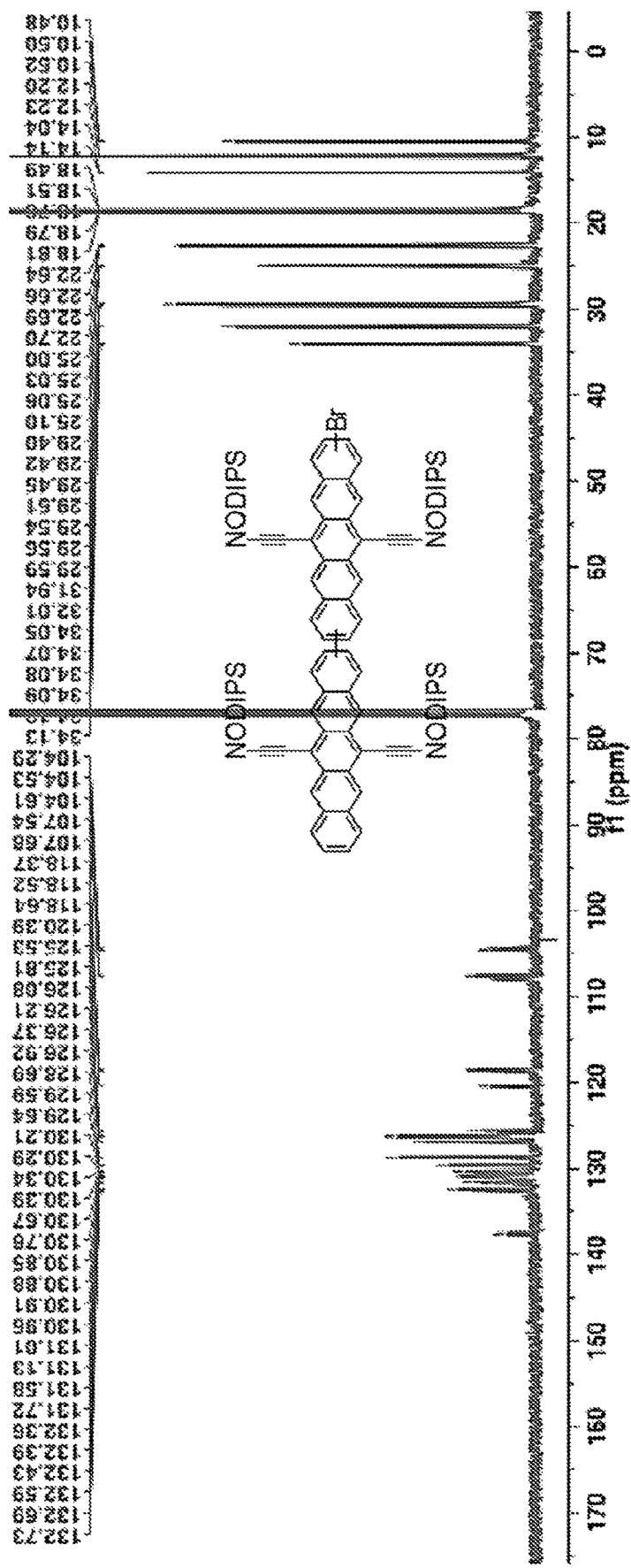
FIG. 45B shows $^{13}$C NMR absorption spectrum for pentacene 2A at its optimum geometry characterized by $^{13}$C-NMR (125 MHz, CDCl$_3$, δ ppm): 137.8, 137.5, 132.7, 132.69, 132.6, 132.4, 132.39, 132.36, 131.8, 131.7, 131.6, 131.3, 131.1, 131.0, 130.96, 130.91, 130.88, 130.85, 130.76, 130.67, 130.57, 130.4, 130.3, 130.29, 130.2, 129.6, 129.59, 128.7, 126.9, 126.4, 126.2, 126.1, 125.8, 125.5, 120.4, 118.8, 118.6, 118.5, 118.4, 118.3, 108.1, 108.0, 107.99, 107.9, 107.7, 107.5, 104.6, 104.5, 104.3, 34.13, 34.1, 34.09, 34.08, 34.07, 34.05, 32.0, 31.9, 29.6, 29.56, 29.54, 29.51, 29.45, 29.42, 29.40, 25.1, 25.06, 25.03, 25.0, 22.7, 22.69, 22.66, 22.64, 18.8, 18.79, 18.76, 18.5, 18.49, 14.1, 14.0, 12.23, 12.20, 10.52, 10.50 and 10.48.
Figure 46A:
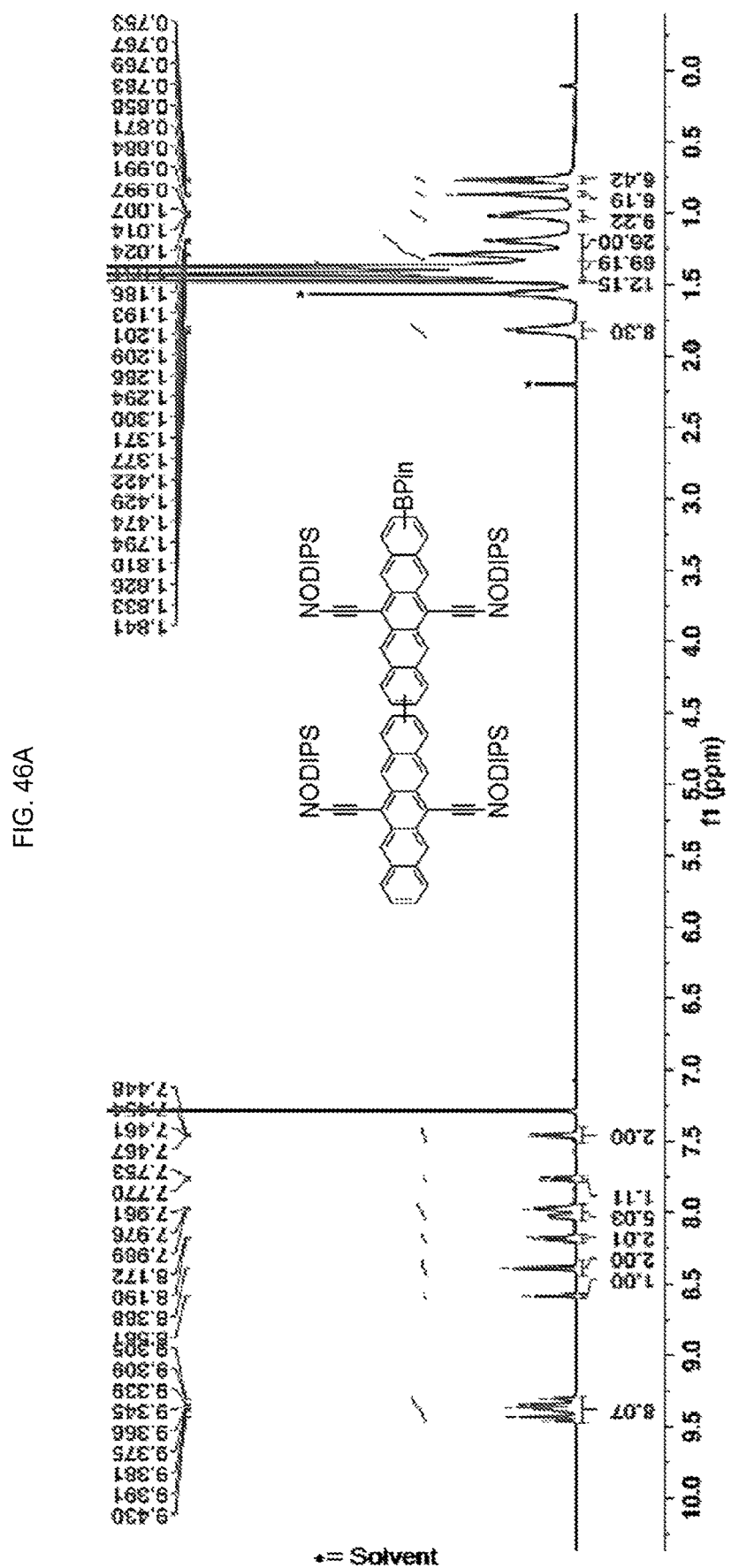
FIG. 46A shows $^1$H NMR absorption spectrum for pentacene 2B at its optimum geometry characterized by $^1$H-NMR (500 MHz, CDCl$_3$, δ ppm): 9.46-9.31 (m, 8H), 8.58 (s, 1H), 8.39 (s, 2H), 8.19-8.17 (m, 2H), 7.99-7.96 (m, 5H), 7.77-7.75 (m, 1H), 7.47-7.45 (m, 2H), 1.84-1.79 (m, 8H), 1.47 (s, 12H), 1.43-1.37 (m, 69H), 1.30-1.19 (m, 26H), 1.03-0.99 (m, 9H), 0.88-0.86 (m, 6H) and 0.78-0.75 (m, 6H).
Figure 46B:
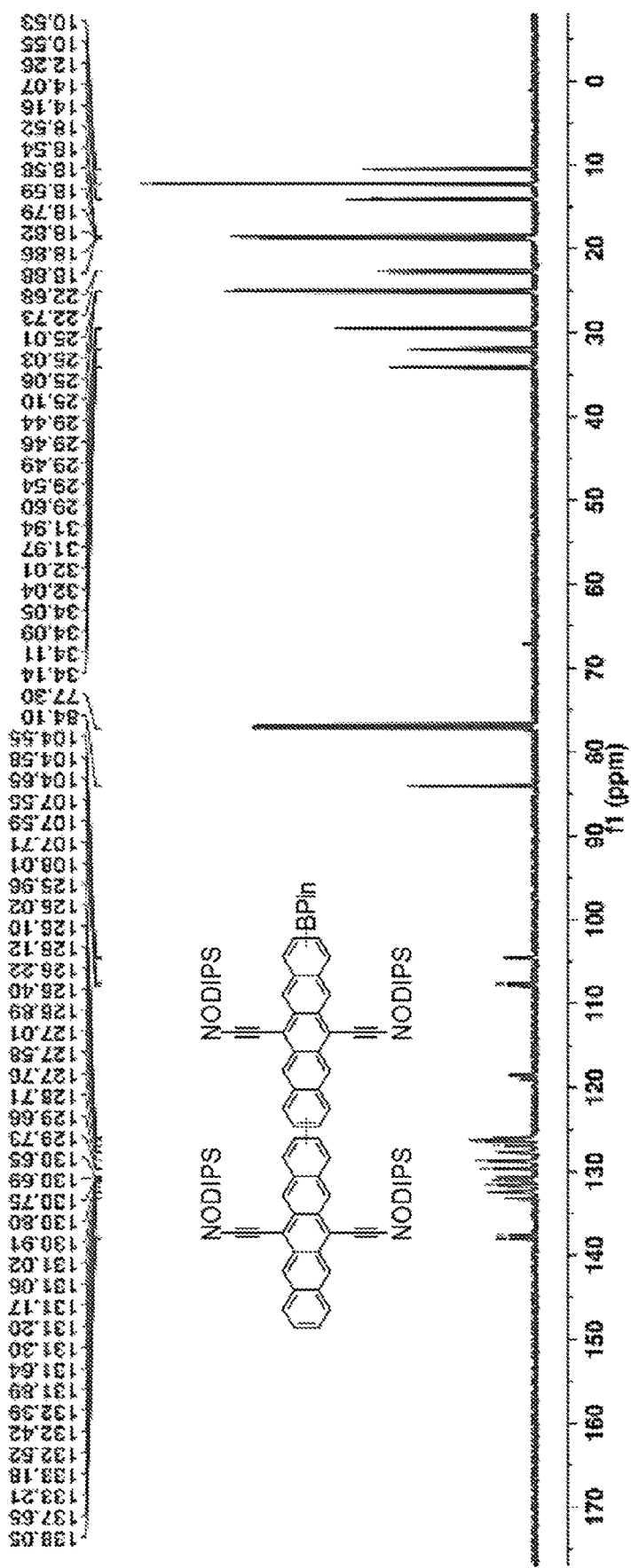
FIG. 46B shows $^{13}$C NMR absorption spectrum for pentacene 2B at its optimum geometry characterized by $^{13}$C-NMR (125 MHz, CDCl$_3$, δ ppm): 138.1, 137.7, 137.65, 133.2, 133.28, 132.6, 132.5, 132.4, 132.39, 131.9, 131.89, 131.7, 131.6, 131.3, 131.22, 131.20, 131.17, 131.06, 131.0, 130.9, 130.8, 130.75, 130.69, 130.65, 129.7, 129.66, 128.7, 127.8, 127.6, 127.0, 126.9, 126.40, 126.2, 126.12, 126.10, 126.0, 125.96, 119.0, 118.9, 118.6, 118.5, 118.4, 118.3, 108.0, 107.9, 107.74, 107.71, 107.59, 107.55, 104.65, 104.58, 104.55, 104.5, 104.4, 84.1, 34.14, 34.1, 34.09, 34.05, 32.04, 32.01, 31.97, 31.9, 29.60, 29.54, 29.49, 29.46, 29.44, 25.10, 25.06, 25.03, 25.01, 22.73, 22.68, 18.88, 18.86, 18.82, 18.79, 18.59, 18.58, 18.54, 18.52, 14.2, 14.1, 12.3, 10.55 and 10.53.
Figure 47A:
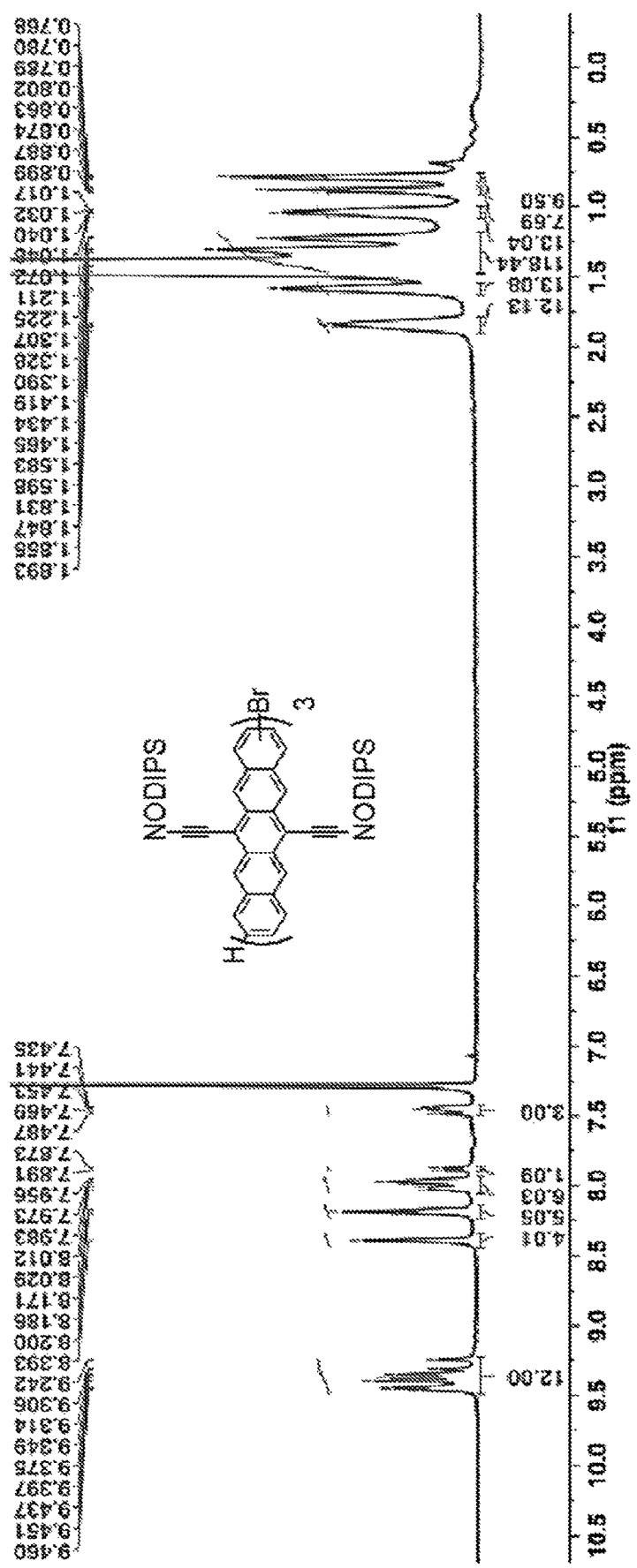
FIG. 47A shows $^1$H NMR absorption spectrum for pentacene 3A at its optimum geometry characterized by $^1$H-NMR (500 MHz, 50° C., CDCl$_3$, δ ppm): 9.46-9.24 (m, 12H), 8.39 (s, 4H), 8.20-8.17 (m, 5H), 8.03-7.96 (m, 6H), 7.89-7.87 (m, 1H), 7.49-7.44 (m, 3H), 1.89-1.83 (m, 13H), 1.59-1.58 (m, 14H), 1.47-1.21 (m, 127H), 1.07-1.02 (m, 14H), 0.89-0.86 (m, 8H) and 0.80-0.77 (m, 10H).
Figure 47B:
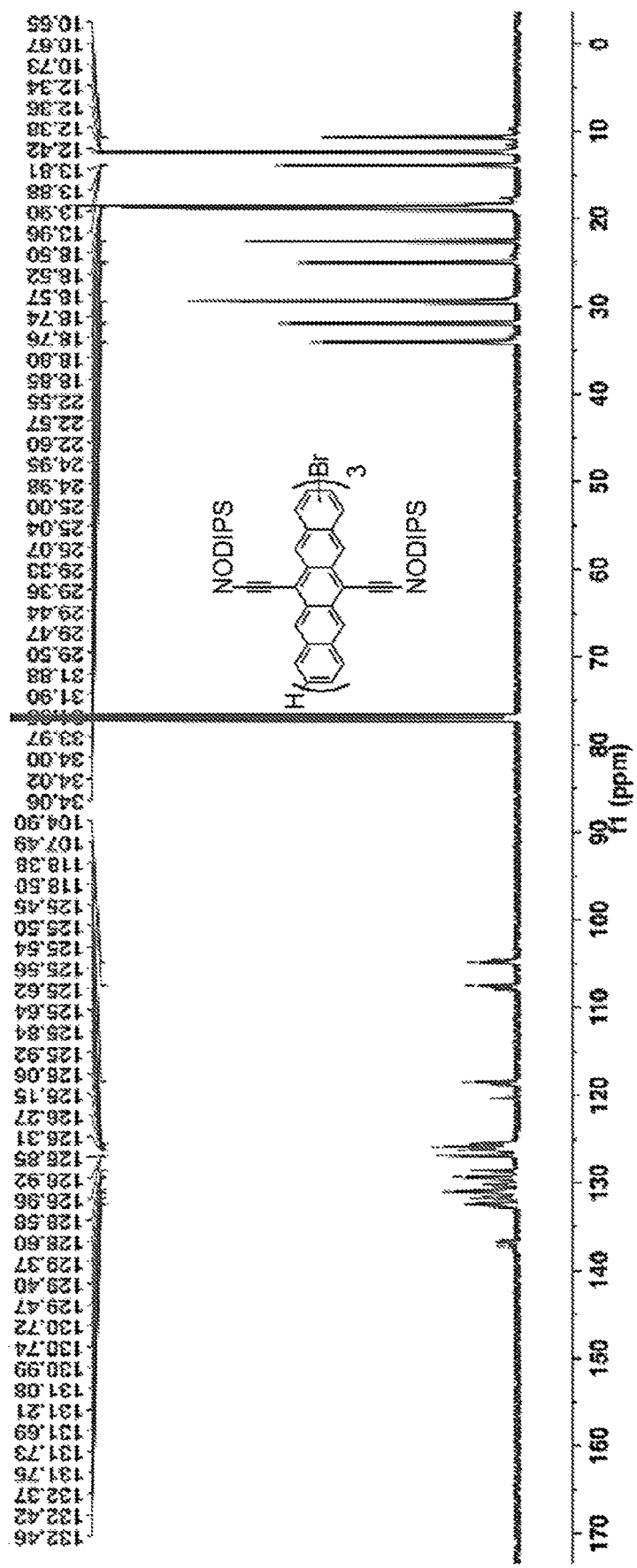
FIG. 47B shows $^{13}$C NMR absorption spectrum for pentacene 3A at its optimum geometry characterized by $^{13}$C-NMR (125 MHz, 50° C., CDCl$_3$, δ ppm): 137.3, 137.2, 136.91, 136.90, 136.88, 136.8, 136.73, 136.72, 136.7, 136.6, 136.5, 132.78, 132.73, 132.68, 132.65, 132.58, 132.52, 132.46, 132.4, 132.37, 132.33, 131.9, 131.86, 131.75, 131.73, 131.69, 131.63, 131.3, 131.27, 131.21, 131.1, 130.99, 130.89, 130.83, 130.81, 130.74, 130.72, 130.63, 130.58, 130.34, 130.31, 130.23, 130.19, 130.15, 130.07, 129.5, 129.4, 129.37, 128.7, 128.6, 128.58, 126.96, 126.9, 126.85, 126.78, 126.31, 126.27, 126.15, 126.1, 125.9, 125.8, 125.6, 125.62, 125.56, 125.54, 125.50, 125.45, 125.37, 125.33, 120.37, 120.34, 120.29, 118.84, 118.81, 118.72, 118.69, 118.65, 118.63, 118.54, 118.50, 118.46, 118.4, 118.38, 108.1, 108.0, 107.99, 107.96, 107.90, 107.85, 107.78, 107.75, 107.63, 107.52, 107.49, 107.39, 104.90, 104.84, 104.82, 104.78, 104.75, 104.59, 104.57, 104.52, 34.06, 34.02, 34.0, 33.97, 31.95, 31.90, 31.88, 29.5, 29.47, 29.44, 29.36, 29.33, 25.1, 25.04, 25.00, 24.98, 24.95, 22.60, 22.57, 22.6, 18.9, 18.8, 18.76, 18.74, 18.57, 18.52, 18.50, 13.96, 13.90, 13.88, 13.81, 12.4, 12.38, 12.36, 12.34, 10.73, 10.7 and 10.65.
Figure 48A:
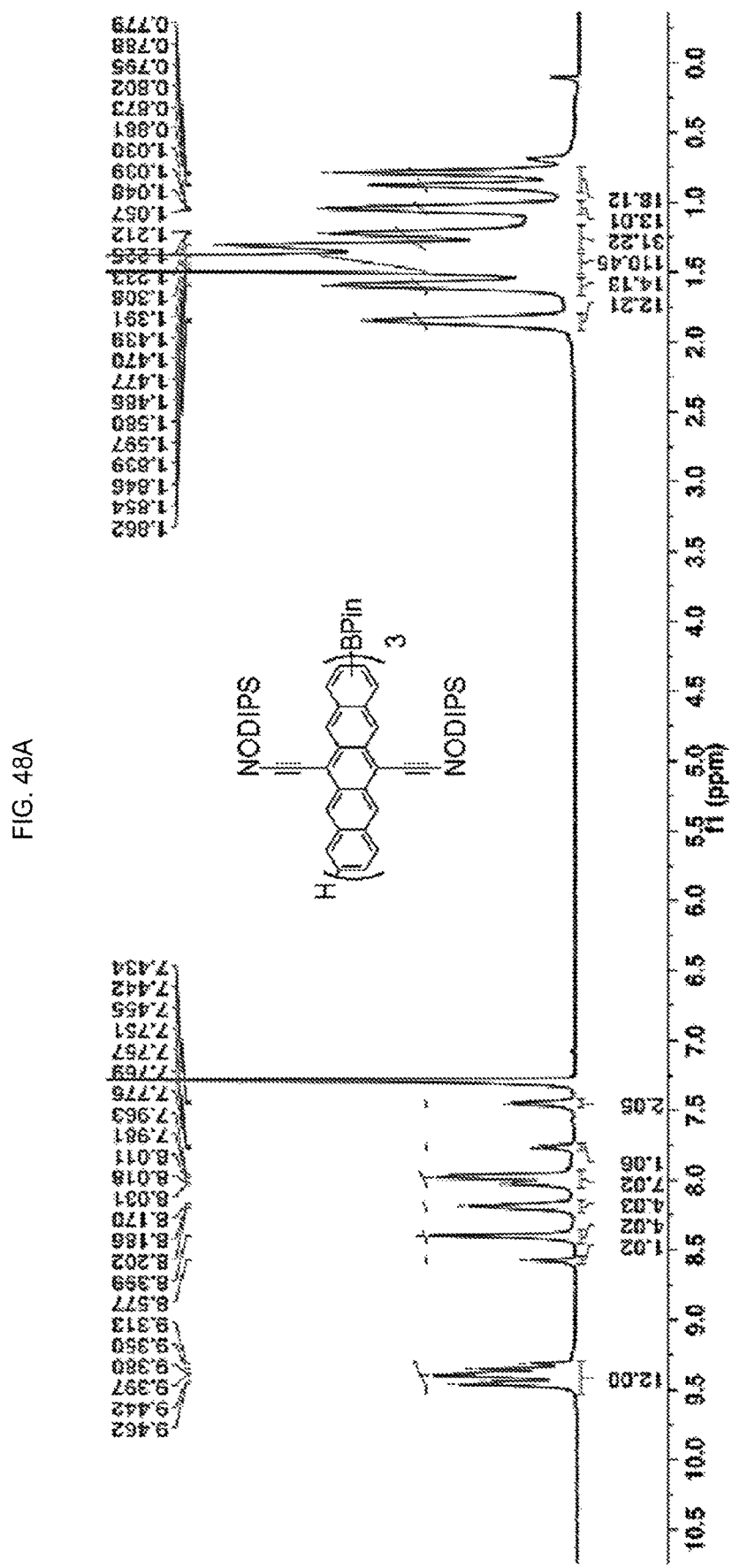
FIG. 48A shows $^1$H NMR absorption spectrum for pentacene 3B at its optimum geometry characterized by $^1$H-NMR (500 MHz, 50° C., CDCl$_3$, δ ppm): 9.46-9.31 (m, 12H), 8.58 (s, 1H), 8.39 (s, 4H), 8.20-8.17 (m, 4H), 8.03-7.98 (m, 7H), 7.78-7.75 (m, 1H), 7.46-7.43 (m, 2H), 1.86-1.84 (m, 12H), 1.59-1.58 (m, 14H), 1.48-1.39 (m, 110H), 1.31-1.21 (m, 31H), 1.06-1.03 (m, 13H) and 0.89-0.78 (m, 18H).
Figure 48B:
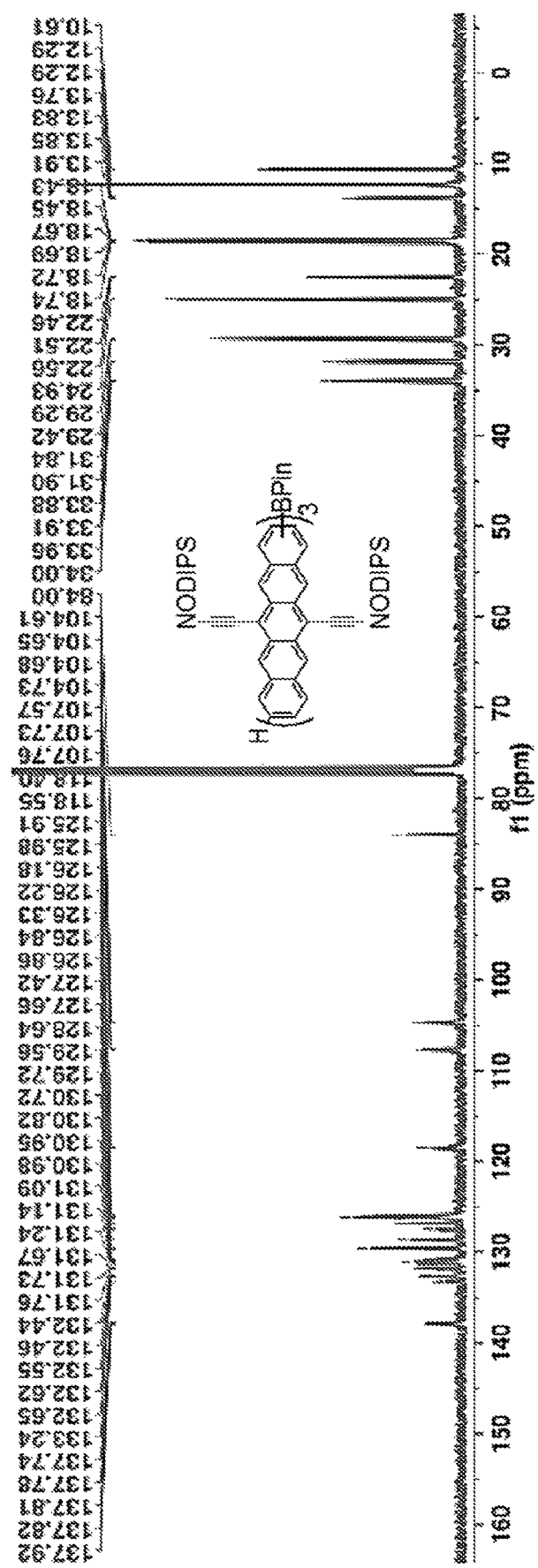
FIG. 48B shows $^{13}$C NMR absorption spectrum for pentacene 3B at its optimum geometry characterized by $^{13}$C-NMR (125 MHz, 50° C., CDCl$_3$, δ ppm): 137.9, 137.85, 137.82, 137.81, 137.78, 137.74, 133.24, 133.22, 132.65, 132.62, 132.55, 132.46, 132.44, 131.97, 131.76, 131.73, 131.67, 131.3, 131.24, 131.14, 131.09, 130.98, 130.95, 130.8, 130.78, 130.72, 130.7, 129.7, 129.6, 128.6, 127.7, 127.4, 126.9, 126.8, 126.33, 126.22, 126.18, 125.98, 125.9, 118.6, 118.4, 107.76, 107.73, 107.57, 104, 73, 104.68, 104.65, 104.61, 104.55, 84.0, 34.0, 33.96, 33.91, 33.88, 31.9, 31.8, 29.4, 29.3, 22.6, 22.5, 22.46, 18.74, 18.72, 18.69, 18.67, 18.45, 18.43, 13.91, 13.85, 13.83, 13.76, 12.29 and 10.6.
Figure 49A:
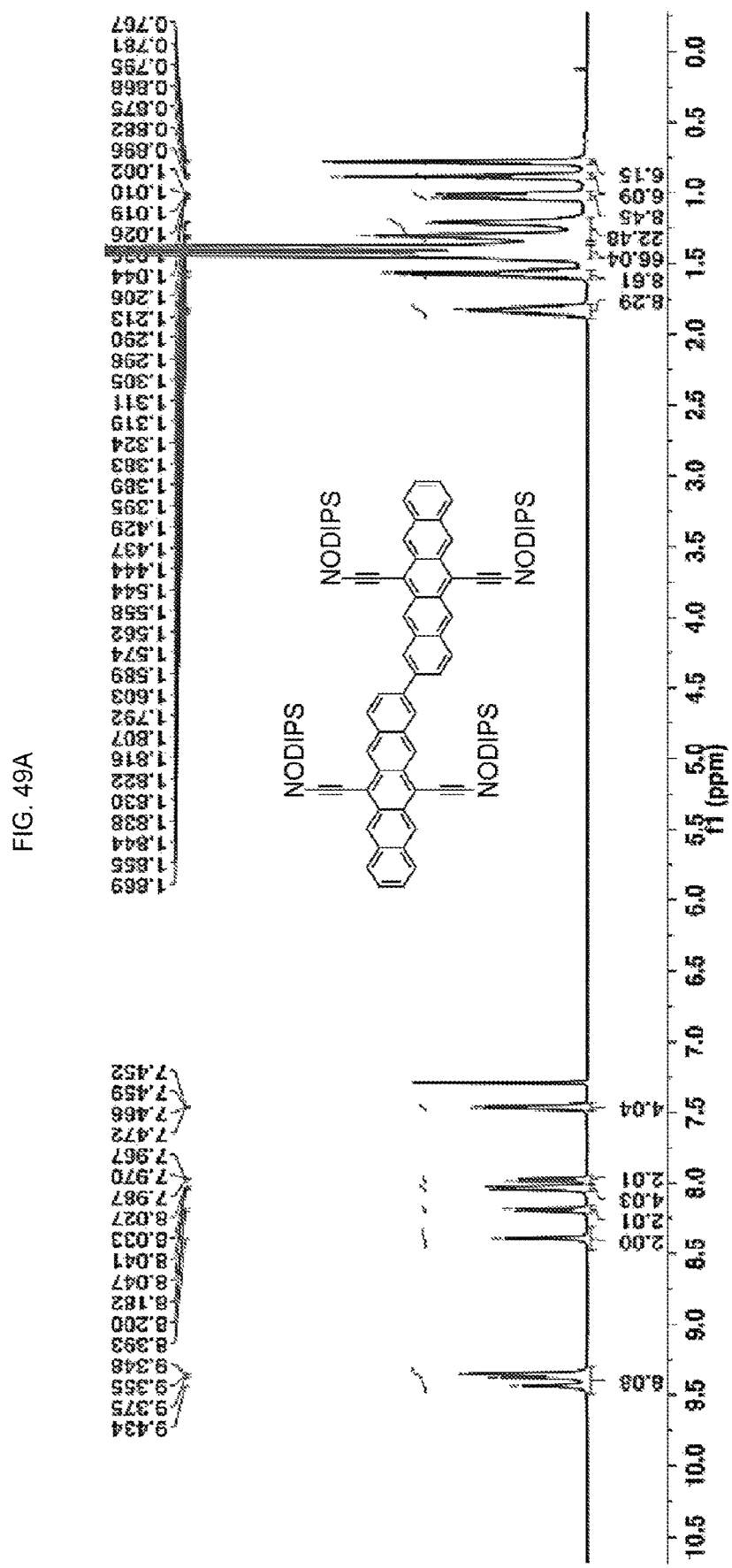
FIG. 49A shows $^1$H NMR absorption spectrum for oligopentacene 2Pc at its optimum geometry characterized by $^1$H-NMR (500 MHz, CDCl$_3$, δ ppm): 9.43-9.35 (m, 8H), 8.39 (s, 2H), 8.20-8.18 (m, 2H), 8.05-8.03 (m, 4H), 7.97-7.97 (m, 2H), 4.47-7.45 (m, 4H), 1.87-1.79 (m, 8H), 1.87-1.79 (m, 8H), 1.60-1.54 (m, 8H), 1.44-1.38 (m, 66H), 1.32-1.21 (m, 22H), 1.04-1.00 (m, 8H), 0.89-0.87 (m, 6H) and 0.79-0.78 (m, 6H).
Figure 49B:
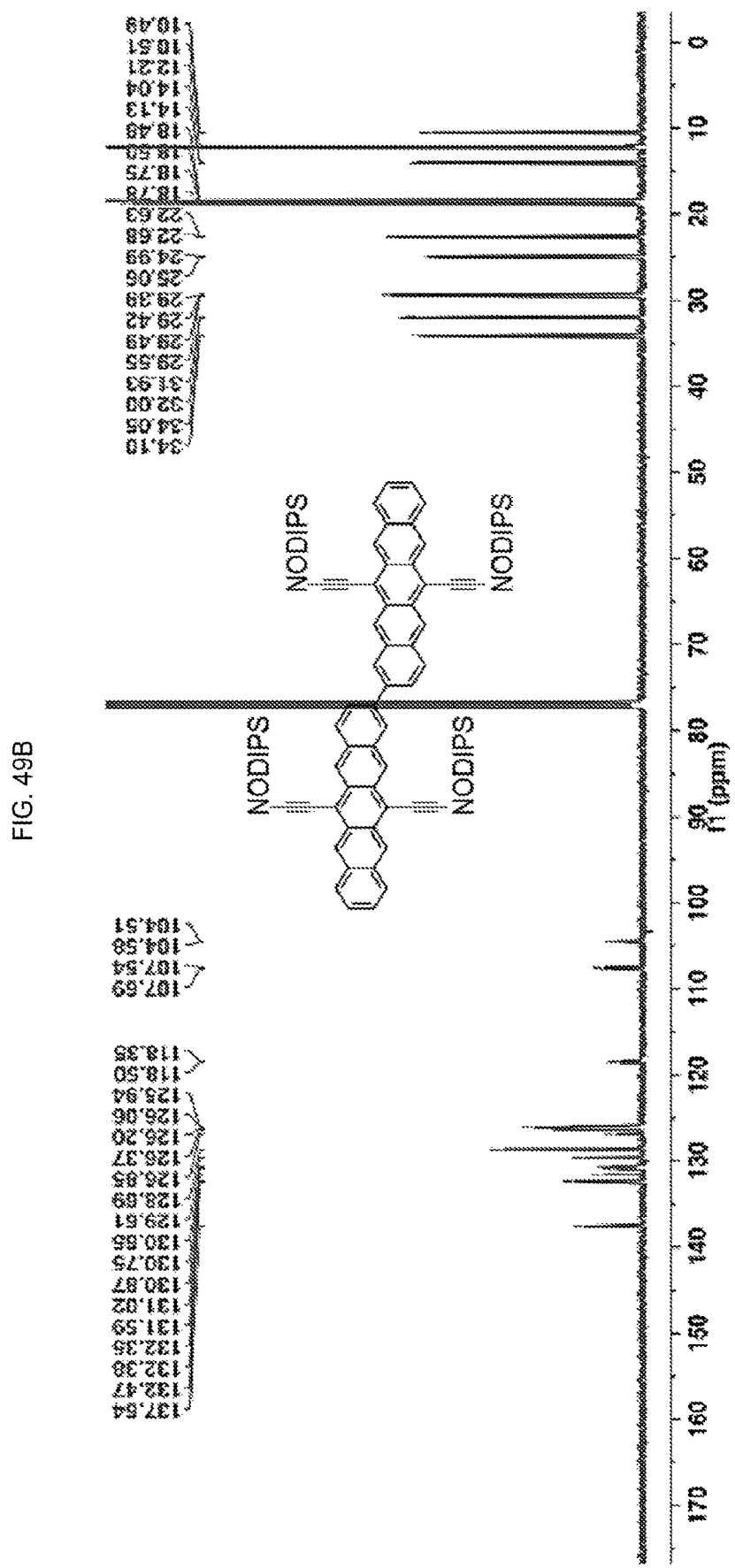
FIG. 49B shows $^{13}$C NMR absorption spectrum for oligopentacene 2Pc at its optimum geometry characterized by $^{13}$C-NMR (125 MHz, CDCl$_3$, δ ppm): 137.6, 132.5, 132.4, 132.35, 131.6, 131.0, 130.9, 130.8, 130.7, 129.6, 128.7, 126.9, 126.4, 126.2, 126.1, 125.9, 118.5, 118.4, 107.7, 107.5, 104.6, 104.5, 34.1, 34.05, 32.0, 31.9, 29.6, 29.5, 29.4, 29.39, 25.1, 24.99, 22.7, 22.6, 18.8, 18.75, 18.5, 18.48, 14.1, 14.0, 12.2, 10.5 and 10.5.
Figure 50A:
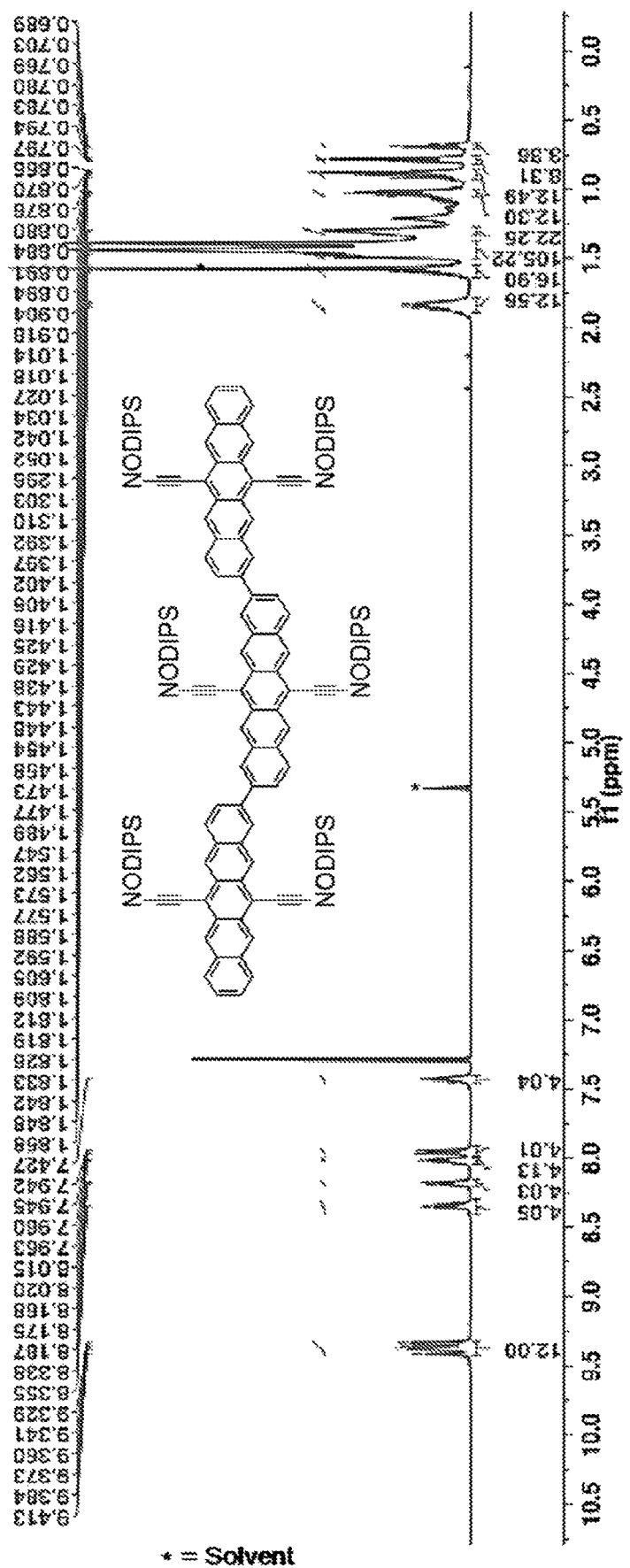
FIG. 50A shows $^1$H NMR absorption spectrum for oligopentacene syn-3Pc at its optimum geometry characterized by $^1$H-NMR (500 MHz, CDCl$_3$, δ ppm): 9.41-9.33 (m, 12H), 8.35-8.32 (m, 4H), 8.19-8.18 (m, 4H), 8.03-8.00 (m, 4H), 7.96-7.94 (m, 4H), 7.45-7.40 (m, 4H), 1.87-1.81 (m, 12H), 1.62-1.55 (m, 12H), 1.49-1.39 (m, 105H), 1.31-1.29 (m, 22H), 1.05-1.01 (m, 12H), 0.92-0.87 (m, 12H), 0.79-0.77 (m, 8H) and 0.70-0.68 (m, 3H).
Figure 50B:
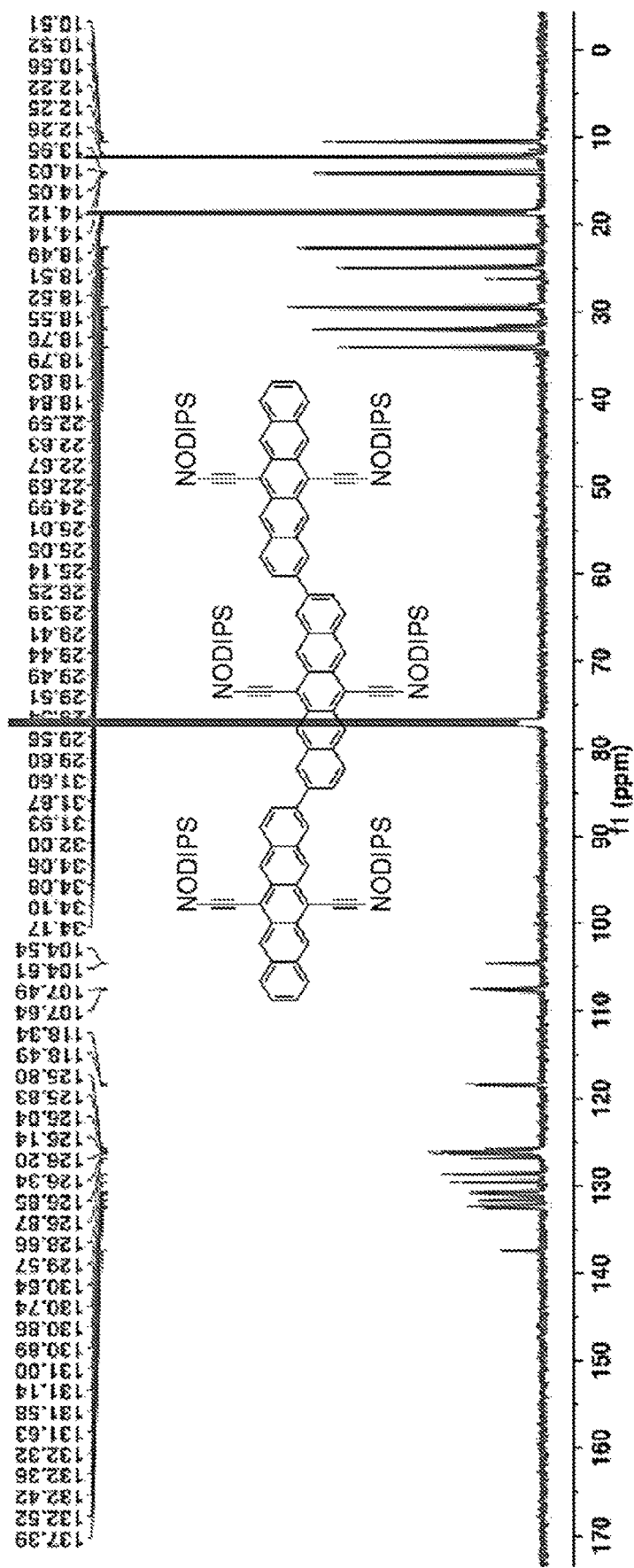
FIG. 50B shows $^{13}$C NMR absorption spectrum for oligopentacene syn-3Pc at its optimum geometry characterized by $^{13}$C-NMR (125 MHz, CDCl$_3$, δ ppm): 137.5, 137.4, 132.5, 132.4, 132.36, 132.3, 131.6, 131.5, 131.1, 131.0, 130.9, 130.86, 130.7, 130.6, 129.6, 128.7, 126.9, 126.85, 126.3, 126.2, 126.1, 125.83, 125.80, 118.7, 118.5, 118.3, 107.8, 107.6, 107.5, 104.7, 104.6, 104.54, 104.51, 34.2, 34.1, 34.08, 34.06, 32.0, 31.9, 31.87, 31.6, 29.6, 29.56, 29.54, 29.51, 29.49, 29.44, 29.41, 29.39, 26.2, 25.1, 25.06, 25.0, 24.99, 24.8, 22.7, 22.67, 22.63, 22.59, 18.84, 18.83, 18.79, 18.76, 18.55, 18.52, 18.49, 14.14, 14.12, 14.05, 14.03, 13.95, 12.26, 12.25, 12.22, 10.56, 10.52 and 10.51.
Figure 51A:
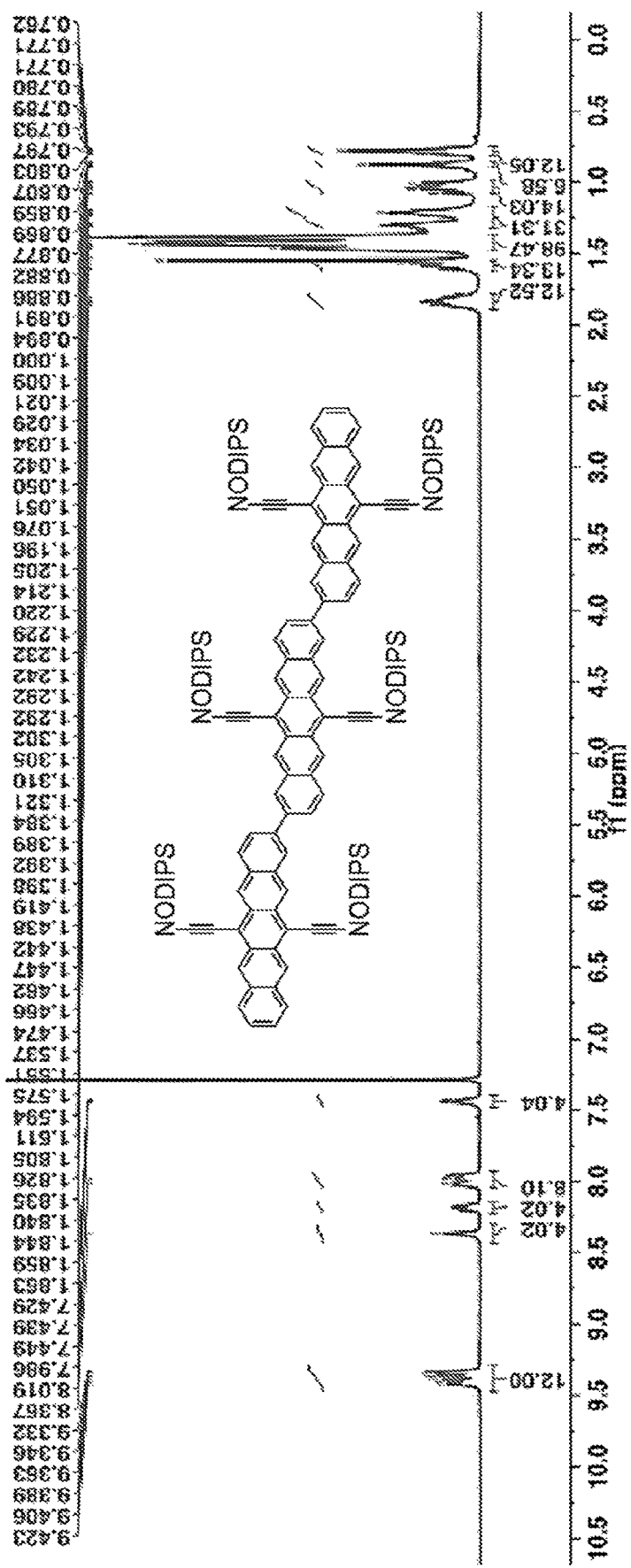
FIG. 51A shows $^1$H NMR absorption spectrum for oligopentacene anti-3Pc at its optimum geometry characterized by $^1$H-NMR (400 MHz, CDCl$_3$, δ ppm): 9.42-9.33 (m, 12H), 8.37 (m, 4H), 8.21-8.17 (m, 4H), 8.04-7.95 (m, 8H), 7.46-7.41 (m, 4H), 1.88-1.79 (m, 12H), 1.62-1.54 (m, 13H), 1.47-1.38 (m, 98H), 1.32-1.19 (m, 31H), 1.08-1.00 (m, 14H) 0.89-0.86 (m, 6H) and 0.81-0.76 (m, 12H).
Figure 51B:
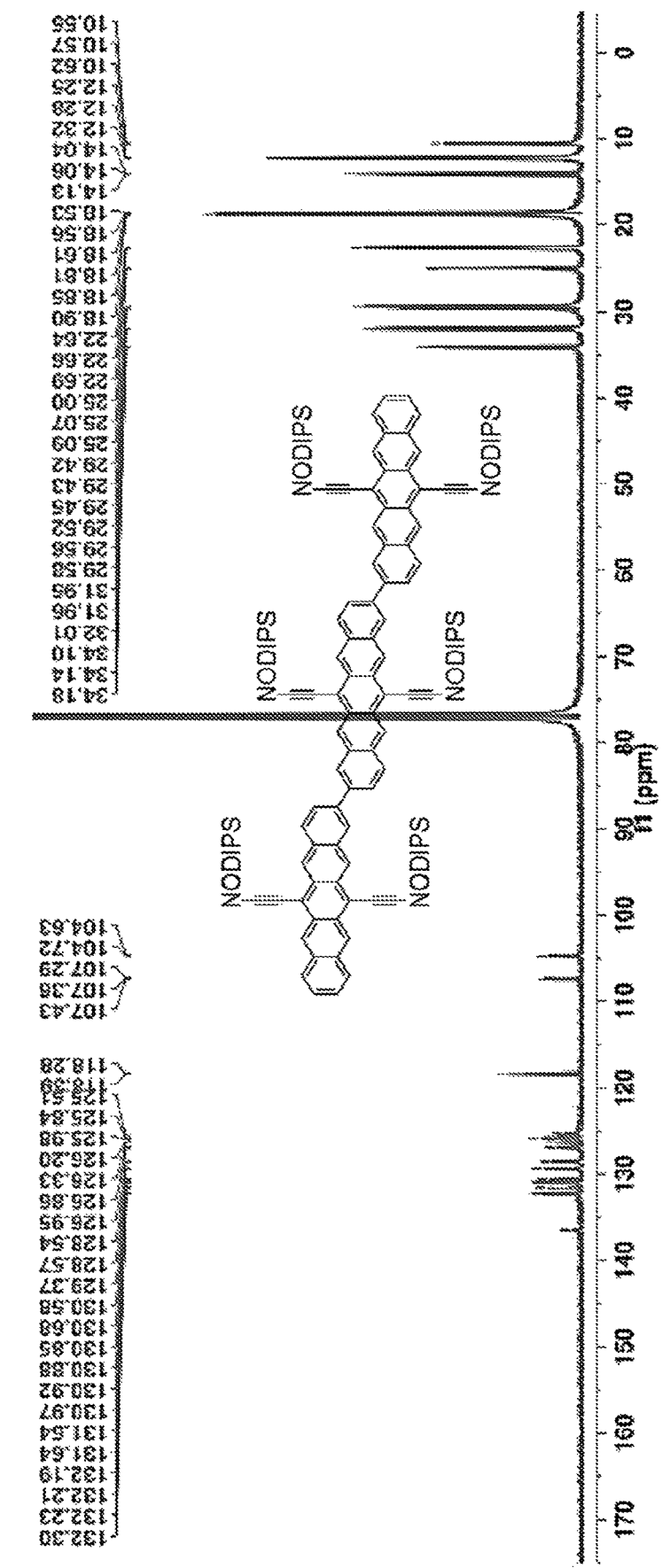
FIG. 51B shows $^{13}$C NMR absorption spectrum for oligopentacene anti-3Pc at its optimum geometry characterized by $^{13}$C-NMR (125 MHz, CDCl$_3$, δ ppm): 136.5, 136.48, 136.45, 132.3, 132.23, 132.21, 132.19, 131.7, 131.6, 131.5, 130.9, 130.92, 130.88, 130.85, 130.7, 130.6, 129.4, 128.57, 128.54, 126.9, 126.86, 126.3, 126.2, 125.9, 125.8, 125.5, 125.4, 125.3, 118.4, 118.3, 107.4, 107.36, 107.29, 104.7, 104.6, 34.18, 34.14, 34.1, 32.0, 31.96, 31.95, 29.58, 29.56, 29.52, 29.45, 29.43, 29.42, 25.1, 25.07, 25.0, 22.7, 22.66, 22.64, 18.9, 18.85, 18.8, 18.6, 18.56, 18.53, 14.1, 14.06, 14.0, 12.32, 12.28, 12.25, 10.62, 10.57 and 10.55.
Figure 52A:
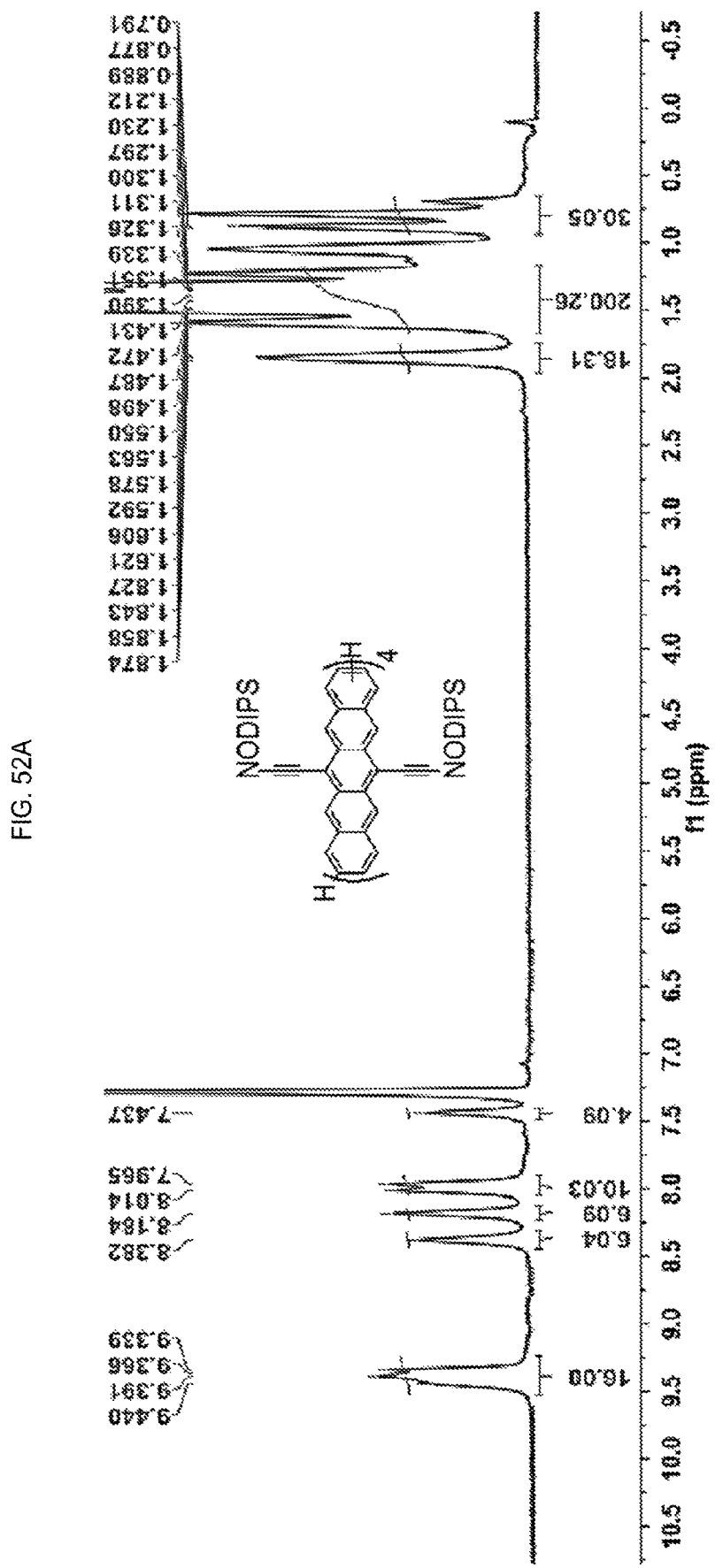
FIG. 52A shows $^1$H NMR absorption spectrum for oligopentacene 4Pc at its optimum geometry characterized by $^1$H-NMR (500 MHz, 50° C., CDCl$_3$, δ ppm): 9.44-9.34 (m, 16H), 8.38 (s, 6H), 8.18 (s, 6H), 8.01-7.97 (m, 10H), 7.44 (s, 4H), 1.87-1.83 (m, 18H), 1.62-1.21 (m, 200H) and 0.89-0.79 (m, 30H).
Figure 52B:
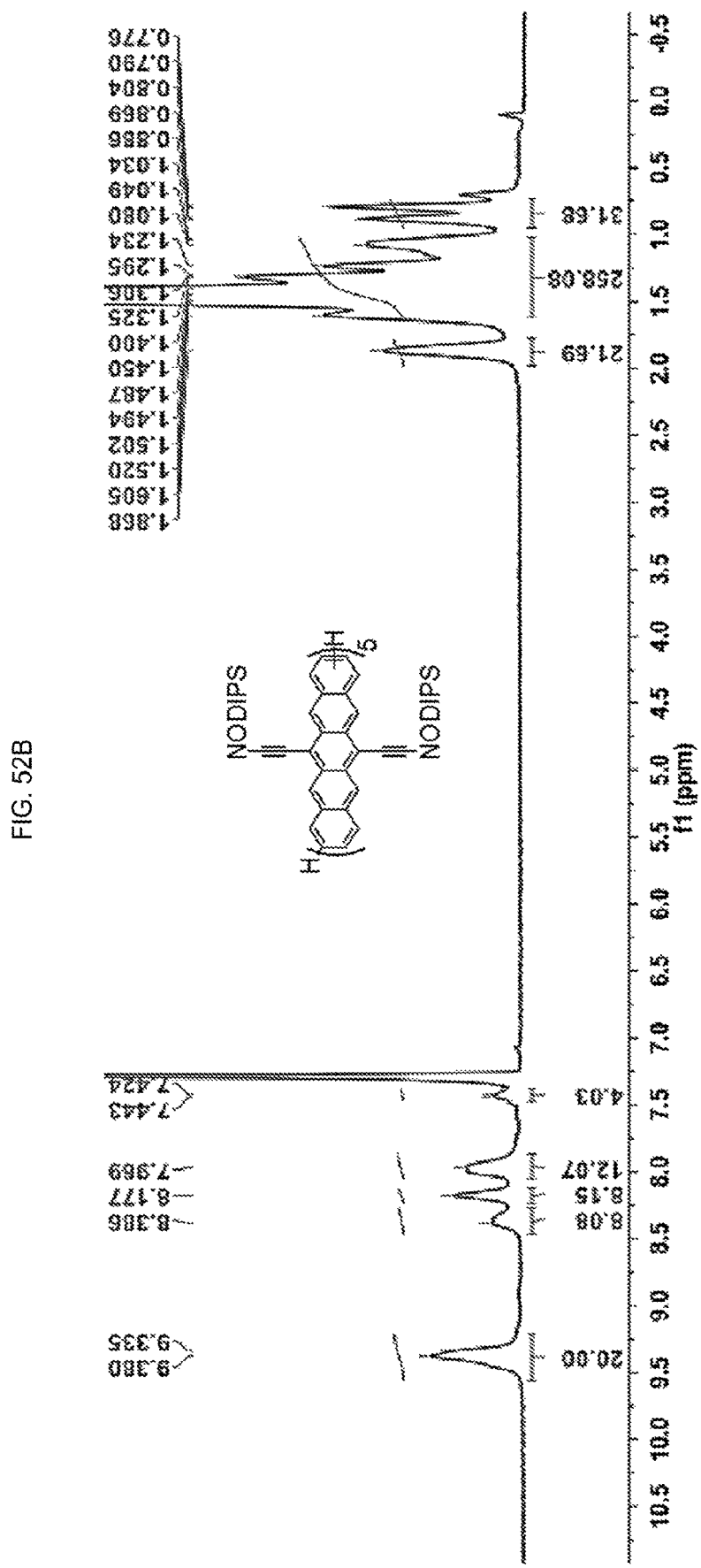
FIG. 52B shows $^{13}$C NMR absorption spectrum for oligopentacene 5Pc at its optimum geometry characterized by $^{13}$C-NMR ((500 MHz, 50° C., CDCl$_3$, δ ppm): 9.38-9.34 (s, 20H), 8.39 (s, 8H), 8.18 (s, 8H), 7.97 (s, 12H), 7.44-7.42 (m, 4H), 1.87 (m, 21H), 1.61-1.03 (m, 258H) and 0.89-0.78 (m, 31H).
Figure 53A:
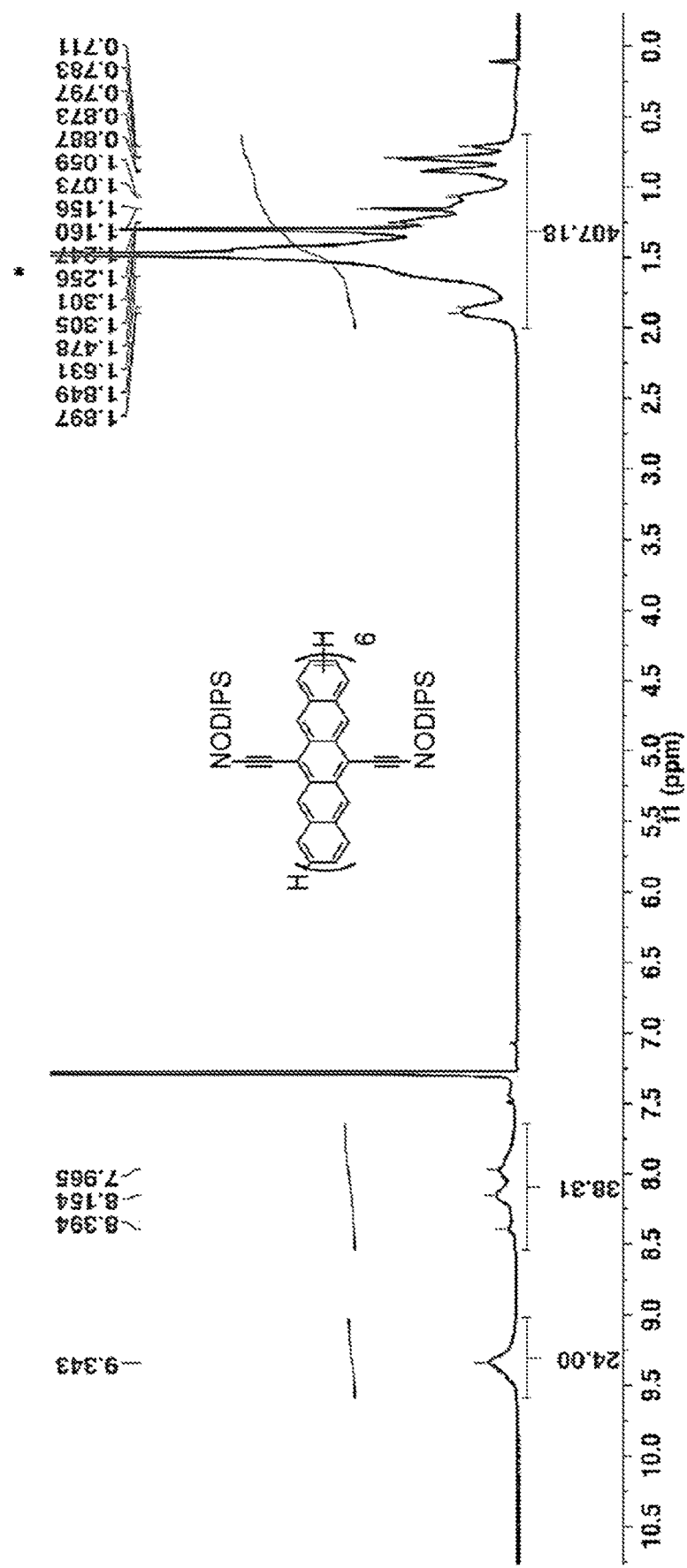
FIG. 53A shows $^1$H NMR absorption spectrum for oligopentacene 6Pc at its optimum geometry characterized by $^1$H-NMR (500 MHz, 50° C., CDCl$_3$, δ ppm): 9.34 (bs, 24H), 8.39-7.97 (m, 38H) and 1.89-0.71 (m, 372H, water peak overlap).
Figure 53B:
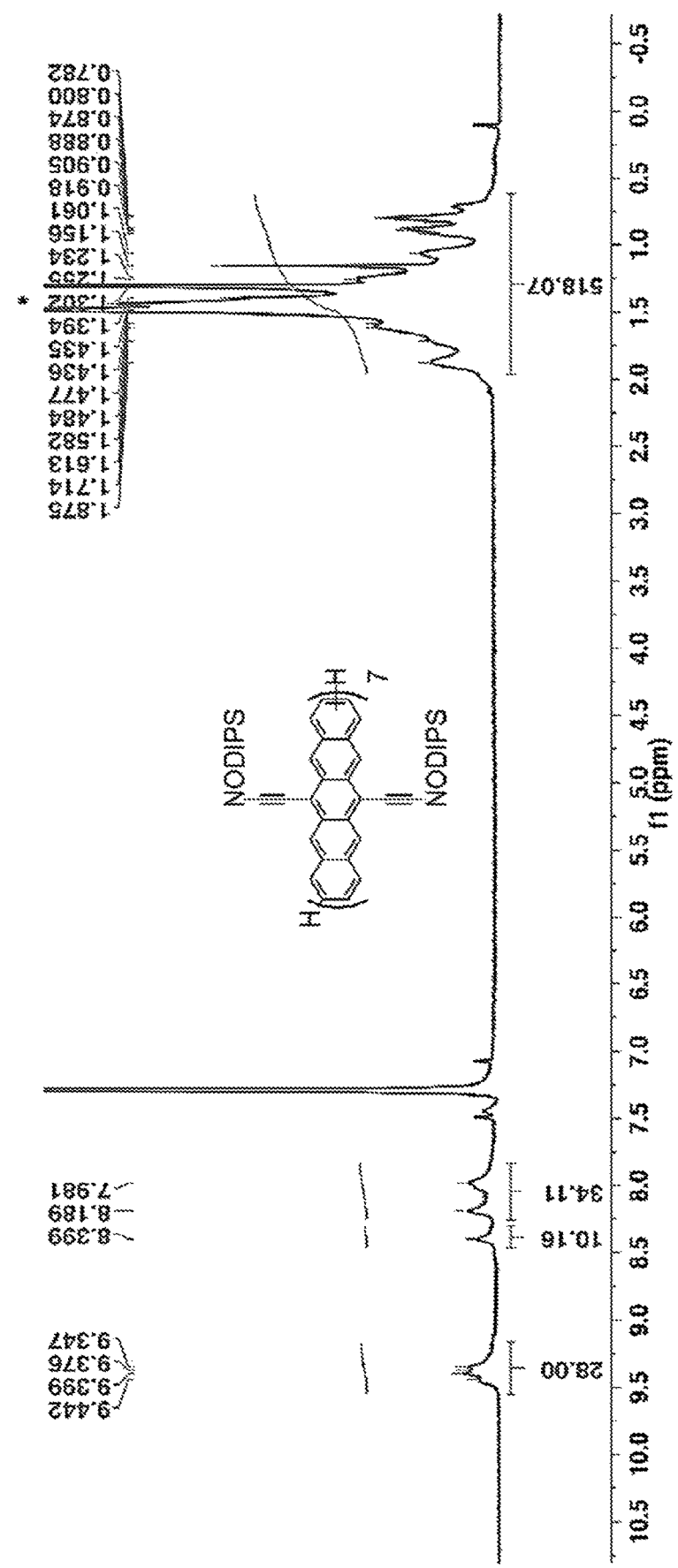
FIG. 53B shows $^1$H NMR absorption spectrum for oligopentacene 7Pc at its optimum geometry characterized by $^1$H-NMR (500 MHz, 50° C., CDCl$_3$, δ ppm): 9.44-9.35 (m, 28H), 8.40 (s, 10H), 8.19-7.98 (m, 34H) and 1.88-0.78 (m, 434H, water peak overlap).
Figure 54A:
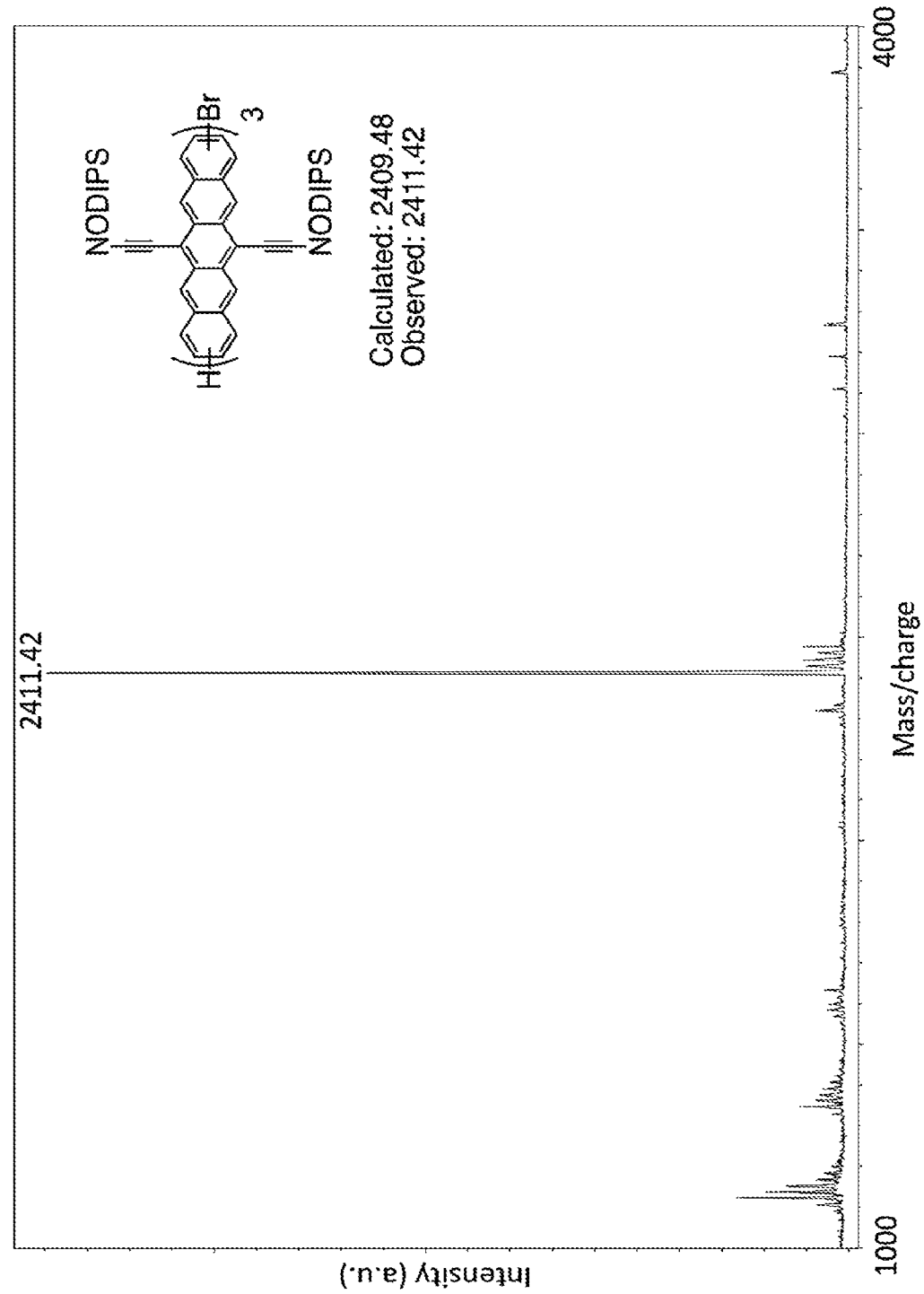
FIG. 54A shows mass spectra for pentacene 3A.
Figure 54B:
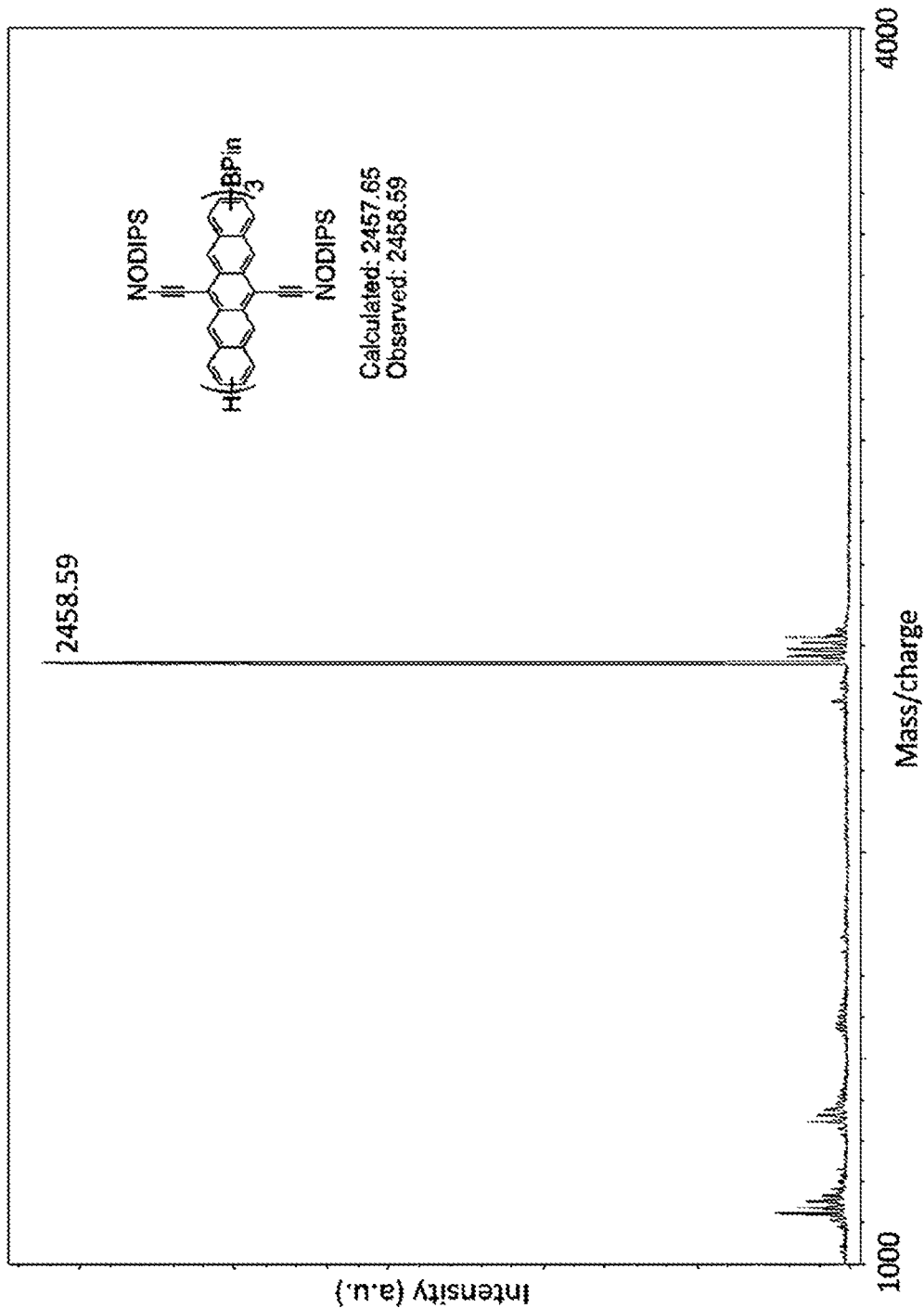
FIG. 54B shows mass spectra for pentacene 3B.
Figure 55A:
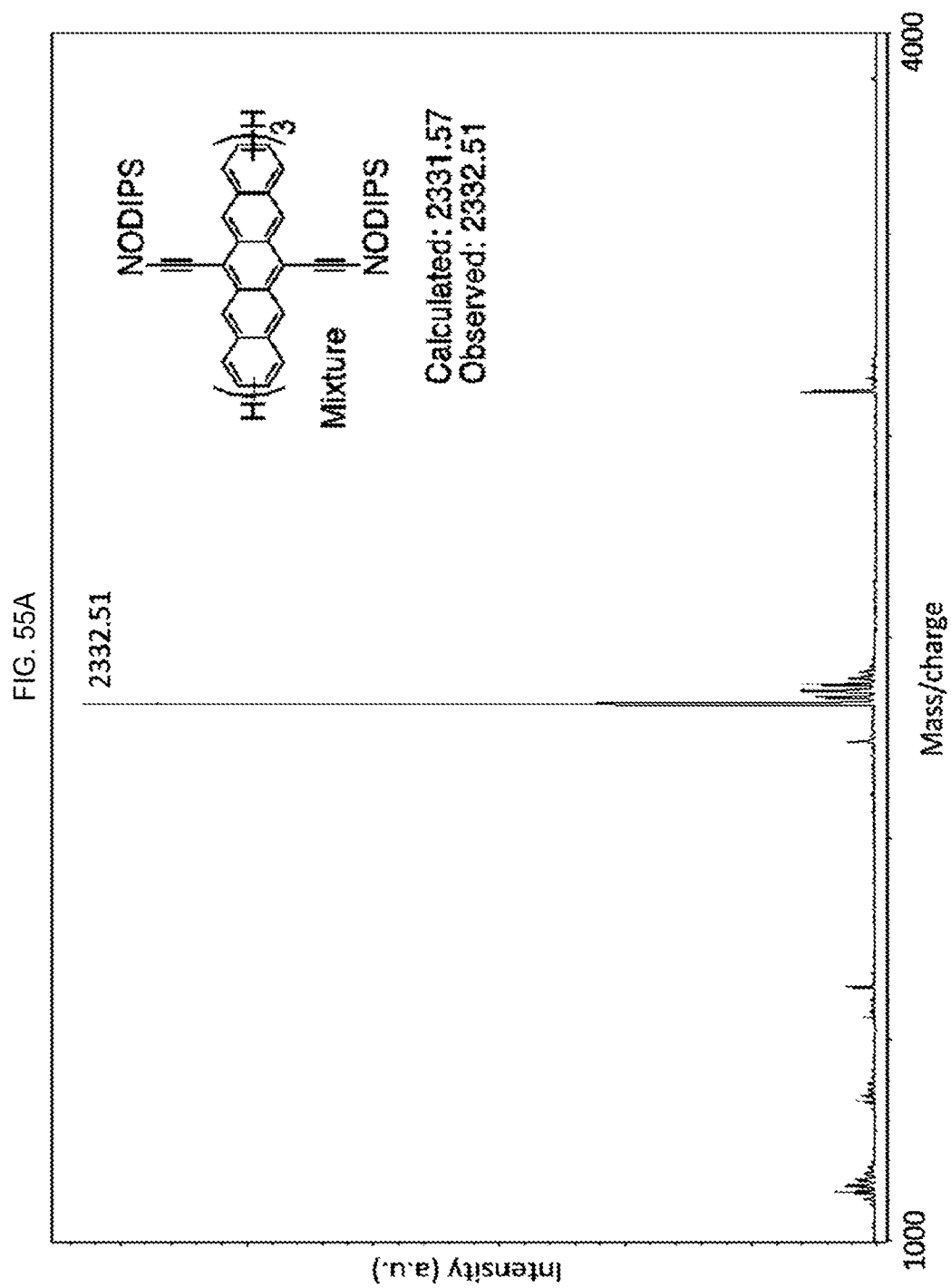
FIG. 55A shows mass spectra for mix-3Pc.
Figure 55B:
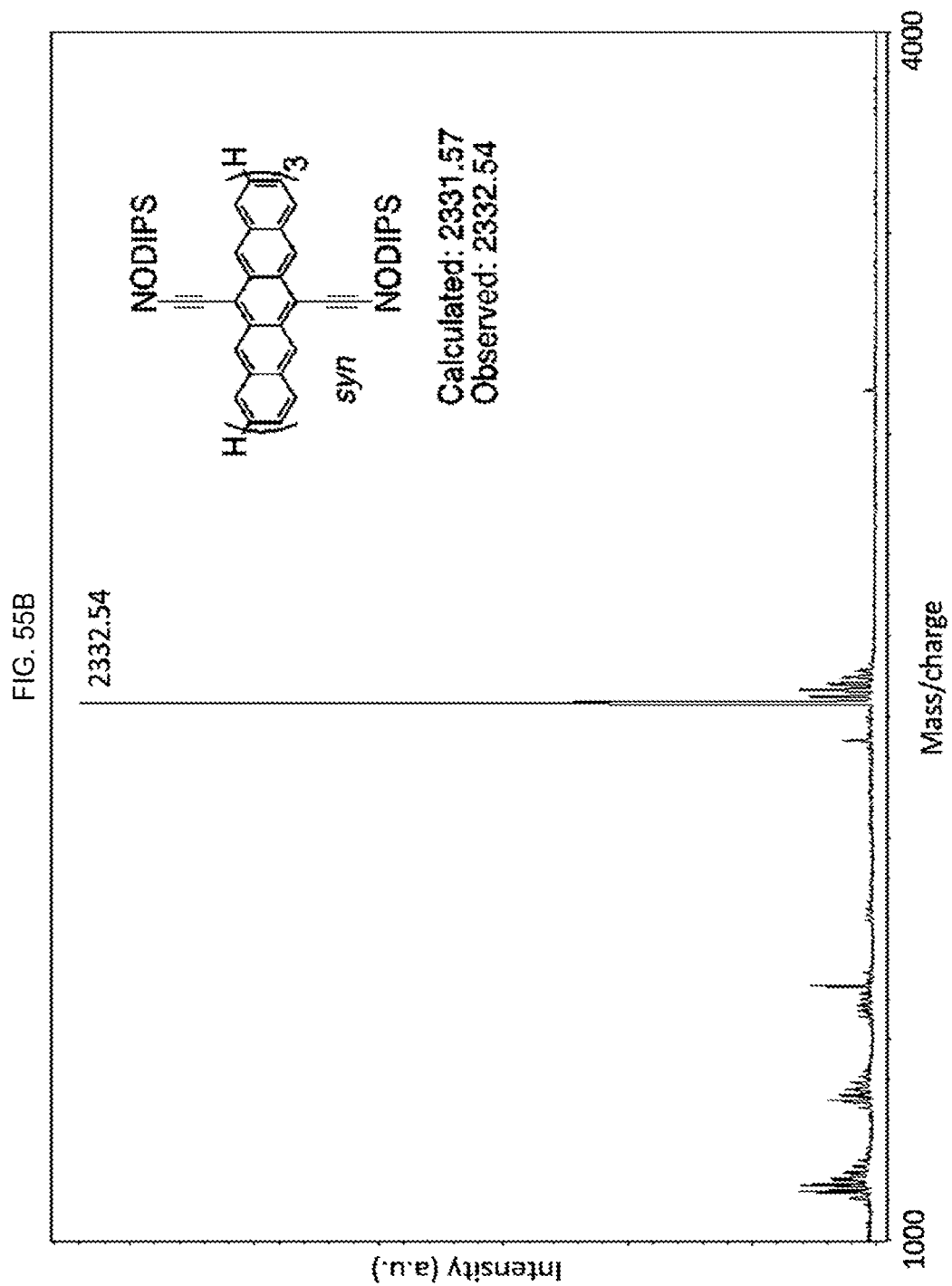
FIG. 55B shows mass spectra for syn-3Pc.
Figure 56A:
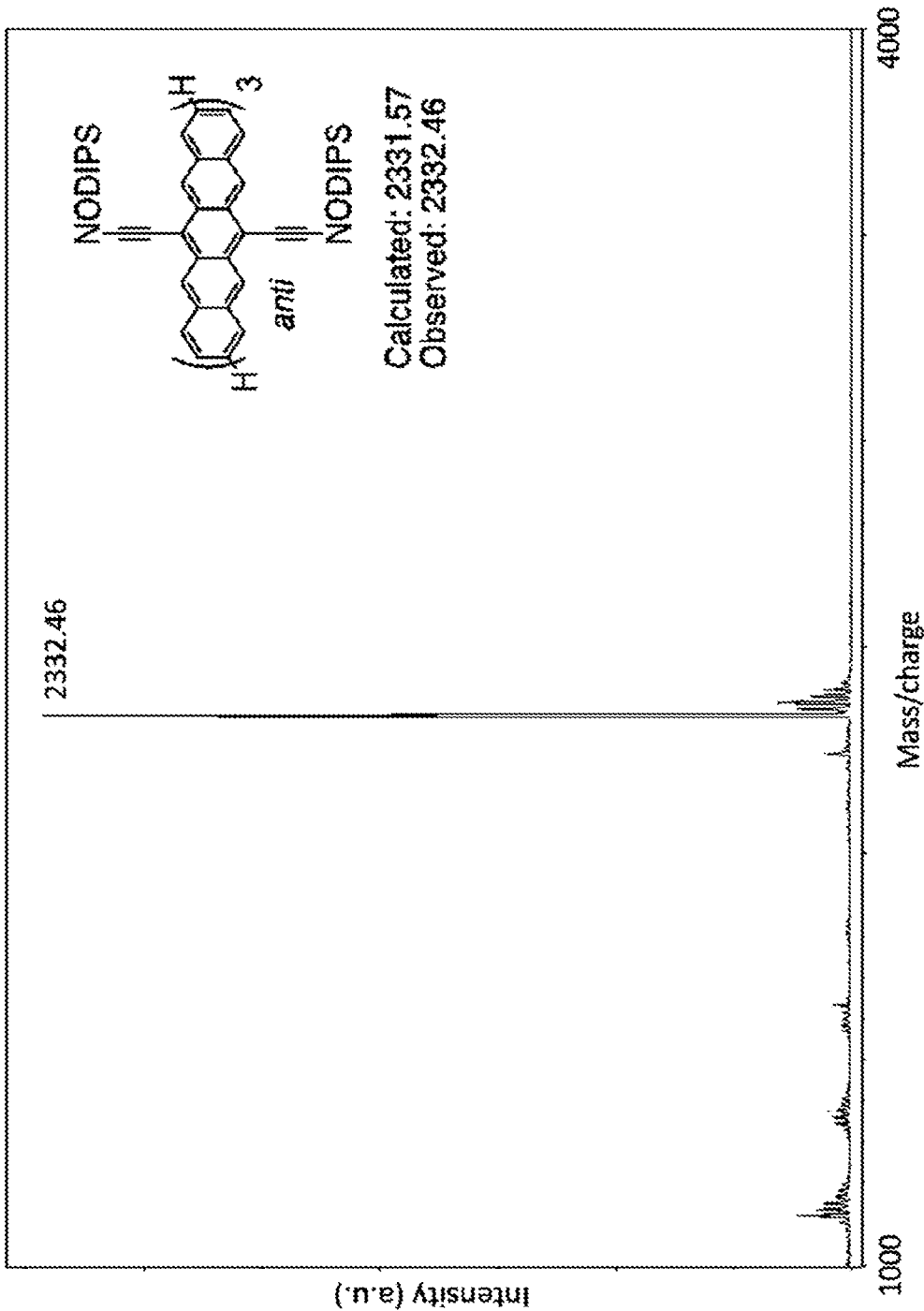
FIG. 56A shows mass spectra for anti-3Pc.
Figure 56B:
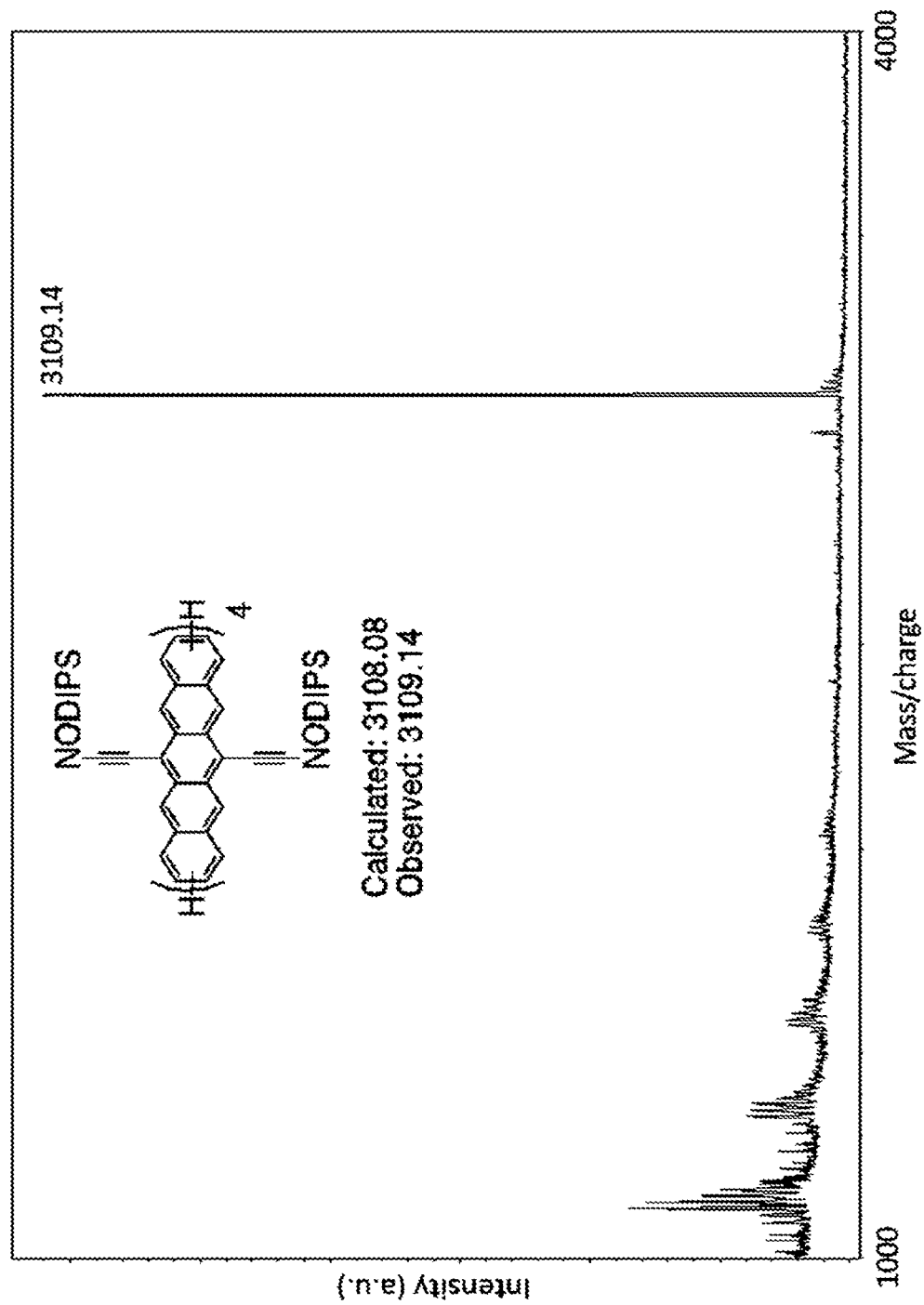
FIG. 56B shows mass spectra for 4Pc.
Figure 57A:
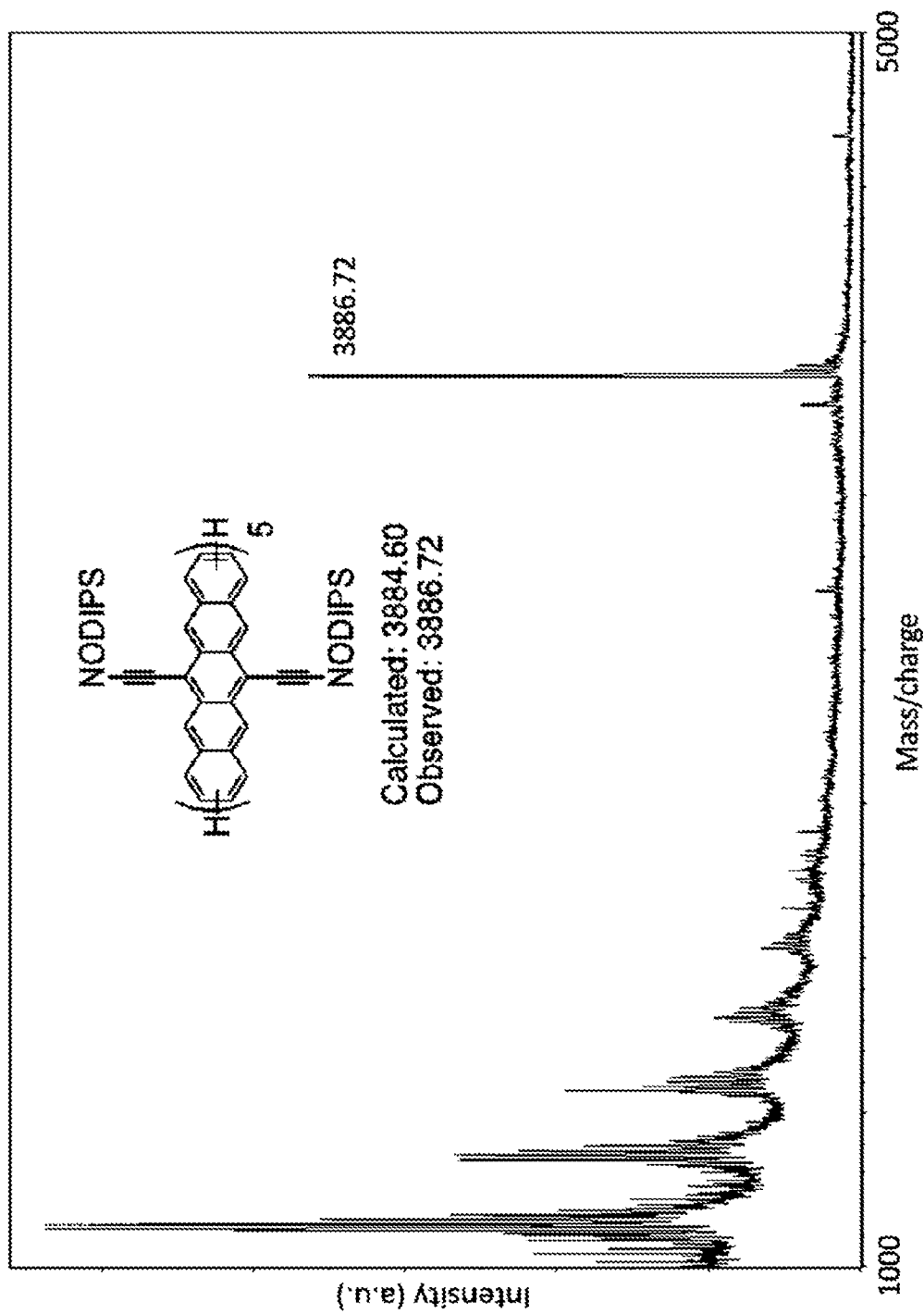
FIG. 57A shows mass spectra for 5Pc.
Figure 57B:
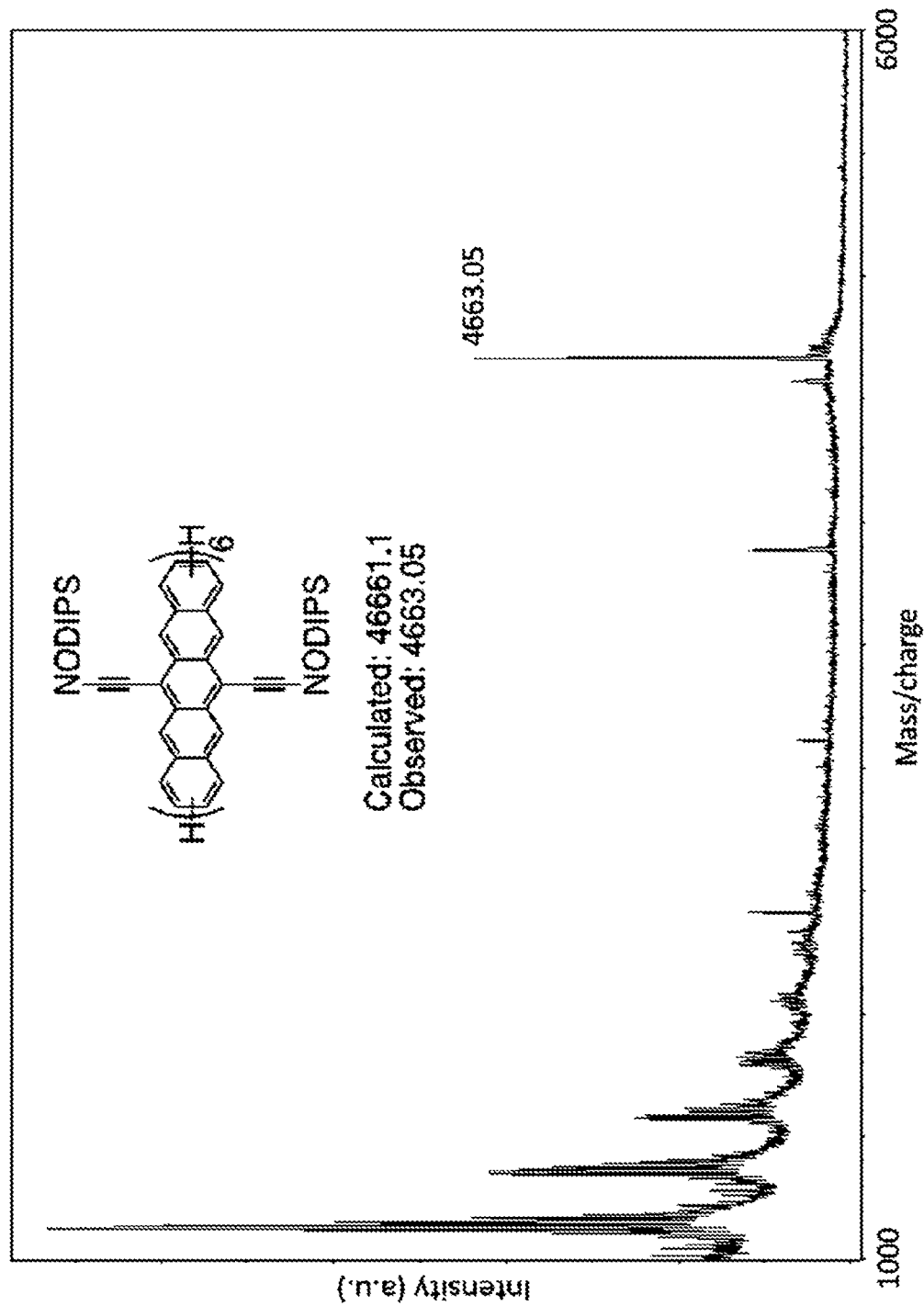
FIG. 57B shows mass spectra for 6Pc.
Figure 58:
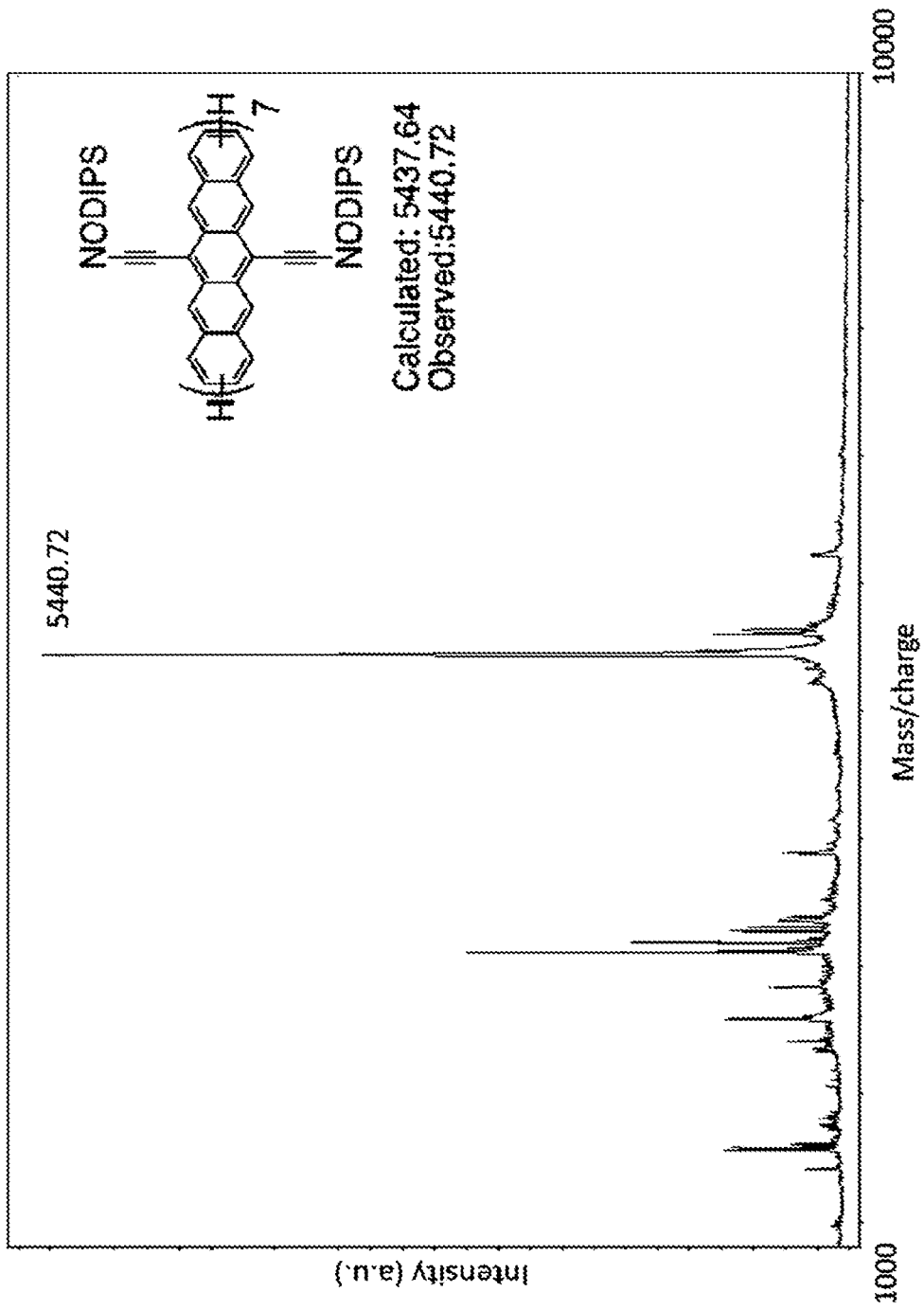
FIG. 58 shows mass spectra for 7Pc.

The NMR spectrum in FIG. 31 compares the aromatic regions of 3a mixture with regiopure syn and anti isomers. The regiopurity of the anti-1A2 is higher compared to syn-1A2 that has small amount of (~12%) of anti-1A2.

Example 26

Synthesis of Bpin Derivatives of Pentacenes

To a dry round bottomed flask was added 1A/1A2/1A2' (4.0 g, 5.57 mmol), Pd(dppf)Cl$_2$.DCM (10 mol % for 1A and 15 mol % for 1A2/1A2'), KOAc (1.5 equiv. for 1A and 3.0 equiv. for 1A2/1A2'), and bis(pinacolato)diboron (1.5 equiv. for 1A and 3.0 equiv. for 1A2/1A2'). Sequential vacuum and argon were used to degas the mixture followed by the addition of dry and degassed 1, 4 dioxane (40 mL). The mixture was heated to 85° C. and maintained for 12 h in the dark. After the reaction, the mixture was cooled to rt and the solvent was removed under reduced pressure. The crude was purified by silica chromatography using mixtures of hexanes/chloroform as an eluent to obtain pure product.

Characteristics:

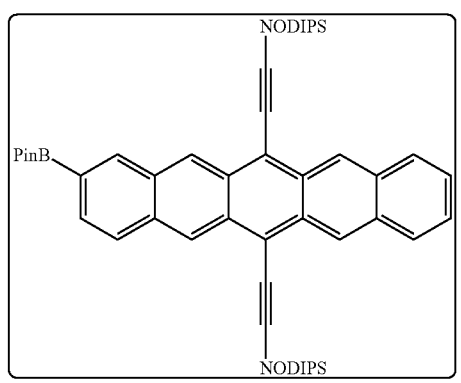

Yield=64%; Blue paste.

$^1$H-NMR (400 MHz, CDCl$_3$, δ ppm): 9.34-9.33 (m, 2H), 9.31 (s, 1H), 9.27 (s, 1H), 8.56 (s, 1H), 8.02-7.95 (m, 3H), 7.75-7.73 (m, 1H), 7.46-7.43 (m, 2H), 1.79-1.74 (m, 4H), 1.56-1.51 (m, 4H), 1.47 (s, 12H), 1.39-1.33 (m, 35H), 1.28-1.24 (m, 8H), 1.02-0.95 (m, 5H) and 0.87-0.82 (m, 6H).

$^{13}$C-NMR (125 MHz, CDCl$_3$, δ ppm): 138.2, 133.3, 132.5, 132.46, 131.98, 131.3, 130.9, 130.85, 130.7, 129.8, 128.8, 127.8, 127.6, 126.5, 126.4, 126.2, 118.96, 118.4, 107.9, 107.6, 104.7, 104.6, 84.1, 34.1, 32.1, 29.6, 29.5, 25.0, 22.8, 18.9, 18.8, 18.6, 18.56, 14.2, 12.3 and 10.6.

Characteristics:

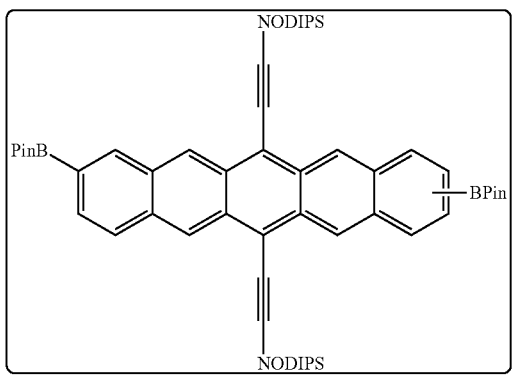

1B2

Yield=61%; Sticky blue paste solidifies over time.

$^1$H-NMR (400 MHz, CDCl$_3$, δ ppm): 9.39 (s, 1H), 9.37 (s, 1H), 9.32 (s, 1H), 9.29 (s, 1H), 8.57 (s, 2H), 7.98-7.96 (m, 2H), 7.77-7.75 (m, 2H), 1.85-1.76 (m, 4H), 1.61-1.53 (m, 5H), 1.47 (s, 24H), 1.41-1.35 (m, 35H), 1.29-1.26 (m, 8H), 1.03-0.99 (m, 4H) and 0.88-0.83 (m, 6H).

$^{13}$C-NMR (125 MHz, CDCl$_3$, δ ppm): 138.1, 138.0, 134.8, 133.2, 133.1, 131.9, 131.86, 131.3, 131.2, 130.8, 130.7, 129.8, 129.7, 127.8, 127.7, 127.6, 127.55, 126.2, 126.1, 119.3, 118.8, 118.3, 108.1, 107.9, 107.6, 104.6, 104.5, 104.4, 84.1, 34.1, 34.0, 33.97, 32.0, 32.01, 29.5, 29.4, 29.40, 29.3, 24.99, 22.7, 18.9, 18.8, 18.78, 18.6, 18.55, 18.5, 14.2, 12.2, 10.5 and 10.49.

MS (APCI): Calculated [M+Na]$^+$: 1053.6931; Observed: 1053.6946.

Characteristics:

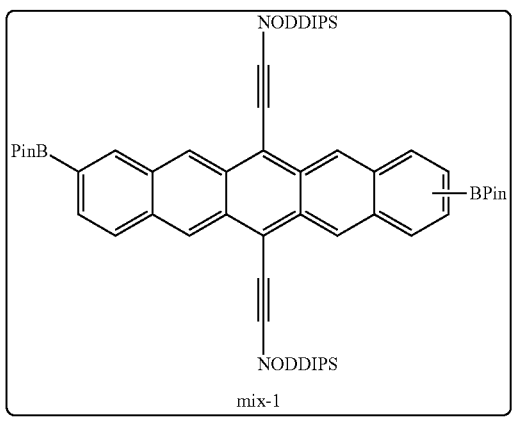

B2'

Yield=80%; Sticky blue paste.

$^1$H-NMR (400 MHz, CDCl$_3$, δ ppm): 9.36-9.34 (m, 2H), 9.29-9.27 (m, 2H), 8.55 (s, 2H), 7.96-7.94 (m, 2H), 7.74-7.72 (m, 2H), 1.81-1.75 (m, 4H), 1.56-1.49 (m, 4H), 1.46 (s, 24H), 1.40-1.19 (m, 88H) and 0.89 (t, 6H).

$^{13}$C-NMR (125 MHz, CDCl$_3$, δ ppm): 138.0, 137.9, 133.1, 133.0, 131.8, 131.7, 131.2, 131.1, 130.7, 130.6, 129.7, 129.6, 127.8, 127.6, 127.52, 127.50, 126.1, 125.99, 119.3, 118.8, 118.2, 108.1, 107.8, 107.5, 104.5, 104.4, 104.3, 84.0, 33.99, 33.96, 33.90, 31.9, 29.8, 29.71, 29.70, 29.7, 29.5, 29.4, 29.37, 29.31, 24.9, 22.7, 18.8, 18.78, 18.72, 18.5, 18.5, 18.45, 14.1, 12.2 and 10.5.

MS (ESI): Calculated [M+H]$^+$: 1312.0242; Observed: 1312.0264.

Example 27

Synthesis of Pentacenes Derivatives 2A and 3A

To a mixture of 1B (to obtain 2A) or 2B (to obtain 3A) (1.0 g, 1.0 equiv.), 1A2 (3.0 equiv.), Pd(dppf)Cl$_2$.DCM (5 mol %), and K$_2$CO$_3$ (5 equiv.) under argon atmosphere added dry and degassed THF:H$_2$O (9:1, 50 mL). The resulting mixture was heated to 65° C. and maintained for 24 h in the dark. After the reaction, the THF was evaporated and the residue was purified by silica chromatography using mixtures of hexanes/chloroform as an eluent to obtain the product.

Characteristics:

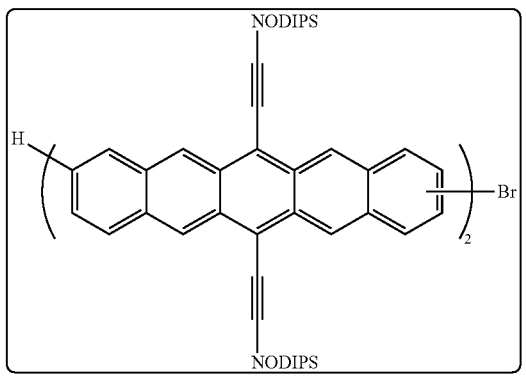

2A

Yield=63%; Dark purple solid.

$^1$H-NMR (400 MHz, CDCl$_3$, δ ppm): 9.43-9.41 (m, 2H), 9.36-9.30 (m, 5H), 9.23-9.22 (m, 1H), 8.38 (s, 2H), 8.19-8.17 (m, 3H), 8.04-7.95 (m, 4H), 7.89-7.88 (m, 1H), 7.49-7.45 (m, 3H), 1.84-1.78 (m, 8H), 1.45-1.28 (m, 85H), 1.22-1.18 (m, 10H), 1.03-0.99 (m, 9H), 0.88-0.85 (m, 6H) and 0.78-0.75 (m, 6H).

$^{13}$C-NMR (125 MHz, CDCl$_3$, δ ppm): 137.8, 137.5, 132.7, 132.69, 132.6, 132.4, 132.39, 132.36, 131.8, 131.7, 131.6, 131.3, 131.1, 131.0, 130.96, 130.91, 130.88, 130.85, 130.76, 130.67, 130.57, 130.4, 130.3, 130.29, 130.2, 129.6, 129.59, 128.7, 126.9, 126.4, 126.2, 126.1, 125.8, 125.5, 120.4, 118.8, 118.6, 118.5, 118.4, 118.3, 108.1, 108.0, 107.99, 107.9, 107.7, 107.5, 104.6, 104.5, 104.3, 34.13, 34.1, 34.09, 34.08, 34.07, 34.05, 32.0, 31.9, 29.6, 29.56, 29.54, 29.51, 29.45, 29.42, 29.40, 25.1, 25.06, 25.03, 25.0, 22.7, 22.69, 22.66, 22.64, 18.8, 18.79, 18.76, 18.5, 18.49, 14.1, 14.0, 12.23, 12.20, 10.52, 10.50 and 10.48.

MS (ESI): Calculated [M+H]$^+$: 1633.9685; Observed: 1633.9662.

Characteristics:

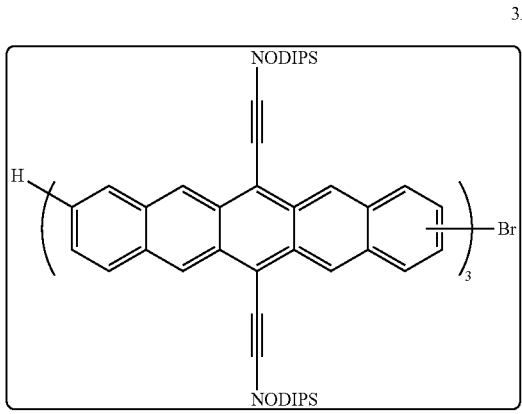

Yield=53%; Dark purple solid.
¹H-NMR (500 MHz, 50° C., CDCl₃, δ ppm): 9.46-9.24 (m, 12H), 8.39 (s, 4H), 8.20-8.17 (m, 5H), 8.03-7.96 (m, 6H), 7.89-7.87 (m, 1H), 7.49-7.44 (m, 3H), 1.89-1.83 (m, 13H), 1.59-1.58 (m, 14H), 1.47-1.21 (m, 127H), 1.07-1.02 (m, 14H), 0.89-0.86 (m, 8H) and 0.80-0.77 (m, 10H).
¹³C-NMR (125 MHz, 50° C., CDCl₃, δ ppm): 137.3, 137.2, 136.91, 136.90, 136.88, 136.8, 136.73, 136.72, 136.7, 136.6, 136.5, 132.78, 132.73, 132.68, 132.65, 132.58, 132.52, 132.46, 132.4, 132.37, 132.33, 131.9, 131.86, 131.75, 131.73, 131.69, 131.63, 131.3, 131.27, 131.21, 131.1, 130.99, 130.89, 130.83, 130.81, 130.74, 130.72, 130.63, 130.58, 130.34, 130.31, 130.23, 130.19, 130.15, 130.07, 129.5, 129.4, 129.37, 128.7, 128.6, 128.58, 126.96, 126.9, 126.85, 126.78, 126.31, 126.27, 126.15, 126.1, 125.9, 125.8, 125.6, 125.62, 125.56, 125.54, 125.50, 125.45, 125.37, 125.33, 120.37, 120.34, 120.29, 118.84, 118.81, 118.72, 118.69, 118.65, 118.63, 118.54, 118.50, 118.46, 118.4, 118.38, 108.1, 108.0, 107.99, 107.96, 107.90, 107.85, 107.78, 107.75, 107.63, 107.52, 107.49, 107.39, 104.90, 104.84, 104.82, 104.78, 104.75, 104.59, 104.57, 104.52, 34.06, 34.02, 34.0, 33.97, 31.95, 31.90, 31.88, 29.5, 29.47, 29.44, 29.36, 29.33, 25.1, 25.04, 25.00, 24.98, 24.95, 22.60, 22.57, 22.6, 18.9, 18.8, 18.76, 18.74, 18.57, 18.52, 18.50, 13.96, 13.90, 13.88, 13.81, 12.4, 12.38, 12.36, 12.34, 10.73, 10.7 and 10.65.
MALDI: Calculated: 2409.48; Observed: 2411.42.

Example 28

Synthesis of Pentacenes Derivatives 2B and 3B

The compound 2B and 3B was obtained according to the procedure described for the synthesis of 1B.

Characteristics:

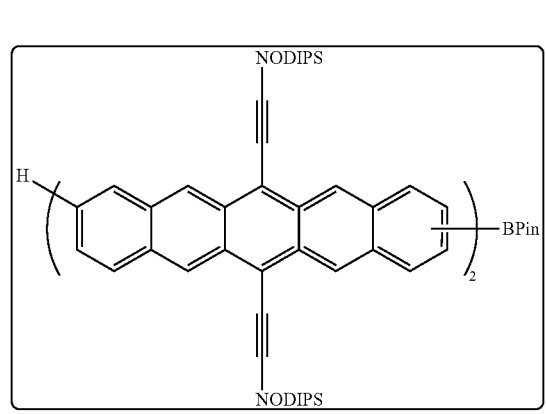

Yield=75%; Dark purple solid.
¹H-NMR (400 MHz, CDCl₃, δ ppm): 9.46-9.31 (m, 8H), 8.58 (s, 1H), 8.39 (s, 2H), 8.19-8.17 (m, 2H), 7.99-7.96 (m, 5H), 7.77-7.75 (m, 1H), 7.47-7.45 (m, 2H), 1.84-1.79 (m, 8H), 1.47 (s, 12H), 1.43-1.37 (m, 69H), 1.30-1.19 (m, 26H), 1.03-0.99 (m, 9H), 0.88-0.86 (m, 6H) and 0.78-0.75 (m, 6H).
¹³C-NMR (125 MHz, CDCl₃, δ ppm): 138.1, 137.7, 137.65, 133.2, 133.28, 132.6, 132.5, 132.4, 132.39, 131.9, 131.89, 131.7, 131.6, 131.3, 131.22, 131.20, 131.17, 131.06, 131.0, 130.9, 130.8, 130.75, 130.69, 130.65, 129.7, 129.66, 128.7, 127.8, 127.6, 127.0, 126.9, 126.40, 126.2, 126.12, 126.10, 126.0, 125.96, 119.0, 118.9, 118.6, 118.5, 118.4, 118.3, 108.0, 107.9, 107.74, 107.71, 107.59, 107.55, 104.65, 104.58, 104.55, 104.5, 104.4, 84.1, 34.14, 34.1, 34.09, 34.05, 32.04, 32.01, 31.97, 31.9, 29.60, 29.54, 29.49, 29.46, 29.44, 25.10, 25.06, 25.03, 25.01, 22.73, 22.68, 18.88, 18.86, 18.82, 18.79, 18.59, 18.58, 18.54, 18.52, 14.2, 14.1, 12.3, 10.55 and 10.53.
MS (ESI): Calculated [M]⁺: 1681.1354; Observed: 1681.1345.
Characteristics:

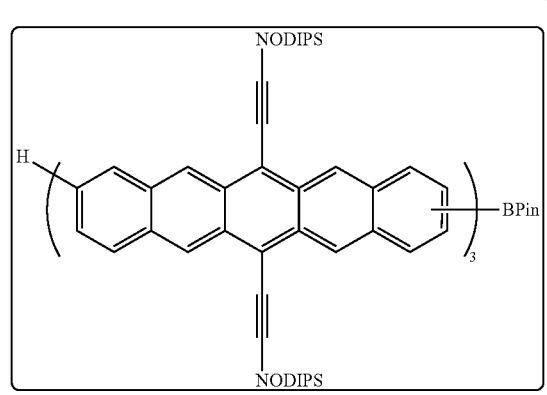

Yield=70%; Dark purple solid.
¹H-NMR (500 MHz, 50° C., CDCl₃, δ ppm): 9.46-9.31 (m, 12H), 8.58 (s, 1H), 8.39 (s, 4H), 8.20-8.17 (m, 4H), 8.03-7.98 (m, 7H), 7.78-7.75 (m, 1H), 7.46-7.43 (m, 2H), 1.86-1.84 (m, 12H), 1.59-1.58 (m, 14H), 1.48-1.39 (m, 110H), 1.31-1.21 (m, 31H), 1.06-1.03 (m, 13H) and 0.89-0.78 (m, 18H).

$^{13}$C-NMR (125 MHz, 50° C., CDCl$_3$, δ ppm): 137.9, 137.85, 137.82, 137.81, 137.78, 137.74, 133.24, 133.22, 132.65, 132.62, 132.55, 132.46, 132.44, 131.97, 131.76, 131.73, 131.67, 131.3, 131.24, 131.14, 131.09, 130.98, 130.95, 130.8, 130.78, 130.72, 130.7, 129.7, 129.6, 128.6, 127.7, 127.4, 126.9, 126.8, 126.33, 126.22, 126.18, 125.98, 125.9, 118.6, 118.4, 107.76, 107.73, 107.57, 104, 73, 104.68, 104.65, 104.61, 104.55, 84.0, 34.0, 33.96, 33.91, 33.88, 31.9, 31.8, 29.4, 29.3, 22.6, 22.5, 22.46, 18.74, 18.72, 18.69, 18.67, 18.45, 18.43, 13.91, 13.85, 13.83, 13.76, 12.29 and 10.6.

MALDI: Calculated: 2457.65; Observed: 2458.59.

Example 29

Synthesis of the Homopolymer of Pentacenes

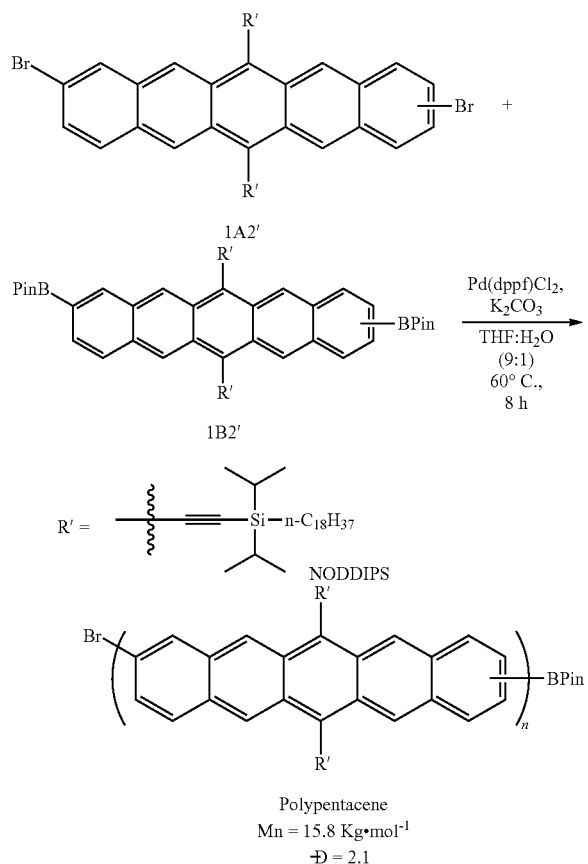

Polypentacene
Mn = 15.8 Kg·mol$^{-1}$
Đ = 2.1

To a dry 20 mL vial added 1B2' (50 mg, 1.0 equiv.), 1A2' (1.1 equiv.), Pd(dppf)Cl$_2$ (5 mol %) and K$_2$CO$_3$ (5.0 equiv.). The vial was capped followed by sequential vacuum and argon was carried out 3 times to degas the mixture. Degassed H$_2$O (1.7 mL) and THF (15.3 mL) was added and the mixture was placed in an oil bath preheated to 60° C. The reaction was carried out in dark for 8 h and then cooled to room temperature. The mixture was precipitated in methanol (75 mL), filtered and the solid was transferred to a Soxhlet thimble. The solid was extracted with hexanes, chloroform and finally chlorobenzene sequentially in dark and under argon atmosphere. The solutions were concentrated and the residue was precipitated in methanol, filtered, dried and stored.

The chloroform fraction yielded 33 mg of product and chlorobenzene fraction yielded 28 mg of the product.

Example 30

Steady State Absorption

The optical properties of oligomers 1-7Pc, regiopure 3Pc and polypentacene were probed by steady state UV-visible absorption spectroscopy in solution and in thin-films (FIGS. 32A to 32D). In solution, the oligomer spectra of 2Pc through 7Pc were qualitatively similar, with minimal red-shift as the number of pentacenes increases. Notably, in solution, there were only minute differences in the UV-vis spectra of syn-3Pc, anti-3Pc and mix-3Pc. In the longer wavelength region (>550 nm) the oligomers all resembled the absorption spectrum of the monomer. However, in the dimer and each of the higher oligomers a new set of absorption peaks appeared between 425 nm and 550 nm (interpreted as a vibrational progression associated with a fundamental absorption described below). These peaks had not been previously observed in other pentacene-containing materials. The height of this new absorption maximum, relative to the height of the peak at the onset of absorption, increased with oligomer length. The strong similarity of the long-wavelength region in the oligomers to that of the monomer led to the conclusion that these long-wavelength features in all of these molecules were due to intra-pentacene vibrational progressions. This was verified with electronic structure calculations on 1Pc, 2Pc, 3Pc, and 4Pc.

FIGS. 33A to 33E show steady state UV-Visible absorption spectra for the oligopentacenes 1Pc, 2Pc, 3Pc, 4PC, 5Pc, 6Pc, and 7Pc. The spectra were taken for known masses of oligomer in a measured volume of chloroform. Variation of the molarity was used to test for aggregation, which typically manifests as red-shifting of the absorbance onset and/or adherence to Beer's Law. The molarities are reported in the legend as molarity of pentacene for ease of comparison, not the molarity of the oligomer (each molarity represents a nearly identical mass of pentacene per volume of solution). The extinction coefficients are listed as $L^{-1}M^{-1}$, where the molarity is the moles of oligomer, in keeping with convention.

Example 31

Solvent Dependence in Steady-State Absorption of Oligopentacenes

Figure 59:
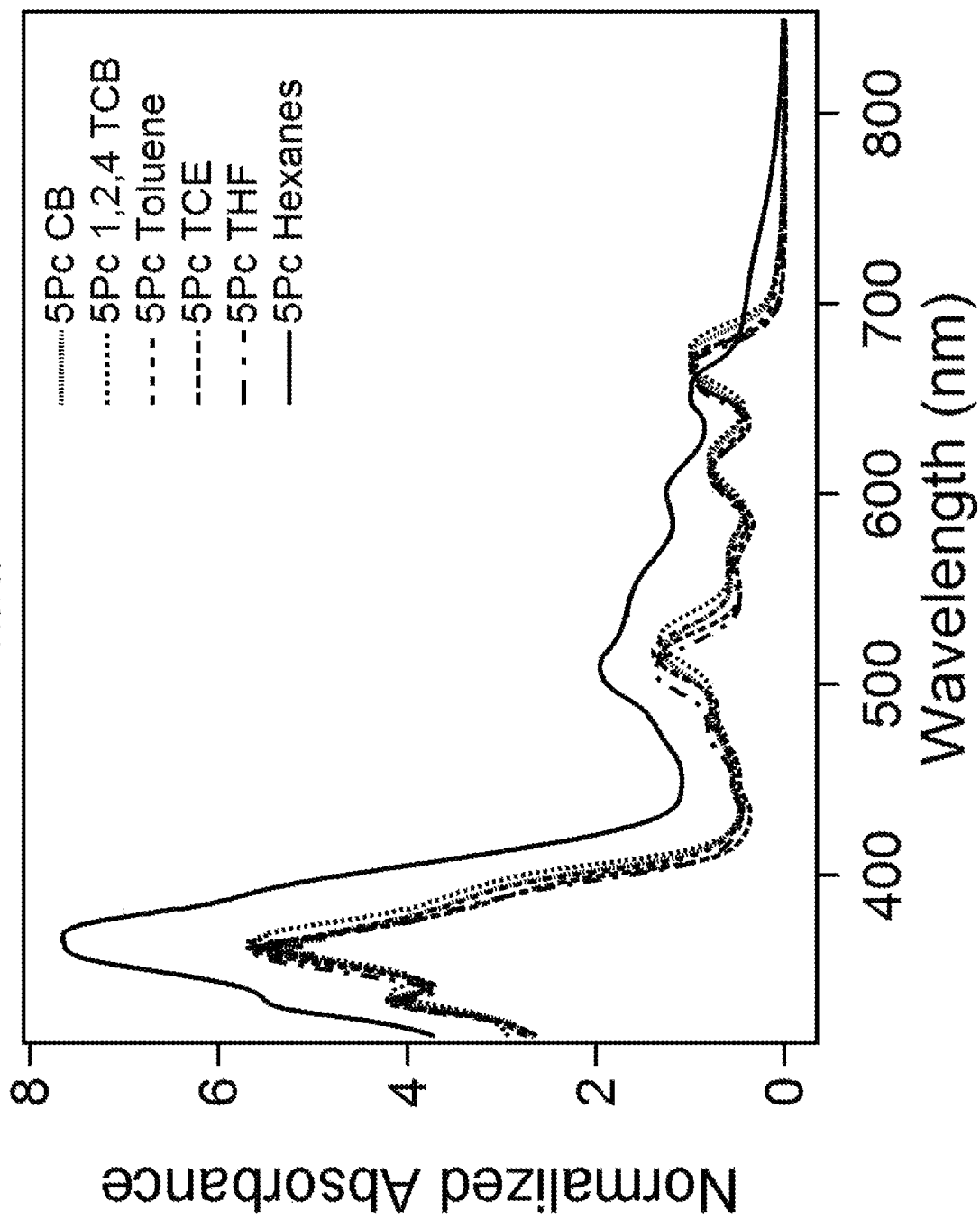
FIG. 59 shows the results of a solvent dependence study of pentamer 5Pc in different solvents.

While the oligopentacenes were not found to have significant concentration-dependent aggregation, there was evidence for solvent-dependent aggregation. 5Pc was chosen for an extensive solvent study. This compound has excellent solubility in a variety of solvents, such as chlorinated solvents trichloroethene (TCE), 1,2,4 trichlorobenzene(1,2,4 TCB), aromatic solvents (toluene) and even polar, non-aromatic tetrahydrofuran, due to the strong solubilizing power of the NODIPS chains. However, while it was readily dispersed in hexanes, and even passed a filter, steady-state absorption suggested significant aggregation in hexanes and other linear hydrocarbon solvents. This aggregation was revealed in a long tail to the absorbance near the onset of absorption and a spectrum which overall resembles the solid-state absorption spectrum. The most prominent peak in FIG. 59 was for 5Pc Hexanes, while the remaining pentamers in solvent (5Pc CB; 5Pc 1,2,4 TCB; 5Pc Toluene; 5Pc TCE; and 5Pc THF) were grouped together at a normalized absorbance less than that of 5 Pc Hexane.

Example 32

Solvent Dependence of Polypentacene

The most significant aggregation was observed for polypentacene. Indeed, at room temperature, significant aggregation was observed in every solvent examined, as shown in FIG. 60.

Figure 60:
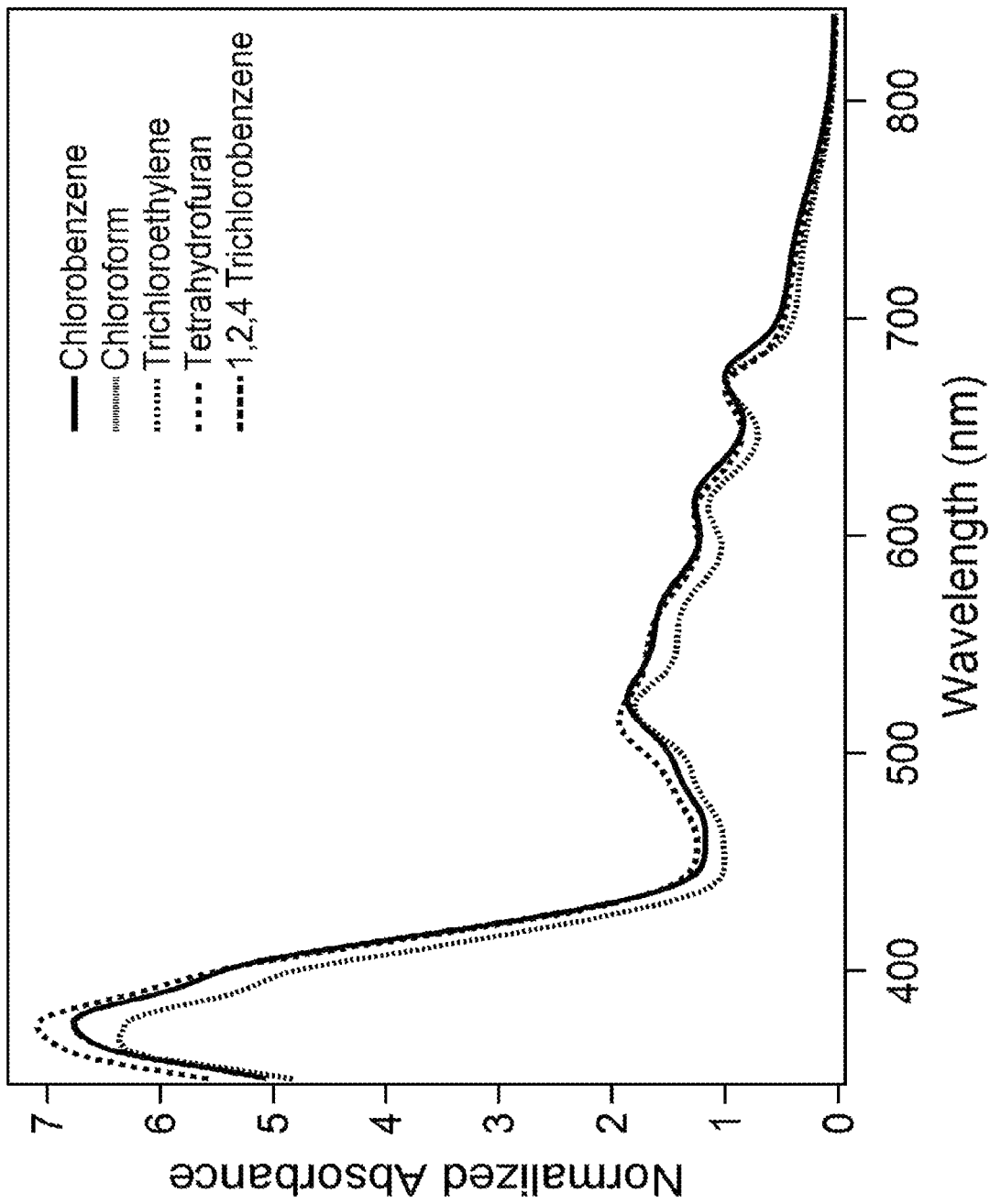
FIG. 60 shows a comparison of UV-Visible steady state absorption of polypentacne in varying solvents, normalized to the height of the peak at the onset of absorption.

Absorption spectra were taken in a variety of solvents, shown in FIG. 60. The optical density of the solutions were comparable, with the peak at the onset of absorption ranging from 0.13 to 0.24 in a 1 cm quartz cuvette. The spectra were normalized to the peak at the onset to allow for a comparison of spectral shape, which revealed significant aggregation in most solvents tested, manifesting in a red-shifting of the absorption spectra. The aggregation also results in less pronounced peaks associated with vibronic effects. The least evidence for aggregation was observed in 1,2,4 trichlorobenzene.

At a wavelength of about 350 nm, the peaks in FIG. 60 represent the polypentacene in solvents: from the uppermost to lowest normalized absorbance peak: tetrahydrofuma, chloroform, chlorobenzene, trichloroethylene, and 1,2,4 trichlorobenzene.

Example 33

DFT and TD-DFT Calculations on Oligopentacenes

All density functional theory (DFT) and time-dependent-DFT (TD-DFT) calculations were carried out using JAGUAR software, version 8.3, Schrodinger, Inc., New York, N.Y., 2014.

The geometries of 1Pc, 2Pc, 3Pc, and 4Pc were fully optimized at the B3LYP/6-31G** level. In the cases of the latter three molecules, the variations in total energy with rotations about the pentacene-pentacene bonds were quite small over a wide range of angles, so there is latitude in the choice of geometrical optima with respect to these coordinates. In the cases of the trimer and tetramer, only the trans regioisomers were studied. The Cartesian coordinates for each molecule are presented in FIG. 34-FIG. 37.

Using TD-DFT, the absorption spectrum for each molecule at its optimum geometry was also calculated.

Figure 61:
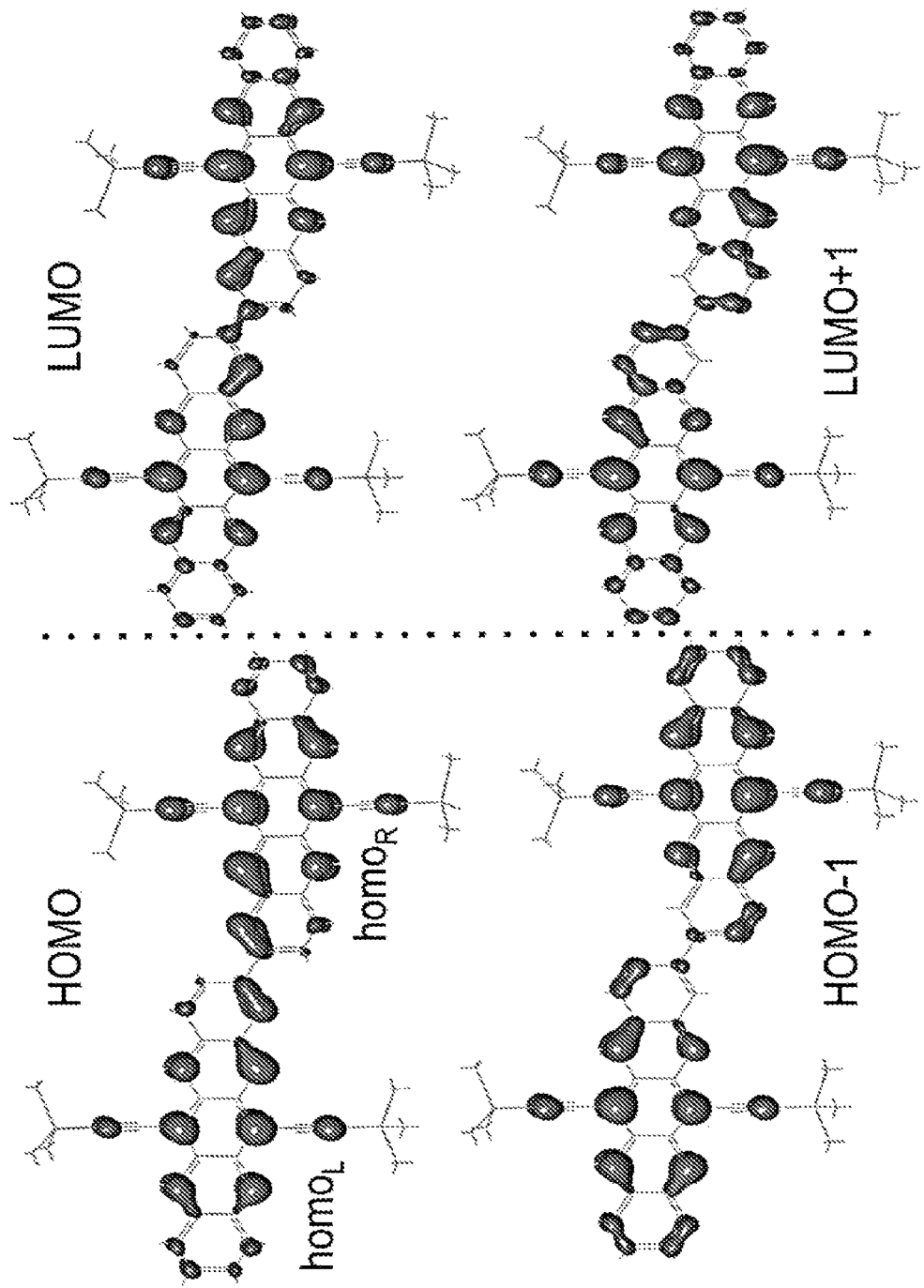
FIG. 61 shows the Highest Occupied and Lowest Unoccupied Molecular Orbitals (HOMO and LUMO, respectively), along with the +1 and −1 orbitals.

Excited state (TD-DFT, see FIGS. 38-53) calculations suggested that the absorption peak at 650 nm in the monomer was due to the fundamental HOMO-to-LUMO transition. However, corresponding calculations on the dimer revealed a more complex situation. The HOMO in the dimer comprised of two parts: one that resembled what would be the HOMO localized on one isolated pentacene (homo$_L$ in FIG. 61), and another that resembled what would be the HOMO localized on the other isolated pentacene (homo$_R$ in FIG. 61). In the full HOMO and HOMO-1 of the molecule, these orbitals were combined with different phases: the HOMO was (homo$_L$−homo$_R$), and the HOMO-1 was (homo$_L$+homo$_R$). The situation for the lowest-energy unoccupied orbitals was similar: the molecular LUMO was approximated by (lumo$_L$+lumo$_R$), and the molecular LUMO+1 by (lumo$_L$−lumo$_R$). The lower-energy transition in the dimer effectively promoted an electron from the HOMO to the LUMO, and the higher-energy transition effectively promoted an electron from the HOMO-1 to the LUMO+1.

The source of the energy separation between the two transitions lies in the *nexus* of the two pentacenes. In the HOMO there is a π-antibonding interaction between the two C atoms that form the pentacene-pentacene link; in the LUMO there is a π-bonding interaction in that space. By comparison in the HOMO-1 there is a π-bond between these two C atoms, and in the LUMO+1 there is a π-antibond. Thus the two "HOMO-to-LUMO" excitations were split by the formation versus destruction of the inter-pentacene π-interaction. In the lower-energy transition an unfavorable interaction was relieved in the ground state and a favorable interaction realized in the excited state; in the higher-energy transition the reverse was the case. Similar effects occurred in the higher oligomers. There are many geometrical degrees of freedom available to the higher oligomers.

In the solution UV-vis, a modest red-shift of the onset of absorption was observed in the highest (n>4) oligomers, indicating weak aggregation in chloroform. This aggregation was weakly concentration dependent, as expected, and strongly solvent dependent. For example, less aggregation was observed in solvents such as toluene, tetrachloroethylene and chloroform, while significant aggregation was observed in hexanes.[105]

Solid-state absorbance spectra were also obtained by drop casting oligomers on to a glass slide from chloroform. In the monomer 1Pc, the solution and solid-state spectra were nearly identical, indicating that the bulky NODIPS chains effectively prevented any significant crystallinity in the solid state and result in a highly amorphous solid. On the other hand, starting from the dimer containing NODIPS, a large degree of interaction was evidenced in the solid-state UV-vis, presumably due to a "bricklayer" type packing that was previously observed in the crystal structure of the dime[107] and possible for all oligomers beyond the monomer, 1Pc. This interaction resulted in a loss of the clear vibronic peaks present in solution, as well as a significant red-shift of the absorption onset. Such significant solid-state interaction in these higher oligomers bodes well for their potential in electronic applications, where strong interactions resulting from planarity and π-π stacking are typically desirable for organic materials.[108-109] These strong interactions also helped to explain the dramatic loss of solubility between monomeric TIPS-pentacene and the TIPS-pentacene dimer, which necessitated the use of the more solubilizing NODIPS chain for higher oligomers. Notably, there were fairly significant differences in the solid-state spectra of syn-3Pc, anti-3Pc and mixture of trimers, despite their similarity in solution. These differences were therefore attributable to different capacities for effective solid-state packing, as confirmed by grazing-incidence wide-angle x-ray scattering (GIWAXS), vide infra. However, beyond the trimer, there were only subtle differences among oligomers 4-7, suggesting that these longer oligomers are starting to converge in their characteristics towards that of a polymer.

Example 34

Cyclic Voltammetry Studies on Oligopentacenes

In order to investigate how the energy levels vary as a function of oligomer length, cyclic voltammetry (CV) was used to determine the oxidation and reduction potentials. The good solubility of the oligopentacenes enabled their measurement in dichloromethane against a Ag/Ag$^+$ reference (see FIG. 62). CV measurements were performed using a single cell set-up on a CH Instruments Electrochemical Analyzer potentiostat with a platinum working electrode, platinum wire counter electrode and Ag/AgCl reference electrode all purchased from BASi. Compounds 1Pc, 2Pc, 3Pc, 4Pc, 5Pc, 6Pc, and 7Pc were measured in dichloromethane solution at a concentration of 1-2 mg/mL and 0.1 M of tetrabutylammoniumhexafluorophosphate (TBAPF$_6$) as supporting electrolyte. A scan rate of 0.2V/s was used throughout.

Figure 62:
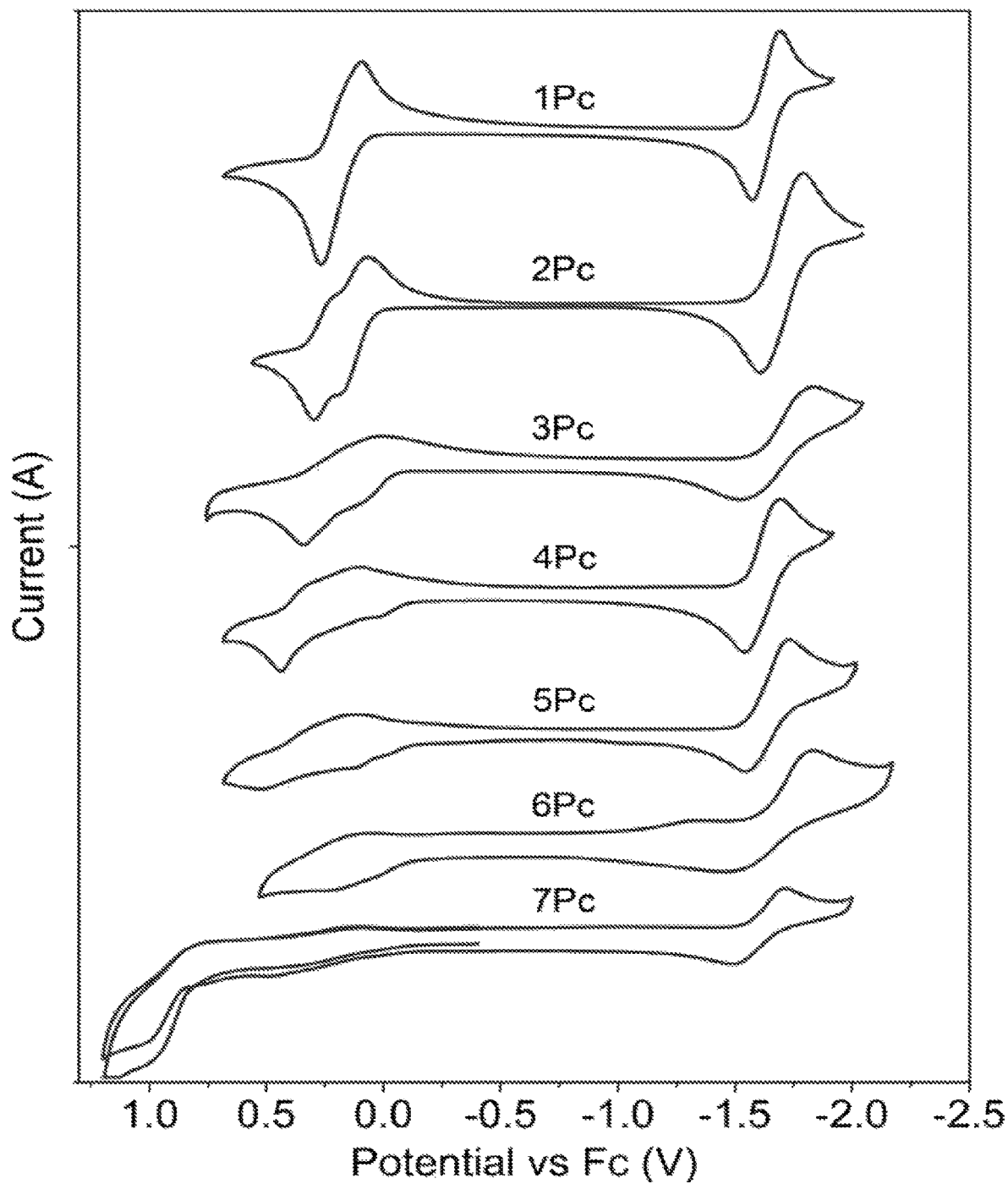
FIG. 62 shows cyclic voltammograms (CVs) of a pentacene oligomer series plotted against the ferrocene oxidation potential. A second sweep of 7Pc is shown to demonstrate the irreversibility.

From the CVs shown in FIG. 62, the HOMO (or LUMO) levels were extracted from the onset of oxidation (or reduction), which were calibrated against the ferrocene/ferrocenium (Fc/Fc$^+$) couple, assumed to be at −4.80 eV relative to vacuum. The oxidation peak of the Fc/Fc$^+$ measured had slight variations and was adjusted using: $E_{Fc}=-(4.80-E_{Fc,measured})$V.[111]

To convert the redox onsets to the HOMO and LUMO levels, the following formulae were used:[111]

$$HOMO=-e(E_{onset,Ox}+(-E_{Fc}))(eV)$$

$$LUMO=-e(E_{onset,Red}+(-E_{Fc}))(eV)$$

The voltammograms for 1Pc-6Pc showed reversible redox waves under the potential ranges measured. Moving out of these ranges generally resulted in irreversible behavior. The reduction wave of the heptamer was irreversible and diminished greatly after the first sweep. The oxidation wave also diminished after successive sweeps. In FIG. 62, a full redox scan, starting with oxidation, is shown along with a 2$^{nd}$ oxidation scan to show that the process is irreversible.

Figure 63:
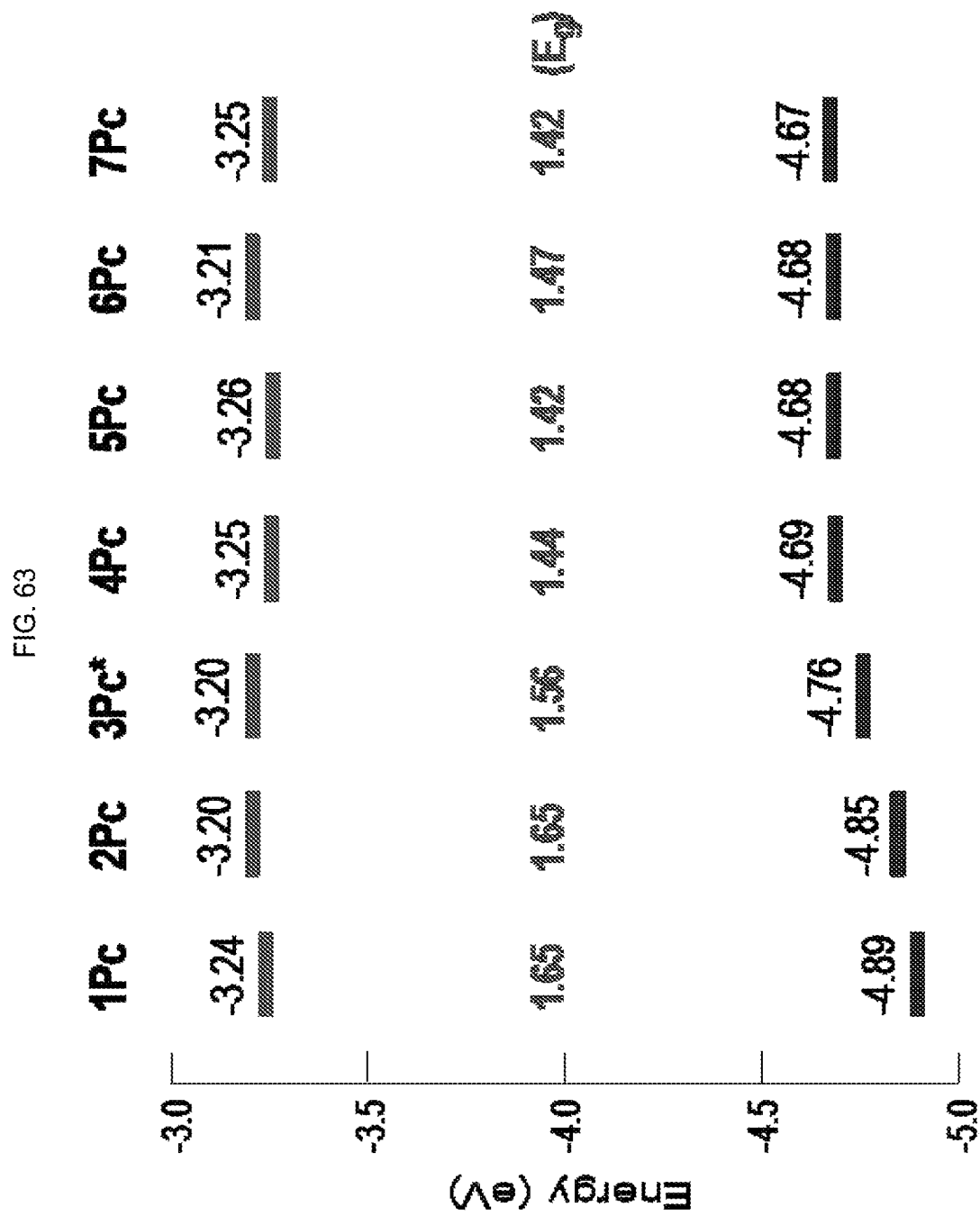
FIG. 63 shows electrochemical properties of oligopentacenes obtained from cyclic voltammetric studies. 3Pc* indicates the sample used was mix-3Pc.
Figure 64B:
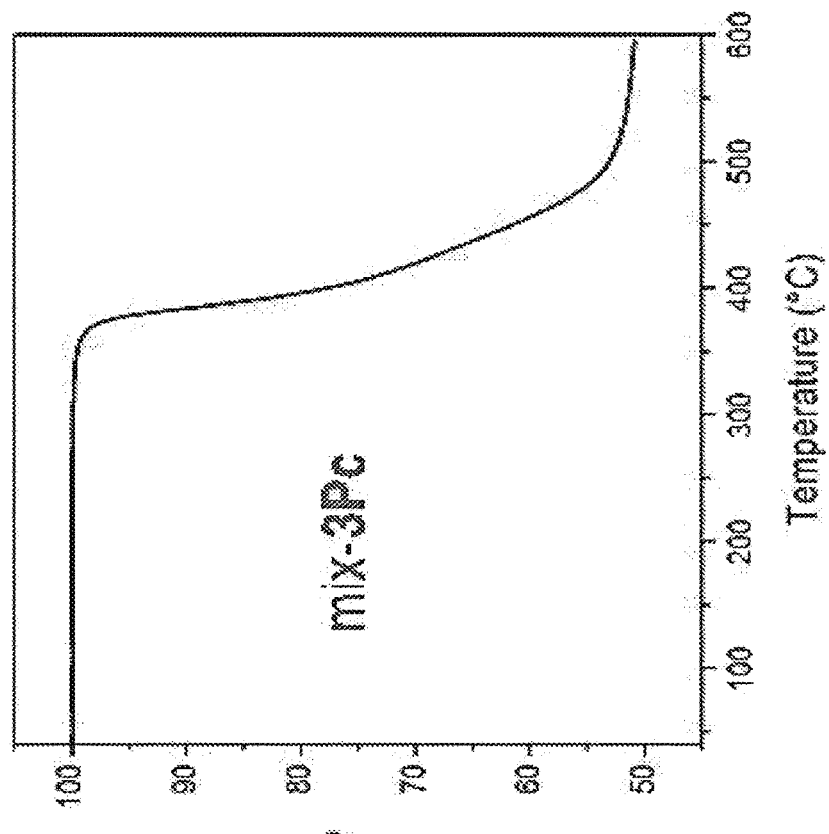
FIGS. 64A to 64D show a thermal gravimetric analysis (TGA) graph of oligopentacenes 2Pc-3Pc.
Figure 64A:
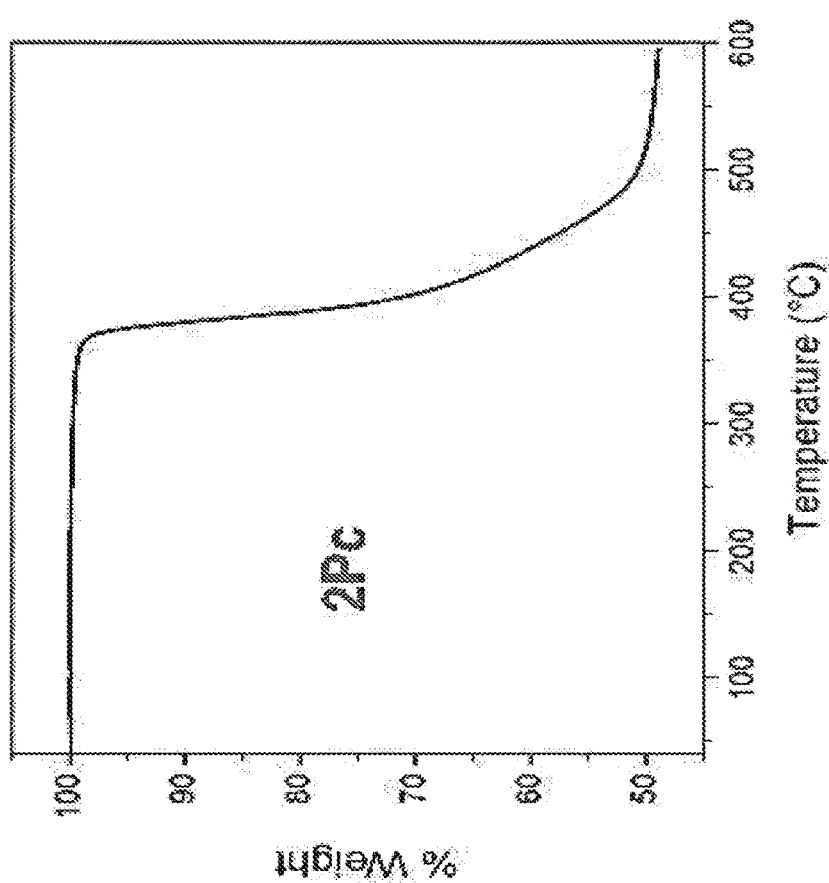
Figure 64C:
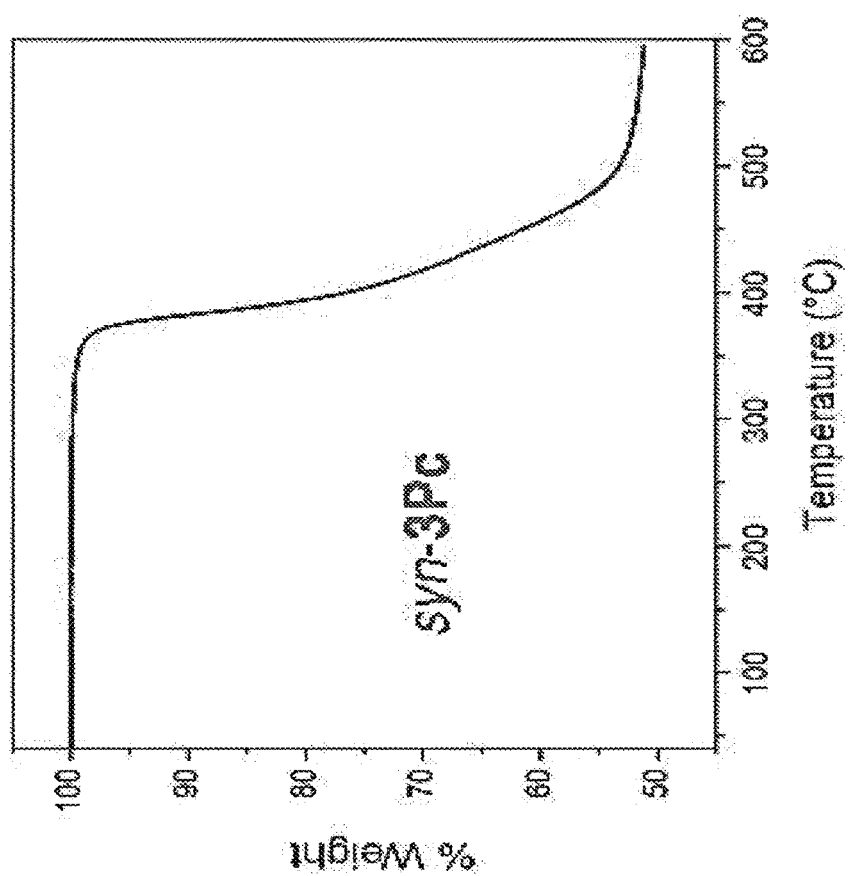
Figure 64D:
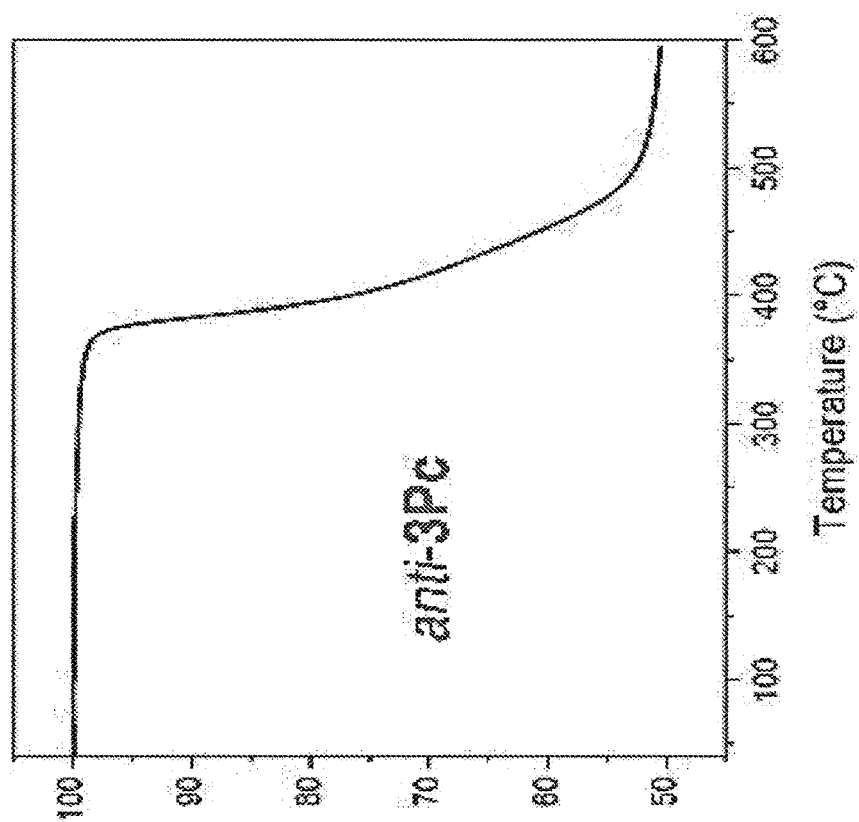
Figure 65B:
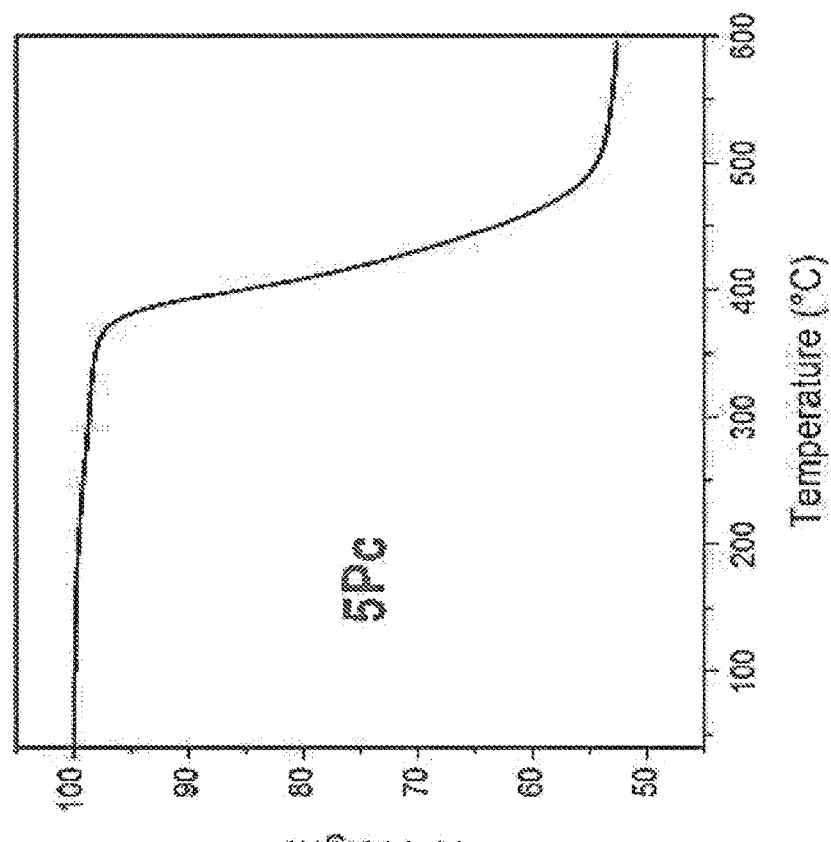
FIGS. 65A to 65D show a TGA graph of oligopentacenes 4Pc-7Pc.
Figure 65A:
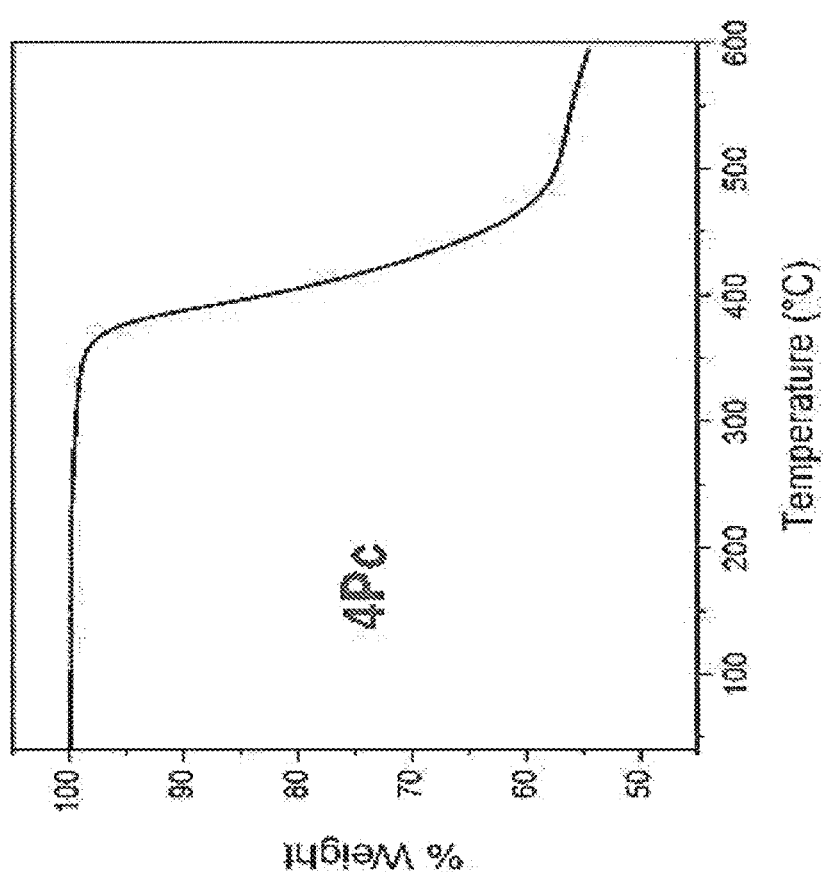
Figure 65D:
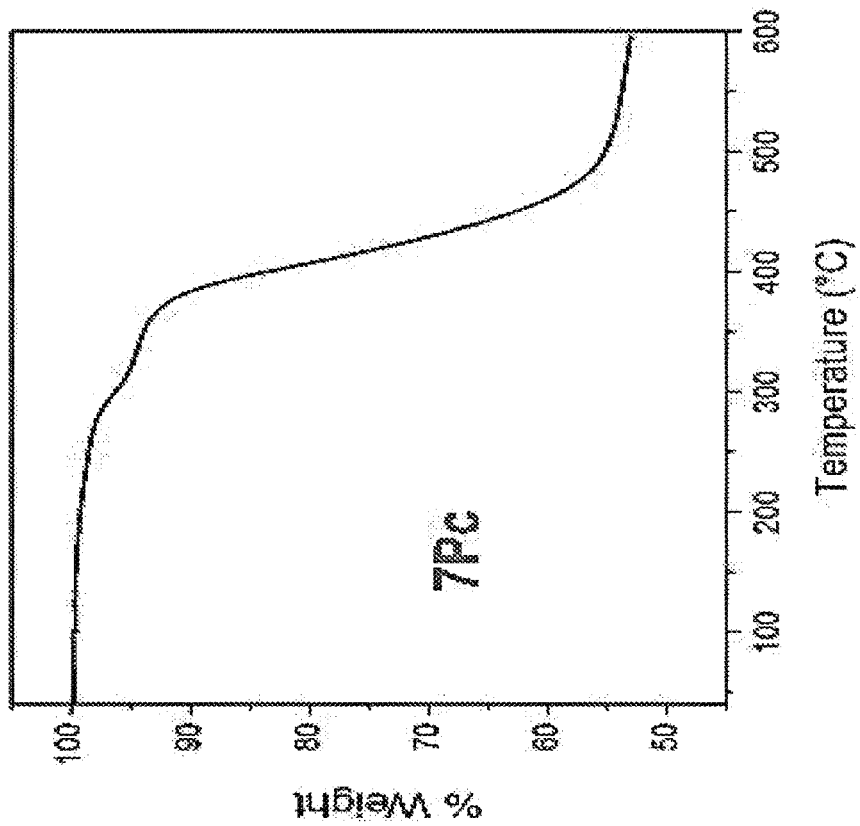
Figure 65C:
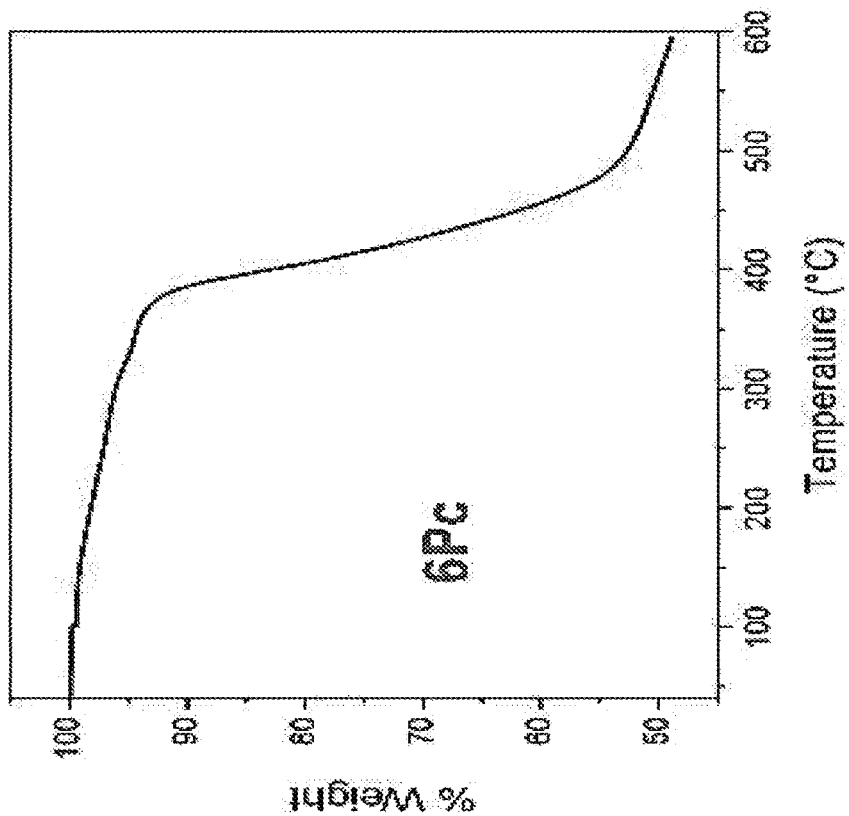
Figure 66A:
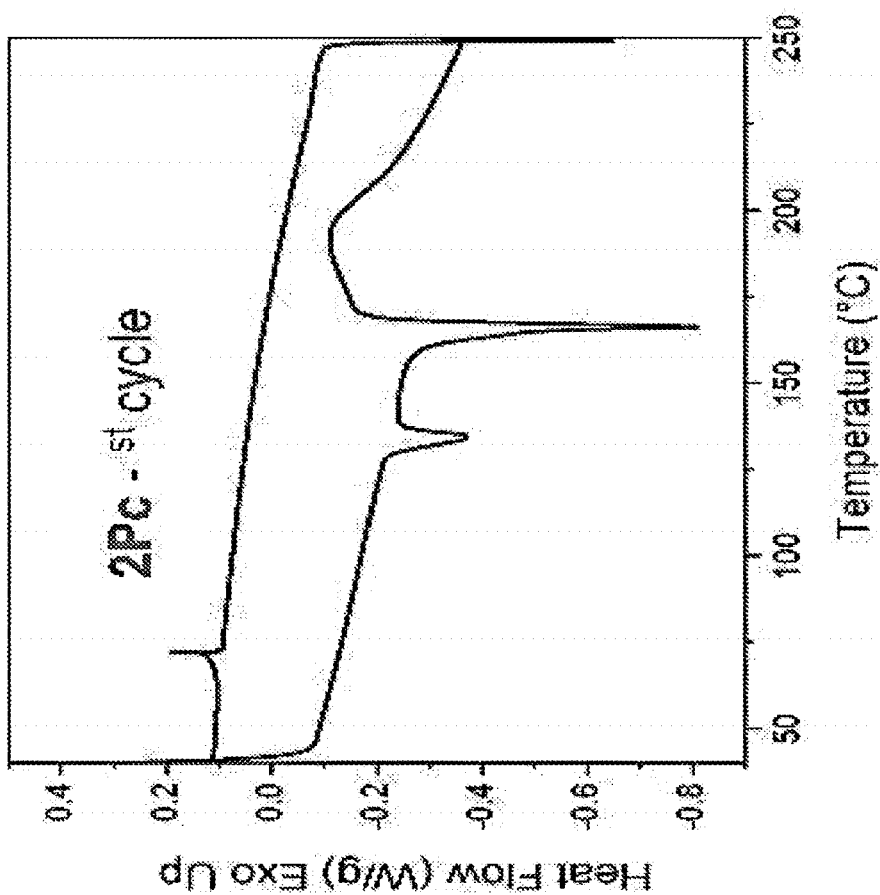
FIG. 66 shows differential scanning calorimetry (DSC) traces of oligopentacenes 2Pc-3Pc.
Figure 66B:
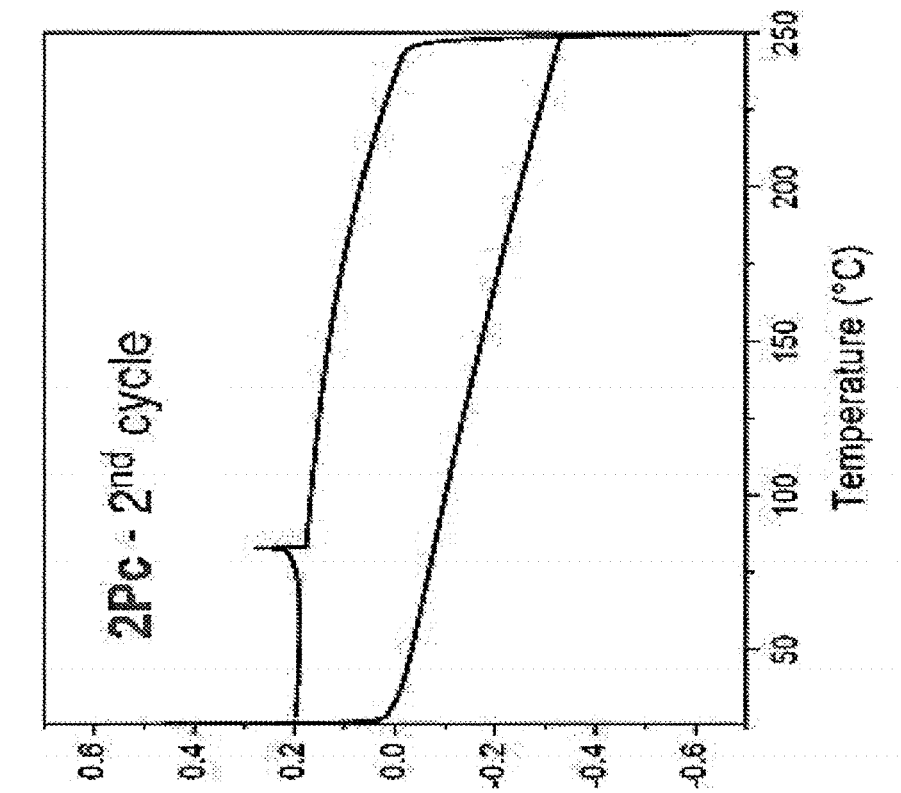
Figure 66D:
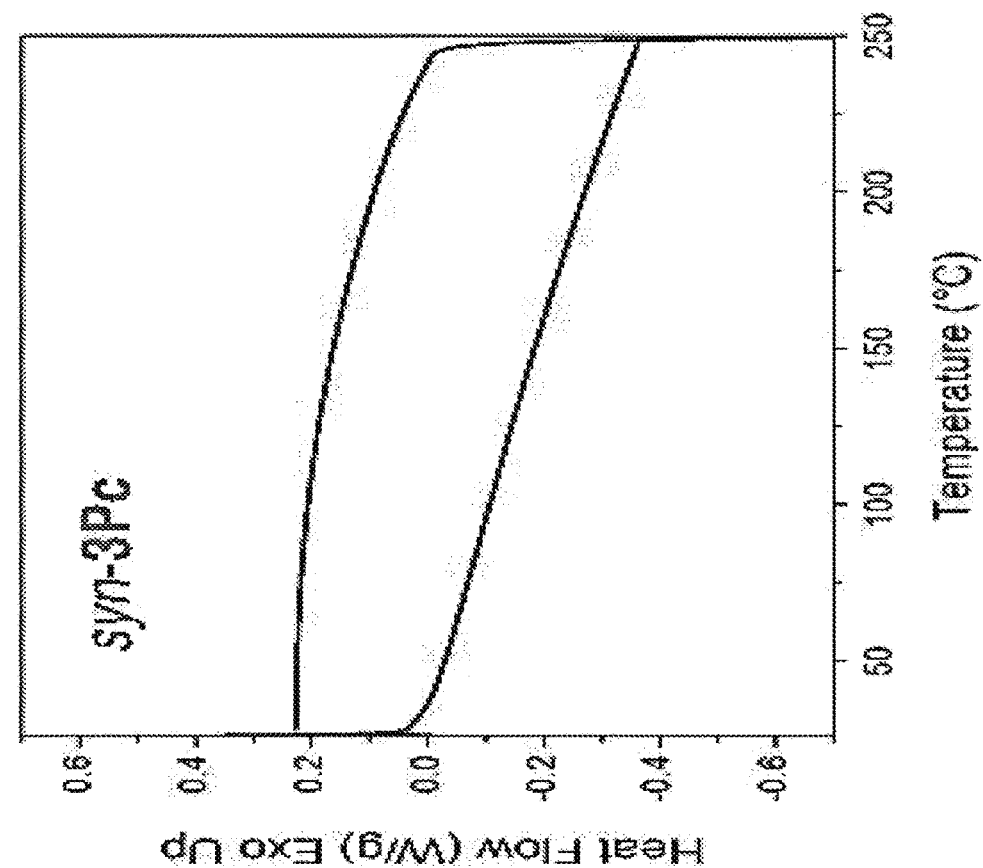
Figure 66C:
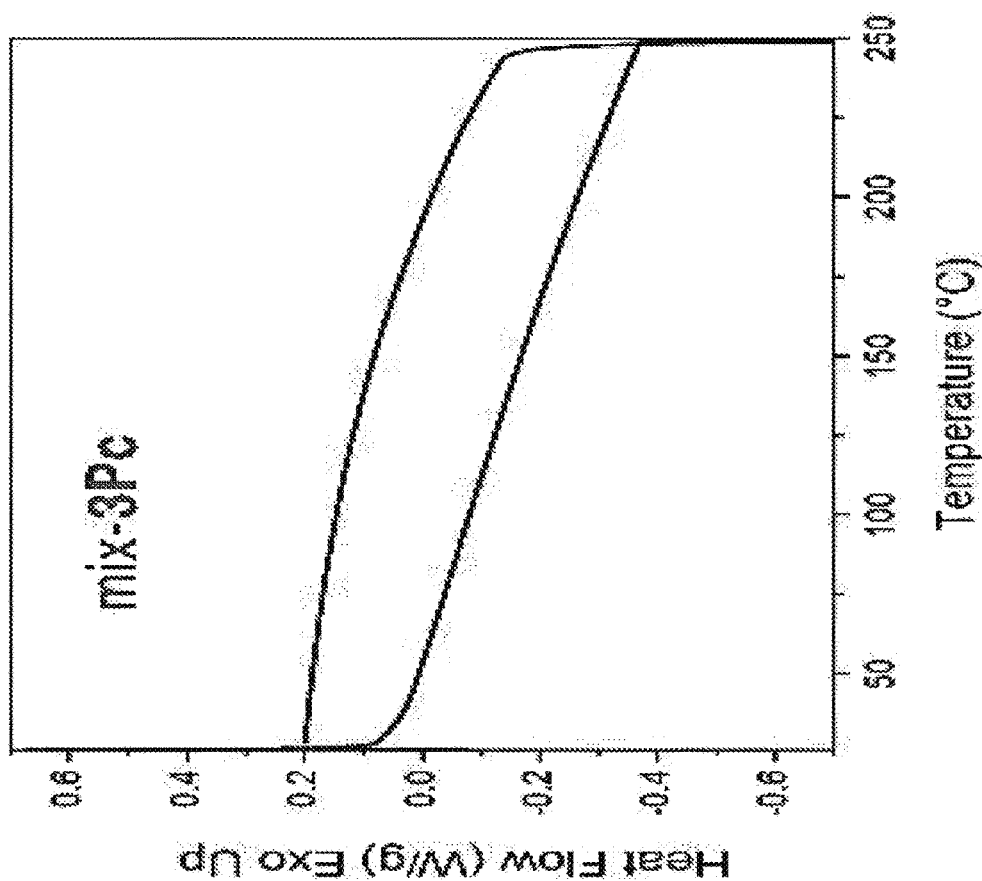
Figure 66E:
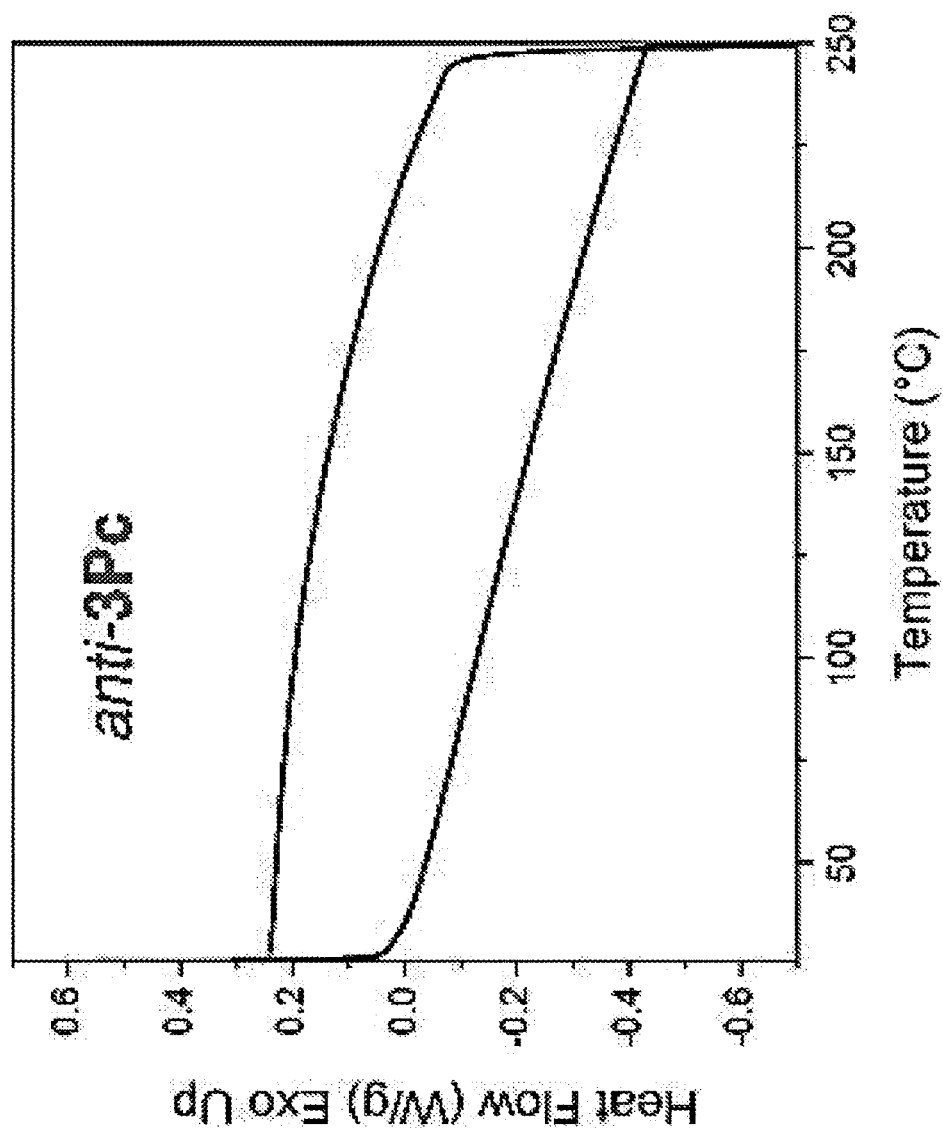
Figure 67B:
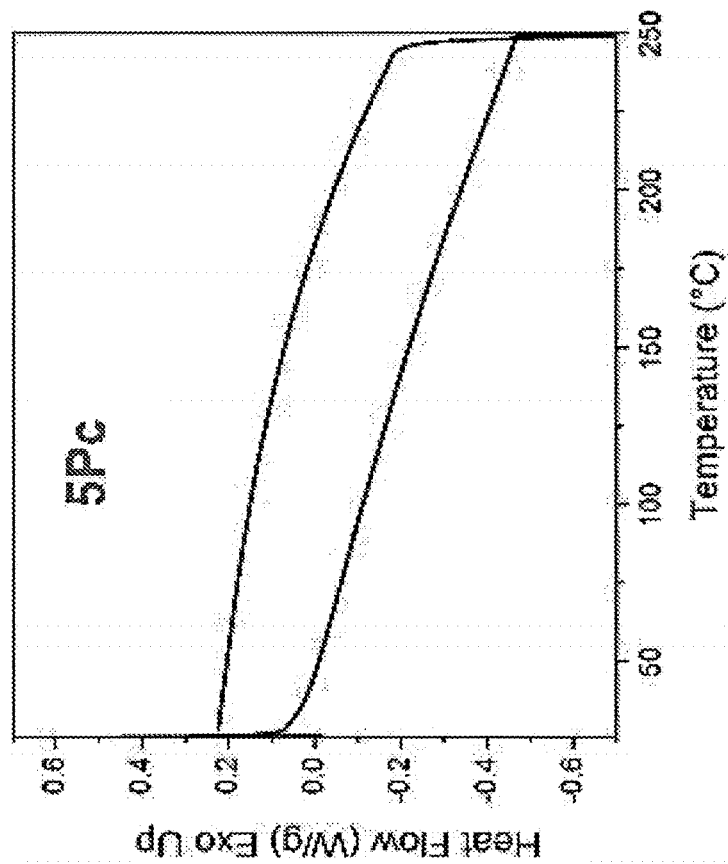
FIGS. 67A to 67D show DSC traces of oligopentacenes 4Pc-7Pc.
Figure 67A:
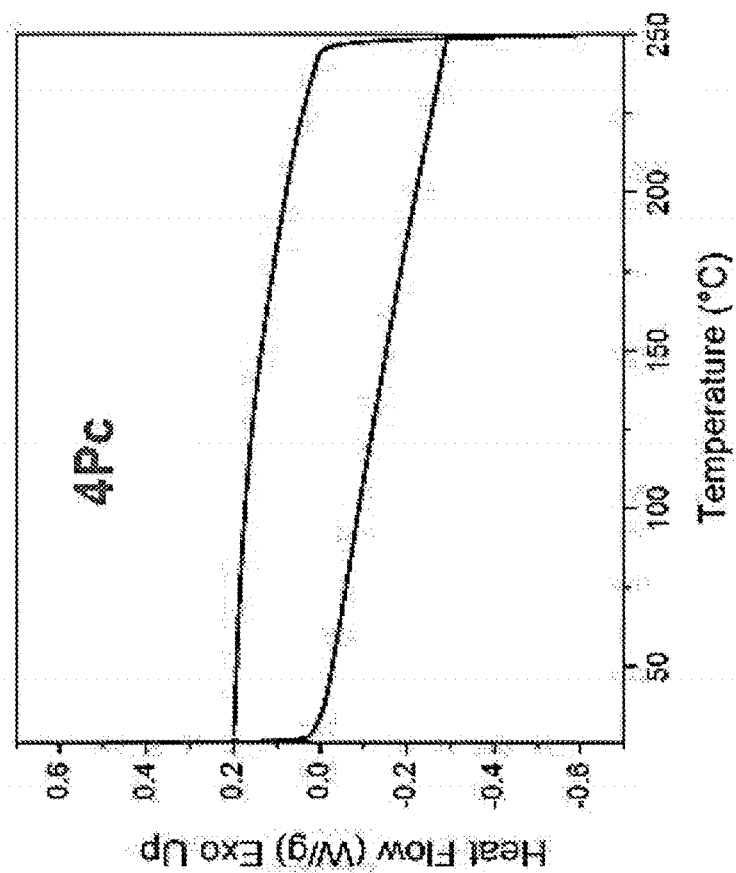
Figure 67D:
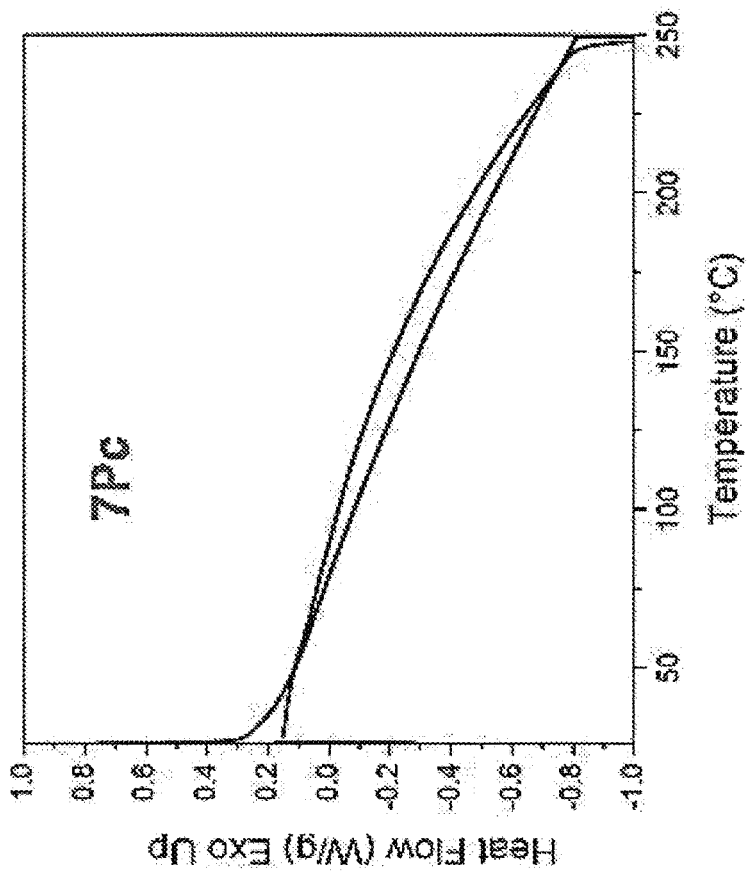
Figure 67C:
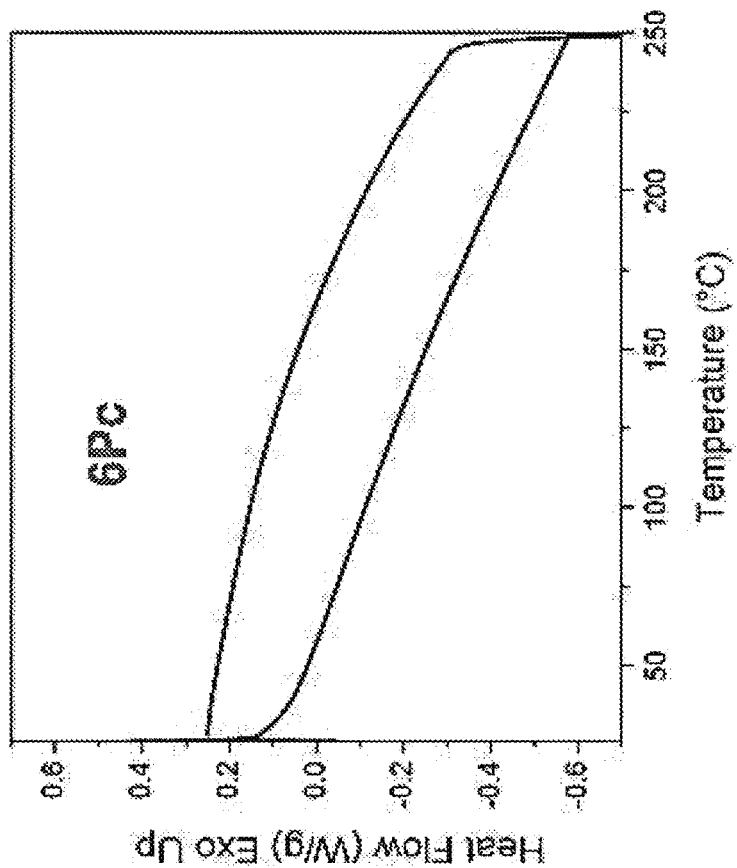
Figure 68:
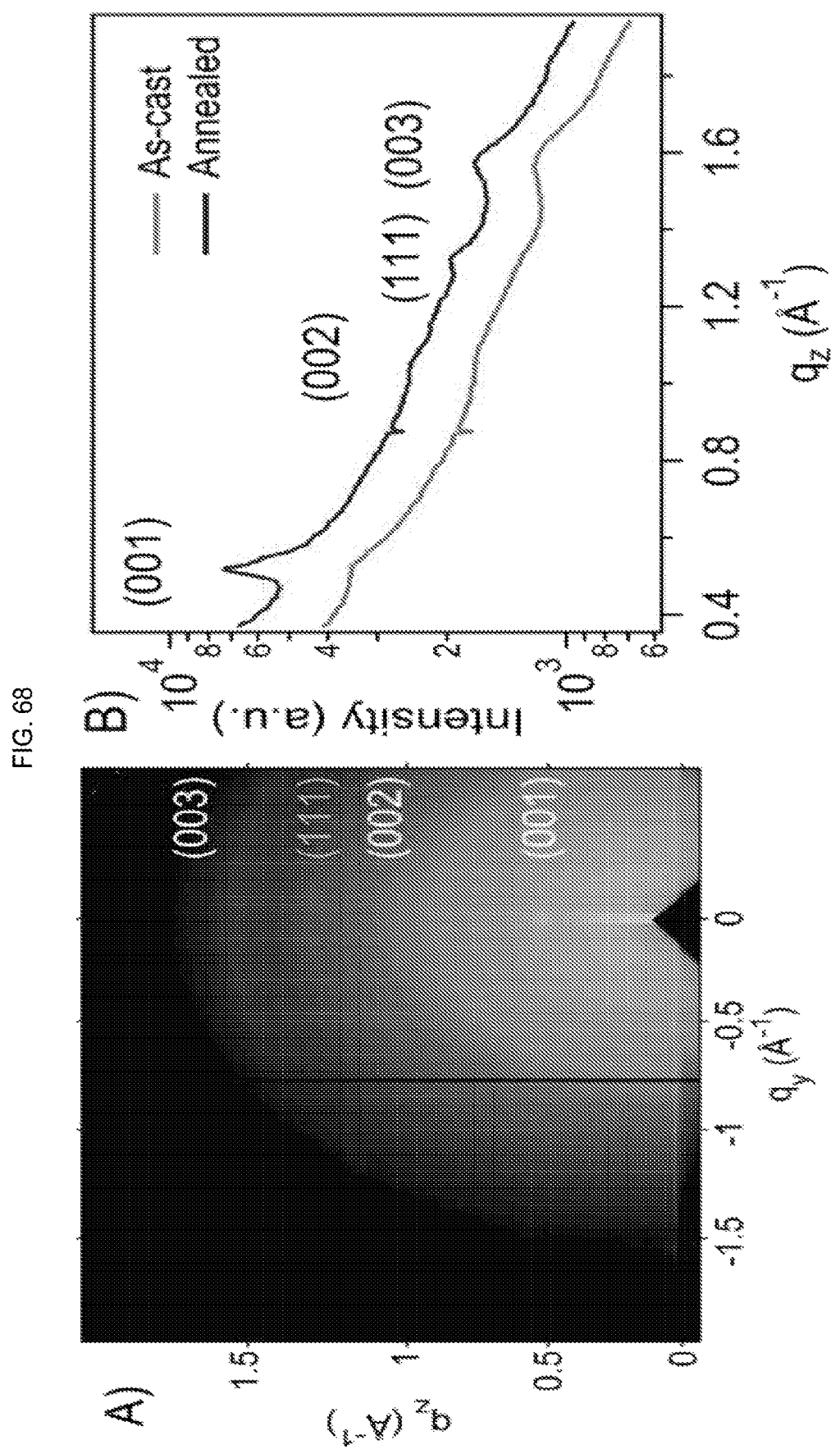
FIG. 68A shows 2D GIWAXS patterns of the annealed anti-3Pc film (incident tangle $\alpha_i$=0.22°).
FIG. 68B shows scattering profiles of as-cast and annealed anti-pentacene trimer (anti-3Pc) along the $q_z$-axis at $q_y$=0 (out-of-plane profile).
Figure 69A:
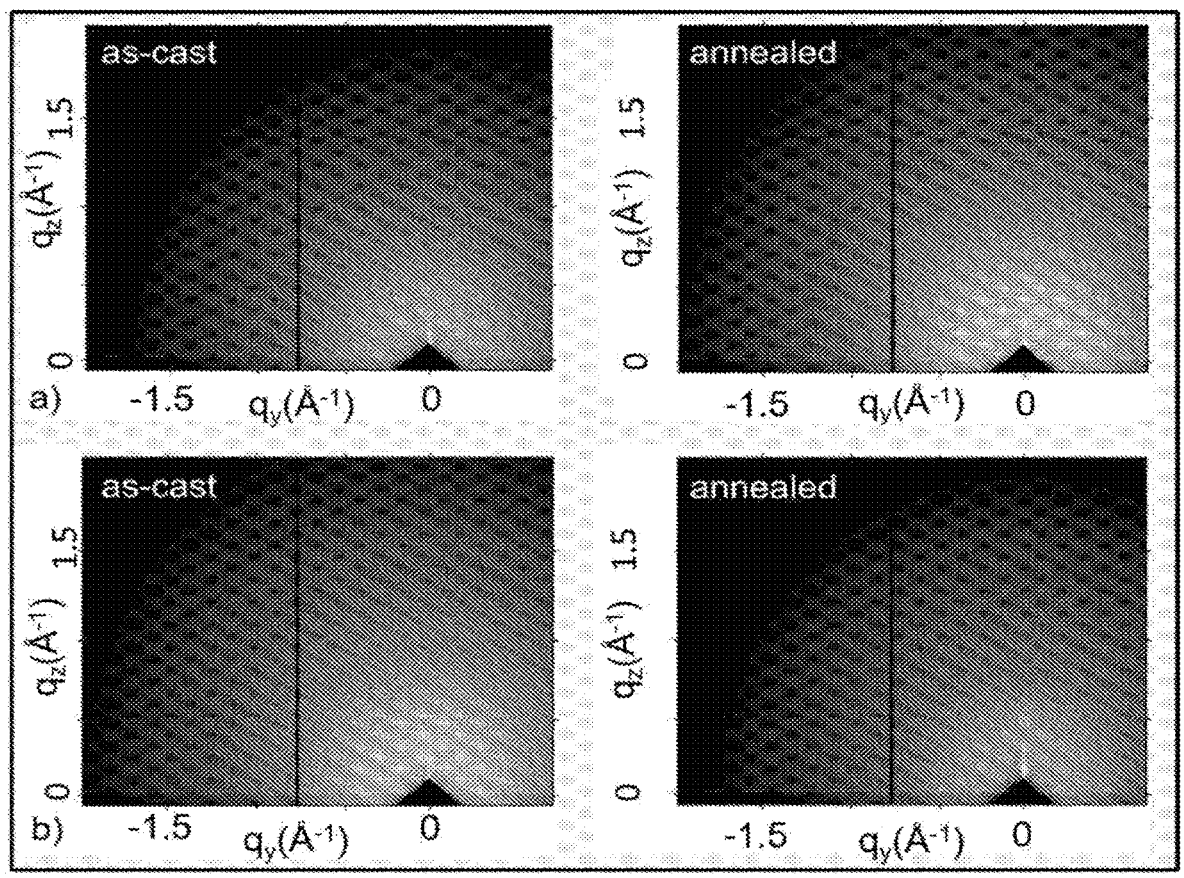
FIG. 69A shows 2D GIWAXS patterns of pentacene dimer (2Pc); left side image is the as-cast, while the image on the right is the annealed thin film; and a mixture of pentacene trimer (mix-3Pc;b)) 2D GIWAXS patterns, for left) as-cast, and right) annealed thin films.
Figure 69B:
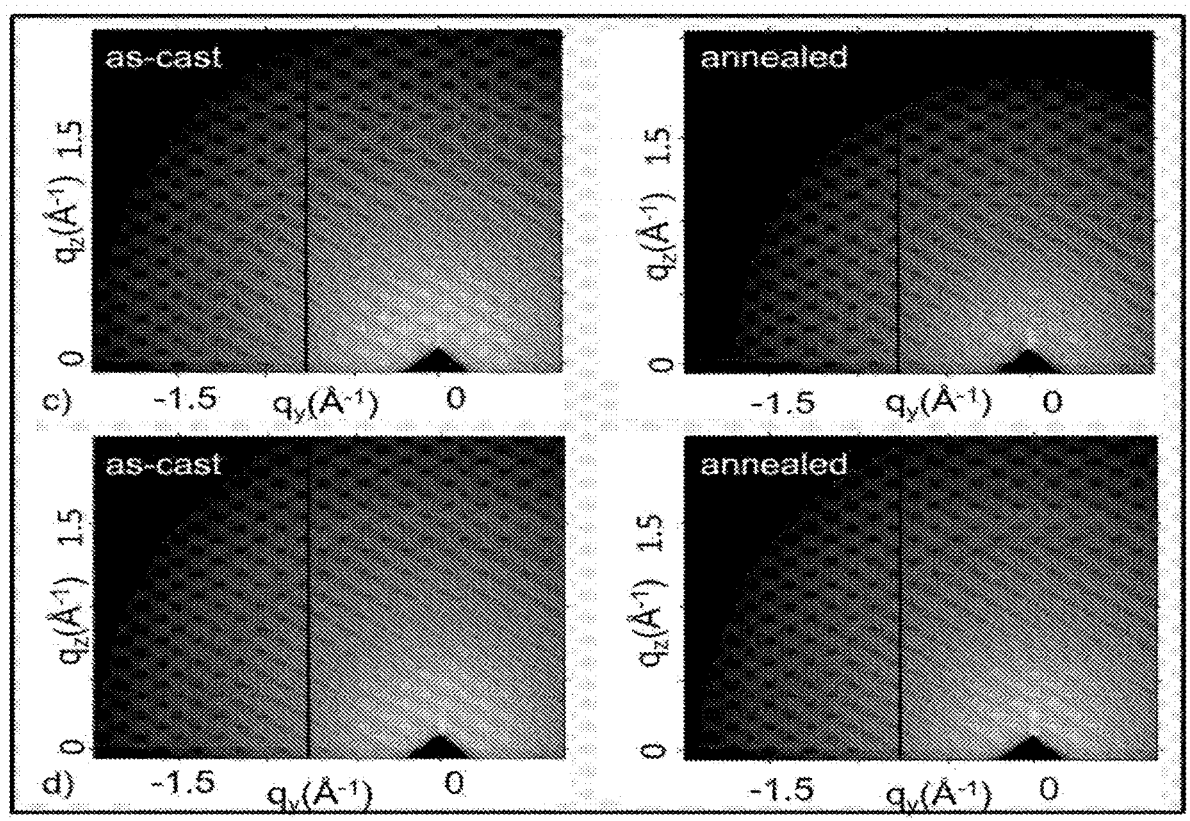
FIG. 69B shows syn-Pentacene trimer (syn-3Pc) 2D GIWAXS patterns; left side image is the as-cast, while the image on the right is the annealed thin film; and 2D GIWAXS patterns of, left) as-cast, and right) annealed anti-pentacene trimer (anti-3Pc;D)) thin-films.
Figure 69C:
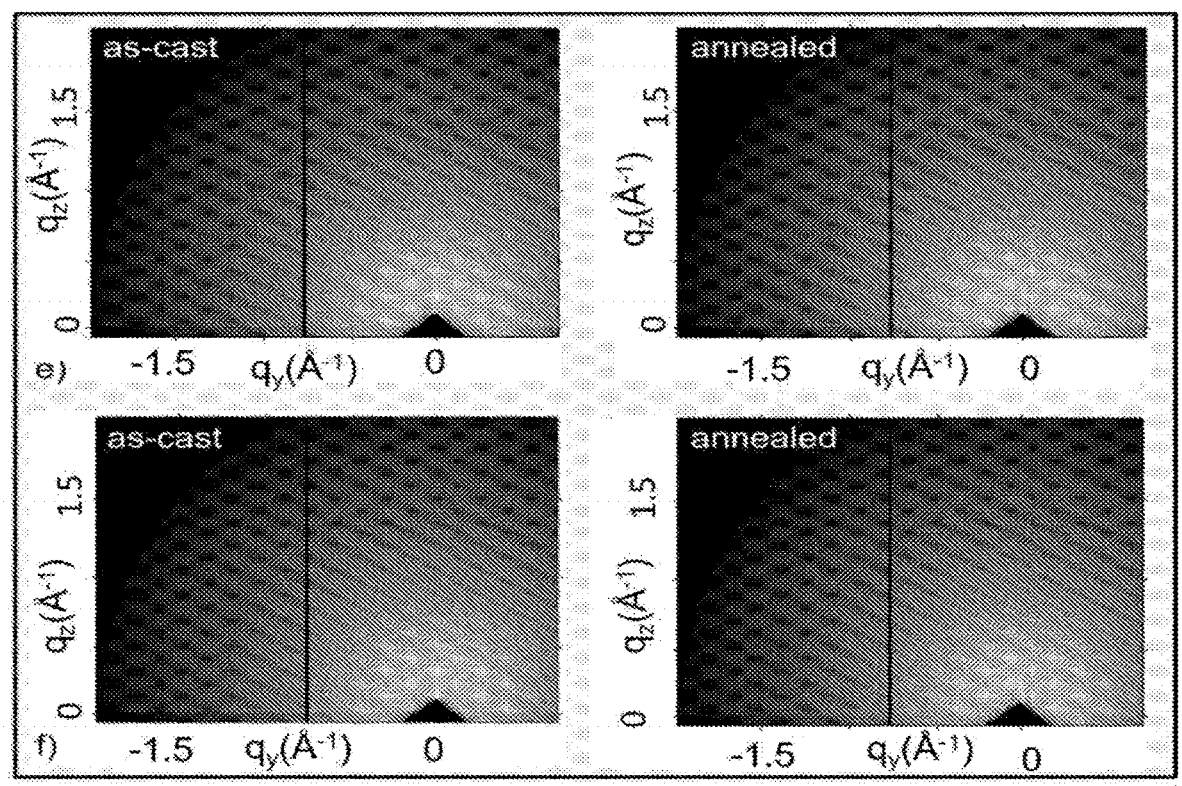
FIG. 69C shows pentacene tetramer (4Pc; e) 2D GIWAXS patterns; left side image is the as-cast, while the image on the right is the annealed thin film; and pentacene pentamer (5Pc; f)) 2D GIWAXS patterns; left side image is the as-cast, and the image on the right is the annealed film..
Figure 69D:
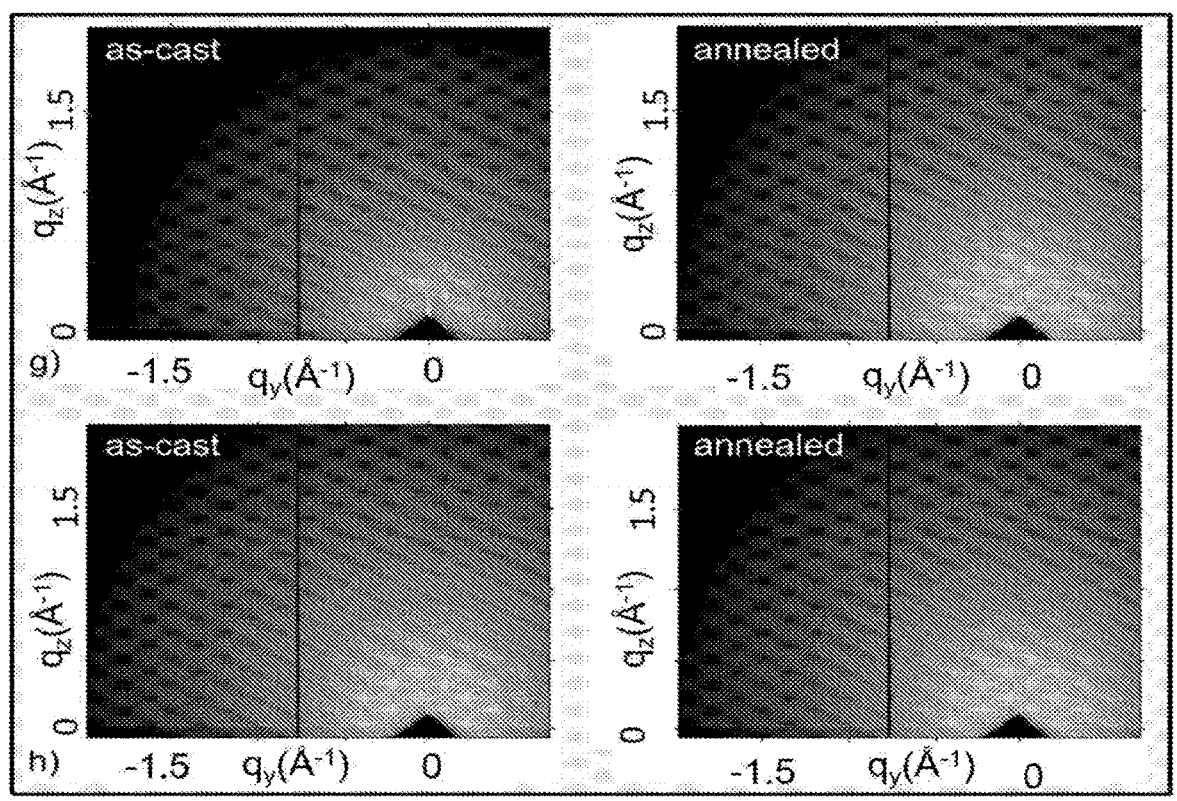
FIG. 69D shows pentacene hexamer (6Pc; g) 2D GIWAXS patterns; left side image is the as-cast, while the image on the right is the annealed thin film; and pentacene heptamer (7Pc; h)) 2D GIWAXS patterns; left side image is the as-cast, and right sid is the annealed thin film.

The highest occupied molecular orbital (HOMO) and lowest unoccupied molecular orbital (LUMO) levels were obtained by calibrating the onset of oxidation (or reduction, for LUMO) to the Fc/Fc$^+$ couple (FIG. 63).[111] The convergence of the band gap in this oligopentacene series is evident both from the frontier energy levels and from the UV-vis data. Similar to the oligopentacenes linked by the central ring reported by Lenherr et al. (shown in Scheme 2), polymer-like behavior is approached starting at 4Pc.[84] The band gap decrease is a result of the HOMO being raised as successive pentacene units are added, while the LUMO remains fairly constant. The raising of the HOMO level with increasing oligomer length has also been reported for phenylene[112] and thiophene systems.[87] Repeated scans revealed that the compounds all display good redox stability within the potential window measured, with the exception of the heptamer which had an irreversible reduction wave.

Example 35

Thermogravimetric Analysis on Oligopentacenes

Thermal gravimetric analysis (TGA) revealed excellent thermal stability of these pentacene oligomers, with all compounds exhibiting a decomposition temperature (T$_d$) of at least 370° C. under nitrogen flow. A summary of these values can be seen in TABLE 3. As the oligomer length increases there is no appreciable change in the T$_d$ of the compounds, which is likely attributable to the almost identical empirical chemical formula of the oligomers. For example, the smallest oligomer (2Pc) has a T$_d$ of 371° C., while the largest oligomer, (7Pc) has a T$_d$ of 382° C.

TABLE 3 provides data regarding thermal properties of oligopentacene obtained by Thermogravimetric analysis (TGA). The measurement was carried out under constant flow of nitrogen with a heating rate of 10° C./min. See, FIGS. 64A-64D and 65A to 65D.

TABLE 3

| Entry | Compound | Decomposition temperature, T$_d$ [° C.] |
|---|---|---|
| 1 | 2Pc | 371 |
| 2 | Mixture-3Pc | 373 |
| 3 | anti-3Pc | 374 |
| 4 | syn-3Pc | 372 |
| 5 | 4Pc | 374 |
| 6 | 5Pc | 380 |
| 7 | 6Pc | 380 |
| 8 | 7Pc | 382 |

Example 36

Differential Scanning Calorimetry Analysis on Oligopentacenes

The thermal transitions of these materials were studied by differential scanning calorimetry (DSC). Differential scanning calorimetry (DSC) was performed on a Q200 instrument (TA-instrument) under N$_2$ flow at a heating/cooling rate of 5° C./min.

Only 2Pc exhibited phase transitions, with a glass transition temperature of 134° C. and a melting point of 166° C.[105] However these transitions are only observed in the first heating cycle, due to the decomposition that is observed after the compound reaches its melting point under oxygen at high temperature. These non-reversible phase transitions agree with DSC performed on similar materials.[93] For the larger oligomers, no phase transitions were observed within the range of temperatures explored. See, FIGS. 66A to 66E and 67A to 67d.

Example 37

Thin Film Morphology Analysis on Oligopentacenes

In order to gain insights into the packing interactions of these materials, grazing incidence wide angle X-ray scattering (GIWAXS) data was collected for all oligopentacene films at incidence angles in the range of 0.2-0.22° C., which is above the critical angle of the oligopentacenes (ca. 0.17°) and below the critical angle of the substrate (ca. 0.24°). The crystal structure of these NODIPS-functionalized oligopentacenes has not been previously reported, and the crystalline content of these samples is too low for a detailed analysis (i.e., too few diffraction peaks). However, the crystal structure of 2Pc was previously reported where the TIPS solubilizing groups are used.[107] This compound, and several other classes of functionalized acenes105[105,113-115] exhibit a triclinic unit cell (space group P$\overline{1}$) in bulk and thin films. These studies were used to guide interpretation of the data.

The morphology of the regiopure trimers were investigated and compared to the mixed product to understand how any differences may arise from these two classes of materials. FIG. 68A displays GIWAXS data for the annealed anti-3Pc thin film, and FIG. 68B shows the out-of-plane line cuts (q$_y$=0) of the same oligomer before and after annealing at 200° C. for 30 min. The 2D scattering pattern is largely diffuse, meaning the film has a high amorphous content, but there are signatures of oriented crystallites along the out-of-plane z-axis (spots/arcs along q$_z$ rather than isotropic rings). Diffraction peaks in the as-cast film are weak and broad along the q$_z$ axis, but annealing increases their intensity and narrows the line shape, which demonstrates that crystallinity is enhanced with heat treatment. Moreover, the first-order peak is detected at $q_z^*=0.52$ Å$^{-1}$, corresponding with a periodicity of $d=2\pi/q_z^*=12.1$ Å, and higher-order peaks are detected at $2q_z^*=1.05$ Å$^{-1}$ and $3q_z^*=1.58$ Å$^{-1}$. Using the lattice parameters for 1Pc,[33] these peaks may be attributed to scattering from {002} and {003} planes. A comparison between the predicted and observed values is included in TABLE 4. An additional peak was observed at $q_z=1.33$ Å$^{-1}$, corresponding to an interlayer periodicity of 0.47 Å, which is consistent with scattering from {111} planes. Scattering from {001} planes is indicative of an edge-on crystallite orientation, where the direction of π-π stacking is in the plane of the film.

TABLE 4 shows the predicted positions of diffraction peaks for 6,13-bis(diisopropyloctylsilylethynyl)pentacene[33] and measured positions for anti-3Pc.

TABLE 4

| Plane | Predicted $q_z$ (Å$^{-1}$) | Measured $q_z$ (Å$^{-1}$) | Measured d (Å) |
|---|---|---|---|
| (001) | 0.51 | 0.52 | 12.1 |
| (002) | 1.03 | 1.05 | 0.60 |
| (111) | 1.24 | 1.33 | 0.47 |
| (003) | 1.54 | 1.58 | 0.40 |

Figure 70:
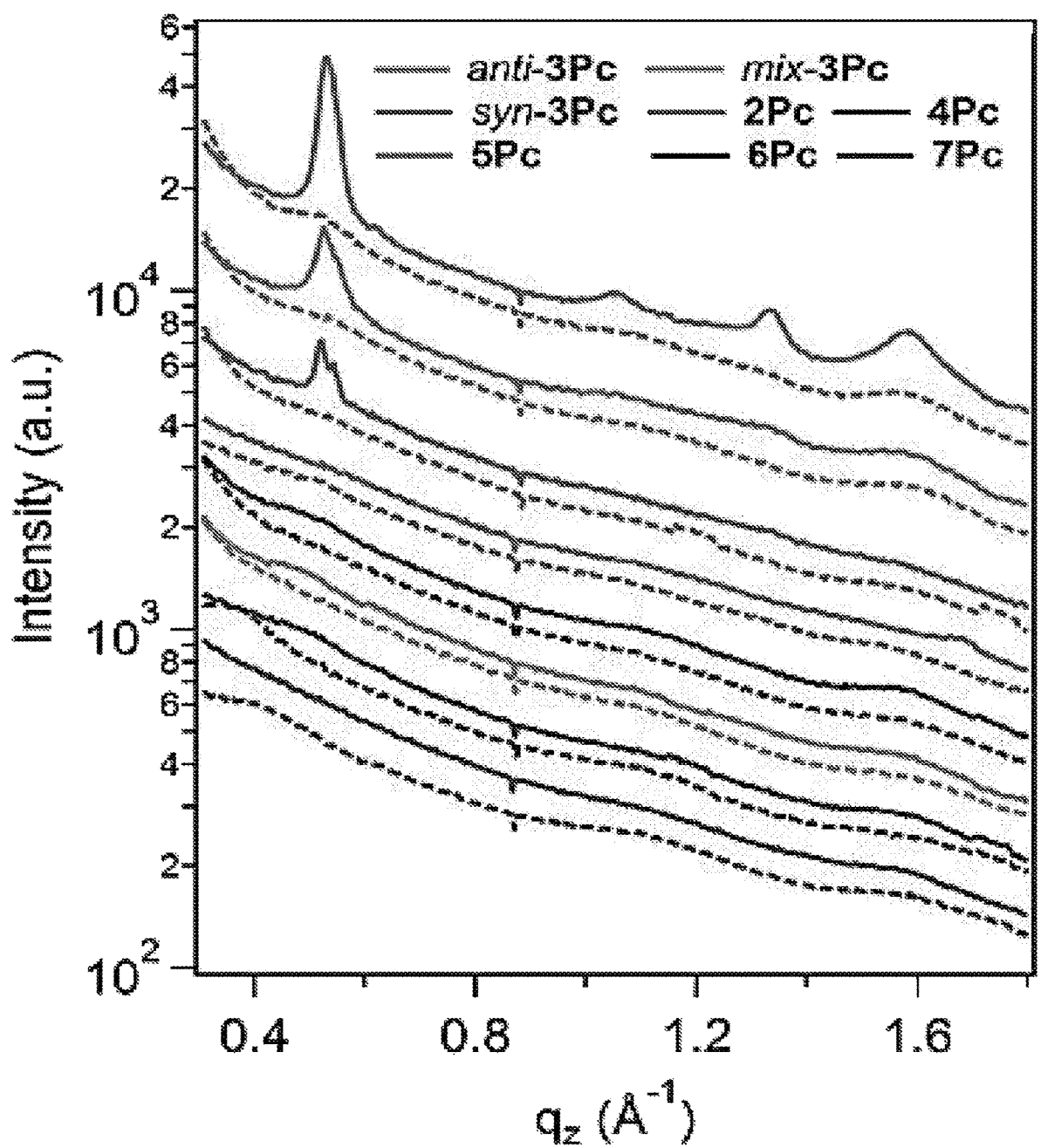
FIG. 70 shows out-of-plane line cuts I($q_z$) for as-cast (dashed lines) and thermally annealed (at 200° C., solid lines) oligopentacene films. Incidence angle is $\alpha_i$=0.20°. From the top having the highest intensity to the bottom having the lowest intensity, the oligopentacenes are as follows: anti-3Pc, mix-3Pc, syn-3Pc, 2Pc, 4Pc, 5Pc, 6Pc, and 7Pc.

Scattering from {111} planes is associated with a face-on orientation that is less favorable for transistors. Anti-3Pc adopts both of these orientations, which is consistent with other thin film studies of functionalized acenes.[93,113] FIG. 70 summarizes the out-of-plane intensity profiles for all of the oligopentacenes discussed here. The highest crystallinity is observed in the annealed trimer series, where it is higher in the order anti-3Pc>mix-3Pc>syn-3Pc. All other higher oligomers (4Pc-7Pc) materials exhibit very low crystallinity, and annealing has little or no impact on ordering. More regioisomers were created for higher oligomers, which can alter packing interactions. Understanding these fundamental details of poly- and oligo-pentacenes is important in designing the appropriate architectures for device fabrication.

The content of all patents, patent applications, published articles, abstracts, books, reference manuals and abstracts, as cited herein are hereby incorporated by reference in their entireties to more fully describe the state of the art to which the disclosure pertains.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variations that fall within the scope of the appended claims.

REFERENCES

1) Hanna, M. C.; Nozik, A. J. *J. Appl. Phys.* 2006, 100(7), 074510-074518.
2) Smith, M. B.; Michl, *J. Annu. Rev. Phys. Chem.* 2013, 64, 361-386.
3) Smith, M. B.; Michl, *J. Chem. Rev.* 2010, 110, 6891-6936.
4) Paci, I. et al., *J. Am. Chem. Soc.* 2006, 128, 16546-16553.
5) Congreve, D. N. et al., *Science* 2013, 340, 334-337.
6) Lee, J. et al., *Acc. Chem. Res.* 2013, 46, 1300-1311.
7) Green, M. A. *Prog. Photovolt: Res. Appl.* 2001, 9, 123-135.
8) Nozik, A. J. *Phys. E* 2002, 14, 115-120.
9) Shockley, W.; Queisser, H. J. *J. Appl. Phys.* 1961, 32, 510-519.
10) Busby, E. et al. *Nat. Mater.* 2014, 14, 426-433.
11) Busby, E. et al., *J. Phys. Chem. B* 2015, 119, 7644-7650.
12) Low, J. Z. et al., *Chem. Mater.* 2015, 27, 5453-5463.
13) Sanders, S. N. et al., *J. Am. Chem. Soc.* 2015, 137, 8965-8972.
14) Zirzlmeier, J. et al., *Proc. Natl Acad. Sci.* 2015, 112, 5325-5330.
15) Lukman, S. et al., *Adv. Funct. Mater.* 2015, 25, 5452-5461.
16) Varnayski, O. P. et al., *J. Phys. Chem. Lett.* 2015, 6, 1375-1384.
17) Singh, S.; et al., *J. Chem. Phys* 1965, 42, 330-342.
18) Monahan, N.; Zhu, X.-Y. *Annu. Rev. Phys. Chem.* 2015, 66, 601-618.
19) Aryanpour, K. et al., *arXiv:* 1508.00071 [cond-mat.mes-hall]2015.
20) Zeng, T. et al., *J. Am. Chem. Soc.* 2014, 136, 5755-5764.
21) Lee, J. et al., *Appl. Phys. Lett.* 2009, 95, 012506.
22) Yost, S. R. et al. *Nat. Chem.* 2014, 6, 492-497.
23) Chan, W.-L. et al. *Science* 2011, 334, 1541-1545.
24) Chan, W.-L. et al. *Acc. Chem. Res.* 2013, 46, 1321-1329.
25) Gradinaru, C. C. et al. *Proc. Nat. Acad. Sci.* 2001, 98, 2364-2369.
26) Musser, A. J. et al., *J. Am. Chem. Soc.* 2013, 135, 12747-12754.
27) Burdett, J. J.; Bardeen, C. *J. Acc. Chem. Res.* 2013, 46, 1312-1320.
28) Vallett, P. J. et al., *J. Phys. Chem. A.* 2013, 117, 10824-10838.
29) Müller, A. M. et al. *Chem. Phys. Lett.* 2006, 421, 518-522.
30) Müller, A. M. et al. *Am. Chem. Soc.* 2007, 129, 14240-14250.
31) Greyson, E. C. et al., *J. Phys. Chem. B.* 2010, 114, 14168-14177.
32) Alguire, E. C. et al., *J. Phys. Chem. A* 2015, 119, 299-311.
32) Trlifaj, M. *Czech J Phys* 1977, 27, 190-199.
33) Charbr, M.; Williams, D. F. *Chem. Phys. Lett.* 1977, 49, 599-603.
34) Geacintov, N. E. et al., *Chem. Phys. Lett.* 1971, 11, 504-508.
35) Mastron, J. N. et al., *J. Phys. Chem. B* 2013, 117, 15519-15526.
36) Roberts, S. T. et al., *J. Am. Chem. Soc.* 2012, 134, 6388-6400.
37) Pensack, R. D. et al., *J. Am. Chem. Soc.,* 2015, 137, 6790-6803.
38) Stern, H. L. et al., *Proc. Natl Acad. Sci.* 2015, 112, 7656-7661.
39) Houk, K. N. et al., *J. Org. Chem.* 2001, 66, 5517-5521.
40) Walker, B. J. et al., *Nat. Chem.* 2013, 5, 1019-1024.

41) Yang, L. et al., *Nano Lett.* 2014, 15, 354-358.
42) Wilson, J. S. et al., *J. Am. Chem. Soc.* 2001, 123, 9412-9417.
43) Caspar, J. V.; Meyer, T. J., *J. Phys. Chem.* 1983, 87, 952-957.
44) Englman, R.; Jortner, J., *Mol. Phys.* 1970, 18, 145-164.
45) Fudickar, W.; Linker, T., *J. Am. Chem. Soc.* 2012, 134, 15071-15082.
46) Anthony, J. E. et al., *Org. Lett.* 2002, 4, 15-18.
47) Anthony, J. E. et al., *J. Am. Chem. Soc.* 2001, 123, 9482-9483.
48) Payne, M. M. et al., *J. Am. Chem. Soc.* 2005, 127, 8028-8029.
49) Purushothaman, B. et al., *Org. Lett.* 2010, 12, 2060-2063.
50) Greyson, E. C. et al., *J. Phys. Chem. B* 2009, 114, 14223-14232.
51) Walker, B. J. et al. *Nat. Chem.* 2013, 5, 1019-1024.
52) Snellenburg, J. J. L. et al., *J. Stat. Softw.* 2012, 49, 1-22.
53) Bensasson, R.; Land, E. J. *Trans. Faraday Soc.* 1971, 67, 1904-1915.
54) Angliker, H. et al., *Chem. Phys. Lett.* 1982, 87, 208-212.
55) Plunkett, K. N. et al. *Organic Letters* 2009, 11, 2225-2228.
56) Brouwer, A. M. *Pure and Applied Chemistry* 2011, 83, 2213-2228.
57) Resch-Genger, U.; Rurack, K. *Pure and Applied Chemistry* 2013, 85, 2005-2013.
58) Busing, W. R.; Levy, H. A. *Acta Crystallographica* 1957, 10, 180-182.
59) Clark, R. C.; Reid, J. S. *Acta Crystallographica* Section A 1995, 51, 887-897.
60) Dolomanov, O. V. et al. *Journal of Applied Crystallography* 2009, 42, 339-341.
61) Sheldrick, G. *Acta Crystallographica Section A* 2008, 64, 112-122.
62) Goto, K. et al. *Angew. Chem. Int. Ed.* 2012, 51, 10333-10336.
63) Katz, H. E. et al. *Acc. Chem. Res.*, 2001, 34, 359-369.
64) Ito, K. et al. *Angew. Chem.*, 2003, 115, 1191-1194.
65) Anthony, J. E. *Angew. Chem. Int. Ed.*, 2008, 47, 452-483.
66) Zade S. S.; Bendikov, M. *Angew. Chem. Int. Ed.*, 2010, 49, 4012-4015.
67) Ball, M. et al. *Acc. Chem. Res.*, 2015, 48, 267-276.
68) Tsefrikas V. M.; Scott, L. T. *Chem. Rev.*, 2006, 106, 4868-4884.
69) Sundar, V. C. et al. *Science*, 2004, 303, 1644-1646.
70) Bunz, U. H. F. *Acc. Chem. Res.*, 2015, 48, 1676-1686.
71) Yen-Yi, L. *Electron Devices, IEEE Transactions on,* 1997, 44, 1325-1331.
72) Park, S. K. *Appl. Phys. Lett.*, 2007, 91, 063514.
73) Afzali, A. *J. Am. Chem. Soc.*, 2002, 124, 8812-8813.
74) Jo, S. B. *ACS Nano*, 2015, 9, 8206-8219.
75) Herwig, P. T.; Müllen, K. *Adv. Mater.*, 1999, 11, 480-483.
76) Shu, Y. *Chem. Sci.*, 2011, 2, 363-368.
77) Anthony, J. E. *Chem. Rev.*, 2006, 106, 5028-5048.
78) Bendikov, M. *Chem. Rev.*, 2004, 104, 4891-4946.
79) Fudickar, W.; Linker, T. *J. Am. Chem. Soc.*, 2012, 134, 15071-15082.
80) Maliakal, A. *Chem. Mater.*, 2004, 16, 4980-4986.
81) Lehnherr, D. et al. *J. Org. Chem.*, 2009, 74, 5017-5024.
82) Okamoto, T.; Bao, Z. *J. Am. Chem. Soc.*, 2007, 129, 10308-10309.
83) Lehnherr, D. et al. *Tetrahedron*, 2008, 64, 11449-11461.
84) Lehnherr, D. et al. *Angew. Chem. Int. Ed.*, 2010, 49, 6190-6194.
85) Tokito, S. et al. *Proc. SPIE-Int. Soc. Opt. Eng.*, 2001, 4105, 69-74.
86) Porz, M. et al. *Macromol. Rapid Commun.*, 2013, 34, 1611-1617.
87) Capozzi, B. et al., *J. Am. Chem. Soc.*, 2014, 136, 10486-10492.
88) Koch, F. P. V. et al., *J. Am. Chem. Soc.*, 2013, 135, 13695-13698.
89) Koch, F. P. V. et al., *J. Am. Chem. Soc.*, 2013, 135, 13699-13709.
90) Zhang, L. et al., *J. Am. Chem. Soc.*, 2013, 135, 844-854.
91) Liu, F. et al., *J. Am. Chem. Soc.*, 2015, 137, 10357-10366.
92) Müllen, K.; Wegner, G. *Electronic Materials: The Oligomer Approach* Wiley-VCH: New York: 1998.
93) Chen, J. et al. *Mater. Chem.*, 2008, 18, 1961-1969.
94) Swartz, C. R. et al. *Org. Lett.*, 2005, 7, 3163-3166.
95) Lehnherr, D. et al. *Org. Lett.*, 2008, 10, 4779-4782.
96) Lehnherr, D. et al. *Org. Lett.*, 2008, 10, 4163-4166.
97) Lehnherr D.; Tykwinski, R. R. *Org. Lett.*, 2007, 9, 4583-4586.
98) Miao, Q. et al., *J. Am. Chem. Soc.*, 2006, 128, 1340-1345.
99) Payne, M. M. et al. *Org. Lett.*, 2004, 6, 3325-3328.
100) Takahashi, T. et al. *Am. Chem. Soc.*, 2000, 122, 12876-12877.
101) Lu, J. e al., *J. Am. Chem. Soc.*, 2006, 128, 17043-17050.
102) Zhao, Y. et al., *J. Org. Chem.*, 2008, 73, 5506-5513.
103) Bénard, C. P. et al. *J. Org. Chem.*, 2007, 72, 7229-7236.
104) Xiao, S. et al. *Chem. Sci.*, 2013, 4, 2018-2023.
105) Kumarasamy, E. et al. *Chem. Rev.*, 2015, 115, 11239-11300.
106) Okamoto, T. et al. *Synth. Met.*, 2010, 160, 2447-2451.
107) Sanders, S. N. et al., *J. Am. Chem. Soc.*, 2015, 137, 8965-8972.
108) Wu, W. et al. *Soc. Rev.*, 2010, 39, 1489-1502.
109) Coropceanu, V. et al. *Chem. Rev.*, 2007, 107, 926-952.
110) Ashton, P. R. et al., *J. Am. Chem. Soc.* 1993, 115, 5422-5429.
111) You, J. et al. *Nat Commun* 2013, 4, 1446.
112) Banerjee, M. et al., *J. Am. Chem. Soc.*, 2009, 131, 1780-1786.
113) Kline, R. J. et al. *Chem. Mater.*, 2011, 23, 1194-1203.
114) Mannsfeld, S. C. B. et al. *Adv. Mater.*, 2011, 23, 127-131.
115) Kang, J. et al., *J. Am. Chem. Soc.*, 2008, 130, 12273-12275.

What is claimed are:

1. A soluble, stable singlet fission material, comprising an oligoacene of at least two covalently bound oligoacene monomers with or without a spacer, wherein the lower singlet exciton energy of one oligoacene monomer is essentially greater than about or essentially equal to about the sum of the energies of the triplet excitons of each of the at least two oligoacene monomers.

2. The material of claim 1, wherein the at least two covalently bound oligoacene monomers are different.

3. The material of claim 1, wherein the at least two covalently bound oligoacene monomers are the same.

4. The material of claim 1, wherein the material comprises asymmetric oligoacene monomers.

5. The material of claim 1, wherein the material is an oligomer of polyoligoacenes.

6. The material of claim 1, wherein the material is a polymer of polyoligoacenes.

7. The material of claim 1, wherein the material is essentially exoergic.

8. The material of claim 1, wherein the material is essentially isoergic.

9. The material of claim 1, wherein the material generates multiple excitons.

10. The material of claim 1, wherein the material is selected from the group consisting of: pentacene-hexacene, 2,2'bipentacene, pentacene-tetracene, an oligomer of 1-10 tetracenes, a polymer of 11-200 tetracenes, an oligomer of 1-10 pentacenes, a polymer of 11-200 tetracenes, and a hetero polymer of pentacenes, tetracenes, and/or hexacenes of 1-200 monomers in length, and any combinations thereof.

11. An electronic, optical, or electrooptical component or device comprising a material of claim 1.

* * * * *

UNITED STATES PATENT AND TRADEMARK OFFICE
CERTIFICATE OF CORRECTION

PATENT NO. : 10,752,730 B2
APPLICATION NO. : 15/536964
DATED : August 25, 2020
INVENTOR(S) : Luis Miguel Campos et al.

It is certified that error appears in the above-identified patent and that said Letters Patent is hereby corrected as shown below:

On the Title Page

Item (73) Assignee should be corrected to read:
The Trustees of Columbia University in the City of New York, New York, NY (US);
Brookhaven Science Associates, LLC, Upton, NY (US)

Signed and Sealed this
Fourth Day of October, 2022

Katherine Kelly Vidal
*Director of the United States Patent and Trademark Office*